(12) United States Patent
Hallows et al.

(10) Patent No.: US 11,970,722 B2
(45) Date of Patent: Apr. 30, 2024

(54) ENGINEERED ACID ALPHA-GLUCOSIDASE VARIANTS

(71) Applicant: Codexis, Inc., Redwood City, CA (US)

(72) Inventors: William Casey Hallows, San Francisco, CA (US); Rachel Cathleen Botham, Burlingame, CA (US); Yu Zhu, Newark, CA (US); Chinping Chng, Menlo Park, CA (US); Nikki Dellas, San Carlos, CA (US); Gjalt W. Huisman, Redwood City, CA (US); Moulay Hicham Alaoui Ismaili, San Mateo, CA (US); David William Homan, San Ramon, CA (US); Adam P. Silverman, San Carlos, CA (US); Jonathan Vroom, South San Francisco, CA (US); Jessica P. Lao, San Carlos, CA (US)

(73) Assignee: Codexis, Inc., Redwood City, CA (US)

( * ) Notice: Subject to any disclaimer, the term of this patent is extended or adjusted under 35 U.S.C. 154(b) by 476 days.

(21) Appl. No.: 17/126,647

(22) Filed: Dec. 18, 2020

(65) Prior Publication Data

US 2021/0189365 A1    Jun. 24, 2021

Related U.S. Application Data

(60) Provisional application No. 62/951,625, filed on Dec. 20, 2019.

(51) Int. Cl.
*A61K 38/00* (2006.01)
*C12N 9/34* (2006.01)

(52) U.S. Cl.
CPC .... *C12N 9/2428* (2013.01); *C12Y 302/01003* (2013.01); *A61K 38/00* (2013.01)

(58) Field of Classification Search
CPC .............................. C12N 9/2428; A61K 38/00
See application file for complete search history.

(56) References Cited

U.S. PATENT DOCUMENTS

| | | | |
|---|---|---|---|
| 5,605,793 A | 2/1997 | Stemmer | |
| 5,811,238 A | 9/1998 | Stemmer et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,180,406 B1 | 1/2001 | Stemmer | |
| 6,251,674 B1 | 6/2001 | Tobin et al. | |
| 6,265,201 B1 | 7/2001 | Wackett et al. | |
| 6,277,638 B1 | 8/2001 | Stemmer | |
| 6,287,861 B1 | 9/2001 | Stemmer et al. | |
| 6,287,862 B1 | 9/2001 | delCardayre et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,323,030 B1 | 11/2001 | Stemmer | |
| 6,326,204 B1 | 12/2001 | delCardayre et al. | |
| 6,335,160 B1 | 1/2002 | Patten et al. | |
| 6,335,198 B1 | 1/2002 | delCardayre et al. | |
| 6,337,186 B1 | 1/2002 | Krebber | |
| 6,344,356 B1 | 2/2002 | Stemmer | |
| 6,352,859 B1 | 3/2002 | delCardayre et al. | |
| 6,355,484 B1 | 3/2002 | Patten et al. | |
| 6,358,740 B1 | 3/2002 | Patten et al. | |
| 6,358,742 B1 | 3/2002 | Stemmer | |
| 6,365,377 B1 | 4/2002 | Patten et al. | |
| 6,365,408 B1 | 4/2002 | Stemmer | |
| 6,368,861 B1 | 4/2002 | Crameri et al. | |
| 6,372,497 B1 | 4/2002 | Stemmer | |
| 6,376,246 B1 | 4/2002 | Crameri et al. | |
| 6,379,964 B1 | 4/2002 | delCardayre et al. | |
| 6,391,552 B2 | 5/2002 | Stemmer | |
| 6,391,640 B1 | 5/2002 | Minshull et al. | |
| 6,395,547 B1 | 5/2002 | Stemmer | |
| 6,406,855 B1 | 6/2002 | Patten et al. | |
| 6,406,910 B1 | 6/2002 | Patten et al. | |
| 6,413,745 B1 | 7/2002 | Patten et al. | |
| 6,413,774 B1 | 7/2002 | Stemmer | |
| 6,420,175 B1 | 7/2002 | Stemmer | |
| 6,423,542 B1 | 7/2002 | Crameri et al. | |
| 6,426,224 B1 | 7/2002 | Crameri et al. | |
| 6,436,675 B1 | 8/2002 | Welch et al. | |
| 6,444,468 B1 | 9/2002 | Stemmer et al. | |
| 6,455,253 B1 | 9/2002 | Patten et al. | |
| 6,479,652 B1 | 11/2002 | Crameri et al. | |
| 6,482,647 B1 | 11/2002 | Stemmer | |
| 6,483,011 B1 | 11/2002 | Stemmer et al. | |
| 6,484,105 B2 | 11/2002 | Zhang | |
| 6,489,146 B2 | 12/2002 | Stemmer et al. | |
| 6,500,617 B1 | 12/2002 | Stemmer et al. | |
| 6,500,639 B2 | 12/2002 | Subramanian | |

(Continued)

FOREIGN PATENT DOCUMENTS

WO    95/22625 A1    8/1995
WO    95/33836 A1    12/1995

(Continued)

OTHER PUBLICATIONS

Altschul, S., et al., "Basic local alignment search tool," J. Mol. Biol., 215: 403-410 [1990].

(Continued)

*Primary Examiner* — Tekchand Saidha
(74) *Attorney, Agent, or Firm* — Codexis, Inc.

(57) ABSTRACT

The present invention provides engineered acid alpha-glucosidase (GAA) polypeptides and compositions thereof. In some embodiments, the engineered GAA polypeptides have been optimized to provide increased expression, stability at neutral pH, and activity in cell lysates. The invention also provides methods for utilization of the compositions comprising the engineered GAA polypeptides for therapeutic and other purposes.

39 Claims, 27 Drawing Sheets

Specification includes a Sequence Listing.

(56) References Cited

U.S. PATENT DOCUMENTS

| | | |
|---|---|---|
| 6,506,602 B1 | 1/2003 | Stemmer |
| 6,506,603 B1 | 1/2003 | Stemmer |
| 6,518,065 B1 | 2/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,605,430 B1 | 8/2003 | Affholter et al. |
| 6,613,514 B2 | 9/2003 | Patten et al. |
| 6,653,072 B1 | 11/2003 | Patten et al. |
| 6,703,240 B1 | 3/2004 | Stemmer et al. |
| 6,716,631 B1 | 4/2004 | delCardayre et al. |
| 6,825,001 B2 | 11/2004 | Wackett et al. |
| 6,686,515 B1 | 12/2004 | Lassner et al. |
| 6,902,922 B2 | 6/2005 | Ness et al. |
| 6,917,882 B2 | 7/2005 | Selifonov et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,220,566 B2 | 5/2007 | Ness et al. |
| 7,288,375 B2 | 10/2007 | Stemmer et al. |
| 7,384,387 B1 | 6/2008 | Raillard et al. |
| 7,421,347 B2 | 9/2008 | Selifonov et al. |
| 7,430,477 B2 | 9/2008 | Selifonov et al. |
| 7,462,469 B2 | 12/2008 | Bass et al. |
| 7,531,341 B1 | 5/2009 | Vellard et al. |
| 7,534,564 B2 | 5/2009 | Patten et al. |
| 7,534,595 B2 | 5/2009 | Vellard et al. |
| 7,560,263 B2 | 7/2009 | Kakkis et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,477 B1 | 1/2011 | Gustafsson et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 7,981,614 B2 | 7/2011 | Stemmer et al. |
| 8,014,961 B2 | 9/2011 | Bass et al. |
| 8,029,988 B2 | 10/2011 | Crameri et al. |
| 8,048,674 B2 | 11/2011 | Minshull et al. |
| 8,058,001 B2 | 11/2011 | Crameri et al. |
| 8,076,138 B2 | 12/2011 | delCardayre et al. |
| 8,108,150 B2 | 1/2012 | Mundorff et al. |
| 8,170,806 B2 | 5/2012 | Selifonov et al. |
| 8,224,580 B2 | 7/2012 | Mundorff et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,504,498 B2 | 8/2013 | Fox |
| 8,589,085 B2 | 11/2013 | Selifonov et al. |
| 8,762,066 B2 | 6/2014 | Fox |
| 8,768,871 B2 | 7/2014 | Fox |
| 9,593,326 B2 | 3/2017 | Clark et al. |
| 9,665,694 B2 | 5/2017 | Cope |
| 9,684,771 B2 | 6/2017 | Cope et al. |
| 2005/0084972 A1 | 4/2005 | Barr et al. |
| 2008/0220990 A1 | 9/2008 | Fox |
| 2009/0312196 A1 | 12/2009 | Colbeck et al. |
| 2012/0064545 A1 | 3/2012 | Khanna et al. |
| 2012/0177722 A1 | 7/2012 | Weiner et al. |
| 2013/0039898 A1 | 2/2013 | Okhamafe et al. |
| 2017/0360900 A1 | 12/2017 | Agard et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2001/75767 A2 | 10/2001 |
| WO | 2006/125141 A2 | 11/2006 |
| WO | 2009/152336 A1 | 12/2009 |
| WO | 2010/144103 A1 | 12/2010 |
| WO | 2013/022721 A1 | 2/2013 |
| WO | 2013/138339 A1 | 9/2013 |
| WO | 2015/048572 A1 | 4/2015 |
| WO | 2015/048573 A1 | 4/2015 |
| WO | 2018/046775 A1 | 3/2018 |
| WO | 2019/222411 A1 | 11/2019 |

OTHER PUBLICATIONS

Altschul, S.F., et al., "Gapped BLAST and PSI-BLAST: a new generation of protein database search programs," Nucleic Acids Res., 25(17):3389-3402 [1997].

Beaucage, S.L., et al., "Deoxynucleoside phosphoamidites-A new class of key intermediates for deoxypolynucleotide synthesis," Tetrahedron Letters, 22(20): 1859-62 [1981].

Black, M.E., et al., "Creation of drug-specific herpes simplex virus type 1 thymidine kinase mutants for gene therapy," Proc Natl Acad Sci USA, 93:3525-3529 [1996].

Botstein, D., et al., "Strategies and applications of in vitro mutagenesis," Science, 229(4719):1193-1201 [1985].

Caldwell, R.C., et al., "Mutagenic PCR," PCR Methods Appl., 3:S136-S140 [1994].

Carter, P., "Site-directed mutagenesis," Biochem. J., 237:1-7 [1986].

Christians, F.C., et al., "Directed evolution of thymidine kinase for AZT phosphorylation using DNA family shuffling," Nat. Biotechnol., 17:259-264 [1999].

Crameri, A., et al., "DNA shuffling of a family of genes from diverse species accelerates directed evolution", Nature, 391:288-291 [1998].

Crameri, A., et al., "Improved green fluorescent protein by molecular evolution using DNA shuffling, "Nat. Biotechnol., 14(3):315-319 [1996].

Crameri, A., et al., "Molecular evolution of an arsenate detoxification pathway by DNA shuffling," Nat. Biotechnol., 15 (5):436-438 [1997].

Dale, S.J., et al., "Oligonucleotide-directed random mutagenesis using the phosphorothioate method," Methods Mol. Biol., 57:369-74 [1996].

De Boer, H.A., et al., "The tac promoter: A functional hybrid derived from the trp and lac promoters," Proc. Natl Acad. Sci. USA, 80: 21-25 [1983].

Guo, Z., et al., "3'-End-Forming Signals of Yeast mRNA," Mol. Cell. Biol., 15(11): 5983-5990 [1995].

Hahn, A., et al., "Long-term outcome and unmet needs in infantile-onset Pompe disease," Ann. Transl. Med., 7(13):283-292 [2019].

Henikoff, S., et al., "Amino acid substitution matrices from protein blocks," Proc. Natl. Acad. Sci., 89:10915-10919 [1992].

Keda, K., et al., "Phenylalanine ammonia-lyase modified with polyethylene glycol: Potential therapeutic agent for phenylketonuria," Amino Acids, 29:283-287 [2005].

Kramer, B., et al., "Different base/base mismatches are corrected with different efficiencies by the methyl-directed DNA mismatch-repair system of E. coli," Cell, 38(3):879-887, [1984].

Leslie, N., et al., "Pompe Disease," NCBI Bookshelf, Adam MP, Ardinger HH, Pagon RA, et al., editors. GeneReviews® [Internet]. Seattle (WA): University of Washington, Seattle; pp. 1-30 [2007].

Ling, M., et al., "Approaches to DNA Mutagenesis:An Overview," Anal. Biochem., 254:157-78 [1997].

(56) References Cited

OTHER PUBLICATIONS

Martiniuk, F., et al., "Isolation and Partial Characterization of the Structural Gene for Human Acid Alpha Glucosidase," DNA Cell. Biol., 10(4):283-292 [1991].
Matthes, H.W.D., et al., "Simultaneous rapid chemical synthesis of over one hundred oligonucleotides on a microscale," EMBO J., 3(4):801-05 [1984].
McIlvaine, T.C., "A Buffer Solution for Colorimetric Comparison," J. Biol. Chem., 49:183-186 [1921].
Minshull, J., et al., "Protein evolution by molecular breeding," Curr. Op. Chem. Biol., 3(3):284-290 [1999].
Morales, J.A., et al., "Glycogen Storage Disease Type II (Pompe Disease)," NCBI Bookshelf, StatPearls [Internet]. Treasure Island (FL): StatPearls Publishing; pp. 1-4 [2019].
Needleman, S., et al., "A general method applicable to the search for similarities in the amino acid sequence of two proteins," J. Mol. Biol. 48:443-453 [1970].
Pearson, W.R., "Improved tools for biological sequence comparison," Proc. Nat'l. Acad. Sci. USA, 85:2444-2448 [1988].
Peruzzo, P., et al. "Molecular genetics of Pompe disease: a comprehensive overview," Ann. Transl. Med., 7 (13):278-287 [2019].
Romanos, M.A., et al., "Foreign gene expression in yeast: a review," Yeast 8:423-488 [1992].
Schoser, B., "Pompe disease: what are we missing?," Ann. Transl. Med., 7(13): 292-298 [2019].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 [1985].
Smith, T., et al., "Comparison of Biosequences," Adv. Appl. Math, 2:482-489 [1981].
Southwood, S., et al., "Several Common HLA-DR Types Share Largely Overlapping Peptide Binding Repertoires," J. Immunol., 160:3363-3373 [1998].
Stemmer, W., "DNA Shuffling by Random Fragmentation and Reassembly: In vitro Recombination for Molecular Evolution," Proc. Natl. Acad. Sci. USA, 91:10747-10751 [1994].
Stemmer, W.P.C., "Rapid evolution of a protein in vitro by DNA shuffling", Nature, 370:389-391 [1994].
Villa-Komaroff, L., et al., "A bacterial clone synthesizing proinsulin," Proc. Natl Acad. Sci. USA, 75(8): 3727-3731 [1978].
Vita, R., et al., "The Immune Epitope Database 2.0," Nucl. Acids Res., 38(Database issue): D854-62 [2010] [Epub Nov. 11, 2009].
Wells, J.A., et al., "Cassette mutagenesis: an efficient method for generation of multiple mutations at defined sites," Gene, 34:315-323 [1985].
Yasuda, K., et al., "Efficient and rapid purification of recombinant human a-galactosidase A by affinity column chromatography," Prot. Exp. Pur,. 37(2):499-506 [2004].
Zhang, J-H., et al., "Directed evolution of a fucosidase from a galactosidase by DNA shuffling and screening ," Proc. Nat. Acad. Sci., U.S.A., 94:4504-4509 [1997].
Zhao, H., et al., "Molecular evolution by staggered extension process (StEP) in vitro recombination," Nat. Biotechnol., 16:258-261 [1998].
Uniprot Accession No. AON1R5 dated Dec. 12, 2006.
International Search Report from PCT/US20/66041 dated May 27, 2021.
Sun et al., "Enhanced Efficacy of an AAV Vector Encoding Chimeric, Highly Secreted Acid alpha-Glucosidase in Glycogen Storage Disease Type II," Molecular Therapy, 2006, 14(6):822-830.

ENGINEERED ACID ALPHA-GLUCOSIDASE VARIANTS

The present application claims priority to U.S. Prov. Appln. Ser. No. 62/951,625, filed Dec. 20, 2019, hereby incorporated by reference in its entirety for all purposes.

FIELD OF THE INVENTION

The present invention provides engineered acid alpha-glucosidase (GAA) polypeptides and compositions thereof. In some embodiments, the engineered GAA polypeptides have been optimized to provide increased expression, stability at neutral and acidic pH, increased uptake into cells, and activity in cell lysates. The invention also provides methods for utilization of the compositions comprising the engineered GAA polypeptides for therapeutic and other purposes.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX7-199US2_ST25.txt", a creation date of Dec. 17, 2020, and a size of 18.2 megabytes. The Sequence Listing filed via EFS-Web is part of the specification and is incorporated in its entirety by reference herein.

BACKGROUND OF THE INVENTION

Pompe disease is an autosomal recessive lysosomal storage disorder that is caused by mutations in the gene encoding acid alpha-glucosidase. This genetic defect leads to reduction of or absence of GAA in the body tissues. The resulting accumulation of glycogen in the lysosomes results in lysosomal swelling and rupture, which can lead to cell damage, organelle dysfunction, and other cellular defects. There are two forms of Pompe disease, including the classical infantile form and late-onset (childhood or adulthood) form. Disease severity is related to the amount of enzyme activity present in the cells of affected individuals. The infantile form is the most severe and rapidly progressive form, typically with GAA activity that is less than 1%, resulting in marked accumulation of glycogen in skeletal muscle, as well as heart and other tissues (See e.g., Hahn and Schänzer, Ann. Transl. Med., 7:283 [2019]). In these patients, there is multi-system storage of accumulated lysosomal and non-lysosomal bound-glycogen in the heart, skeletal muscle, and brain tissue (See, Schoser, Ann. Transl. Med., 7:292 [2019]). Patients present with elevated creatinine kinase levels, hypertrophic cardiomyopathy, failure to thrive, muscular hypotonia, and axial muscle weakness. If untreated, patients typically die within the first year of life due to cardiorespiratory insufficiency. Survival beyond 18 months of age is exceptional. This form is distinguished from non-classic or late-infantile Pompe disease, in which patients present with much less severe cardiac hypertrophy. Patients with late-onset Pompe disease typically experience progressive limb-girdle myopathy and respiratory dysfunction. These patients present with predominant, but not exclusive, muscle involvement. The patients eventually become wheelchair and/or ventilator-dependent. Respiratory insufficiency is the leading cause of death in these patients. Some patients may synthesize a non-functional form of GAA, but others are incapable of producing any type of native enzyme. The human GAA gene encoding GAA has been localized to chromosome 17q25.2-q25.3 and has been cloned and sequenced (See, Peruzzo et all, Ann. Transl. Med., 7:278-287 [2019]; and Martiniuk et al., DNA Cell. Biol., 10:283-292 [1991]). Although numerous mutations in the gene have been reported, the pathological mechanisms that lead to the wide range of phenotypes observed in affected patients remains unknown. Despite the availability of enzyme replacement therapy (ERT) utilizing recombinant GAA, there remains the need for better treatment and management options for affected patients.

SUMMARY OF THE INVENTION

The present invention provides engineered acid alpha-glucosidase (GAA) polypeptides and compositions thereof. In some embodiments, the engineered GAA polypeptides have been optimized to provide increased expression, stability at neutral and acidic pH, increased uptake into cells, and activity in cell lysates. The invention also provides methods for utilization of the compositions comprising the engineered GAA polypeptides for therapeutic and other purposes.

In some embodiments, the present invention provides engineered GAA polypeptides (also referred to herein as "recombinant GAA polypeptides") and biologically active fragments and analogs thereof having improved properties when compared to a wild-type GAA enzyme and/or a reference GAA polypeptide under essentially the same conditions. The invention is further directed to methods of using the engineered GAA polypeptides and biologically active fragments and analogs thereof in therapeutic and/or other compositions.

The present invention provides recombinant acid alpha-glucosidases and/or biologically active recombinant acid alpha-glucosidase fragments comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 2, 6, 8, 12, 14, 16, 18, 20, 946, 1956, 2496, 2880, and/or 3104. In some embodiments, the present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2, 6, 8, 12, 14, 16, 18, 20, 946, 1956, 2496, 2880, and/or 3104. In some embodiments, the present invention also provides recombinant acid alpha-glucosidases and/or biologically active recombinant acid alpha-glucosidase fragments comprising an amino acid sequence comprising SEQ ID NO: 2, 6, 8, 12, 14, 16, 18, 20, 946, 1956, 2496, 2880, and/or 3104. In some embodiments, the present invention further provides recombinant acid alpha-glucosidases and/or biologically active recombinant acid alpha-glucosidase fragments comprising an amino acid sequence consisting of SEQ ID NO: 2, 6, 8, 12, 14, 16, 18, 20, 946, 1956, 2496, 2880, and/or 3104. In some embodiments, the recombinant acid alpha-glucosidase sequences include a signal peptide sequence (e.g., SEQ ID NO: 3382 or 3384) encoded by the polynucleotides set forth in SEQ ID NO: 3381 and 3383, respectively. In some embodiments, the recombinant polynucleotides encoding the recombinant acid alpha-glucosidases of the present invention comprise a 57 base pair sequence that encodes a signal peptide. In some embodiments, the polypeptides of the recombinant acid alpha-glucosidases of the present invention comprise a 19 amino acid signal peptide. In some alternative embodiments, the recombinant polynucleotides encoding recombinant acid alpha-glucosidases do not include a sequence encoding a signal peptide. In some additional embodiments, the recombinant polypeptides comprising recombinant acid alpha-glucosidases do not include a signal peptide. It is not intended that the present invention be limited to recombinant acid alpha-glucosidase polynucleotide or polypeptide sequences comprising the signal peptide nucleotide or polypeptide sequence. It is also not intended that the present invention be limited to recombinant acid alpha-glucosidase polynucleotide or polypeptide sequences that do not comprise a signal peptide nucleotide or polypeptide sequence.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2. In some embodiments, the acid alpha-glucosidase comprises at least one substitution at position or set of positions selected from 27, 27/944, 28, 29/478, 30, 88, 107, 109, 109/842, 110, 113, 135, 137, 138, 148, 150, 247, 274, 276, 278, 375, 403, 414, 418, 418/499, 421, 426, 437, 444, 455, 463, 471, 471/478, 476, 489, 527, 547, 581, 610, 642, 668, 670, 692, 725/732, 750, 753, 786, 820, 862, 871, 895, 897, 930, 934, and 944, wherein the positions are numbered with reference to SEQ ID NO: 2. In some embodiments, the acid alpha-glucosidase comprises at least one substitution or substitution sets at one or more positions selected from 27P, 27P/944W, 27R, 28P, 28R, 28S, 29T/478T, 30G, 30K, 30T, 88G, 88S, 107G, 107P, 109G/842E, 109P, 110G, 110L, 113S, 135A, 135Q, 137P, 138A, 148G, 148Y, 150G, 247R, 274G, 276F, 276Y, 278A, 278G, 375E, 403W, 414P, 418E/499R, 418R, 421S, 426R, 437S, 444T, 455V, 463A, 471Q/478S, 471S, 476A, 476H, 489R, 527R, 547G, 581G, 581T, 610A, 610G, 610S, 642M, 642Q, 642S, 668H, 670N, 692Q, 725N/732I, 750P, 753T, 786P, 786Y, 820E, 862G, 871E, 895R, 897V, 930R, 934R, 944G, and 944R, wherein the positions are numbered with reference to SEQ ID NO: 2. In some embodiments, the acid alpha-glucosidase comprises at least one substitution or substitution sets at one or more positions selected from F27P, F27P/C944W, F27R, L28P, L28R, L28S, L29T/A478T, V30G, V30K, V30T, K88G, K88S, Q107G, Q107P, L109G/G842E, L109P, Q110G, Q110L, Q113S, S135A, S135Q, E137P, M138A, T148G, T148Y, T150G, Q247R, D274G, A276F, A276Y, T278A, T278G, I375E, R403W, R414P, A418E/H499R, A418R, Q421S, G426R, A437S, A444T, R455V, E463A, K471Q/A478S, K471S, S476A, S476H, A489R, N527R, A547G, K581G, K581T, W610A, W610G, W610S, L642M, L642Q, L642S, S668H, L670N, T692Q, K725N/V732I, A750P, A753T, R786P, R786Y, G820E, R862G, L871E, K895R, T897V, C930R, L934R, C944G, and C944R, wherein the positions are numbered with reference to SEQ ID NO: 2. In some embodiments, the acid alpha-glucosidase comprises at least one substitution at position or set of positions selected from 29/218/240/668/700/744/869, 29/218/240/700/869, 29/240/596/668/700/744/869, 29/240/596/668/869, 36/106/150/218/527/750/883/894, 106/112/150/218/414/527/793/883, 106/150/169/218/414/486/527/750/894, 106/150/169/218/414/486/527/894, 106/150/169/218/414/486/749/793/883/894, 106/150/169/218/414/486/750/793/883/894, 106/150/169/218/414/486/793/883, 106/150/169/218/414/486/894, 106/150/169/218/414/749/793/883, 106/150/169/218/414/749/793, 106/150/169/218/414/749/793/883, 106/150/169/218/486/527/749/793/894, 106/150/169/218/486/749/883, 106/150/169/218/486/883, 106/150/169/218/749/800, 106/150/169/414/486/749/750/883, 106/150/169/527/749/793/883, 106/150/169/749/793/883/894, 106/150/218/331/414/486/527/733/749/793, 106/150/218/414/486/642750/793/883, 106/150/218/414/486/750/793/894, 106/150/218/414/527/749/750/883, 106/150/218/414/527/749/793/883/894, 106/150/218/414/749/750/793/883/894, 106/150/218/414/749/793/883, 106/150/218/486/527/749/894, 106/150/218/486/793/883, 106/150/218/527/749/750/93, 106/150/218/527/793/894, 106/150/218/749/750/793, 106/150/218/793, 106/150/218/793/894, 106/150/245/793/883/894, 106/150/414/749/750/793/894, 106/150/414/749/793/894, 106/150/486/527/750/793, 106/150/486/749/793/883/894, 106/150/749/793/883, 106/169/185/218/414/749/750/793, 106/191/280/402/414/444/727, 106/191/414/444/522/928/944, 106/191/414/489/928/944, 106/280/402/414/444/489/727/944, 150/169/218/414/527/793, 150/218/414/486/749/750, 150/218/414/486/750/793, 150/218/414/486/750/793/883, 150/218/414/749/750/793/894, 150/218/414/749/793, 150/218/527/749/793, 150/218/749/750/793, 150/218/749/793, 150/414/486/527/750/894, 150/414/486/749/750/93, 150/486/750/883/894, 169/486/750/793/883, 180/275/402/518/547/610/638/669/671, 180/402/431/507/547/610/669/671/793, 180/402/507/547/610/671, 191/280/402/414/444/465/842/928, 191/280/402/414/444/489/500/944, 191/280/414/444/489/500/522/842/928/944, 191/280/414/444/489/522/727/944, 191/280/414/489/842/928/944, 191/280/414/944, 191/414/522/842/944, 196/402/431/547/610/638, 218/668/700/869, 224/402/507/518/547/638/668, 269/275/431/518/547/638/668/669, 275/281/402/431/507/518/610/668, 275/281/402/431/518/547/610/669/671, 275/281/402/507/518/547/638/669/671, 275/281/402/518/547/610/638/671, 275/281/402/518/547/610/668/669/887, 275/281/402/547/610/638/669/671, 275/281/431/518/547/638/669/671, 275/281/507/547/669/671, 275/281/610/638/668/669, 275/281/671, 275/377/402/507/518/669/671/715, 275/402/431/507/547/671, 275/402/431/518/610/638/669/671/922, 275/402/507/547/610/638/668/669, 275/402/507/547/610/638/669/671, 275/402/507/547/610/638/669/671, 275/402/507/547/610/638/669/671, 275/402/547/638/669/671, 275/402/638/669/671, 275/431/507/518/547/668/669/671, 275/431/507/518/610/669/671, 275/431/507/547/610/638/671, 275/431/518/547/638/668, 275/431/518/610/638/669/671, 275/431/638, 275/507/518/547/610/638/668/669, 275/507/518/547/638/669/671, 275/507/547/610/638/669/671, 275/507/547/668/669/671, 275/518/671, 280/402/536/928, 281/402/507/518/547/610/638/669/671, 281/402/507/547/638/669/671, 281/402/518/547/610/638/668/669, 281/402/518/547/668, 281/431/507/518/547/610/638/668, 402/431/518/547/610/668, 402/431/518/547/671, 402/431/518/610, 402/431/547/638/671, 431/507/518/541/547/638/669/671, 431/507/518/669/671, 507/547/610, 507/547/638/669/671, 547/610/638/671, and 547/638/668, wherein the positions are numbered with reference to SEQ ID NO: 2. In some embodiments, the acid alpha-glucosidase comprises at least one substitution or substitution sets at one or more positions selected from 29Q/218S/240I/668D/700F/744V/869L, 29Q/240I/596P/668D/869L, 29Q/240I/596S/668D/700F/744V/869T, 29V/218S/240I/700F/869T, 36R/106P/150S/218S/527D/750P/883H/894R, 106P/112S/150S/218S/414G/527D/793K/883H, 106P/150S/169S/218S/414G/486E/527D/750P/894R, 106P/150S/169S/218S/414G/486E/527D/894R, 106P/150S/169S/218S/414G/486E/749E/793K/883H/ 894R, 106P/150S/169S/218S/414G/486E/750P/793K/ 883H/894R, 106P/150S/169S/218S/414G/486E/793K/ 883H, 106P/150S/169S/218S/414G/486E/894R, 106P/ 150S/169S/218S/414G/749E/750P/793K/883H, 106P/ 150S/169S/218S/414G/749E/793K, 106P/150S/169S/218S/ 414G/749E/793K/883H, 106P/150S/169S/218S/486E/ 527D/749E/793K/894R, 106P/150S/169S/218S/486E/ 749E/883H, 106P/150S/169S/218S/486E/883H, 106P/ 150S/169S/218s/749E/800A, 106P/150S/169S/414G/486E/ 749E/750P/883H, 106P/150S/169S/527D/749E/793K/ 883H, 106P/150S/169S/749E/793K/883H/894R, 106P/ 150S/218S/331A/414G/486E/527D/733E/749E/793K, 106P/150S/218S/414G/486E/642F/750P/793K/883H, 106P/150S/218S/414G/486E/750P/793K/894R, 106P/ 150S/218S/414G/527D/749E/750P/883H, 106P/150S/ 218S/414G/527D/749E/793K/883H/894G, 106P/150S/ 218S/414G/749E/750P/793K/883H/894R, 106P/150S/ 218S/414G/749E/793K/883H, 106P/150S/218S/486E/ 527D/749E/894R, 106P/150S/218S/486E/793K/883H, 106P/150S/218S/527D/749E/750P/793K, 106P/150S/218S/ 527D/793K/894G, 106P/150S/218S/749E/50P/793K, 106P/ 150S/218S/793K, 106P/150S/218S/793K/894R, 106P/ 150S/245S/793K/883H/894R, 106P/150S/414G/749E/ 750P/793K/894R, 106P/150S/414G/749E/793K/894R, 106P/150S/486E/527D/750P/793K, 106P/150S/486F/749F/ 1793K/883H/894G, 106P/150S/749E/793K/883H, 106P/ 169S/185G/218S/414G/749E/750P/793K, 106P/191R/ 280D/402A/414G/444P/727P, 106P/191R/414G/444P/ 522V/928T/944S, 106P/191R/414G/489D/928T/944S, 106P/280D/402A/414G/444P/489D/727P/944S, 150S/ 169S/218S/414G/527D/793K, 150S/218S/414G/486A/ 750P/793K, 150S/218S/414G/486E/749E/750P, 150S/ 218S/414G/486E/750P/793K/883H, 150S/218S/414G/ 749E/750P/793K/894R, 150S/218S/414G/749E/793K, 150S/218S/527D/749E/793K, 150S/218S/749E/750P/ 793K, 150S/218s/749E/793K, 150S/414G/486E/527D/ 750P/894R, 150S/414G/486E/749E/750P/793K, 150S/ 486E/750P/883H/894G, 169S/486E/750P/793K/883H, 180H/275M/402A/518V/547G/610R/638I/669H/671N, 180H/402A/431V/507L/547G/610R/669H/671N/793G, 180H/402A/507L/547G/610R/671N, 191R/280D/402A/ 414G/444P/465E/842S/928T, 191R/280D/402A/414G/ 444P/489D/500A/944S, 191R/280D/414G/444P/489D/ 500A/522V/842S/928T/944S, 191R/280D/414G/444P/ 489D/522V/727P/944S, 191R/280D/414G/489D/842S/ 928T/944S, 191R/280D/414G/944S, 191R/414G/522V/ 842S/944S, 196V/402A/431V/547G/610R/638I, 218S/ 668D/700F/869T, 224F/402A/507U/518V/547G/638I/ 668D, 269N/275M/431V/518V/547G/638I/668D/669H, 275M/281V/402A/431V/507L/518V/610R/668D, 275M/ 281V/402A/507V/518V/547G/638I/669H/671N, 275M/ 281V/402A/518V/547G/610R/638I/671N, 275M/281V/ 402A/518V/547G/610R/668D/669H/887D, 275M/281V/ 402A/547G/610R/638I/669H/671N, 275M/281V/507L/ 547G/669H/671N, 275M/281V/610R/638I/668D/669H, 275M/402A/431V/507L/547G/671N, 275M/402A/507L/ 547G/610R/671N, 275M/402A/547G/638I/669H/671N, 275M/431V/518V/547G/638I/668D, 275M/431V/518V/ 610R/638I/669H/671N, 275M/431V/638I, 275M/507L/ 547G/668D/669H/671N, 275V/281V/402A/431V/518V/ 547G/610R/669H/671N, 275V/281V/431V/518V/547G/ 638I/669H/671N, 275V/281V/671N, 275V/377K/402A/ 507L/518V/669H/671N/715G, 275V/402A/431V/518V/ 610R/638I/669H/671N/922L, 275V/402A/507L/547G/ 610R/638I/668D/669H, 275V/402A/507L/547G/610R/ 638I/669H/671N, 275V/402A/547G/610R/638I/669H/ 671N, 275V/402A/638I/669H/671N, 275V/431V/507L/ 518V/547G/668D/669H/671N, 275V/431V/507L/518V/ 610R/669H/671N, 275V/431V/507L/547G/610R/638I/ 671N, 275V/507L/518V/547G/610R/638I/668D/669H, 275V/507L/518V/547G/638I/669H/671N, 275V/507L/ 547G/610R/638I/669H/671N, 275V/518V/671N, 280D/ 402A/536I/928T, 281V/402A/507L/518V/547G/610R/ 638I/669H/671N, 281V/402A/507L/547G/638I/669H/ 671N, 281V/402A/518V/547G/610R/638I/668D/669H, 281V/402A/518V/547G/668D, 281V/431V/507L/518V/ 547G/610R/638I/668D, 402A/431V/518V/547G/610R/ 668D, 402A/431V/518V/547G/671N, 402A/431V/518V/ 610R, 402A/431V/547G/638I/671N, 431V/507L/518V/ 541E/547G/638I/669H/671N, 431V/507L518V/669H/ 671N, 507L/547G/610R, 507L/547G/638I/669H/671N, 547G/610R/638I/671N, and 547G/638I/668D, wherein the positions are numbered with reference to SEQ ID NO: 2. In some embodiments, the acid alpha-glucosidase comprises at least one substitution or substitution sets at one or more positions selected from L29Q/L218S/L240I/S668D/H700F/ I744V/I869L, L29Q/L240I/A596P/S668D/I869L, L29Q/ L240I/A596S/S668D/H700F/I744V/I869T, L29V/L218S/ L240I/H700F/I869T, G36R/K106P/T150S/L218S/N527D/ A750P/R883H/Q894R, K106P/A112S/T150S/L218S/ R414G/N527D/E793K/R883H, K106P/T150S/N169S/ L218S/R414G/T486E/N527D/A750P/Q894R, K106P/ T150S/N169S/L218S/R414G/T486E/N527D/Q894R, K106P/T150S/N169S/L218S/R414G/T486E/Q749E/ E793K/R883H/Q894R, K106P/T150S/N169S/L218S/ R414G/T486E/A750P/E793K/R883H/Q894R, K106P/ T150S/N169S/L218S/R414G/T486E/E793K/R883H, K106P/T150S/N169S/L218S/R414G/T486E/Q894R, K106P/T150S/N169S/L218S/R414G/Q749E/A750P/ E793K/R883H, K106P/T150S/N169S/L218S/R414G/ Q749E/E793K, K106P/T150S/N169S/L218S/R414G/ Q749E/E793K/R883H, K106P/T150S/N169S/L218S/ T486E/N527D/Q749E/E793K/Q894R, K106P/T150S/ N169S/L218S/T486E/Q749E/R883H, K106P/T150S/ N169S/L218S/T486E/R883H, K106P/T150S/N169S/ L218S/Q749E/P800A, K106P/T150S/N169S/R414G/ T486E/Q749E/A750P/R883H, K106P/T150S/N169S/ N527D/Q749E/E793K/R883H, K106P/T150S/N169S/ Q749E/E793K/R883H/Q894R, K106P/T150S/L218S/ V331A/R414G/T486E/N527D/D733E/Q749E/E793K, K106P/T150S/L218S/R414G/T486E/L642F/A750P/ E793K/R883H, K106P/T150S/L218S/R414G/T486E/ A750P/E793K/Q894R, K106P/T150S/L218S/R414G/ N527D/Q749E/A750P/R883H, K106P/T150S/L218S/ R414G/N527D/Q749E/E793K/R883H/Q894G, K106P/ T150S/L218S/R414G/Q749E/A750P/E793K/R883H/ Q894R, K106P/T150S/L218S/R414G/Q749E/E793K/ R883H, K106P/T150S/L218S/T486E/N527D/Q749E/ Q894R, K106P/T150S/L218S/T486E/E793K/R883H, K106P/T150S/L218S/N527D/Q749E/A750P/E793K, K106P/T150S/L218S/N527D/E793K/Q894G, K106P/ T150S/L218S/Q749E/A750P/E793K, K106P/T150S/ L218S/E793K, K106P/T150S/L218S/E793K/Q894R, K106P/T150S/P245S/E793K/R883H/Q894R, K106P/ T150S/R414G/Q749E/A750P/E793K/Q894R, K106P/ T150S/R414G/Q749E/E793K/Q894R, K106P/T150S/ T486E/N527D/A750P/E793K, K106P/T150S/T486E/ Q749E/E793K/R883H/Q894G, K106P/T150S/Q749E/ E793K/R883H, K106P/N169S/V185G/L218S/R414G/ Q749E/A750P/E793K, K106P/H191R/G280D/S402A/ R414G/A444P/S727P, K106P/H191R/R414G/A444P/ E522V/D928T/C944S, K106P/H191R/R414G/A489D/ D928T/C944S, K106P/G280D/S402A/R414G/A444P/

A489D/S727P/C944S, T150S/N169S/L218S/R414G/ N527D/E793K, T150S/L218S/R414G/T486A/A750P/ E793K, T150S/L218S/R414G/T486E/Q749E/A750P, T150S/L218S/R414G/T486E/A750P/E793K/R883H, T150S/L218S/R414G/Q749E/A750P/E793K/Q894R, T150S/L218S/R414G/Q749E/E793K, T150S/L218S/ N527D/Q749E/E793K, T150S/L218S/Q749E/A750P/ E793K, T150S/L218S/Q749E/E793K, T150S/R414G/ T486E/N527D/A750P/Q894R, T150S/R414G/T486E/ Q749E/A750P/E793K, T150S/T486E/A750P/R883H/ Q894G, N169S/T486E/A750P/E793K/R883H, N180H/ L275M/S402A/I518V/A547G/W610R/V638I/L669H/ S671N, N180H/S402A/M431V/M507L/A547G/W610R/ L669H/S671N/E793G, N180H/S402A/M507L/A547G/ W610R/S671N, H191R/G280D/S402A/R414G/A444P/ G465E/G842S/D928T, H191R/G280D/S402A/R414G/ A444P/A489D/D500A/C944S, H191R/G280D/R414G/ A444P/A489D/D500A/E522V/G842S/D928T/C944S, H191R/G280D/R414G/A444P/A489D/E522V/S727P/ C944S, H191R/G280D/R414G/A489D/G842S/D928T/ C944S, H191R/G280D/R414G/C944S, H191R/R414G/ E522V/G842S/C944S, A196V/S402A/M431V/A547G/ W610R/V638I, L218S/S668D/H700F/I869T, T224F/ S402A/M507L/I518V/A547G/V638I/S668D, T269N/ L275M/M431V/I518V/A547G/V638I/S668D/L669H, L275M/A281V/S402A/M431V/M507L/I518V/W610R/ S668D, L275M/A281V/S402A/M507L/I518V/A547G/ V638I/L669H/S671N, L275M/A281V/S402A/I518V/ A547G/W610R/V638U/S671N, L275M/A281V/S402A/ I518V/A547G/W610R/S668D/L669H/E887D, L275M/ A281V/S402A/A547G/W610R/V638I/L669H/S671N, L275M/A281V/M507L/A547G/L669H/S671N, L275M/ A281V/W610R/V638/S668D/L669H, L275M/S402A/ M431V/M507L/A547G/S671N, L275M/S402A/M507L/ A547G/W610R/S671N, L275M/S402A/A547G/V638I/ L669H/S671N, L275M/M431V/I518V/A547G/V638I/ S668D, L275M/M431V/I518V/W610R/V638I/L669H/ S671N, L275M/M431V/V638I, L275M/M507L/A547G/ S668D/L669H/S671N, L275V/A281V/S402A/M431V/ I518V/A547G/W610R/L669H/S671N, L275V/A281V/ M431V/I518V/A547G/V638I/L669H/S671N, L275V/ A281V/S671N, L275V/R377K/S402A/M507L/I518V/ L669H/S671N/V715G, L275V/S402A/M431V/I518V/ W610R/V638I/L669H/S671N/P922L, L275V/S402A/ M507L/A547G/W610R/V638I/S668D/L669H, L275V/ S402A/M507L/A547G/W610R/V638I/L669H/S671N, L275V/S402A/A547G/W610R/V638I/L669H/S671N, L275V/S402A/V638I/L669H/S671N, L275V/M431V/ M507L/I518V/A547G/S668D/L669H/S671N, L275V/ M431V/M507L/I518V/W610R/L669H/S671N, L275V/ M431V/M507L/A547G/W610R/V638I/S671N, L275V/ M507L/I518V/A547G/W610R/V638I/S668D/L669H, L275V/M507L/I518V/A547G/V638I/L669H/S671N, L275V/M507L/I547G/W610R/V638I/L669H/S671N, L275V/I518V/S671N, G280D/S402A/V536V/D928T, A281V/S402A/M507L/I518V/A547G/W610R/V638I/ L669H/S671N, A281V/S402A/M507L/A547G/V638I/ L669H/S671N, A281V/S402A/I518V/A547G/W610R/ V638I I/S668D/L669H, A281V/S402A/I518V/A547G/ S668D, A281V/M431V/M507L/I518V/A547G/W610R/ V638I/S668D, S402A/M431V/I518V/A547G/W610R/ S668D, S402A/M431V/I518V/A547G/S671N, S402A/ M431V/I518V/W610R, S402A/M431V/A547G/V638I/ S671N, M431V/M507L/I518V/G541E/A547G/V638I/ L669H/S671N, M431V/M507L/I518V/L669H/S671N, M507L/A547G/W610R, M507L/A547G/V638I/L669H/ S671N, A547G/W610R/V638I/S671N, and A547G/V638I/ S668D, wherein the positions are numbered with reference to SEQ ID NO: 2. In some embodiments, the acid alpha-glucosidase comprises at least one substitution or substitution sets at one or more positions selected from 27, 27/944, 28, 29/218/240/668/700/744/869, 29/218/240/700/869, 29/240/596/668/700/744/869, 29/240/596/668/869, 29/478, 30, 36/106/150/218/527/750/883/894, 106/112/150/218/ 414/527/793/883, 106/150/169/218/414/486/527/750/894, 106/150/169/218/414/486/527/894, 106/150/169/218/414/ 486/749/793/883/894, 106/150/169/218/414/486/750/793/ 883/894, 106/150/169/218/414/486/793/883, 106/150/169/ 218/414/486/894, 106/150/169/218/414/749/750/793/883, 106/150/169/218/414/749/793, 106/150/169/218/414/749/ 793/883, 106/150/169/218/486/749/883, 106/150/169/218/ 486/883, 106/150/169/414/486/749/750/883, 106/150/169/ 527/749/793/883, 106/150/169/749/793/883/894, 106/ 1501218/331/414/486/527/733/749/793, 106/150/218/414/ 486/642/750/793/883, 106/1501218/414/486/750/793/894, 106/150/218/414/527/749/750/883, 106/150/218/414/527/ 749/793/883/894, 106/150/218/414/749/750/793/883/894, 106/1501218/414/749/793/883, 106/150/218/486/527/749/ 894, 106/150/218/486/793/883, 106/1501218/527/793/894, 106/150/245/793/883/894, 106/150/414/749/750/793/894, 106/150/414/749/793/894, 106/150/486/527/750/793, 106/ 150/486/749/793/883/894, 106/150/749/793/883, 106/169/ 185/218/414/749/750/793, 106/191/280/402/414/444/727, 106/280/402/414/444/489/727/944, 107, 109, 109/842, 110, 135, 138, 148, 150, 150/218/414/486/749/750, 150/218/414/ 486/750/793, 150/218/414/486/750/793/883, 150/218/414/ 749/750/793/894, 1501218/414/749/793, 150/414/486/527/ 750/894, 150/414/486/149/750/793, 150/486/750/883/894, 169/486/750/793/883, 180/275/402/518/547/610/638/669/ 671, 180/402/431/507/547/610/669/671/793, 180/402/507/ 547/610/671, 191/280/402/414/444/489/500/944, 191/280/ 414/444/489/522/127/944, 191/280/414/944, 191/414/522/ 842/944, 196/402/431/547/610/638, 218/668/700/869, 224/ 402/507/518/547/638/668, 269/275/431/518/547/638/668/ 669, 274, 275/281/402/431/507/518/610/668, 275/281/402/ 431/518/547/610/669/671, 275/281/402/507/518/547/638/ 669/671, 275/281/402/518/547/610/638/671, 275/281/402/ 518/547/610/668/669/887, 275/281/402/547/610/638/669/ 671, 275/281/431/518/547/638/669/671, 275/281/507/547/ 669/671, 275/281/610/638/668/669, 275/377/402/507/518/ 669/671/715, 275/402/431/507/547/671, 275/402/431/518/ 610/638/669/671/922, 275/402/507/547/610/638/668/669, 275/402/507/547/610/638/669/671, 275/402/507/547/610/ 671, 275/402/547/610/638/669/671, 275/402/547/638/669/ 671, 275/402/638/669/671, 275/431/507/518/547/668/669/ 671, 275/431/507/518/610/669/671, 275/431/507/547/610/ 638/671, 275/431/518/547/638/668, 275/431/518/610/638/ 669/671, 275/431/638, 275/507/518/547/610/638/668/669, 275/507/518/547/638/669/671, 275/507/547/610/638/669/ 671, 275/507/547/668/669/671, 276, 281/402/507/518/547/ 610/638/669/671, 281/402/507/547/638/669/671, 281/402/ 518/547/610/638/668/669, 281/402/518/547/668, 281/431/ 507/518/547/610/638/668, 375, 402/431/518/547/610/668, 402/431/518/547/671, 402/431/518/610, 402/431/547/638/ 671, 403, 414, 418/499, 431/507/518/541/547/638/669/671, 431/507/518/669/671, 437, 471/478, 507/547/610, 507/547/ 638/669/671, 547, 547/610/638/671, 547/638/668, 581, 642, 670, 692, 750, 753, 820, 871, and 944, wherein the positions are numbered with reference to SEQ ID NO: 2. In some embodiments, the acid alpha-glucosidase comprises at least one substitution or substitution sets at one or more positions selected from 27P, 27P/944W, 27R, 28P, 28S, 29Q/218S/ 240I/668D/700F/744V/869L, 29Q/240I/596P/668D/869L, 29Q/240I/596S/668D/700F/744V/869T, 29T/478T, 29V/

218S/240I/700F/869T, 30G, 30K, 30T, 36R/106P/150S/ 218S/527D/750P/883H/894R, 106P/112S/150S/218S/ 414G/527D/793K/883H, 106P/150S/169S/218S/414G/ 486E/527D/750P/894R, 106P/150S/169S/218S/414G/ 486E/527D/894R, 106P/150S/169S/218S/414G/486F/ 749F/793K/883H/894R, 106P/150S/169S/218S/414G/ 486F/750P/793K/883H/894R, 106P/150S/169S/218S/ 414G/486F/793K/883H, 106P/150S/169S/218S/414G/ 486E/894R, 106P/150S/169S/218S/414G/749F/750P/ 793K/883H, 106P/150S/169S/218S/414G/749F/793K, 106P/150S/169S/218S/414G/749F/793K/883H, 106P/ 150S/169S/218S/486E/749E/883H, 106P/150S/169S/218S/ 486E/883H, 106P/150S/169S/414G/486F/749F/750P/ 883H, 106P/150S/169S/527D/749E/793K/883H, 106P/ 150S/169S/749F/793K/883H/894R, 106P/150S/218S/ 331A/414G/486E/527D/733F/749F/793K, 106P/150S/ 218S/414G/486E/642F/750P/793K/883H, 106P/150S/ 218S/414G/486F/750P/793K/894R, 106P/150S/218S/ 414G/527D/749E/750P/883H, 106P/150S/218S/414G/ 527D/749E/793K/883H/894G, 106P/150S/218S/414G/ 749E/750P/793K/883H/894R, 106P/150S/218S/414G/ 749E/793K/883H, 106P/150S/218S/486E/527D/749E/ 894R, 106P/150S/218S/486E/793K/883H, 106P/150S/ 218S/527D/793K/894G, 106P/150S/245S/793K/883H/ 894R, 106P/150S/414G/749E/750P/793K/894R, 106P/ 150S/414G/749E/793K/894R, 106P/150S/486E/527D/ 750P/793K, 106P/150S/486E/749E/793K/883H/894G, 106P/150S/749E/793K/883H, 106P/169S/185G/218S/ 414G/749E/750P/793K, 106P/191R/280D/402A/414G/ 444P/727P, 106P/280D/402A/414G/444P/489D/727P/ 944S, 107G, 109G/842E, 109P, 110G, 110L, 135Q, 138A, 148G, 148Y, 150G, 150S/218S/414G/486A/750P/793K, 150S/218S/414G/486E/749E/750P, 150S/218S/414G/486E/ 750P/793K/883H, 150S/218S/414G/749E/750P/793K/ 894R, 150S/218S/414G/749E/793K, 150S/414G/486E/ 527D/750P/894R, 150S/414G/486E/749E/750P/793K, 150S/486E/750P/883H/894G, 169S/486E/750P/793K/ 883H, 180H/275M/402A/518V/547G/610R/638I/669H/ 671N, 180H/402A/431V/507L/547G/610R/669H/671N/ 793G, 180H/402A/507L/547G/610R/671N, 191R/280D/ 402A/414G/444P/489D/500A/944S, 191R/280D/414G/ 444P/489D/522V/727P/944S, 191R/280D/414G/944S, 191R/414G/522V/842S/944S, 196V/402A/431V/547G/ 610R/638I, 218S/668D/700F/869T, 224F/402A/507L/ 518V/547G/638I1668D, 269N/275M/431V/518V/547G/ 638I1668D/669H, 274G, 275M/281V/402A/431V/507L/ 518V/610R/668D, 275M/281V/402A/507L/518V/547G/ 638I/669H/671N, 275M/281V/402A/518V/547G/610R/ 638I/671N, 275M/281V/402A/518V/547G/610R/668D/ 669H/887D, 275M/281V/402A/547G/610R/638I669H/ 671N, 275M/281V/507L/547G/669H/671N, 275M/281V/ 610R/638I/668D/669H, 275M/402A/431V/507L/547G/ 671N, 275M/402A/507L/547G/610R/671N, 275M/402A/ 547G/638I/669H/671N, 275M/431V/518V/547G/638I/ 668D, 275M/431V/518V/610R/638I/669H/671N, 275M/ 431V/638I, 275M/507L/547G/668D/669H/671N, 275V/ 281V/402A/431V/518V/547G/610R/669H/671N, 275V/ 281V/431V/518V/547G/638I669H/671N, 275V/377K/ 402A/507L/518V/669H/671N/715G, 275V/402A/431V/ 518V/610R/638I/669H/671N/922L, 275V/402A/507L/ 547G/610R/638I1668D/669H, 275V/402A/507L/547G/ 610R/638I1669H/671N, 275V/402A/547G/610R/638I/ 669H/671N, 275V/402A/638I/669H/671N, 275V/431V/ 507L/518V/547G/668D/669H/671N, 275V/431V/507L/ 518V/610R/669H/671N, 275V/431V/507L/547G/610R/ 638I/671N, 275V/507L/518V/547G/610R/638I1668D/ 669H, 275V/507L/518V/547G/610R/638I/669H/671N, 275V/ 507L/547G/610R/638I/669H/671N, 276Y, 281V/402A/ 507L/518V/547G/610R/638I/669H/671N, 281V/402A/ 507L/547G/638I/669H/671N, 281V/402A/518V/547G/ 610R/638I1668D/669H, 281V/402A/518V/547G/668D, 281V/431V/507L/518V/547G/610R/638I/668D, 375E, 402A/431V/518V/547G/610R/668D, 402A/431V/518V/ 547G/671N, 402A/431V/518V/610R, 402A/431V/547G/ 638I/671N, 403W, 414P, 418E/499R, 431V/507L/518V/ 541E/547G/638I/669H/671N, 431V/507L518V/669H/ 671N, 437S, 471Q/478S, 507L/547G/610R, 507L/547G/ 638I/669H/671N, 547G, 547G/610R/638I/671N, 547G/ 638I/668D, 581G, 581T, 642Q, 642S, 670N, 692Q, 750P, 753T, 820E, 871E, and 944G, wherein the positions are numbered with reference to SEQ ID NO: 2. In some embodiments, the acid alpha-glucosidase comprises at least one substitution or substitution sets at one or more positions selected from F27P, F27P/C944W, F27R, L28P, L28S, L29Q/L218S/L240I1S668D/H700F/I744V/I869L, L29Q/ L240I/A596P/S668D/I869L, L29Q/L240I/A596S/S668D/ H700F/I744V/I869T, L29T/A478T, L29V/L218S/L240I/ H700F/I869T, V30G, V30K, V30T, G36R/K106P/T150S/ L218S/N527D/A750P/R883H/Q894R, K106P/A112S/ T150S/L218S/R414G/N527D/E793K/R883H, K106P/ T150S/N169S/L218S/R414G/T486E/N527D/A750P/ Q894R, K106P/T150S/N169S/L218S/R414G/T486E/ N527D/Q894R, K106P/T150S/N169S/L218S/R414G/ T486E/Q749E/E793K/R883H/Q894R, K106P/T150S/ N169S/L218S/R414G/T486E/A750P/E793K/R883H/ Q894R, K106P/T150S/N169S/L218S/R414G/T486E/ E793K/R883H, K106P/T150S/N169S/L218S/R414G/ T486E/Q894R, K106P/T150S/N169S/L218S/R414G/ Q749E/A750P/E793K/R883H, K106P/T150S/N169S/ L218S/R414G/Q749E/E793K, K106P/T150S/N169S/ L218S/R414G/Q749E/E793K/R883H, K106P/150S/ N169S/L218S/T486E/Q749E/R883H, K106P/T150S/ N169S/L218S/T486E/R883H, K106P/T150S/N169S/ R414G/T486E/Q749E/A750P/R883H, K106P/T150S/ N169S/N527D/Q749E/E793K/R883H, K106P/T150S/ N169S/Q749E/E793K/R883H/Q894R, K106P/T150S/ L218S/V331A/R414G/T486E/N527D/D733E/Q749E/ E793K, K106P/T150S/L218S/R414G/T486E/L642F/ A750P/E793K/R883H, K106P/T150S/L218S/R414G/ T486E/A750P/E793K/Q894R, K106P/T150S/L218S/ R414G/N527D/Q749E/A750P/R883H, K106P/T150S/ L218S/R414G/N527D/Q749E/E793K/R883H/Q894R, K106P/T150S/L218S/R414G/Q749E/A750P/E793K/ R883H/Q894R, K106P/T150S/L218S/R414G/Q749E/ E793K/R883H, K106P/T150S/L218S/T486E/N527D/ Q749E/Q894R, K106P/T150S/L218S/T486E/E793K/ R883H, K106P/T150S/L218S/N527D/E793K/Q894G, K106P/T150S/P245S/E793K/R883H/Q894R, K106P/ T150S/R414G/Q749E/A750P/E793K/Q894R, K106P/ T150S/R414G/Q749E/E793K/Q894R, K106P/T150S/ T486E/N527D/A750P/E793K, K106P/T150S/T486E/ Q749E/E793K/R883H/Q894G, K106P/T150S/Q749E/ E793K/R883H, K106P/N169S/V185G/L218S/R414G/ Q749E/A750P/E793K, K106P/H191R/G280D/S402A/ R414G/A444P/S727P, K106P/G280D/S402A/R414G/ A444P/A489D/S727P/C944S, Q107G, L109G/G842E, L109P, Q110G, Q110L, S135Q, M138A, T148G, T148Y, T150G, T150S/L218S/R414G/T486A/A750P/E793K, T150S/L218S/R414G/T486E/Q749E/A750P, T150S/ L218S/R414G/T486E/A750P/E793K/R883H, T150S/ L218S/R414G/Q749E/A750P/E793K/Q894R, T150S/ L218S/R414G/Q749E/E793K, T150S/R414G/T486F/ N527D/A750P/Q894R, T150S/R414G/T486E/Q749E/ A750P/E793K, T150S/T486E/A750P/R883H/Q894G, N169S/T486E/A750P/E793K/R883H, N180H/L275M/ S402A/I518V/A547G/W610R/V638I/L669H/S671N, N180H/S402A/M431V/M507L/A547G/W610R/L669H/ S671N/E793G, N180H/S402A/M507L/A547G/W610R/ S671N, H191R/G280D/S402A/R414G/A444P/A489D/ D500A/C944S, H191R/G280D/R414G/A444P/A489D/ E522V/S727P/C944S, H191R/G280D/R414G/C944S, H191R/R414G/E522V/G842S/C944S, A196V/S402A/ M431V/A547G/W610R/V638I, L218S/S668D/H700F/ I869T, L224F/S402A/M507L/I518V/A547G/V638I/ S668D, T269N/L275M/M431V/I518V/A547G/V638I/ S668D/L669H, D274G, L275M/A281V/S402A/M431V/ M507L/I518V/W610R/S668D, L275M/A281V/S402A/ M507L/I518V/A547G/V638I/L669H/S671N, L275M/ A281V/S402A/I518V/A547G/W610R/V638I/S671N, L275M/A281V/S402A/I518V/A547G/W610R/S668D/ L669H/E887D, L275M/A281V/S402A/A547G/W610R/ V638I/L669H/S671N, L275M/A281V/M507L/A547G/ L669H/S671N, L275M/A281V/W610R/V638/S668D/ L669H, L275M/S402A/M431V/M507L/A547G/S671N, L275M/S402A/M507L/A547G/W610R/S671N, L275M/ S402A/A547G/V638I/L669H/S671N, L275M/M431V/ I518V/A547G/V638I/S668D, L275M/M431V/I518V/ W610R/V638I/L669H/S671N, L275M/M431V/V638I, L275M/M507L/A547G/S668D/L669H/S671N, L275V/ A281V/S402A/M431V/I518V/A547G/W610R/L669H/ S671N, L275V/A281V/M431V/I518V/A547G/V638I/ L669H/S671N, L275V/R377K/S402A/M507L/A518V/ L669H/S671N/V715G, L275V/S402A/M431V/I518V/ W610R/V638I/L669H/S671N/P922L, L275V/S402A/ M507L/A547G/W610R/V638I/S668D/L669H, L275V/ S402A/M507L/A547G/W610R/V638I/L669H/S671N, L275V/S402A/A547G/W610R/V638I/L669H/S671N, L275V/S402A/V638I/L669H/S671N, L275V/M431V/ M507L/I518V/A547G/S668D/L669H/S671N, L275V/ M431V/M507L/I518V/W610R/L669H/S671N, L275V/ M431V/M507L/A547G/W610R/V638I/S671N, L275V/ M507L/I518V/A547G/W610R/V638I/S668D/L669H, L275V/M507L/I518V/A547G/V638I/L669H/S671N, L275V/M507L/A547G/W610R/V638I/L669H/S671N, A276Y, A281V/S402A/M507L/I518V/A547G/W610R/ V638I/L669H/S671N, A281V/S402A/M507L/A547G/ V638I/L669H/S671N, A281V/S402A/I518V/A547G/ W610R/V638I/S668D/L669H, A281V/S402A/I518V/ A547G/S668D, A281V/M431V/M507L/I518V/A547G/ W610R/V638I/S668D, I375E, S402A/M431V/I518V/ A547G/W610R/S668D, S402A/M431V/I518V/A547G/ S671N, S402A/M431V/I518V/W610R, S402A/M431V/ A547G/V638I/S671N, R403W, R414P, A418E/H499R, M431V/M507L/I518V/G541E/A547G/V638I/L669H/ S671N, M431V/M507L/I518V/L669H/S671N, A437S, K471Q/A478S, M507L/A547G/W610R, M507L/A547G/ V638I/L669H/S671N, A547G, A547G/W610R/V638I/ S671N, A547G/V638I/S668D, K581G, K581T, L642Q, L642S, L670N, T692Q, A750P, A753T, G820E, L871E, and C944G, wherein the positions are numbered with reference to SEQ ID NO: 2.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 6. In some embodiments, the acid alpha-glucosidase comprises at least one substitution at position or set of positions selected from 27, 27/944, 28, 29/218/240/668/700/ 744/869, 29/218/240/700/869, 29/240/596/668/700/744/ 869, 29/240/596/668/869, 29/478, 30, 36/106/150/218/527/ 750/883/894, 88, 106/112/150/218/414/527/793/883, 106/ 150/169/218/414/486/527/750/894, 106/150/169/218/414/ 486/527/894, 106/150/169/218/414/486/749/793/883/894, 106/150/169/218/414/486/750/793/883/894, 106/150/169/ 218/414/486/793/883, 106/150/169/218/414/486/894, 106/ 150/169/218/414/749/750/793/883, 106/150/169/218/414/ 749/793, 106/150/169/218/414/749/793/883, 106/150/169/ 218/486/527/749/793/894, 106/150/169/218/486/749/883, 106/150/169/218/486/883, 106/150/169/218/749/800, 106/ 150/169/414/486/749/750/883, 106/150/169/527/749/793/ 883, 106/150/169/749/793/883/894, 106/150/218/331/414/ 486/527/733/749/793, 106/150/218/414/486/642/750/793/ 883, 106/150/218/414/486/750/793/894, 106/150/218/414/ 527/749/750/883, 106/150/218/414/527/749/793/883/894, 106/150/218/414/749/750/793/883/894, 106/150/218/414/ 749/793/883, 106/150/218/486/527/749/894, 106/150/218/ 486/793/883, 106/1501218/527/749/750/793, 106/150/218/ 527/793/894, 106/150/218/749/750/793, 106/150/218/793, 106/150/218/793/894, 106/150/245/793/883/894, 106/150/ 414/749/750/793/894, 106/150/414/749/793/894, 106/150/ 486/527/750/793, 106/150/486/749/793/883/894, 106/150/ 749/793/883, 106/169/185/218/414/749/750/793, 106/191/ 280/402/414/444/727, 106/191/414/444/522/928/944, 106/ 191/414/489/928/944, 106/280/402/414/444/489/727/944, 107, 109, 109/842, 110, 113, 135, 137, 138, 148, 150, 150/169/218/414/527/793, 150/218/414/486/749/750, 150/ 218/414/486/750/793, 150/218/414/486/750/793/883, 150/ 218/414/749/750/793/894, 150/218/414/749/793, 150/218/ 527/749/793, 150/218/749/750/793, 150/218/749/793, 150/ 414/486/527/750/894, 150/414/486/749/750/793, 150/486/ 750/883/894, 169/486/750/793/883, 180/275/402/518/547/ 610/638/669/671, 180/402/431/507/547/610/669/671/793, 180/402/507/547/610/671, 191/280/402/414/444/465/842/ 928, 191/280/402/414/444/489/500/944, 191/280/414/444/ 489/500/522/842/928/944, 191/280/414/444/489/522/727/ 944, 191/280/414/489/842/928/944, 191/280/414/944, 191/ 414/522/842/944, 196/402/431/547/610/638, 218/668/700/ 869, 224/402/507/518/547/638/668, 247, 269/275/431/518/ 547/638/668/669, 274, 275/281/402/431/507/518/610/668, 275/281/402/431/518/547/610/669/671, 275/281/402/507/ 518/547/638/669/671, 275/281/402/518/547/610/638/671, 275/281/402/518/547/610/668/669/887, 275/281/402/547/ 610/638/669/671, 275/281/431/518/547/638/669/671, 275/ 281/507/547/669/671, 275/281/610/638/668/669, 275/281/ 671, 275/377/402/507/518/669/671/715, 275/402/431/507/ 547/671, 275/402/431/518/610/638/669/671/922, 275/402/ 507/547/610/638/668/669, 275/402/507/547/610/638/669/ 671, 275/402/507/547/610/671, 275/402/547/610/638/669/ 671, 275/402/547/638/669/671, 275/402/638/669/671, 275/ 431/507/518/547/668/669/671, 275/431/507/518/610/669/ 671, 275/431/507/547/610/638/671, 275/431/518/547/638/ 668, 275/431/518/610/638/669/671, 275/431/638, 275/507/ 518/547/610/638/668/669, 275/507/518/547/638/669/671, 275/507/547/610/638/669/671, 275/507/547/668/669/671, 275/518/671, 276, 278, 280/402/536/928, 281/402/507/518/ 547/610/638/669/671, 281/402/507/547/638/669/671, 281/ 402/518/547/610/638/668/669, 281/402/518/547/668, 281/ 431/507/518/547/610/638/668, 375, 402/431/518/547/610/ 668, 402/431/518/547/671, 402/431/518/610, 402/431/547/ 638/671, 403, 414, 418, 418/499, 421, 426, 431/507/518/ 541/547/638/669/671, 431/507/518/669/671, 437, 444, 455, 463, 471, 471/478, 476, 489, 507/547/610, 507/547/638/ 669/671, 527, 547, 547/610/638/671, 547/638/668, 581, 610, 642, 668, 670, 692, 725/732, 750, 753, 786, 820, 862, 871, 895, 897, 934, and 944, wherein the positions are numbered with reference to SEQ ID NO: 6. In some embodiments, the acid alpha-glucosidase comprises at least one substitution at position or set of positions selected from 27P, 27P/944W, 27R, 28P, 28R, 28S, 29Q/218S/240I/668D/ 700F/744V/869L, 29Q/240I/596P/668D/869L, 29Q/240I/ 596S/668D/700F/744V/869T, 29T/478T, 29V/218S/240I/ 700F/869T, 30G, 30K, 30T, 36R/106P/150S/218S/527D/ 750P/883H/894R, 88G, 88S, 106P/112S/150S/218S/414G/ 527D/793K/883H, 106P/150S/169S/218S/414G/486E/ 527D/750P/894R, 106P/150S/169S/218S/414G/486E527D/ 894R, 106P/150S/169S/218S/414G/486F/749F/793K/ 883H/894R, 106P/150S/169S/218S/414G/486E/750P/ 793K/883H/894R, 106P/150S/169S/218S/414G/486E/ 793K/883H, 106P/150S/169S/218S/414G/486E/894R, 106P/150S/169S/218S/414G/749E/750P/793K/883H, 106P/150S/169S/218S/414G/749E/793K, 106P/150S/169S/ 218S/414G/749E/793K/883H, 106P/150S/169S/218S/ 486E/527D/749E/793K/894R, 106P/150S/169S/218S/ 486E/749E/883H, 106P/150S/169S/218S/486E/883H, 106P/150S/169S/218s/749E/800A, 106P/150S/169S/414G/ 486E/749E/750P/883H, 106P/150S/169S/527D/749E/ 793K/883H, 106P/150S/169S/749E/793K/883H/894R, 106P/150S/218S/331A/414G/486E/527D/733E/749E/ 793K, 106P/150S/218S/414G/486E/642F/750P/793K/ 883H, 106P/150S/218S/414G/486E/750P/793K/894R, 106P/150S/218S/414G/527D/749E/750P/883H, 106P/ 150S/218S/414G/527D/749E/793K/883H/894G, 106P/ 150S/218S/414G/749E/750P/793K/883H/894R, 106P/ 150S/218S/414G/749E/793K/883H, 106P/150S/218S/ 486E/527D/749E/894R, 106P/150S/218S/486E/793K/ 883H, 106P/150S/218S/527D/749E/750P/793K, 106P/ 150S/218S/527D/793K/894G, 106P/150S/218S/749E/ 750P/793K, 106P/150S/218S/793K, 106P/150S/218s/ 793K/894R, 106P/150S/245s/793K/883H/894R, 106P/ 150S/414G/749E/750P/793K/894R, 106P/150S/414G/ 749E/793K/894R, 106P/150S/486E/527D/750P/793K, 106P/150S/486E/749E/793K/883H/894G, 106P/150S/ 749E/793K/883H, 106P/169S/185G/218S/414G/749E/ 750P/793K, 106P/191R/280D/402A/414G/444P/727P, 106P/191R/414G/444P/522V/928T/944S, 106P/191R/ 414G/489D/928T/944S, 106P/280D/402A/414G/444P/ 489D/727P/944S, 107G, 107P, 109G/842E, 109P, 110G, 110L, 113S, 135A, 135Q, 137P, 138A, 148G, 148Y, 150G, 150S/169S/218S/414G/527D/793K, 150S/218S/414G/ 486A/750P/793K, 150S/218S/414G/486E/749E/750P, 150S/218S/414G/486E/750P/793K/883H, 150S/218S/ 414G/749E/750P/793K/894R, 150S/218S/414G/749E/ 793K, 150S/218S/527D/749E/793K, 150S/218S/749E/ 750P/793K, 150S/218s/749E/793K, 150S/414G/486E/ 527D/750P/894R, 150S/414G/486E/749E/750P/793K, 150S/486E/750P/883H/894G, 169S/486E/750P/793K/ 883H, 180H/275M/402A/518V/547G/610R/638I/669H/ 671N, 180H/402A/431V/507L/547G/610R/669H/671N/ 793G, 180H/402A/507L/547G/610R/671N, 191R/280D/ 402A/414G/444P/465E/842S/928T, 191R/280D/402A/ 414G/444P/489D/500A/944S, 191R/280D/414G/444P/ 489D/500A/522V/842S/928T/944S, 191R/280D/414G/ 444P/489D/522V/727P/944S, 191R/280D/414G/489D/ 842S/928T/944S, 191R/280D/414G/944S, 191R/414G/ 522V/842S/944S, 196V/402A/431V/547G/610R/638I, 218S/668D/700F/869T, 224F/402A/507L/518V/547G/ 638I668D, 247R, 269N/275M/431V/518V/547G/ 638I1668D/669H, 274G, 275M/281V/402A/431V/507U/ 518V/610R/668D, 275M/281V/402A/507U/518V/547G/ 638I/669H/671N, 275M/281V/402A/518V/547G/610R/ 638I/671N, 275M/281V/402A/518V/547G/610R/668D/ 669H/887D, 275M/281V/402A/547G/610R/638I/669H/ 671N, 275M/281V/507L/547G/669H/671N, 275M/281V/ 610R/638I/668D/669H, 275M/402A/431V/507L/547G/ 671N, 275M/402A/507L547G/610R/671N, 275M/402A/ 547G/638I/669H/671N, 275M/431V/518V/547G/638I/ 668D, 275M/431V/518V/610R/638I/669H/671N, 275M/ 431V/638I, 275M/507L/547G/668D/669H/671N, 275V/ 281V/402A/431V/518V/547G/610R/669H/671N, 275V/ 281V/431V/518V/547G/638I/669H/671N, 275V/281V/ 671N, 275V/377K/402A/507L/518V/669H/671N/715G, 275V/402A/431V/518V/610R/638I/669H/671N/922L, 275V/402A/507L/547G/610R/638I1668D/669H, 275V/ 402A/507L/547G/610R/638I1669H/671N, 275V/402A/ 547G/610R/638I/669H/671N, 275V/402A/638I/669H/ 671N, 275V/431V/507L/518V/547G/668D/669H/671N, 275V/431V/507L/518V/610R/669H/671N, 275V/431V/ 507L/547G/610R/638I/671N, 275V/507L/518V/547G/ 610R/638I/668D/669H, 275V/507L/518V/547G/638I/ 669H/671N, 275V/507L/547G/610R/638I/669H/671N, 275V/518V/671N, 276F, 276Y, 278A, 278G, 280D/402A/ 536I/928T, 281V/402A/507L/518V/547G/610R/638I/ 669H/671N, 281V/402A/507L/547G/638I/669H/671N, 281V/402A/518V/547G/610R/638I/668D/669H, 281V/ 402A/431V/507L/518V/547G/668D, 281V/431V/507L/518V/547G/ 610R/638I/668D, 375E, 402A/431V/518V/547G/610R/ 668D, 402A/431V/518V/547G/671N, 402A/431V/518V/ 610R, 402A/431V/547G/638I/1671N, 403W, 414P, 418E/ 499R, 418R, 421S, 426R, 431V/507L/518V/541E/547G/ 638I1669H/671N, 431V/507L/518V/669H/671N, 437S, 444T, 455V, 463A, 471Q/478S, 471S, 476A, 476H, 489R, 507L/547G/610R, 507L/547G/638I/669H/671N, 527R, 547G, 547G/610R/638I/671N, 547G/638I/668D, 581G, 581T, 610A, 610G, 610S, 642M, 642Q, 642S, 668H, 670N, 692Q, 725N/732I, 750P, 753T, 786P, 786Y, 820E, 862G, 871E, 895R, 897V, 934R, 944G, and 944R, wherein the positions are numbered with reference to SEQ ID NO: 6. In some embodiments, the acid alpha-glucosidase comprises at least one substitution at position or set of positions selected from F27P, F27P/C944W, F27R, L28P, L28R, L28S, L29Q/ L218S/L240I/S668D/H700F/I744V/I869L, L29Q/L240I/ A596P/S668D/I869L, L29Q/L240I/A596S/S668D/H700F/ I744V/I869T, L29T/A478T, L29V/L218S/L240I/H700F/ I869T, V30G, V30K, V30T, G36R/K106P/T150S/L218S/ N527D/A750P/R883H1Q894R, K88G, K88S, K106P/ A112S/T150S/L218S/R414G/N527D/E793K/R883H, K106P/T150S/N169S/L218S/R414G/T486E/N527D/ A750P/Q894R, K106P/T150S/N169S/L218S/R414G/ T486E/N527D/Q894R, K106P/T150S/N169S/L218S/ R414G/T486E/Q749E/E793K/R883H/Q894R, K106P/ T150S/N169S/L218S/R414G/T486E/A750P/E793K/ R883H/Q894R, K106P/T150S/N169S/L218S/R414G/ T486E/E793K/R883H, K106P/T150S/N169S/L218S/ R414G/T486E/Q894R, K106P/T150S/N169S/L218S/ R414G/Q749E/A750P/E793K/R883H, K106P/T150S/ N169S/L218S/R414G/Q749E/E793K, K106P/T150S/ N169S/L218S/R414G/Q749E/E793K/R883H, K106P/ T150S/N169S/L218S/T486E/N527D/Q749E/E793K/ Q894R, K106P/T150S/N169S/L218S/T486E/Q749E/ R883H, K106P/T150S/N169S/L218S/T486E/R883H, K106P/T150S/N169S/L218S/Q749E/P800A, K106P/ T150S/N169S/R414G/T486E/Q749E/A750P/R883H, K106P/T150S/N169S/N527D/Q749E/E793K/R883H, K106P/T150S/N169S/Q749E/E793K/R883H/Q894R, K106P/T150S/L218S/V331A/R414G/T486E/N527D/ D733E/Q749E/E793K, K106P/T150S/L218S/R414G/ T486E/L642F/A750P/E793K/R883H, K106P/T150S/ L218S/R414G/T486E/A750P/E793K/Q894R, K106P/ T150S/L218S/R414G/N527D/Q749E/A750P/R883H, K106P/T150S/L218S/R414G/N527D/Q749E/E793K/ R883H/Q894G, K106P/T150S/L218S/R414G/Q749E/ A750P/E793K/R883H/Q894R, K106P/T150S/L218S/ R414G/Q749E/E793K/R883H, K106P/T150S/L218S/ T486E/N527D/Q749E/Q894R, K106P/T150S/L218S/ T486E/E793K/R883H, K106P/T150S/L218S/N527D/ Q749E/A750P/E793K, K106P/T150S/L218S/N527D/ E793K/Q894G, K106P/T150S/L218S/Q749E/A750P/ E793K, K106P/T150S/L218S/E793K, K106P/T150S/ L218S/E793K/Q894R, K106P/T150S/P245S/E793K/ R883H/Q894R, K106P/T150S/R414G/Q749E/A750P/ E793K/Q894R, K106P/T150S/R414G/Q749E/E793K/ Q894R, K106P/T150S/T486E/N527D/A750P/E793K, K106P/T150S/T486E/Q749E/E793K/R883H/Q894G, K106P/T150S/Q749E/E793K/R883H, K106P/N169S/ V185G/L218S/R414G/Q749E/A750P/E793K, K106P/ H191R/G280D/S402A/R414G/A444P/S727P, K106P/ H191R/R414G/A444P/E522V/D928T/C944S, K106P/ H191R/R414G/A489D/D928T/C944S, K106P/G280D/ S402A/R414G/A444P/A489D/S727P/C944S, Q107G, Q107P, L109G/G842E, L109P, Q110G, Q110L, Q113S, S135A, S135Q, E137P, M138A, T148G, T148Y, T150G, T150S/N169S/L218S/R414G/N527D/E793K, T150S/ L218S/R414G/T486A/A750P/E793K, T150S/L218S/ R414G/T486E/Q749E/A750P, T150S/L218S/R414G/ T486E/A750P/E793K/R883H, T150S/L218S/R414G/ Q749E/A750P/E793K/Q894R, T150S/L218S/R414G/ Q749E/E793K, T150S/L218S/N527D/Q749E/E793K, T150S/L218S/Q749E/A750P/E793K, T150S/L218S/ Q749E/E793K, T150S/R414G/T486E/N527D/A750P/ Q894R, T150S/R414G/T486E/Q749E/A750P/E793K, T150S/486E/A750P/R883H/Q894G, N169S/T486E/ A750P/E793K/R883H, N180H/L275M/S402A/I518V/ A547G/W610R/V638I/L669H/S671N, N180H/S402A/ M431V/M507U/A547G/W610R/L669H/S671N/E793G, N180H/S402A/M507L/A547G/W610R/S671N, H191R/ G280D/S402A/R414G/A444P/G465E/G842S/D928T, H191R/G280D/S402A/R414G/A444P/A489D/D500A/ C944S, H191R/G280D/R414G/A444P/A489D/D500A/ E522V/G842S/D928T/C944S, H191R/G280D/R414G/ A444P/A489D/E522V/S727P/C944S, H191R/G280D/ R414G/A489D/G842S/D928T/C944S, H191R/G280D/ R414G/C944S, H191R/R414G/E522V/G842S/C944S, A196V/S402A/M431V/A547G/W610R/V638I, L218S/ S668D/H700F/I869T, L224F/S402A/M507L/I518V/ A547G/V638I/S668D, Q247R, T269N/L275M/M431V/ I518V/A547G/V638I/S668D/L669H, D274G, L275M/ A281V/S402A/M431V/M507L/I518V/W610R/S668D, L275M/A281V/S402A/M507L/I518V/A547G/V638I/ L669H/S671N, L275M/A281V/S402A/I518V/A547G/ W610R/V638I/S671N, L275M/A281V/S402A/I518V/ A547G/W610R/S668D/L669H/E887D, L275M/A281V/ S402A/A547G/W610R/V638I/L669H/S671N, L275M/ A281V/M507L/A547G/L669H/S671N, L275M/A281V/ W610R/V638/S668D/L669H, L275M/S402A/M431V/ M507L/A547G/S671N, L275M/S402A/M507L/A547G/ W610R/S671N, L275M/S402A/A547G/V638I/L669H/ S671N, L275M/M431V/I518V/A547G/V638I/S668D, L275M/M431V/I518V/W610R/V638I/L669H/S671N, L275M/M431V/V638I, L275M/M507L/A547G/S668D/ L669H/S671N, L275V/A281V/S402A/M431V/I518V/ A547G/W610R/L669H/S671N, L275V/A281V/M431V/ I518V/A547G/V638I/L669H/S671N, L275V/A281V/ S671N, L275V/R377K/S402A/M507L/A518V/L669H/ S671N/V715G, L275V/S402A/M431V/I518V/W610R/ V638I/L669H/S671N/P922L, L275V/S402A/M507L/ A547G/W610R/V638I/S668D/L669H, L275V/S402A/ M507L/A547G/W610R/V638I/L669H/S671N, L275V/ S402A/A547G/W610R/V638I/L669H/S671N, L275V/ S402A/V638I/L669H/S671N, L275V/M431V/M507L/ I518V/A547G/S668D/L669H/S671N, L275V/M431V/ M507L/I518V/W610R/L669H/S671N, L275V/M431V/ M507L/A547G/W610R/V638I/S671N, L275V/ M507A518V/A547G/W610R/V638I/S668D/L669H, L275V/M507A518V/A547G/V638I/L669H/S671N, L275V/M507L/A547G/W610R/V638I/L669H/S671N, L275V/I518V/S671N, A276F, A276Y, T278A, T278G, G280D/S402A/V536U/D928T, A281V/S402A/M507L/ I518V/A547G/W610R/V638I/L669H/S671N, A281V/ S402A/M507L/A547G/V638I/L669H/S671N, A281V/ S402A/I518V/A547G/W610R/V638I/S668D/L669H, A281V/S402A/I518V/A547G/S668D, A281V/M431V/ M507A518V/A547G/W610R/V638I/S668D, I375E, S402A/M431V/I518V/A547G/W610R/S668D, S402A/ M431V/I518V/A547G/S671N, S402A/M431V/I518V/ W610R, S402A/M431V/A547G/V638I/S671N, R403W, R414P, A418E/H499R, A418R, Q421S, G426R, M431V/ M507V/I518V/G541E/A547G/V638I/L669H/S671N, M431V/M507L/I518V/L669H/S671N, A437S, A444T, R455V, E463A, K471Q/A478S, K471S, S476A, S476H, A489R, M507L/A547G/W610R, M507L/A547G/V638I/ L669H/S671N, N527R, A547G, A547G/W610R/V638I/ S671N, A547G/V638I/S668D, K581G, K581T, W610A, W610G, W610S, L642M, L642Q, L642S, S668H, L670N, T692Q, K725N/V732I, A750P, A753T, R786P, R786Y, G820E, R862G, L871E, K895R, T897V, L934R, C944G, and C944R, wherein the positions are numbered with reference to SEQ ID NO: 6.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 8. In some embodiments, the acid alpha-glucosidase comprises at least one substitution at position or set of positions selected from 4, 27, 27/28/489, 27/418/478, 28, 28/29, 28/29/113/135/138, 28/29/113/135/418, 28/29/135, 28/29/418, 29/113/126/135/193, 29/113/135, 29/113/135/ 455, 29/113/138, 29/148, 29/478, 106, 106/138/218/431/ 671/749, 106/218/281, 106/218/455, 106/218/455/507/749, 106/489/671, 106/638, 106/671/934, 113, 113/135/418, 113/ 418/455/478/581, 113/418/478/489/581, 135, 135/148/150/ 418, 135/478/489/581, 135/489, 135/944, 138/218/668/671, 138/218/749/934, 138/671/749/934, 157, 218, 218/281, 218/ 281/431, 218/281/671, 218/431, 218/431/489/507/749/934, 218/455, 218/507/749, 218/507/934, 218/638/671, 218/749, 281/431/489/668, 345/934, 418, 418/489, 431/668/671, 489/ 638/934, 489/671/934, 489/749, 489/934, 507/668, 507/671/ 934, 671/749, 671/934, and 749/784, wherein the positions are numbered with reference to SEQ ID NO: 8. In some embodiments, the acid alpha-glucosidase comprises at least one substitution or substitution sets at one or more positions selected from 4H, 27P/28S/489R, 27P/418E/478T, 27R, 28S, 28S/29T, 28S/29T/113S/135/138A, 28S/29T/113/ 135Q/418E, 28S/29T/135Q, 28S/29T/418E, 29T/113S/ 126Q/135Q/193Q, 29T/113S/135Q, 29T/113S/135Q/455V, 29T/113S/138A, 29T/148G, 29T/478T, 106P, 106P/138A/ 218S/431S/671N/749E, 106P/218S/281V, 106P/218S/ 455V, 106P/218S/455/507/749E, 106P/489R/671N, 106P/638I, 106P/671N/934R, 113S, 113S/135Q/418E, 113S/418E/455V/478T/581T, 113S/418E/478T/489R/581T, 135P/944Y, 135Q, 135Q/148G/150G/418E, 135Q/478T/

489R/581T, 135Q/489R, 138A/218S/668D/671N, 138A/218S/749E/934R, 138A/671N/749E/934R, 157M, 218S, 218S/281V, 218S/281V/431V, 218S/281V/671N, 218S/431V, 218S/431V/489R/507L/749E/934R, 218S/455V, 218S/507L/749E, 218S/507L/934R, 218S/638I/671N, 218S/749E, 281V/431V/489R/668D, 345K/934R, 418E, 418E/489R, 431V/668D/671N, 489R/638I/934R, 489R/671N/934R, 489R/749E, 489R/934R, 507L/668D, 507L/671N/934R, 671N/749E, 671N/934R, and 749E/784T, wherein the positions are numbered with reference to SEQ ID NO: 8. In some embodiments, the acid alpha-glucosidase comprises at least one substitution or substitution sets at one or more positions selected from P4H, F27P/L28S/A489R, F27P/A418E/A478T, F27R, L28S, L28S/L29T, L28S/L29T/Q113S/S135Q/M138A, L28S/L29T/Q113S/S135Q/A418E, L28S/L29T/S135Q, L28S/L29T/A418E, L29T/Q113S/P126Q/S135Q/H193Q, L29T/Q113S/S135Q, L29T/Q113S/S135Q/R455V, L29T/Q113S/M138A, L29T/T148G, L29T/A478T, K106P, K106P/M138A/L218S/M431V/S671N/Q749E, K106P/L218S/A281V, K106P/L218S/R455V, K106P/L218S/R455V/M507L/Q749E, K106P/A489R/S671N, K106P/V638I, K106P/S671N/L934R, Q113S, Q113S/S135Q/A418E, Q113S/A418E/R455V/A478T/K581T, Q113S/A418E/A478T/A489R/K581T, S135P/C944Y, S135Q, S135Q/T148G/S150G/A418E, S135Q/A478T/A489R/K581T, S135Q/A489R, M138A/L218S/S668D/S671N, M138A/L218S/Q749E/L934R, M138A/S671N/Q749E/L934R, L157M, L218S, L218S/A281V, L218S/A281V/M431V, L218S/A281V/S671N, L218S/M431V, L218S/M431V/A489R/M507L/Q749E/L934R, L218S/R455V, L218S/M507/Q749E, L218S/M507L/L934R, L218S/V638I/S671N, L218S/Q749E, A281V/M431V/A489R/S668D, Q345K/L934R, A418E, A418E/A489R, M431V/S668D/S671N, A489R/V638I/L934R, A489R/S671N/L934R, A489R/Q749E, A489R/L934R, M507L/S668D, M507L/S671N/L934R, S671N/Q749E, S671N/L934R, and Q749E/A784, wherein the positions are numbered with reference to SEQ ID NO: 8. In some embodiments, the acid alpha-glucosidase comprises at least one substitution or substitution sets at one or more positions selected from 27, 27/418/478, 28, 28/29, 28/29/113/135/138, 28/29/113/135/418, 28/29/135, 28/29/418, 29/113/126/135/193, 29/113/135, 29/113/135/455, 29/113/138, 29/148, 29/478, 106, 106/138/218/431/671/749, 106/489/671, 106/638, 113/135/418, 113/418/455/478/581, 113/418/478/489/581, 135, 135/148/150/418, 135/478/489/581, 135/944, 138/218/668/671, 157, 218/638/671, 418, 418/489, 431/668/671, 507/668, and 671/749, wherein the positions are numbered with reference to SEQ ID NO: 8. In some embodiments, the acid alpha-glucosidase comprises at least one substitution or substitution sets at one or more positions selected from 27P/418E/478T, 27R, 28S, 28S/29T, 28S/29T/113S/135Q/138A, 28S/29T/113S/135Q/418E, 28S/29T/135Q, 28S/29T/418E, 29T/113S/126Q/135Q/193Q, 29T/113S/135Q, 29T/113S/135Q/455V, 29T/113S/138A, 29T/148G, 29T/478T, 106P, 106P/138A/218S/431V/671N/749E, 106P/489R/671N, 106P/638I, 113S/135Q/418E, 113S/418E/455V/478T/581T, 113S/418E/478T/489R/581T, 135P/944Y, 135Q, 135Q/148G/150G/418E, 135Q/478T/489R/581T, 138A/218S/668D/671N, 157M, 218S/638I/671N, 418E, 418E/489R, 431V/668D/671N, 507L/668D, and 671N/749E, wherein the positions are numbered with reference to SEQ ID NO: 8. In some embodiments, the acid alpha-glucosidase comprises at least one substitution or substitution sets at one or more positions selected from F27P/A418E/A478T, F27R, L28S, L28S/L29T, L28S/L29T/Q113S/S135Q/M138A, L28S/L29T/Q113S/S135Q/A418E, L28S/L29T/S135Q, L28S/L29T/A418E, L29T/Q113S/P126Q/S135Q/H193Q, L29T/Q113S/S135Q, L29T/Q113S/S135Q/R455V, L29T/Q113S/M138A, L29T/T148G, L29T/A478T, K106P, K106P/M138A/L218S/M431V/S671N/Q749E, K106P/A489R/S671N, K106P/V638I, Q113S/S135Q/A418E, Q113S/A418E/R455V/A478T/K581T, Q113S/A418E/A478T/A489R/K581T, S135P/C944Y, S135Q, S135Q/T148G/S150G/A418E, S135Q/A478T/A489R/K581T, M138A/L218S/S668D/S671N, L157M, L218S/V638I/S671N, A418E, A418E/A489R, M431V/S668D/S671N, M507L/S668D, and S671N/Q749E, wherein the positions are numbered with reference to SEQ ID NO: 8.

The present invention also provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 12. In some embodiments, the acid alpha-glucosidase comprises at least one substitution at position or set of positions selected from 4, 27, 27/28/489, 27/418/478, 28, 28/29, 28/29/113/135/138, 28/29/113/135/418, 28/29/135, 28/29/418, 29/113/126/135/193, 29/113/135, 29/113/135/455, 29/113/138, 29/148, 29/478, 106, 106/138/218/431/671/749, 106/218/281, 106/218/455, 106/218/455/507/749, 106/489/671, 106/638, 106/671/934, 113, 113/135/418, 113/418/455/478/581, 113/418/478/489/581, 135, 135/148/150/418, 135/478/489/581, 135/489, 135/944, 138/218/668/671, 138/218/749/934, 138/671/749/934, 157, 218, 218/281/431, 218/281/671, 218/431, 218/455, 218/507/749, 218/638/671, 218/749, 281/431/489/668, 345/934, 418, 418/489, 431/668/671, 489/638/934, 489/671/934, 489/749, 489/934, 507/668, 507/671/934, 671/749, 671/934, and 749/784, wherein the positions are numbered with reference to SEQ ID NO: 12. In some embodiments, the acid alpha-glucosidase comprises at least one substitution at position or set of positions selected from 4H, 27P/28S/489R, 27P/418E/478T, 27R, 28S, 28S/29T, 28S/29T/113S/135Q/138A, 28S/29T/113S/135Q/418E, 28S/29T/135Q, 28S/29T/418E, 29T/113S/126Q/135Q/193Q, 29T/113S/135Q, 29T/113S/135Q/455V, 29T/113S/138A, 29T/148G, 29T/478T, 106P, 106P/138A/218S/431V/671N/749E, 106P/218S/281V, 106P/218S/455V, 106P/218S/455V/507L/749E, 106P/489R/671N, 106P/638I, 106P/671N/934R, 113S, 113S/135Q/418E, 113S/418E/455V/478T/581T, 113S/418E/478T/489R/581T, 135P/944Y, 135Q, 135Q/148G/150G/418E, 135Q/478T/489R/581T, 135Q/489R, 138A/218S/668D/671N, 138A/218S/749E/934R, 138A/671N/749E/934R, 157M, 218S, 218S/281V/431V, 218S/281V/671N, 218S/431V, 218S/455V, 218S/507L/749E, 218S/638I/671N, 218S/749E, 281V/431V/489R/668D, 345K/934R, 418E, 418E/489R, 431V/668D/671N, 489R/638I/934R, 489R/671N/934R, 489R/749E, 489R/934R, 507L/668D, 507L/671N/934R, 671N/749E, 671N/934R, and 749E/784T, wherein the positions are numbered with reference to SEQ ID NO: 12. In some embodiments, the acid alpha-glucosidase comprises at least one substitution at position or set of positions selected from P4H, F27P/L28S/A489R, F27P/A418E/A478T, F27R, L28S, L28S/L29T, L28S/L29T/Q113S/S135Q/M138A, L28S/L29T/Q113S/S135Q/A418E, L28S/L29T/S135Q, L28S/L29T/A418E, L29T/Q113S/P126Q/S135Q/1H193Q, L29T/Q113S/S135Q, L29T/Q113S/S135Q/R455V, L29T/Q113S/M138A, L29T/T148G, L29T/A478T, K106P, K106P/M138A/L218S/M431V/S671N/Q749E, K106P/L218S/A281V, K106P/L218S/R455V, K106P/L218S/R455V/M507L/Q749E, K106P/A489R/S671N, K106P/

V638I, K106P/S671N/L934R, Q113S, Q113S/S135Q/ A418E, Q113S/A418E/R455V/A478T/K581T, Q113S/ A418E/A478T/A489R/K581T, S135P/C944Y, S135Q, S135Q/T148G/S150G/A418E, S135Q/A478T/A489R/ K581T, S135Q/A489R, M138A/L218S/S668D/S671N, M138A/L218S/Q749E/L934R, M138A/S671N/Q749E/ L934R, L157M, L218S, L218S/A281V/M431V, L218S/ A281V/S671N, L218S/M431V, L218S/R455V, L218S/ M5071L/Q749E, L218S/V638I/S671N, L218S/Q749E, A281V/M431V/A489R/S668D, Q345K/L934R, A418E, A418E/A489R, M431V/S668D/S671N, A489R/638I/ L934R, A489R/S671N/L934R, A489R/Q749E, A489R/ L934R, M507L/S668D, M507L/S671N/L934R, S671N/ Q749E, S671N/L934R, and Q749E/A784T, wherein the positions are numbered with reference to SEQ ID NO: 12.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 14. The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 16. In some embodiments, the acid alpha-glucosidase comprises at least one substitution at position or set of positions selected from 22, 24, 27, 27/165, 30, 33, 34, 37/62, 37/62/79/196/696/862, 37/62/523, 37/62/523/793, 37/64/66/ 79/154/523/681/793/862, 37/79/154/793, 37/196, 37/528/ 696/793, 37/528/790, 37/528/790/793/862, 37/790/793, 39, 39/58/489/725/830/842/930/944, 39/70/109/830/842, 39/70/489/612, 39/70/725, 39/267, 39/267/489/522/612/ 830/842, 39/267/489/830/944, 39/489/500/612, 39/500/612, 40, 44/157, 47, 49, 50, 55, 60/500/612, 6279/154/862, 62/79/196/681/862, 62/79/523/528/790, 62/79/790/793, 62/79/862, 62/92, 62/92/790/793, 62/106/523/528/696/793/ 862, 62/154/696/793/862, 62793/862, 68, 70, 70/267/725/ 944, 70/267/930/944, 70/489/930, 70/725/830/860/930/944, 77, 79/154/681, 79/154/793/862, 79/862, 89, 97, 106/154, 107, 109, 109/522/612/725, 109/522/830/944, 109/612, 118, 149, 157, 158, 178, 179, 196/528/681/790/793, 207, 208, 217, 267/489/500/725/830/930, 267/522/725, 352, 385, 424, 448, 463, 489/830/944, 500, 500/612/830/860, 500/860/930, 500/930/944, 522/725, 523, 523/790/793, 528/681, 528/793, 528/862, 672, 673, 725, 734, 740, 753, 774, 778, 793, 830, 844, 862, 875, 880, 892, 902, 922, 925, 930, 932, 934, 938, and 944, wherein the positions are numbered with reference to SEQ ID NO: 14 and/or 16. In some embodiments, the acid alpha-glucosidase comprises at least one substitution or substitution sets at one or more positions selected from 22R, 24E, 24R, 24W, 27A, 27G, 27G/165I, 27K, 27R, 27S, 27V, 27W, 30D, 30L, 33G, 33P, 34D, 34M, 34T, 37F/62E, 37F/ 62E/79S/196T/696S/862Q, 37F/62E/523N, 37F/62E/523N/ 793K, 37F/64Q/66G/79S/154R/523N/681Q/793K/862Q, 37F/79S/154R/793K, 37F/196T, 37F/528S/696S/793K, 37F/528S/790V, 37F/528S/790V/793K/862Q, 37F/790V/ 793K, 39D, 39H, 39Q, 39Q/58L/489D/725E/830K/842S/ 930P/944S, 39Q/70A/109P/830K/842S, 39Q/70A/489D/ 612D, 39Q/70A/725E, 39Q/267K, 39Q/267K/489D/522V/ 612D/830K/842S, 39Q/267K/489D/830K/944S, 39Q/ 489D/500A/612D, 39Q/500A/612D, 40W, 44I/157V, 47G, 47R, 49A, 49G, 50G, 50L, 50V, 55C, 55L, 60V/500A/612D, 62E/79S/154R/862Q, 62E/79S/196T/681Q/862Q, 62E179S/523N/528S/790V, 62E/79S/790V/793K, 62E/79S/ 862Q, 62E/92R, 62E/92R/790V/793K, 62E/106R/523N/ 528S/696S/793K/862Q, 62E/154R/696S/793K/862Q, 62E/ 793K/862Q, 68N, 685, 68W, 70A/267K/725E/944S, 70A/ 267K/930P/944S, 70A/489D/930P, 70A/725E/830K/860F/ 930P/944S, 70Q, 77W, 79S/154R/681Q, 79S/154R/793K/ 862Q, 79S/862Q, 89R, 97D, 97G, 106/154R, 107G, 109D, 109P/522V/612D/725E, 109P/522V/830K/944S, 109P/ 612D, 118F, 149R, 157Q, 158E, 158F, 178G, 178V, 179L, 196T/528S/681Q/790V/793K, 207R, 207Y, 208G, 208I, 217A, 217D, 267K/489D/500A/725E/830K/930P, 267K/ 522V/725E, 352K, 352V, 385G, 424K, 448L, 463A, 489D/ 830K/944S, 500A, 500A/612D/830K/860F, 500A/860F/ 930P, 500A/930P/944S, 522V/725E, 523N, 523N/790V/ 793K, 528S/681Q, 528S/793K, 528S/862Q, 672E, 672K, 673N, 673R, 725F, 725V, 734K, 740G, 740Q, 753S, 774G, 774S, 778Q, 793K, 830V, 844R, 862Q, 875D, 880R, 892L, 902L, 922E, 925A, 925W, 930P, 932A, 934F, 938A, 938P, 944R, and 944S, wherein the positions are numbered with reference to SEQ ID NO: 14 and/or 16. In some embodiments, the acid alpha-glucosidase comprises at least one substitution or substitution sets at one or more positions selected from I22R, L24E, L24R, L24W, F27A, F27G, F27G/M165I, F27K, F27R, F27S, F27V, F27W, V30D, V30L, E33G, E33P, L34D, L34M, L34T, S37F/A62E, S37F/ A62E/N79S/A196T/A696S/R862Q, S37F/A62E/D523N, S37F/A62E/D523N/E793K, S37F/P64Q/R66G/N79S/ K154R/D523N/E681Q/E793K/R862Q, S37F/N79S/ K154R/E793K, S37F/A196T, S37F/N528S/A696S/E793K, S37F/N528S/I790V, S37F/N528S/I790V/E793K/R862Q, S37F/I790V/E793K, P39D, P39H, P39Q, P39Q/R58L/ A489D/K725E/Q830K/G842S/C930P/C944S, P39Q/ V70A/L109P/Q830K/G842S, P39Q/V70A/A489D/S612D, P39Q/V70A/K725E, P39Q/R267K, P39Q/R267K/A489D/ E522V/S612D/Q830K/G842S, P39Q/R267K/A489D/ Q830K/C944S, P39Q/A489D/D500A/S612D, P39Q/ D500A/S612D, V40W, T44I/L157V, A47G, A47R, Q49A, Q49G, Q50G, Q50L, Q50V, P55C, P55L, A60V/D500A/ S612D, A62E/N79S/K154R/R862Q, A62E/N79S/A196T/ E681Q/R862Q, A62E/N79S/D523N/N528S/I790V, A62E/ N79S/I790V/E793K, A62E/N79S/R862Q, A62E/Q92R, A62E/Q92R/I790V/E793K, A62E/K106R/D523N/N528S/ A696S/E793K/R862Q, A62E/K154R/A696S/E793K/ R862Q, A62E/E793K/R862Q, R68N, R68S, R68W, V70A/ R267K/K725E/C944S, V70A/R267K/C930P/C944S, V70A/A489D/C930P, V70A/K725E/Q830K/L860F/C930P/ C944S, V70Q, P77W, N79S/K154R/E681Q, N79S/K154R/ E793K/R862Q, N79S/R862Q, A89R, A97D, A97G, K106R/ K154R, Q107G, L109D, L109P/E522V/S612D/K725E, L109P/E522V/Q830K/C944S, L109P/S612D, WI 18F, P149R, L157Q, T158E, T158F, P178G, P178V, A179L, A196T/N528S/E681Q/I790V/E793K, E207R, E207Y, E208G, E208I, Q217A, Q217D, R267K/A489D/D500A/ K725E/Q830K/C930P, R267K/E522V/K725E, Y352K, Y352V, R385G, H424K, R448L, E463A, A489D/Q830K/ C944S, D500A, D500A/S612D/Q830K/L860F, D50A/ L860F/C930P, D500A/C930P/C944S, E522V/K725E, D523N, D523N/I790V/E793K, N528S/E681Q, N528S/ E793K, N528S/R862Q, L672E, L672K, P673N, P673R, K725F, K725V, H734K, E/740G, E/740Q, A753S, A774G, A774S, L778Q, E/793K, Q830V, E844R, R862Q, N875D, E880R, Q892L, A902L, P922E, K925A, K925W, C930P, S932A, L934F, Q938A, Q938P, C944R, and C944S, wherein the positions are numbered with reference to SEQ ID NO: 14 and/or 16.

The present invention also provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 18, wherein the positions are numbered with reference to SEQ ID NO: 18. In some embodiments, the acid alpha-glucosidase comprises at least one substitution at position or set of positions selected from 22, 24, 27, 27/165, 30, 33, 34, 37/62, 37/62/79/196/696/862, 37/62/523, 37/1%, 37/528/790, 39, 39/70/109/830/842, 39/70/725, 39/267, 39/267/489/522/612/830/842, 39/267/489/830/944, 40, 70/267/725/944, 70/267/930/944, 70/489/930, 107, 109, 109/522/830/944, 217, 267/489/500/725/830/930, 267/522/725, 352, 385, 500/930/944, 673, 734, 774, 778, 875, 930, 932, and 934, wherein the positions are numbered with reference to SEQ ID NO: 18. In some embodiments, the acid alpha-glucosidase comprises at least one substitution at position or set of positions selected from 22R, 24E, 24R, 24W, 27G, 27G/165I, 27K, 27R, 27W, 30D, 33G, 34D, 34M, 34T, 37F/62E, 37F/62E/79S/196T/696S/862Q, 37F/62E/523N, 37F/196T, 37F/528S/790V, 39D, 39Q, 39Q/70A/109P/830K/842S, 39Q/70A/725E, 39Q/267K, 39Q/267K/489D/522V/612D/830K/842S, 39Q/267K/489D/830K/944S, 40W, 70A/267K/725E/944S, 70A/267K/930P/944S, 70A/489D/930P, 107G, 109D, 109P/522V/830K/944S, 217D, 267K/489D/500A/725E/830K/930P, 267K/522V/725E, 352K, 352V, 385G, 500A/930P/944S, 673N, 734K, 774G, 778Q, 875D, 930P, 932A, and 934F, wherein the positions are numbered with reference to SEQ ID NO: 18. In some embodiments, the acid alpha-glucosidase comprises at least one substitution at position or set of positions selected from I22R, L24E, L24R, L24W, F27G, F27G/M165I, F27K, F27R, F27W, V30D, E33G, L34D, L34M, L34T, S37F/A62E, S37F/A62E/N79S/A196T/A696S/R862Q, S37F/A62E/D523N, S37F/A196T, S37F/N528S/I790V, P39D, P39Q, P39Q/V70A/L109P/Q830K/G842S, P39Q/V70A/K725E, P39Q/R267K, P39Q/R267K/A489D/E522V/S612D/Q830K/G842S, P39Q/R267K/A489D/Q830K/C944S, V40W, V70A/R267K/K725E/C944S, V70A/R267K/C930P/C944S, V70A/A489D/C930P, Q107G, L109D, L109P/E522V/Q830K/C944S, Q217D, R267K/A489D/D500A/K725E/Q830K/C930P, R267K/E522V/K725E, Y352K, Y352V, R385G, D500A/C930P/C944S, P673N, H734K, A774G, L778Q, N875D, C930P, S932A, and L934F, wherein the positions are numbered with reference to SEQ ID NO: 18.

The present invention also provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 20, wherein the positions are numbered with reference to SEQ ID NO: 20. In some embodiments, the acid alpha-glucosidase comprises at least one substitution at position or set of positions selected from 22/24, 22/24/27/50/107/109/489/612/725, 22/24/27/489, 22/24/27/489/612/774, 22/24/27/612/944, 22/24/50/109/267/489/774/944, 22/24/50/267/612/922/944, 22/24/107/267/489/922, 22/24/489, 22/24/612/725/944, 22/50/107/267/489/612/944, 22/50/109/267/489, 22/267/489/612, 24, 24/27/50/107/267/774/944, 24/27/89/500/842, 24/27/107/267/612/944, 24/27/267/944, 24/27/500/842, 24/27/500/842/932, 24/27/944, 24/39/49/89/97/842/932, 24/39/68/89/107/500/842, 24/39/89/97/842/932, 24/39/842/932, 24/50/489/944, 24/50/612, 24/70/107/109/489/612/725, 24/70/267/774, 24/89/500, 24/107/109/267/489/612/725/774, 24/109/612, 24/109/944, 24/267/725/944, 24/489/944, 24/725, 24/842/932, 24/944, 27/39/49/97/500/842, 27/49/68/500/842, 34/39/500/932, 39/89/97/500, 42, 48, 50/109/489/612, 50/489/774, 50/612/944, 57, 62, 68, 68/89/97/932, 71, 88, 89/97/107, 89/97/500, 89/842, 107/109, 107/500/842, 108, 109/612/774/944, 112, 123, 124, 148, 188, 193, 197, 204, 253, 264, 305, 312, 333, 381, 402, 402/181, 489, 489/944, 500/842, 500/932, 523, 527, 612, 612/725/944, 612/922, 614, 727, 742, 748, 820, 823, 832, 842/932, 858, 862, 911, 913, 914, 916, 923, 937, and 940, wherein the positions are numbered with reference to SEQ ID NO: 20. In some embodiments, the acid alpha-glucosidase comprises at least one substitution at position or set of positions selected from 22R/24W, 22R/24W/27A/50V/107G/109D/489A/612S/725E, 22R/24W/27A/489A, 22R/24W/27A/489A/612S/774S, 22R/24W/27A/612S/944R, 22R/24W/50V/109D/267R/489A/774S/944R, 22R/24W/50V/267R/612S/922E/944R, 22R/24W/107G/267R/489A/922E, 22R/24W/489A, 22R/24W/612S/725E/944R, 22R/50V/107G/267R/489A/612S/944S, 22R/50V/109D/267R/489A, 22R/267R/489A/612S, 24R, 24R/27G/89R/500A/842G, 24R/27G/500A/842G, 24R/27G/500A/842G/932A, 24R/39D/68S/89R/107G/500A/842G, 24R/39H149G/89R/97G/842G/932A, 24R/39H189R/97D/842G/932A, 24R/39H1842G/932A, 24R/89R/500A, 24R/842G/932A, 24W, 24W/27A/50V/107G/267R/774S/944S, 24W/27A/107G/267R/612S/944S, 24W/27A/267R/944R, 24W/27A/944R, 24W/50V/489A/944S, 24W/50V/612S, 24W/70A/107G/109D/489A/612S/725E, 24W/70A/267R/774S, 24W/107G/109D/267R/489A/612S/725E/774S, 24W/109D/612S, 24W/109D/944S, 24W/267R/725E/944S, 24W/489A/944R, 24W/725E, 24W/944S, 27G/39H/49G/97G/500A/842G, 27G/49G/68S/500A/842G, 34T/39D/500A/932A, 39D/89R/97G/500A, 42G, 48Q, 48V, 48W, 50V/109D/489A/612S, 50V/489A/1774S, 50V/612S/944S, 57F, 57L, 57M, 62F, 62L, 62W, 68N/89R/97G/932A, 68S, 71G, 71L, 71V, 71W, 71Y, 88L, 88R, 89R/97G/107G, 89R/97G/500A, 89R/842G, 107G/109D, 107G/500A/842G, 108R, 109D/612S/774S/944S, 112H, 123L, 123V, 124G, 124M, 124V, 148K, 148R, 188R, 188W, 193E, 193P, 197G, 204A, 253M, 264M, 305F, 312A, 333L, 381R, 381V, 381W, 402N, 402V/781Q, 489A, 489A/944R, 500A/842G, 500A/932A, 523E, 527R, 527V, 612S, 612S/725E/944S, 612S/922E, 614Q, 614R, 614W, 727W, 742V, 748V, 820A, 820V, 823F, 823V, 832A, 832R, 842G/932A, 858C, 858W, 862I, 862M, 862Q, 862Y, 911G, 911R, 913G, 913R, 913W, 914G, 914I, 914K, 914Q, 914R, 914S, 914T, 916G, 916H, 916R, 923L, 923V, 923W, 937K, and 940Q, wherein the positions are numbered with reference to SEQ ID NO: 20. In some embodiments, the acid alpha-glucosidase comprises at least one substitution at position or set of positions selected from I22R/L24W, I22R/L24W/F27A/Q50V/Q107G/L109D/D489A/D612S/K725E, I22R/L24W/F27A/D489A, I22R/L24W/F27A/D489A/D612S/A774S, I22R/L24W/F27A/D612S/C944R, I22R/L24W/Q50V/L109D/K267R/D489A/A774S/C944R, I22R/L24W/Q50V/K267R/D612S/P922E/C944R, I22R/L24W/Q107G/K267R/D489A/P922E, I22R/L24W/D489A, I22R/L24W/D612S/K725E/C944R, I22R/Q50V/Q107G/K267R/D489A/D612S/C944S, I22R/Q50V/L109D/K267R/D489A, I22R/K267R/D489A/D612S, L24R, L24R/F27G/A89R/D500A/S842G, L24R/F27G/D500A/S842G, L24R/F27G/D500A/S842G/S932A, L24R/Q39D/R68S/A89R/Q107G/D500A/S842G, L24R/Q39H/Q49G/A89R/A97G/S842G/S932A, L24R/Q39H/A89R/Q49G/A89R/

A97D/S842G/S932A, L24R/Q39H/S842G/S932A, L24R/ A89R/D500A, L24R/S842G/S932A, L24W, L24W/F27A/ Q50V/Q107G/K267R/A774S/C944S, L24W/F27A/Q107G/ K267R/D612S/C944S, L24W/F27A/K267R/C944R, L24W/F27A/C944R, L24W/Q50V/D489A/C944S, L24W/ Q50V/D612S, L24W/V70A/Q107G/L109D/D489A/ D612S/K725E, L24W/V70A/K267R/A774S, L24W/ Q107G/L109D/K267R/D489A/D612S/K725E/A774S, L24W/L109D/D612S, L24W/L109D/C944S, L24W/ K267R/K725E/C944S, L24W/D489A/C944R, L24W/ K725E, L24W/C944S, F27G/Q39H/Q49G/A97G/D500A/ S842G, F27G/Q49G/R68S/D500A/S842G, L34T/Q39D/ D500A/S932A, Q39D/A89R/A97G/D500A, E42G, H48Q, H48V, H48W, Q50V/L109D/D489A/D612S, Q50V/ D489A/A774S, Q50V/D612S/C944S, P57F, P57L, P57M, A62F, A62L, A62W, R68N/A89R/A97G/S932A, R68S, P71G, P71L, P71V, P71W, P71Y, K88L, K88R, A89R/ A97G/Q107G, A89R/A97G/D500A, A89R/S842G, Q107G/ L109D, Q107G/D500A/S842G, G108R, L109D/D612S/ A774S/C944S, A112H, P123L, P123V, S124G, S124M, S124V, T148K, T148R, E188R, E188W, H193E, H193P, P197G, E204A, A253M, S264M, L305F, V312A, I333L, E381R, E381V, E381W, S402N, S402V/P781Q, D489A, D489A/C944R, D500A/S842G, D500A/S932A, D523E, N527R, N527V, D612S, D612S/K725E/C944S, D612S/ P922E, E614Q, E614R, E614W, S727W, L742V, L748V, G820A, G820V, L823F, L823V, P832A, P832R, S842G/ S932A, E858C, E858W, R862I, R862M, R862Q, R862Y, N911G, N911R, V913G, V913R, V913W, P914E, P914I, P914K, P914Q, P914R, P914S, P914T, S916G, S916H, S916R, D923L, D923V, D923W, E937K, and L940Q, wherein the positions are numbered with reference to SEQ ID NO: 20. In some additional embodiments, the acid alpha-glucosidase comprises at least one substitution at position or set of positions selected from 22/24, 22/24/27/ 50107/109/489/612/725, 22/24/27/489, 22/24/27/489/612/ 774, 22/24/27/612/944, 22/24/50/109/267/489/774/944, 22/24/50/267/612/922/944, 22/24/107/267/489/922, 22/24/ 489, 22/24/612/725/944, 22/50/107/267/489/612/944, 22/50/109/267/489, 22/267/489/612, 24, 24/27/50/107/267/ 774/944, 24/27/89/500/842, 24/27/107/267/612/944, 24/27/ 267/944, 24/27/500/842, 24/27/500/842/932, 24/27/944, 24/39/49/89/97/842/932, 24/39/68/89/107/500/842, 24/39/ 89/97/842/932, 24/39/842/932, 24/50/489/944, 24/50/612, 24/70/107/109/489/612/725, 24/70267/774, 24/89/500, 24/107/109/267/489/612/725/774, 24/109/612, 24/109/944, 24/267/725/944, 24/489/944, 24/725, 24/842/932, 24/944, 27/39/49/97/500/842, 27/49/68/500/842, 34/39/500/932, 50/109/489/612, 50/612/944, 68/89/97/932, 89/97/107, 89/842, 106, 107/109, 107/500/842, 108, 109/612/774/944, 112, 148, 148/772, 188/377, 238, 240, 240/374, 243, 244, 246, 248, 249/777, 252, 253, 259, 260, 261, 262, 264, 279, 305, 309, 312, 319, 320, 329, 333, 387, 402, 421, 432, 500/842, 500/932, 556, 612, 612/725/944, 612/922, 727, 736, 737, 741, 742, 748, 815, 816, 818, 823, 832, 842/932, 911, 913, 914, 916, 923, 937, and 940, wherein the positions are numbered with reference to SEQ ID NO: 20. In some embodiments, the acid alpha-glucosidase comprises at least one substitution at position or set of positions selected from 22R/24W, 22R/24W/27A/50V/107G/109D/489/612S/ 725E, 22R/24W/27A/489A, 22R/24W/27A/489A/612S/ 774S, 22R/24W/27A/612S/944R, 22R/24W/50V/109D/ 267R/489A/774S/944R, 22R/24W/50V/267R/612S/922E/ 944R, 22R/24W/107G/267R/489A/922E, 22R/24W/489A, 22R/24W/612S/725E/944R, 22R/50V/107G/267R/489A/ 612S/944S, 22R/50V/109D/267R/489A, 22R/267R/489A/ 612S, 24R, 24R/27G/89R/500A/842G, 24R/27G/500A/ 842G, 24R/27G/500A/842G/932A, 24R/39D/68S/89R/ 107G/500A/842G, 24R/39D/89R/97G/842G/932A, 24R/39H/49G/89R/97G/842G/932A, 24R/39H/89R/97D/842G/932A, 24R/39H1842G/932A, 24R/89R/500A, 24R/842G/932A, 24W, 24W/27A/50V/ 107G/267R/774S/944S, 24W/27A/107G/267R/612S/944S, 24W/27A/267R/944R, 24W/27A/944R, 24W/50V/489A/ 944S, 24W/50V/612S, 24W/70A/107G/109D/489A/612S/ 725E, 24W/70A/267R/774S, 24W/107G/109D/267R/489A/ 612S/725E/774S, 24W/109D/612S, 24W/109D/944S, 24W/ 267R/725E/944S, 24W/489A/944R, 24W/725E, 24W/944S, 27G/39H/49G/97G/500A/842G, 27G/49G/68S/500A/842G, 34T/39D/500A/932A, 50V/109D/489A/612S, 50V/612S/ 944S, 68N/89R/97G/932A, 89R/97G/107G, 89R/842G, 106A, 106G, 106N, 106T, 107G/109D, 107G/500A/842G, 108H, 108N, 108R, 108S, 108V, 109D/612S/774S/944S, 112H, 112P, 148E, 148G, 148H, 148K, 148R/772I, 188Q/ 377Q, 238Q, 240I, 240W/374T, 240Y, 243E, 243G, 243R, 243V, 244I, 244V, 246A, 246G, 248A, 248R, 248V, 249V/ 777N, 252V, 253G, 253P, 259G, 259N, 259S, 260W, 261E, 262P, 264C, 279E, 305F, 305G, 305R, 305V, 305Y, 309C, 309G, 312A, 319F, 320M, 329F, 333L, 333V, 387L, 402G, 402N, 421P, 432C, 500A/842G, 500A/932A, 556H, 556R, 556S, 556Y, 612S, 612S/725E/944S, 612S/922E, 727G, 727Q, 727T, 727W, 736A, 736V, 736W, 737M, 741C, 741D, 741E, 741G, 741T, 742V, 748I, 748T, 748V, 815A, 815M, 816V, 818T, 818V, 823A, 823F, 823G, 823R, 832E, 832G, 842G/932A, 911G, 913A, 913E, 913G, 913H, 913L, 913Q, 913R, 913W, 914E, 914G, 914H, 914K, 914Q, 914R, 914S, 914T, 916A, 916G, 916H, 916I, 916R, 916V, 923W, 937Q, 940G, 940Q, 940T, and 940W, wherein the positions are numbered with reference to SEQ ID NO: 20. In some embodiments, the acid alpha-glucosidase comprises at least one substitution at position or set of positions selected from I22R/L24W, I22R/L24W/F27A/Q50V/Q107G/L109D/ D489A/D612S/K725E, I22R/L24W/F27A/D489A, I22R/ L24W/F27A/D489A/D612S/A774S, I22R/L24W/F27A/ D612S/C944R, I22R/L24W/Q50V/L109D/K267R/D489A/ A774S/C944R, I22R/L24W/Q50V/K267R/D612S/P922E/ C944R, I22R/L24W/Q07G/K267R/D489A/P922E, I22R/ L24W/D489A, I22R/L24W/D612S/K725E/C944R, I22R/ Q50V/Q107G/K267R/D489A/D612S/C944S, I22R/Q50V/ L109D/K267R/D489A, I22R/K267R/D489A/D612S, L24R, L24R/F27G/A89R/D500A/S842G, L24R/F27G/ D500A/S842G, L24R/F27G/D500A/S842G/S932A, L24R/ Q39D/R68S/A89R/Q107G/D500A/S842G, L24R/ Q39H1Q49G/A89R/A97G/S842G/S932A, L24R/ Q39H1A89R/A97D/S842G/S932A, L24R/Q39H/S842G/ S932A, L24R/A89R/D500A, L24R/S842G/S932A, L24W, L24W/F27A/Q50V/Q107G/K267R/A774S/C944S, L24W/ F27A/Q107G/K267R/D612S/C944S, L24W/F27A/K267R/ C944R, L24W/F27A/C944R, L24W/Q50V/D489A/C944S, L24W/Q50V/D612S, L24W/V70A/Q107G/L109D/D489A/ D612S/K725E, L24W/V70A/K267R/A774S, L24W/ Q107G/L109D/K267R/D489A/D612S/K725E/A774S, L24W/L109D/D612S, L24W/L109D/C944S, L24W/ K267R/K725E/C944S, L24W/D489A/C944R, L24W/ K725E, L24W/C944S, F27G/Q39H/Q49G/A97G/D500A/ S842G, F27G/Q49G/R68S/D500A/S842G, L34T/Q39D/ D500A/S932A, Q50V/L109D/D489A/D612S, Q50V/ D612S/C944S, R68N/A89R/A97G/S932A, A89R/A97G/ Q107G, A89R/S842G, K106A, K106G, K106N, K106T, Q107G/L109D, Q107G/D500A/S842G, G108H, G108N, G108R, G108S, G108V, L109D/D612S/A774S/C944S, A112H, A112P, T148E, T148G, T148H, T148K, T148R/ V772I, E188Q/R377Q, L238Q, L240I, L240W/A374T, L240Y, S243E, S243G, S243R, S243V, L244I, L244V, S246A, S246G, Y248A, Y248R, Y248V, I249V/S777N, L252V, A253G, A253P, L259G, L259N, L259S, M260W, L261E, S262P, S264C, P279E, L305F, L305G, L305R, L305V, L305Y, A309G, V312A, A319F, L320M, L329F, I333L, I333V, H387L, S402G, S402N, Q421P, M432C, D500A/S842G, D500A/S932A, F556H, F556R, F556S, F556Y, D612S, D612S/K725E/C944S, D612S/ P922E, S727G, S727Q, S727T, S727W, L736M, L736V, L736W, L737M, A741C, A741D, A741E, A741G, A741T, L742V, L748I, L748T, L748V, I815A, I815M, I816V, L818T, L818V, L823A, L823F, L823G, L823R, P832E, P832G, S842G/S932A, N911G, V913A, V913E, V913G, V913H, V913L, V913Q, V913R, V913W, P914E, P914G, P914H, P914K, P914Q, P914R, P914S, P914T, S916A, S916G, S916H, S916I, S916R, S916V, D923W, E937Q, L940G, L940Q, L940T, and L940W, wherein the positions are numbered with reference to SEQ ID NO: 20.

The present invention further provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 946, wherein the positions are numbered with reference to SEQ ID NO: 946. In some embodiments, the acid alpha-glucosidase comprises at least one substitution at position or set of positions selected from 19/124/149/381/ 727, 24/39/489/862, 24/57/62/89/489/823/862, 24/57/823/ 862, 24/62/89/188/823/842/862, 24/89/489, 24/89/489/727/ 862, 24/489/500/842, 39/57/62/188/500/842, 39/57/500/ 862, 57, 57/62/120/527/913/916, 57/62/305/437/500/614/ 727/916, 57/62/305/437/500/727/913/916, 57/62/305/437/ 614/683/913/916/932, 57/62/305/489/907/913/916, 57/62/ 305/489/913/916, 57/62/305/500/913/916, 57/62/305/913, 57/62/305/916, 57/62/437/500/761/914/916, 57/62/437/ 527/727, 57/62/437/913/916, 57/62/913/916/932, 57/62/ 916, 57/188/489/823/862, 57/305, 57/305/437/916, 57/437/ 500/527/727/916, 57/437/500/614/727/914, 57/437/913/ 914, 57/489/527/914/916, 57/614/916/932, 62/89, 62/89/ 124/148/381/858, 62/89/124/381/858, 62/89/148/381/614/ 858, 62/89/148/923, 62/89/149/381, 62/89/149/381/832, 62/89/188/489/500/727/823, 62/89/381, 62/89/381/858, 62/89/381/923, 62/89/858, 62/96/614, 62/124/148/149/381/ 614, 62/124/149/381/832/858/937, 62/124/188/823/842/ 862, 62/124/381/832, 62/148/149/381/858/937, 62/148/381/ 614/937, 62/148/381/727, 62/148/381/858, 62/149/381/614/ 937, 62/149/381/858/937, 62/149/727, 62/305/437/500/727/ 913, 62/305/727, 62/381, 62/437/489/527/727/913/932, 62/437/489/614/727/913, 62/437/527/727, 62/437/527/916/ 932, 62/437/913/916, 62/489/500/932, 62/489/527/916/932, 62/489/614/916, 62/500, 62/527, 62/527/727/916, 62/614, 62/727, 62/916, 89/148/149, 89/148/149/381, 89/381, 124/ 148/381/727/858/937, 124/381/614, 124/500/842/862, 124/ 832/937, 148/832/858/937, 381, 381/614/832, 381/858/937, 437, 437/489/914/916, 437/727/914, 437/914/916, 489/500, 489/614/916, 500/727/913/916, 500/914/916, and 923, wherein the positions are numbered with reference to SEQ ID NO: 946. In some embodiments, the acid alpha-glucosidase comprises at least one substitution at position or set of positions selected from 19T/124V/149R/381V/727W, 24R/ 39H/489A/862Q, 24R/57L/62W/89R/489A/823F/862Q, 24R/57L/823F/862Q, 24R/62W/89R/188W/823V/842G/ 862Q, 24R/89R/489A, 24R/89R/489A/727W/862Q, 24R/ 489A/500A/842G, 39H/57L/62W/188W/500A/842G, 39H/ 57L/500A/862Q, 57F/62L/305F/437G/500A/614Q/727W/ 916R, 57F/62L305F/437G/614Q/683S/913R/916A/932A, 57F/62L/305F/500A/913R/916G, 57F/62L/305F/913R, 57F/62L/437G/500A/761F/914K/916R, 57F/62L/437G/ 527R/127W, 57F/62L/913R/916R/932A, 57F/62L/916G, 57F/62W/120I/527R/913R/916R, 57F/62W/305F/437G/ 500A/727W/913R/916R, 57F/62W/305F/489A/907K/ 913R/916G, 57F/62W/305F/489A/913R/916G, 57F/62W/ 305F/916R, 57F/62W/437G/913R/916G, 57F/305F, 57F/ 305F/437G/916G, 57F/437G/500A/527R/727W/916R, 57F/ 437G/500A/614Q/727W/914R, 57F/437G/913R/914R, 57F/489A/527R/914R/916G, 57F/614Q/916G/932A, 57L, 57L/188W/489A/823F/862Q, 62F/89R, 62F/89R/124V/ 148R/381W/858W, 62F/89R/148R/381V/614R/858W, 62F/ 89R/148R/923W, 62F/89R/149R/381W/832R, 62F/89R/ 381V/923W, 62F/89R/858C, 62F/96K/614R, 62F/124V/ 381W/832R, 62F/149R/381V/858W/937K, 62F/149R/ 727W, 62F/381V, 62F/614R, 62L/305F/437G/500A/727W/ 913R, 62L/305F/727W, 62L/437G/489A/527R/727W/ 913R/932A, 62L/437G/527R/727W, 62L/437G/527R/ 916G/932A, 62L/437G/913R/916R, 62L/489A/500A/932A, 62L/489A/614Q/916R, 62L/527R, 62L/527R/727W/916G, 62W/89R/124V/381W/858C, 62W/89R/149R/381W, 62W/ 89R/188W/489A/500A/727W/823F, 62W/89R/381V, 62W/ 89R/381W/858C, 62W/124V/148R/149R/381W/614R, 62W/124V/149R/381V/832R/858C/937K, 62W/124V/ 188W/823F/842G/862Q, 62W/148R/149R/381V/858C/ 937K, 62W/148R/381W/614R/937K, 62W/148R/381W/ 727W, 62W/148R/381W/858C, 62W/149R/381W/614R/ 937K, 62W/381V, 62W/437G/489A/614Q/727W/913R, 62W/489A/527R/916R/932A, 62W/500A, 62W/727W, 62W/916G, 89R/148R/149R, 89R/148R/149R/381W, 89R/ 381W, 124V/148R/381W/727W/858W/937K, 124V/381W/ 614R, 124V/500A/842G/862Q, 124V/832R/937K, 148R/ 832R/858W/937K, 381V, 381V/614R/832R, 381W/858C/ 937K, 437G, 437G/489A/914R/916R, 437G/727W/914K, 437G/914R/916G, 489A/500A, 489A/614Q/916G, 500A/ 727W/913R/916R, 500A/914R/916G, and 923W, wherein the positions are numbered with reference to SEQ ID NO: 946. In some embodiments, the acid alpha-glucosidase comprises at least one substitution at position or set of positions selected from S19T/S124V/P149R/E381V/S727W, W24R/ Q39H/D489A/R862Q, W24R/P57/A62W/A89R/D489A/ L823F/R862Q, W24R/P57L/L823F/R862Q, W24R/A62W/ A89R/E188W/L823V/S842G/R862Q, W24R/A89R/ D489A, W24R/A89R/D489A/S727W/R862Q, W24R/ D489A/D500A/S842G, Q39H/P57L/A62W/E188W/ D500A/S842G, Q39H/P57L/D500A/R862Q, P57F/A62L/ L305F/A437G/D500A/E614Q/S727W/S916R, P57F/A62L/ L305F/A437G/E614Q/A683S/V913R/S916R/S932A, P57F/A62L/L305F/D500A/V913R/S916G, P57F/A62L/ L305F/V913R, P57F/A62L/A437G/D500A/L761F/P914K/ S916R, P57F/A62L/A437G/N527R/S727W, P57F/A62L/ V913R/S916R/S932A, P57F/A62L/S916G, P57F/A62W/ F120I/N527R/V913R/S916R, P57F/A62W/L305F/A437G/ D500A/S727W/V913R/S916R, P57F/A62W/L305F/ D489A/Q907K/V913R/S916G, P57F/A62W/L305F/ D489A/V913R/S916G, P57F/A62W/L305F/S916R, P57F/ A62W/A437G/V913R/S916G, P57F/L305F, P57F/L305F/ A437G/S916G, P57F/A437G/D500A/N527R/S727W/ S916R, P57F/A437G/D500A/E614Q/S727W/P914R, P57F/ A437G/V913R/P914R, P57F/D489A/N527R/P914R/ S916G, P57F/E614Q/S916G/S932A, P57L, P57/E188W/ D489A/L823F/R862Q, A62F/A89R, A62F/A89R/S124V/ T148R/E381W/E858W, A62F/A89R/T148R/E381V/ E614R/E858W, A62F/A89R/T148R/D923W, A62F/A89R/ P149R/E381W/P832R, A62F/A89R/E381V/D923W, A62F/ A89R/E858C, A62F/E96K/E614R, A62F/S124V/E381W/ P832R, A62F/P149R/E381V/E858W/E937K, A62F/P149R/ S727W, A62F/E381V, A62F/E614R, A62L/L305F/A437G/

D500A/S727W/V913R, A62L/L305F/S727W, A62L/ A437G/D489A/N527R/S727W/V913R/S932A, A62L/ A437G/N527R/S727W, A62L/A437G/N527R/S916G/ S932A, A62L/A437G/V913R/S916R, A62L/D489A/ D500A/S932A, A62L/D489A/E614Q/S916R, A62L/ N527R, A62L/N527R/S727W/S916G, A62W/A89R/ S124V/E381W/E858C, A62W/A89R/P149R/E381W, A62W/A89R/E188W/D489A/D500A/S727W/L823F, A62W/A89R/E381V, A62W/A89R/E381W/E858C, A62W/ S124V/T148R/P149R/E381W/E614R, A62W/S124V/ P149R/E381V/P832R/E858C/E937K, A62W/S124V/ E188W/L823F/S842G/R862Q, A62W/T148R/P149R/ E381V/E858C/E937K, A62W/T148R/E381W/E614R/ E937K, A62W/T148R/E381W/S727W, A62W/T148R/ E381W/E858C, A62W/P149R/E381W/E614R/E937K, A62W/E381V, A62W/A437G/D489A/E614Q/S727W/ V913R, A62W/D489A/N527R/S916R/S932A, A62W/ D500A, A62W/S727W, A62W/S916G, A89R/T148R/ P149R, A89R/T48R/P149R/E381W, A89R/E381W, S124V/ T148R/E381W/S727W/E858W/E937K, S124V/E381W/ E614R, S124V/D500A/S842G/R862Q, S124V/P832R/ E937K, T148R/P832R/E858W/E937K, E381V, E381V/ E614R/P832R, E381W/E858C/E937K, A437G, A437G/ D489A/P914R/S916R, A437G/S727W/P914K, A437G/ P914R/S916G, D489A/D500A, D489A/E614Q/S916G, D500A/S727W/V913R/S916R, D500A/P914R/S916G, and D923W, wherein the positions are numbered with reference to SEQ ID NO: 946. In some embodiments, the acid alpha-glucosidase comprises at least one substitution at position or set of positions selected from 57/62/120/527/ 913/916, 57/62/305/437/500/614/727/916, 57/62/305/437/ 500/727/913/916, 57/62/305/437/614/683/913/916/932, 57/62/305/489/907/913/916, 57/62/305/489/913/916, 57/62/305/500/913/916, 57/62/305/913, 57/62/305/916, 57/62/437/500/761/914/916, 57/62/437/527/727, 57/62/ 437/913/916, 57/62/913/916/932, 57/62/916, 57/188/489/ 823/862, 57/305, 57/305/437/916, 57/437/500/527/727/916, 57/437/500/614/727/914, 57/437/913/914, 57/489/527/914/ 916, 57/614/916/932, 62/89/188/489/500/727/823, 62/124/ 188/823/842/862, 62/305/437/500/727/913, 62/305/727, 62/437/489/527/727/913/932, 62/437/489/614/727/913, 62/437/527/727, 62/437/527/916/932, 62/437/913/916, 62/489/500/932, 62/489/527/916/932, 62/527/727/916, 62/727, 62/916, 124/500/842/862, 437, 437/489/914/916, 437/727/914, 437/914/916, 489/614/916,500/727/913/916, 500/914/916, and 923, wherein the positions are numbered with reference to SEQ ID NO: 946. In some embodiments, the acid alpha-glucosidase comprises at least one substitution at position or set of positions selected from 57F/62L/ 305F/437G/500A/614Q/727W/916R, 57F/62L/305F/437G/ 614Q/683S/913R/916R/932A, 57F/62L/305F/500A/913R/ 916G, 57F/62L/305F/913R, 57F/62L/437G/500A/761F/ 914K/916R, 57F/62L/437G/527R/727W, 57F/62L/913R/ 916R/932A, 57F/62L/916G, 57F/62W/120I/527R/913R/ 916R, 57F/62W/305F/437G/500A/727W/913R/916R, 57F/ 62W/305F/489A/907K/913R/916G, 57F/62W/305F/489A/ 913R/916G, 57F/62W/305F/916R, 57F/62W/437G/913R/ 916G, 57F/305F, 57F/305F/437G/916G, 57F/437G/500A/ 527R/727W/916R, 57F/437G/500A/614Q/727W/914R, 57F/437G/913R/914R, 57F/489A/527R/914R/916G, 57F/ 614Q/916G/932A, 57L/188W/489A/823F/862Q, 62L/ 305F/437G/500A/727W/913R, 62L/305F/727W, 62L/ 437G/489A/527R/727W/913R/932A, 62L/437G/527R/ 727W, 62L/437G/527R/916G/932A, 62L/437G/913R/ 916R, 62L/489A/500A/932A, 62L/527R/727W/916G, 62W/89R/188W/489A/500A/727W/823F, 62W/124V/ 188W/823F/842G/862Q, 62W/437G/489A/614Q/727W/ 913R, 62W/489A/527R/916R/932A, 62W/727W, 62W/ 916G, 124V/500A/842G/862Q, 437G, 437G/489A/914R/ 916R, 437G/727W/914K, 437G/914R/916G, 489A/614Q/ 916G, 500A/727W/913R/916R, 500A/914R/916G, and 923W, wherein the positions are numbered with reference to SEQ ID NO: 946. In some embodiments, the acid alpha-glucosidase comprises at least one substitution at position or set of positions selected from P57F/A62L/L305F/A437G/ D500A/E614Q/S727W/S916R, P57F/A62L/L305F/A437G/ E614Q/A683S/V913R/S916R/S932A, P57F/A62L/L305F/ D500A/V913R/S916G, P57F/A62L/L305F/V913R, P57F/ A62L/A437G/D500A/L761F/P914K/S916R, P57F/A62L/ A437G/N527R/S727W, P57F/A62L/V913R/S916R/S932A, P57F/A62L/S916G, P57F/A62W/F120I/N527R/V913R/ S916R, P57F/A62W/L305F/A437G/D500A/S727W/ V913R/S916R, P57F/A62W/L305F/D489A/Q907K/ V913R/S916G, P57F/A62W/L305F/D489A/V913R/ S916G, P57F/A62W/L305F/S916R, P57F/A62W/A437G/ V913R/S916G, P57F/L305F, P57F/L305F/A437G/S916G, P57F/A437G/D500A/N527R/S727W/S916R, P57F/ A437G/D500A/E614Q/S727W/P914R, P57F/A437G/ V913R/P914R, P57F/D489A/N527R/P914R/S916G, P57F/ E614Q/S916G/S932A, P57F/E188W/D489A/L823F/ R862Q, A62L/L305F/A437G/D500A/S727W/V913R, A62L1L305F/S727W, A62L/A437G/D489A/N527R/S727W/ V913R/S932A, A62L/A437G/N527R/S727W, A62L/ A437G/N527R/S916G/S932A, A62L/A437G/V913R/ S916R, A62L/D489A/D500A/S932A, A62L/N527R/ S727W/S916G, A62W/A89R/E188W/D489A/D500A/ S727W/L823F, A62W/S124V/E188W/L823F/S842G/ R862Q, A62W/A437G/D489A/E614Q/S727W/V913R, A62W/D489A/N527R/S916R/S932A, A62W/S727W, A62W/S916G, S124V/D500A/S842G/R862Q, A437G, A437G/D489A/P914R/S916R, A437G/S727W/P914K, A437G/P914R/S916G, D489A/E614Q/S916G, D500A/ S727W/V913R/S916R, D500A/P914R/S916G, and D923W, wherein the positions are numbered with reference to SEQ ID NO: 946.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 1956, wherein the positions are numbered with reference to SEQ ID NO: 1956. In some embodiments, the acid alpha-glucosidase comprises at least one substitution at position or set of positions selected from, 3/569, 41/53, 44, 44/347, 56, 65, 78, 78/87/176/266/536/615, 78/87/266, 78/87/266/372/386/777, 78/87/266/372/536, 78/87/266/ 483/924, 78/87/483/777, 78/87/536, 78/266/483/536/615, 78/266/483/795, 78/266/763, 78/372/390, 78/390, 78/536/ 615, 87, 87/266, 87/266/372/483, 87/266/483, 87/266/924, 87/372/777, 87/536/777, 87/615, 87/195, 105, 136, 141, 145, 154/588, 156, 157, 199, 202, 222, 225, 227, 229, 266, 266/372/536/615/763/777, 266/372/924, 266/536/615/795, 344, 348, 390/615, 412, 423, 425/678/894, 430, 446, 484, 488, 496, 499/711, 503, 530, 543, 569, 572, 573, 574, 577, 578, 579, 580, 581, 583, 585, 588, 589/663, 615, 628, 629, 631, 633, 656, 663, 669, 670, 671, 678, 679, 687, 690, 691, 692, 693, 705, 706, 708, 709, 710, 711, 726, 768, 773, 777, 779, 795, 797, 816, 826, 834, 857, 859, 868, 869, 871, 873, 877, 878, and 909, wherein the positions are numbered with reference to SEQ ID NO: 1956. In some embodiments, the acid alpha-glucosidase comprises at least one substitution at position or set of positions selected from 3L/569F, 41I/53M, 44E, 44G, 44L, 44P/347I, 44R, 56A, 56L, 56R, 65L, 65V, 78E, 78E/87E/176T/266N/536T/615D, 78E/87E/266N, 78E/87E/266N/372T/386Y/777G, 78E/87E/266N/372T/536T, 78E/87E/266N/483S/924N, 78E/87E/483S/777G, 78E/87E/536T, 78E/266N/483S/536T/615D, 78E/266N/483S/795E, 78E/266N/763L, 78E/372T/390Q, 78E/390Q, 78E/536T/615D, 87E, 87E/266N, 87E/266N/372T/483S, 87E/266N/483S, 87E/266N/924N, 87E/372T/777G, 87E/536T/777G, 87E/615D, 87F/795E, 105T, 136G, 141S, 141W, 145I, 145R, 154R/588L, 156L, 157S, 199V, 202K, 202L, 202N, 202R, 202T, 222C, 222P, 225D, 227A, 229C, 266N, 266N/372T/536T/615D/763L/777G, 266N/372T/924N, 266N/536T/615D/795E, 344G, 344M, 348G, 390Q/615D, 412Y, 423V, 425R/678I/894C, 430F, 446T, 484L, 488G, 488K, 488M, 496G, 499Y/711F, 503S, 503T, 530V, 543C, 543Q, 543S, 543V, 569H, 569I, 569Q, 569S, 569T, 569V, 569Y, 572G, 572S, 573C, 573D, 573H, 573M, 573Q, 574S, 577A, 577D, 577E, 577M, 577T, 577V, 578S, 579V, 580E, 580G, 580I, 580L, 580W, 580Y, 581F, 581G, 581H, 581L, 581S, 581T, 581V, 581Y, 583C, 583G, 583K, 583L, 585F, 585L, 585M, 585Q, 585V, 588L, 588V, 589I/663F, 615G, 628I, 628M, 628V, 629A, 629C, 629G, 629I, 631I, 631L, 631M, 633V, 656M, 656V, 663A, 663F, 669R, 670E, 670F, 670I, 670Q, 670R, 670S, 670T, 670V, 670W, 671A, 671G, 671M, 671T, 678H, 678L, 678T, 678Y, 679W, 687L, 690V, 691F, 691V, 692C, 692F, 692G, 692I, 692L, 692R, 692S, 692V, 692Y, 693F, 693I, 693Y, 705M, 706F, 706M, 706V, 708C, 709S, 710K, 710L, 710M, 710N, 710S, 711C, 711F, 711G, 711H, 711L, 711R, 711W, 726E, 768S, 773V, 777G, 777I, 777R, 779E, 779H, 779R, 795E, 797L, 797M, 816L, 826G, 834H, 857T, 859T, 859Y, 868I, 868L, 869L, 869S, 871E, 871K, 871R, 873A, 873F, 873Y, 877L, 877V, 878A, 878F, 878G, 878K, 878L, 878Q, 878R, 878S, 878W, and 909F, wherein the positions are numbered with reference to SEQ ID NO: 1956. In some embodiments, the acid alpha-glucosidase comprises at least one substitution at position or set of positions selected from W3L/L569F, L41I/S53M, T44E, T44G, T44L, T44P/L347I, T44R, G56A, G56L, G56R, G65L, G65V, P78E, P78E/D87E/K176T/T266N/V536T/Q615D, P78E/D87E/T266N, P78E/D87E/T266N/S372T/A386Y/S777G, P78E/D87E/T266N/S372T/V536T, P78E/D87E/T266N/T483S/T924N, P78E/D87E/T483S/S777G, P78E/D87E/V536T, P78E/T266N/T483S/V536T/Q615D, P78E/T266N/T483S/Q795E, P78E/T266N/T763L, P78E/S372T/L390Q, P78E/L390Q, P78E/V536T/Q615D, D87E, D87E/T266N, D87E/T266N/S372T/T483S, D87E/T266N/T483S, D87E/T266N/I924N, D87E/S372T/S777G, D87E/T536T/S777G, D87E/Q615D, D87E/Q795E, A105T, S136G, T141S, T141W, T145I, T145R, K154R/F588L, I156L, L157S, P199V, S202K, S202L, S202N, S202R, S202T, V222C, V222P, N225D, T227A, A229C, T266N, T266N/S372T/V536T/Q615D/T763L/S777G, T266N/S372T/T924N, T266N/V536T/Q615D/Q795E, Q344G, Q344M, D348G, L390Q/Q615D, G412Y, L423V, Q425R/S678I/G894C, Y430F, S446T, N484L, L488G, L488K, L488M, A496G, H499Y/A711F, P503S, P503T, L530V, T543C, T543Q, T543S, T543V, L569H, L569I, L569Q, L569S, L569T, L569V, L569Y, A572G, A572S, I573C, I573D, I573H, I573M, I573Q, A574S, R577A, R577D, R577E, R577M, R577T, R577V, A578S, L579V, V580E, V580G, V580I, V580L, V580W, V580Y, K581F, K581G, K581H, K581L, K581S, K581T, K581V, K581Y, R583C, R583G, R583E, R583L, T585F, T585L, T585M, T585V, F588L, F588V, V589I/M663F, Q615G, L628I, L628M, L628V, L629A, L629C, L629G, L629I, V631I, V631L, V631M, L633V, L656M, L656V, M663A, M663F, L669R, L670E, L670F, L670I, L670Q, L670R, L670S, L670T, L670V, L670W, S671A, S671G, S671M, S671T, S678H, S678L, S678T, S678Y, F679W, M687L, A690V, L691F, L691V, T692C, T692F, T692G, T692I, T692L, T692R, T692S, T692V, T692Y, L693F, L693I, L693Y, F705M, H706F, H706M, H706V, A708C, H709S, V710K, V710L, V710M, V710N, V710S, A711C, A711F, A711G, A711H, A711L, A711R, A711W, D726E, Q768S, E/773V, S777G, S777I, S777R, P779E, P779H, P779R, Q795E, V797L, V797M, I816L, T826G, A834H, L857T, V859T, V859Y, V868I, V868L, I869L, I869S, L871E, L871K, L871R, R873A, R873F, R873Y, I877L, I877V, V878A, V878F, V878G, V878K, V878L, V878Q, V878R, V878S, V878W, and L909F, wherein the positions are numbered with reference to SEQ ID NO: 1956. In some embodiments, the acid alpha-glucosidase comprises at least one substitution at position selected from 44, 53, 56, 63, 65, 105, 125, 129, 136, 139, 141, 142, 145, 152, 156, 162, 176, 177, 185, 186, 187, 199, 199/775, 202, 265, 267, 337, 344, 348, 350, 354, 372, 373, 401, 412, 446, 469, 484, 488, 493, 496, 499, 503, 526, 543, 612, 615, 649, 677, 678, 679, 730, 752, 765, 768, 773, 777, 779, 788, 797, 822, 826, 834, 855, 856, 857, 859, 860, 924, 926, 931, and 936, wherein the positions are numbered with reference to SEQ ID NO: 1956. In some embodiments, the acid alpha-glucosidase comprises at least one substitution at position selected from 44A, 44F, 44V, 44W, 44Y, 53I, 56S, 56W, 63N, 65A, 65F, 65R, 65Y, 105V, 105W, 125H, 125W, 129E, 129I, 129S, 129T, 129V, 129W, 136K, 136R, 136V, 139E, 141K, 141R, 142G, 145A, 145L, 152L, 152S, 152W, 156C, 156K, 156R, 156S, 162T, 176R, 177Q, 185L, 186H, 187I, 199A, 199G, 199I, 199R, 199T, 199V/775I, 199W, 202A, 202D, 202G, 202H, 202Q, 202Y, 265D, 265F, 265H, 267E, 267G, 267R, 337H, 344C, 348E, 348W, 350F, 350I, 354L, 354S, 372D, 373A, 373S, 401G, 401S, 412R, 412S, 412W, 446C, 446D, 446G, 446I, 446K, 469M, 469T, 469V, 484A, 484K, 484R, 488C, 488E, 488S, 493L, 496M, 496W, 499A, 499E, 499I, 499M, 499Q, 499V, 503C, 503H, 503N, 526L, 526V, 543G, 543H, 543K, 543L, 543R, 612G, 612L, 612R, 612T, 615M, 615S, 649M, 677T, 678Q, 678R, 678V, 678W, 679Y, 730K, 730L, 730R, 752F, 752G, 752L, 752N, 752S, 752W, 765W, 768I, 768K, 768V, 773P, 777M, 777W, 779I, 779M, 779S, 788A, 788H, 788I, 788L, 788N, 788Q, 788S, 788T, 788Y, 797E, 797F, 797I, 797R, 797W, 822R, 826I, 826M, 834G, 834S, 834V, 834W, 855G, 855L, 856A, 856G, 857A, 857E, 857R, 857S, 857V, 859A, 859G, 860S, 924N, 926M, 926T, 931L, 936N, 936R, and 936S, wherein the positions are numbered with reference to SEQ ID NO: 1956. In some embodiments, the acid alpha-glucosidase comprises at least one substitution at position selected from T44A, T44F, T44V, T44W, T44Y, 553I, G56S, G56W, H63N, G65A, G65F, G65R, G65Y, A105V, A105W, Y125H, Y125W, K129E, K129I, K129S, K129T, K129V, K129W, S136K, S136R, S136V, G139E, T141K, T141R, A142G, T145A, T145L, F152L, F152S, F152W, I156C, I156K, I156R, I156S, D162T, K176R, D177Q, V185L, P186H, L187I, P199A, P199G, P199I, P199R, P199T, P199V/L775I, P199W, S202A, S202D, S202G, S202H, S202Q, S202Y, W265D, W265F, W265H, K267E, K267G, K267R, P337H, Q344C, D348E, D348W, V350F, V350I, F354L, F354S, S372D, T373A, T373S, D401G, D401S, G412R, G412S, G412W, S446C, S446D, S446G, S446I, S446K, I469M, I469T, I469V, N484A, N484K, N484R, L488C, L488E, L488S, D493L, A496M, A496W, H499A, H499E, H499I, H499M, H499Q, H499V, P503C, P503H, P503N, P526L, P526V, T543G, T543H, T543K, T543L, T543R, S612G, S612L, S612R, S612T, Q615M, Q615S, L649M, Y677T, S678Q, S678R, S678V, S678W, F679Y, W730K, W730L, W730R, K752F, K752G, K752L, K752N, K752S, K752W, Y765W, Q768I, Q768K, Q768V, E773P, S777M, S777W, P779I, P779M, P779S, P788A, P788H, P788I, P788W, P788N, P788Q, P788S, P788T, P788Y, V797E, V797F, V797I, V797R, V797W, G822R, T826I, T826M, A834G, A834S, A834V, A834W, E855G, E855L, S856A, S856G, L857A, L857E, L857R, L857S, L857V, V859A, V859G, L860S, T924A, V926M, V926T, V931L, G936N, G936R, and G936S, wherein the positions are numbered with reference to SEQ ID NO: 1956. In some embodiments, the acid alpha-glucosidase comprises at least one substitution at position or set of positions selected from 78/87/176/266/536/615, 78/87/266/372/386/777, 78/87/266/372/536, 78/266/763, 78/372/390, 87/266/372/483, 87/372/777, 105, 125, 129, 136, 139, 141, 142, 152, 154/588, 156, 222, 225, 227, 229, 266/372/536/615/763/777, 266/372/924, 267, 372, 401, 493, 496, 499, 569, 572, 573, 574, 577, 579, 580, 581, 583, 585, 588, 589/663, 628, 629, 631, 663, 669, 670, 671, 691, 692, 693, 706, 708, 710, 711, 765, 768, 779, 797, 826, 834, 855, 856, 857, 869, 871, 873, 878, 909, 924, and 926, wherein the positions are numbered with reference to SEQ ID NO: 1956. In some embodiments, the acid alpha-glucosidase comprises at least one substitution at position or set of positions selected from 78E/87E/176T/266N/536T/615D, 78E/87E/266N/372T/386Y/777G, 78E/87E/266N/372T/536T, 78E/266N/763L, 78E/372T/390Q, 87E/266N/372T/483S, 87E/372T/777G, 105T, 105W, 125W, 129E, 129S, 136G, 136K, 136V, 139E, 141S, 142G, 152S, 152W, 154R/588L, 156C, 156L, 222C, 222P, 225D, 227A, 229C, 266N/372T/536T/615D/763L/777G, 266N/372T/924N, 267E, 372D, 401G, 493L, 496G, 499E, 499I, 499M, 499Q, 569H, 569Q, 569S, 569T, 569V, 569Y, 572G, 572S, 573C, 573D, 573H, 573M, 573Q, 574S, 577A, 577D, 577E, 577T, 579V, 580E, 580G, 580W, 581G, 581H, 581T, 583C, 583G, 585Q, 588L, 588V, 589I/663F, 628V, 629A, 629C, 629I, 631I, 631L, 631M, 663A, 663F, 669R, 670E, 670F, 670I, 670Q, 670R, 670S, 670T, 670V, 670W, 671A, 671G, 671T, 691V, 692C, 692F, 692G, 692I, 692L, 692Y, 693F, 693I, 693Y, 706F, 708C, 710K, 710L, 710M, 710N, 710S, 711C, 711G, 711H, 711W, 765W, 768I, 779E, 797E, 797F, 797I, 797L, 797M, 797W, 826G, 834G, 834H, 834S, 834W, 855G, 856G, 857A, 857E, 857S, 857T, 857V, 869L, 869S, 871E, 871K, 873A, 873F, 873Y, 878A, 878G, 878K, 878Q, 878S, 878W, 909F, 924A, 926M, and 926T, wherein the positions are numbered with reference to SEQ ID NO: 1956. In some embodiments, the acid alpha-glucosidase comprises at least one substitution at position or set of positions selected from P78E/D87E/K176T/T266N/V536T/Q615D, P78E/D87E/T266N/S372T/A386Y/S777G, P78E/D87E/T266N/S372T/V536T, P78E/T266N/T763L, P78E/S372T/L390Q, D87E/T266N/S372T/T483S, D87E/S372T/S777G, A105T, A105W, Y125W, K129E, K129S, S136G, S136K, S136V, G139E, T141S, A142G, F152S, F152W, K154R/F588L, I156C, I156L, V222C, V222P, N225D, T227A, A229C, T266N/S372T/V536T/Q615D/T763L/S777G, T266N/S372T/T924N, K267E, S372D, D401G, D493L, A496G, H499E, H499I, H499M, H499Q, L569H, L569Q, L569S, L569T, L569V, L569Y, A572G, A572S, I573C, I573D, I573H, I573M, I573Q, A574S, R577A, R577D, R577E, R577T, L579V, V580E, V580G, V580W, K581G, K581H, K581T, R583C, R583G, T585Q, F588L, F588V, V589I/M663F, L628V, L629A, L629C, L629G, L629I, V631I, V631L, V631M, M663A, M663F, L669R, L670E, L670F, L670I, L670Q, L670R, L670S, L670T, L670V, L670W, S671A, S671G, S671T, L691V, T692C, T692F, T692G, T692I, T692L, T692Y, L693F, L693I, L693Y, H706F, A708C, V710K, V710L, V710M, V710N, V710S, A711C, A711G, A711H, A711W, Y765W, Q768I, P779E, V797E, V797F, V797I, V797L, V797M, V797W, T826G, A834G, A834H, A834S, A834W, E855G, S856G, L857A, L857E, L857S, L857T, L857V, I869L, I869S, L871E, L871K, R873A, R873F, R873Y, V878A, V878G, V878K, V878Q, V878S, V878W, L909F, T924A, V926M, and V926T, wherein the positions are numbered with reference to SEQ ID NO: 1956.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2496, wherein the positions are numbered with reference to SEQ ID NO: 2496. In some embodiments, the acid alpha-glucosidase comprises at least one substitution at position or set of positions selected from 246, 304, 313, 569, 569/588, 569/588/589/628/629/692/711, 569/588/678/692, 569/588/711/869/871/878, 569/588/878, 569/589/628/670/678/692/711/795/871, 569/589/628/670/692/711, 569/589/628/692/711/795, 569/589/670, 569/589/670/678/692/711/795, 569/589/670/871, 569/589/678/871/878, 569/589/692/795/871/878, 569/589/711/871, 569/589/871, 569/628, 569/628/670, 569/628/670/678, 569/628/670/692/711/871, 569/628/670/711, 569/628/678/711, 569/628/692, 569/670, 569/670/678, 569/670/678/692/871, 569/670/692, 569/670/711, 569/670/711/871, 569/678/692/795, 569/678/869/878, 569/678/878, 569/692, 569/692/711, 569/692/711/869/871/878, 569/711, 569/711/795/871/878, 569/711/869/878, 569/711/871, 569/795, 569/871, 572/588/678/692/869/878, 572/588/795, 572/692/869/878, 572/692/878, 582, 584, 585, 588/589/628/678, 589, 589/670/692/795/871, 589/670/795/871, 589/871, 628/629/692/871/878, 628/670, 628/670/692/711/795, 628/711/795, 628/871, 628/878, 629/869/878, 670/678, 670/678/692/871, 670/692/871, 678/692/711/869, 678/692/795/869, 678/692/869, 678/795/871/878, 692, 692/711, 692/711/795/869, 692/711/795/869/871/878, 692/711/869/878, 692/711/871/878, 692/869, 692/869/871/878/916, 692/871, 711, 711/795/869/878, 711/869/878, 711/871, 795/878, 812, 871, and 878, wherein the positions are numbered with reference to SEQ ID NO: 2496. In some embodiments, the acid alpha-glucosidase comprises at least one substitution at position or set of positions selected from 246T, 304M, 313I, 313L, 569H/589I/628M/670T/678T/692G/711H/795E/871S, 569H/628M, 569H/628M/670F/678T, 569H/628M/670T, 569H/628M/670T/692Y/711H/871K, 569H/670F/678T/692G/871S, 569H/670T/692G, 569H/678T/692G/795E, 569H/692G, 569H/692Y, 569H/711H/795E/871S/878S, 569H/711H/869S/878S, 569H/711H/871K, 569T, 569T/588L, 569T/588L/589I/628M/629I/692Y/711H, 569T/588L/678T/692Y, 569T/588L/711H/869L/871K/878S, 569T/588L/878S, 569T/589I/628M/670F/692G/711H, 569T/589I/678T/871K/878S, 569T/589I/692G/795E/871K/8785, 569T/589I/871S, 569T/628M/678T/711H, 569T/628M/692Y, 569T/670T/678T/692G/871K, 569T/670T/711H/871E, 569T/678T/869S/878S, 569T/678T/878S, 569T/692Y, 569T/692Y/711H/869L/871K/878A, 569T/711H, 569T/795E, 569T/871K, 569T/871S, 569Y/589I/628M/670T/692Y/711H, 569Y/589I/628M/692G/711H/795E, 569Y/589I/670F, 569Y/589I/670T/678T/692G/711H/795E, 569Y/589I/670T/871K, 569Y/589I/711H/871K, 569Y/628M/670T/692Y/711H/871S, 569Y/628M/670T/711H, 569Y/670F/678T, 569Y/670T, 569Y/670T/711H, 569Y/692Y/711H, 569Y/711H, 569Y/871E, 572S/588L/678T/692G/869L/878A, 572S/588L/795E, 572S/692G/869S/878S, 572S/692G/878S, 572S/692L/869S/

878S, 582T, 584E, 585K, 588L/589I/628M/678T, 589I, 589I/670T/692G/795E/871K, 589I/670T/795E/871S, 589I/871E, 628M/629I/692Y/871S/878S, 628M/670F, 628M/670T/692G/711H/795E, 628M/711H/795E, 628M/871S, 628M/878S, 629I/869L/878S, 670T/678T, 670T/678T/692Y/871S, 670T/692G/871K, 678T/692G/711H/869S, 678T/692G/795E/869S, 678T/692G/869S, 678T/795E/871K/878A, 692G/711H, 692G/711H/795E/869L/871K/878A, 692G/711H/795E/869S, 692G/711H/869L/878S, 692G/711H/869S/878A, 692G/711H/871S/878A, 692G/869L871K/878S/916R, 692G/869S, 692G/871K, 692Y, 711H, 711H/795E/869S/878S, 711H/869S/878S, 711H/871K, 795E/878S, 812E, 871K, 871S, and 878S, wherein the positions are numbered with reference to SEQ ID NO: 2496. In some embodiments, the acid alpha-glucosidase comprises at least one substitution at position or set of positions selected from S246T, L304M, V313I, V313L, L569H/V589I/L628M/L670T/S678T/T692G/A711H/Q795E/L871S, L569H/L628M, L569H/L628M/L670F/S678T, L569H/L628M/L670T, L569H/L628M/L670T/T692Y/A711H/L871K, L569H/L670F/S678T/T692G/L871S, L569H/L670T/T692G, L569H/S678T/T692G/Q795E, L569H/T692G, L569H/T692Y, L569H/A711H/Q795E/L871S/V878S, L569H/A711H/I869S/V878S, L569H/A711H/L871K, L569T, L569T/F588L, L569T/F588L/V589I/L628M/L629I/T692Y/A711H, L569T/F588L/S678T/T692Y, L569T/F588L/A711H/I869L187IK/V878S, L569T/F588L/V878S, L569T/589I/L628M/L670F/T692G/A711H, L569T/V589I/S678T/L871K/V878S, L569T/V589I/T692G/Q795E/L871K/V878S, L569T/V589I/L871S, L569T/L628M/S678T/A711H, L569T/L628M/T692Y, L569T/L670T/S678T/T692G/L871K, L569T/L670T/A711H/L871E, L569T/S678T/I869S/V878S, L569T/S678T/V878S, L569T/T692Y, L569T/T692Y/A711H/I869L/L871K/V878A, L569T/A711H, L569T/Q795E, L569T/L871K, L569T/L871S, L569Y/L589I/L628M/L670T/T692Y/A711H, L569Y/L589I/L628M/T692G/A711H/Q795E, L569Y/L589/L670F, L569Y/L589I/L670T/S678T/T692G/A711H/Q795E, L569Y/L589/L670T/L871K, L569Y/L589I/A711H/L871K, L569Y/L628M/L670T/T692Y/A711H/L871S, L569Y/L628M/L670T/A711H, L569Y/L670F/S678T, L569Y/L670T, L569Y/L670T/A711H, L569Y/T692Y/A711H, L569Y/A711H, L569Y/L871E, A572S/F588L/S678T/T692G/I869L/V878A, A572S/F588L/Q795E, A572S/T692G/I869S/V878S, A572S/T692G/V878S, A572S/T692I869S/V878S, A582T, G584E, T585K, F588L/V589V/L628M/S678T, V589I, V589/L670T/T692G/Q795E/L871K, V589M/670/Q795E/L871S, V589I/L871E, L628M/L629I/T692Y/L871S/V878S, L628M/L670F, L628M/L670T/T692G/A711H/Q795E, L628M/A711H/Q795E, L628M/L871S, L628M/V878S, L629I/I869L/V878S, L670T/S678T, L670T/S678T/T692Y/L871S, L670T/T692G/L871K, S678T/T692G/A711H/I869S, S678T/T692G/Q795E/I869S, S678T/T692G/I869S, S678T/Q795E/L871K/V878A, T692G/A711H, T692G/A711H/Q795E/I869L/L871K/V878A, T692G/A711H/Q795E/I869S, T692G/A711H/I869L/V878S, T692G/A711H/I869S/V878A, T692G/A711H/L871S/V878A, T692G/I869L/L871K/V878S/S916R, T692G/I869S, T692G/L871K, T692Y, A711H, A711H/Q795E/I869S/V878S, A711H/I869S/V878S, A711H/L871K, Q795E/V878S, A812E, L871K, L871S, and V878S, wherein the positions are numbered with reference to SEQ ID NO: 2496. In some embodiments, the acid alpha-glucosidase comprises at least one substitution at position or set of positions selected from 60/589, 307, 313, 584, and 810, wherein the positions are numbered with reference to SEQ ID NO: 2496. In some embodiments, the acid alpha-glucosidase comprises at least one substitution at position or set of positions selected from 60V/589A, 307T, 313T, 584C, and 810V, wherein the positions are numbered with reference to SEQ ID NO: 2496. In some embodiments, the acid alpha-glucosidase comprises at least one substitution at position or set of positions selected from A60V/V589A, S307T, V313T, G584C, and L810V, wherein the positions are numbered with reference to SEQ ID NO: 2496. In some embodiments, the acid alpha-glucosidase comprises at least one substitution at position or set of positions selected from 60/589, 246, 304, 307, 313, 569, 569/588, 569/588/589/628/629/692/711, 569/588/678/692, 569/588/711/869/871/878, 569/588/878, 569/589/628/670/678/692/711/795/871, 569/589/628/670/692/711, 569/589/628/692/711/795, 569/589/670, 569/589/670/678/692/711/795, 569/589/670/871, 569/589/678/871/878, 569/589/692/795/871/878, 569/589/711/871, 569/589/871, 569/628, 569/628/670, 569/628/670/678, 569/628/670/692/711/871, 569/628/670/711, 569/628/678/711, 569/628/692, 569/670, 569/670/678, 569/670/678/692/871, 569/670/692, 569/670/711, 569/670/711/871, 569/678/692/795, 569/678/869/878, 569/678/878, 569/692, 569/692/711, 569/692/711/869/871/878, 569/711, 569/711/795/871/878, 569/711/869/878, 569/711/871, 569/795, 569/871, 572/588/678/692/869/878, 572/588/795, 572/692/869/878, 572/692/878, 582, 584, 585, 588/589/628/678, 589, 589/670/692/795/871, 589/670/795/871, 589/871, 628/629/692/871/878, 628/670, 628/670/692/711/795, 628/711/795, 628/871, 628/878, 629/869/878, 670/678, 670/678/692/871, 670/692/871, 678/692/711/869, 678/692/795/869, 678/692/869, 678/795/871/878, 692, 692/711, 692/711/795/869, 692/711/795/869/871/878, 692/711/869/878, 692/711/871/878, 692/869, 692/869/871/878/916, 692/871, 711, 711/795/869/878, 711/869/878, 711/871, 795/878, 810, 812, 871, and 878, wherein the positions are numbered with reference to SEQ ID NO: 2496. In some embodiments, the acid alpha-glucosidase comprises at least one substitution at position or set of positions selected from 60V/589A, 246T, 304M, 307T, 313I, 313L, 313T, 569H/589I/628M/670T/678T/692G/711H/795E/871S, 569H/628M, 569H/628M/670F/678T, 569H/628M/670T, 569H/628M/670T/692Y/711H/871K, 569H/670F/678T/692G/871S, 569H/670T/692G, 569H/678T/692G/795E, 569H/692G, 569H/692Y, 569H/711H/795E/871S/878S, 569H/711H/869S/878S, 569H/711H/871K, 569T, 569T/588L, 569T/588L/589I/628M/629I/692Y/711H, 569T/588L/678T/692Y, 569T/588L/711H/869I/871K/878S, 569T/588L/878S, 569T/589I/628M/670F/692G/711H, 569T/589I/678T/871K/878S, 569T/589I/692G/795E/871K/8785, 569T/589I/871S, 569T/628M/678T/711H, 569T/628M/692Y, 569T/670T/678T/692G/871K, 569T/670T/711H/871E, 569T/678T/869S/878S, 569T/678T/878S, 569T/692Y, 569T/692Y/711H/869L/871K/878A, 569T/711H, 569T/795E, 569T/871K, 569T/871S, 569Y/589I/628M/670T/692Y/11H, 569Y/589I/628M/692G/711H/795E, 569Y/589I/670F, 569Y/589I/670T/678T/692G/711H/795E, 569Y/589I/670T/871K, 569Y/589I/711H/871K, 569Y/628M/670T/692Y/711H/871S, 569Y/628M/670T/711H, 569Y/670F/678T, 569Y/670T, 569Y/670T/711H, 569Y/692Y/711H, 569Y/711H, 569Y/871E, 572S/588L/678T/692G/869L/878A, 572S/588L/795E, 572S/692G/869S/878S, 572S/692G/878S, 572S/692L/869S/878S, 582T, 584C, 584E, 585K, 588L/589I/628M/678T, 589I, 589I/670T/692G/795E/871K, 589I/670T/795E/871S, 589I/871E, 628M/629I/692Y/871S/878S, 628M/670F, 628M/670T/692G/711H/795E, 628M/711H/795E, 628M/871S, 628M/878S, 629I/869L/878S, 670T/678T, 670T/678T/692Y/871S, 670T/692G/871K, 678T/

692G/711H/869S, 678T/692G/795E/869S, 678T/692G/869S, 678T/795E/871K/878A, 692G/711H, 692G/711H/795E/869L/871K/878A, 692G/711H/795E/869S, 692G/711H/869L/878S, 692G/711H/869S/878A, 692G/711H/871S/878A, 692G/869L/871K/878S/916R, 692G/869S, 692G/871K, 692Y, 711H, 711H/795E/869S/878S, 711H/869S/878S, 711H/871K, 795E/878S, 810V, 812E, 871K, 871S, and 878S, wherein the positions are numbered with reference to SEQ ID NO: 2496. In some embodiments, the acid alpha-glucosidase comprises at least one substitution at position or set of positions selected from A60V/V589A, S246T, L304M, S307T, V313I, V313L, V313T, L569H/V589I/L628M/L670T/S678T/T692G/A711H/Q795E/L871S, L569H/L628M, L569H/L628M/L670F/S678T, L569H/L628M/L670T, L569H/L628M/L670T/T692Y/A711H/L871K, L569H/L670F/S678T/T692G/L871S, L569H/L670T/T692G, L569H/S678T/T692G/Q795E, L569H/T692G, L569H/T692Y, L569H/A711H/Q795E/L871S/V878S, L569H/A711H/I869S/V878S, L569H/A711H/L871K, L569T, L569T/F588L, L569T/F588L/V589I/L628M/L629I/T692Y/A711H, L569T/F588L/S678T/T692Y, L569T/F588L/A711H/I869L/871K/V878S, L569T/F588L/V878S, L569T/V589I/L628M/L670F/T692G/A711H, L569T/V589I/S678T/L871K/V878S, L569T/V589I/T692G/Q795E/L871K/V878S, L569T/V589I/L871S, L569T/L628M/S678T/A711H, L569T/L628M/T692Y, L569T/L670T/S678T/T692G/L871K, L569T/L670T/A711H/L871E, L569T/S678T/I869S/V878S, L569T/S678T/V878S, L569T/T692Y, L569T/T692Y/A711H/I869L/L871K/V878A, L569T/A711H, L569T/Q795E, L569T/L871K, L569T/L871S, L569Y/V589I/L628M/L670T/T692Y/A711H, L569Y/V589I/L628M/T692G/A711H/Q795E, L569Y/V589/L670F, L569Y/V589I/L670T/S678T/T692G/A711H/Q795E, L569Y/V589I/L670T/L871K, L569Y/V589I/A711H/L871K, L569Y/L628M/L670T/T692Y/A711H/L871S, L569Y/L628M/L670T/A711H, L569Y/L670F/S678T, L569Y/L670T, L569Y/L670T/A711H, L569Y/T692Y/A711H, L569Y/A711H, L569Y/L871E, A572S/F588L/S678T/T692G/I869L/V878A, A572S/F588L/Q795E, A572S/T692G/I869S/V878S, A572S/T692G/V878S, A572S/T692I869S/V878S, A582T, G584C, G584E, T585K, F588L/V589I/L628M/S678T, V589I, V589I/L670T/T692G/Q795E/L871K, V589M/670T/Q795E/L871S, V589I/L871E, L628M/L629L/692Y/L871S/V878S, L628M/L670F, L628M/L670T/T692G/A711H/Q795E, L628M/A711H/Q795E, L628M/L871S, L628M/V878S, L629I/I869L/V878S, L670T/S678T, L670T/S678T/T692Y/L871S, L670T/T692G/L871K, S678T/T692G/A711H/I869S, S678T/T692G/Q795E/I869S, S678T/T692G/I869S, S678T/Q795E/L871K/V878A, T692G/A711H, T692G/A711H/Q795E/I869L/L871K/V878A, T692G/A711H/Q795E/I869S, T692G/A711H/I869L/V878S, T692G/A711H/I869S/V878A, T692G/A711H/L871S/V878A, T692G/I869I/L871K/V878S/S916R, T692G/I869S, T692G/L871K, T692Y, A711H, A711H/Q795E/I869S/V878S, A711H/I869S/V878S, A711H/L871K, Q795E/V878S, L810V, A812E, L871K, L871S, and V878S, wherein the positions are numbered with reference to SEQ ID NO: 2496.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2880, wherein the positions are numbered with reference to SEQ ID NO: 2880. In some embodiments, the acid alpha-glucosidase comprises at least one substitution at position or set of positions selected from 24/28/29/39/50/62/78/87/135/150/266/267/522/527/551/670727/750/830/842/871/883/894/932, 24/28/39/50/62/78/87/135/150/266/267/522/527/551/569/727/830/842/871/883/894/913, 24/28/50/135/150/437/522/527/871/883/894/932, 24/28/62/522/569/932, 24/28/437/486/527, 24/29/39/50/62/78/87/135/150/267/437/486/522/527/551/711/727/750/830/842/871/883/894/913/932, 24/50/78/87/135/150/267/486/522/527/551/670/727/750/830/842/871/883/894/913/932, 24/50/486/527/711/727, 24/62/87/486/727, 24/62/727/830/932, 24/87/135/522/670/711/830/842/913, 24/150/522/527/727/883/894, 24/527/727/842/871/883/913/932, 24/670/727/750/842/871, 28, 28/50/78/87/135/266/267/437/486/527/551/670/727/750/830/842/871/883/894/913/932, 28/50/522/527/711/727/871, 28/62, 28/62/267/932, 28/437/527/871, 28/522/527/569/711/830/894, 28/727, 28/727/871, 29/39/50/62/65/78/87/135/150/437/551/569/670/727/750/830/842/883/894/932, 29/62/437/527, 29/78/87/150/527/727, 29/78/135/727/830, 29/87, 29/135/150/527/670/727/883, 29/150/267/727/750/871/883/932, 29/150/437/727, 29/522/670/711/871, 29/670/932, 39/50, 39/727/750/932, 50/135/150/932, 50/437/522/527, 50/711, 50727/750/883/894, 62, 62/87/150, 62/87/150/727, 62/135/522/711/727/750/842/871/894, 62/437, 62/437/727, 78/87/486/527/670/727/750/830/842/871/913/932, 87/750, 89/109/527/678/727/842, 89/109/678/727/736/812/878, 89/109/727/932, 89/109/932, 89/527, 89/527/678/692/736/842/878/932, 89/527/678/932, 89/527/727/812/860, 89/678/692/736/932, 89/678/812/878, 89/842/878, 109/527/678/812, 109/678/692/842/860/878/932, 109/678/727/860, 109/678/736/812/878, 109/678/812, 109/678/842/878, 109/692/727/736/812, 109/692/727/812/842/860, 109/727/860/878, 109/736/932, 109/812, 109/842, 109/932, 135/670/727, 135/711/750/932, 150/527/842/871/913, 150/871/932, 150/883/932, 267/527/727, 403/527/678/692/736/812/842/860, 437/522/527/670/871, 437/750/830/932, 522, 522/527/569/727, 522/830, 527, 527/678/692/727/736/878, 527/678/692/812/932, 527/692/727/736/812, 527/692/727/736/842/860/878, 527/727/736, 527/736/932, 527/812, 670/711/871, 670/830/871, 678/692/727/812/842, 678/692/812, 678/812, 678/860/878, 678/913, 678/932, 692/727/736/842/913, 692/812, 727, 727/932, 871, and 878/932, wherein the positions are numbered with reference to SEQ ID NO: 2880. In some embodiments, the acid alpha-glucosidase comprises at least one substitution at position or set of positions selected from wherein the positions are numbered with reference to SEQ ID NO: 2880. In some embodiments, the acid alpha-glucosidase comprises at least one substitution at position or set of positions selected from 24L/28L29L/39P/50Q/62A/78P/87D/135S/150T/266T/267R/522E/527N/551V/670L/727S/750A/830Q/842G/871L/883R/894Q/932S, 24L/28L/39P/50Q/62A178P/87D/135S/150T/266T/267R/522E/527N/551V/569L/727S/830Q/842G/871L/883R/894Q/913V, 24L/28L/50Q/135S/150T/437A/522E/527N/871L/883R/894Q/932S, 24L/28L/62A/522E/569L/932S, 24L/28L/437A/486T/527N, 24L/29L/39P/50Q/62A178P/87D/135S/150T/267R/437A/486T/522E/527N/551V/711A/727S/150A/830Q/842G/871L/883R/894Q/913V/932S, 24L/50Q/78P/87D/135S/150T/267R/486T/522E/527N/551V/670L/727S/750A/830Q/842G/871L/883R/894Q/913V/932S, 24L/50Q/486T/527N/711A/727S, 24L/62A/87D/486T/727S, 24L/62A/727S/830Q/932S, 24L/87D/135S/522E/670L711A/830Q/842G/913V, 24L/150T/522E/527N/727S/883R/894Q, 24L/527N/727S/842G/871L/883R/913V/932S, 24L/670L/727S/750A/842G/871L, 28L, 28L/50Q/78P/87D/135S/

266T/267R/437A/486T/527N/551V/670L/727S/750A/ 830Q/842G/871L/883R/894Q/913V/932S, 28L/50Q/522E/ 527N/711A/727S/871L, 28L/62A, 28L/62A/267R/932S, 28L/437A/527N/871L, 28L/522E/527N/569L/711A/830Q/ 894Q, 28L/727S, 28L/727S/871L, 29L/39P/50Q/62A/65R/ 78P/87D/135S/150T/437A/551V/569L/670L/727S/750A/ 830Q/842G/883R/894Q/932S, 29L/62A/437A/527N, 29L/ 78P/87D/150T/527N/727S, 29L178P/135S/727S/830Q, 29L/87D, 29L/135S/150T/527N/670L/727S/883R, 29L/ 150T/267R/727S/750A/871L/883R/932S, 29L150T/437A/ 727S, 29L/522E/670L/711A/871L, 29L/670L/932S, 39P/ 50Q, 39P/727S/750A/932S, 50Q/135S/150T/932S, 50Q/ 437A/522E/527N, 50Q/711A, 50Q/727S/750A/883R/894Q, 62A, 62A/87D/150T, 62A/87D/150T/727S, 62A/135S/ 522E/711A/727S/750A/842G/871L/894Q, 62A/437A, 62A/ 437A/727S, 78P/87D/486T/527N/670L/727S/750A/830Q/ 842G/871L/913V/932S, 87D/750A, 89R/109D/527N/678T/ 727S/842G, 89R/109D/678T/727S/736M/812E/878S, 89R/ 109D/727S/932S, 89R/109D/932S, 89R/527N, 89R/527N/ 678T/692G/736M/842G/878S/932S, 89R/527N/678T/ 932S, 89R/527N/727S/812E/860F, 89R/678T/692G/736M/ 932S, 89R/678T/812E/878S, 89R/842G/878S, 109D/527N/ 678T/812E, 109D/678T/692G/842G/860F/878S/932S, 109D/678T/727S/860F, 109D/678T/736M/812E/878S, 109D/678T/812E, 109D/678T/842G/878S, 109D/692G/ 727S/736M/812E, 109D/692G/127S/812E/842G/860F, 109D/727S/860F/878S, 109D/736M/932S, 109D/812E, 109D/842G, 109D/932S, 135S/670L/1727S, 135S/711A/ 750A/932S, 150T/527N/842G/871L/913V, 150T/871L/ 932S, 150T/883R/932S, 267R/527N/727S, 403H1527N/ 678T/692G/736M/812E/842G/860F, 437A/522E/527N/ 670L/871L, 437A/750A/830Q/932S, 522E, 522E/527N/ 569L/727S, 522E/830Q, 527N, 527N/678T/692G/127S/ 736M/878S, 527N/678T/692G/812E/932S, 527N/692G/ 727S/736M/812E, 527N/692G/127S/736M/842G/860F/ 878S, 527N/727S/736M, 527N/736M/932S, 527N/812E, 670L/711A/871L, 670L/830Q/871L, 678T/692G/727S/ 812E/842G, 678T/692G/812E, 678T/812E, 678T/860F/ 878S, 678T/913V, 678T/932S, 692G/727S/736M/842G/ 913V, 692G/812E, 727S, 727S/932S, 871L, and 878S/932S, wherein the positions are numbered with reference to SEQ ID NO: 2880. In some embodiments, the acid alpha-glucosidase comprises at least one substitution at position or set of positions selected from W24L/S28L/T29L/Q39P/V50Q/ L62A/E78P/E87D/Q135S/S150T/N266T/K267R/V522E/ R527N/A551V/T670L/W727S/P750A/K830Q/S842G/ E871L/H883R/G894Q/A932S, W24L/S28L/Q39P/V50Q/ L62A/E78P/E87D/Q135S/S150T/N266T/K267R/V522E/ R527N/A551V/T 569L/W727S/K830Q/S842G/E871L/ H883R/G894Q/R913V, W24L/S28L/V50Q/Q135S/S150T/ G437A/V522E/R527N/E871L/H883R/G894Q/A932S, W24L/S28U/L62A/V522E/T569L/A932S, W24L/S28L/ G437A/E486T/R527N, W24L/T29L/Q39P/V50Q/L62A/ E78P/E87D/Q135S/S150T/K267R/G437A/E486T/V522E/ R527N/A 551V/H711A/W727S/P750A/K830Q/S842G/ E871L/H883R/G894Q/R913V/A932S, W24L/V50Q/E78P/ E87D/Q135S/S150T/K267R/E486T/V522E/R527N/ A551V/T670L/W727S/P750A/K830Q/S842G/E871L/ H883R/G894Q/R913V/A932S, W24L/V50Q/E486T/ R527N/H711A/W727S, W24L/L62A/E87D/E486T/ W727S, W24L/L62A/W727S/K830Q/A932S, W24L/ E87D/Q135S/V522E/T670L/H711A/K830Q/S842G/ R913V, W24L/S150T/V522E/R527N/W727S/H883R/ G894Q, W24L/R527N/W727S/S842G/E871L/H883R/ R913V/A932S, W24L/T670L/W727S/P750A/S842G/ E871L, S28L, S28L/V50Q/E78P/E87D/Q135S/N266T/ K267R/G437A/E486T/R527N/A551V/T670L/W727S/ P750A/K830Q/S842G/E871L/H883R/G894Q/R913V/ A932S, S28L/V50Q/V522E/R527N/H711A/W727S/ E871L, S28L62A, S28L/L62A/K267R/A932S, S28L/ G437A/R527N/E87L, S28L/V522E/R527N/T569L/H711A/ K830Q/G894Q, S28L/W727S, S28L/W727S/E871L, T29L/ Q39P/V50Q/L62A/G65R/E78P/E87D/Q135S/S150T/ G437A/A551V/T569L/T670L/W727S/P750A/K830Q/ S842G/H883R/G894Q/A932S, T29L/L62A/G437A/ R527N, T29L/E78P/E87D/S150T/R527N/W727S, T29L/ E78P/Q135S/W727S/K830Q, T29L/E87D, T29L/Q135S/ S150T/R527N/T670L/W727S/H883R, T291L/S150T/ K267R/W727S/P750A/E871L/H883R/A932S, T29L/ S150T/G437A/W727S, T29L/V522E/T670L/H711A/ E871L, T29L/T670L/A932S, Q39P/V50Q, Q39P/W727S/ P750A/A932S, V50Q/Q135S/S150T/A932S, V50Q/ G437A/V522E/R527N, V50Q/H711A, V50Q/W727S/ P750A/H883R/G894Q, L62A, L62A/E87D/S150T, L62A/ E87D/S150T/W727S, L62A/Q135S/V522E/H711A/ W727S/P750A/S842G/E871L/G894Q, L62A/G437A, L62A/G437A/W727S, E78P/E87D/E486T/R527N/T670U/ W727S/P750A/K830Q/S842G/E871L/R913V/A932S, E87D/P750A, E89R/L109D/R527N/S678T/W727S/S842G, A89R/L109D/S678T/W727S/L736M/A812E/V878S, A89R/L109D/W727S/A932S, A89R/L109D/A932S, A89R/ R527N, A89R/R527N/S678T/T692G/L736M/S842G/ V878S/A932S, A89R/R527N/S678T/A932S, A89R/ R527N/W727S/A812E/L860F, A89R/S678T/T692G/ L736M/A932S, A89R/S678T/A812E/V878S, A89R/ S842G/V878S, L109D/R527N/S678T/A812E, L109D/ S678T/T692G/S842G/L860F/V878S/A932S, L109D/ S678T/W727S/L860F, L109D/S678T/L736M/A812E/ V878S, L109D/S678T/A812E, L109D/S678T/S842G/ V878S, L109D/T692G/W727S/L736M/A812E, L109D/ T692G/W727S/A812E/S842G/L860F, L109D/W727S/ L860F/V878S, L109D/L736M/A932S, L109D/A812E, L109D/S842G, L109D/A932S, Q135S/T670L/W727S, Q135S/H711A/P750A/A932S, S150T/R527N/S842G/ E871L/R913V, S150T/E871L/A932S, S150T/H883R/ A932S, K267R/R527N/W727S, R403H/R527N/S678T/ T692G/L736M/A812E/S842G/L860F, G437A/V522E/ R527N/T670U/E871L, G437A/P750A/K830Q/A932S, V522E, V522E/R527N/T569L/W727S, V522E/K830Q, R527N, R527N/S678T/T692G/W727S/L736M/V878S, R527N/S678T/T692G/A812E/A932S, R527N/T692G/ W727S/L736M/A812E, R527N/T692G/W727S/L736M/ S842G/L860F/V878S, R527N/W727S/L736M, R527N/ L736M/A932S, R527N/A812E, T670L/H711A/E871L, T670L/K830Q/E871L, S678T/T692G/W727S/A812E/ S842G, S678T/T692G/A812E, S678T/A812E, S678T/ L860F/V878S, S678T/R913V, S678T/A932S, T692G/ W727S/L736M/S842G/R913V, T692G/A812E, W727S, W727S/A932S, E871L, and V878S/A932S, wherein the positions are numbered with reference to SEQ ID NO: 2880. In some embodiments, the acid alpha-glucosidase comprises at least one substitution at position or set of positions selected from 62/87/150, 89/109/527/678/727/842, 89/109/ 678/727/736/812/878, 89/109/932, 89/527/678/692/736/ 842/878/932, 89/527/727/812/860, 89/678/692/736/932, 89/678/812/878, 109/527/678/812, 109/678/692/842/860/ 878/932, 109/678/736/812/878, 109/678/812, 109/692/727/ 736/812, 109/692/727/812/842/860, 109/736/932, 109/812, 109/842, 109/932, 403/527/678/692/736/812/842/860, 522/ 830, 527/678/692/727/736/878, 527/678/692/812/932, 527/ 692/727/736/812, 527/692/727/736/842/860/878, 527/727/ 736, 527/736/932, 527/812, 678/692/727/812/842, 678/692/ 812, 678/812, 692/727/736/842/913, and 692/812, wherein the positions are numbered with reference to SEQ ID NO:

2880. In some embodiments, the acid alpha-glucosidase comprises at least one substitution at position or set of positions selected from 62A/87D/150T, 89R/109D/527N/ 678T/727S/842G, 89R/109D/678T/727S/736M/812E/878S, 89R/109D/932S, 89R/527N/678T/692G/736M/842G/878S/ 932S, 89R/527N/727S/812E/860F, 89R/678T/692G/736M/ 932S, 89R/678T/812E/878S, 109D/527N/678T/812E, 109D/678T/692G/842G/860F/878S/932S, 109D/678T/ 736M/812E/878S, 109D/678T/812E, 109D/692G/727S/ 736M/812E, 109D/692G/727S/812E/842G/860F, 109D/ 736M/932S, 109D/812E, 109D/842G, 109D/932S, 403H1527N/678T/692G/736M/812E/842G/860F, 522E/ 830Q, 527N/678T/692G/727S/736M/878S, 527N/678T/ 692G/812E/932S, 527N/692G/727S/736M/812E, 527N/ 692G/727S/736M/842G/860F/878S, 527N/727S/736M, 527N/736M/932S, 527N/812E, 678T/692G/727S/812E/ 842G, 678T/692G/812E, 678T/812E, 692G/727S/736M/ 842G/913V, and 692G/812E, wherein the positions are numbered with reference to SEQ ID NO: 2880. In some embodiments, the acid alpha-glucosidase comprises at least one substitution at position or set of positions selected from L62A/E87D/S150T, A89R/L109D/R527N/S678T/W727S/ S842G, A89R/L109D/S678T/W727S/L736M/A812E/ V878S, A89R/L109D/A932S, A89R/R527N/S678T/ T692G/L736M/S842G/V878S/A932S, A89R/R527N/ W727S/A812E/L860F, A89R/S678T/T692G/L736M/ A932S, A89R/S678T/A812E/V878S, L109D/R527N/ S678T/A812E, L109D/S678T/T692G/S842G/L860F/ V878S/A932S, L109D/S678T/L736M/A812E/V878S, L109D/S678T/A812E, L109D/T692G/W727S/L736M/ A812E, L109D/T692G/W727S/A812E/S842G/L860F, L109D/L736M/A932S, L109D/A812E, L109D/S842G, L109D/A932S, R403H/R527N/S678T/T692G/L736M/ A812E/S842G/L860F, V522E/K830Q, R527N/S678T/ T692G/W727S/L736M/V878S, R527N/S678T/T692G/ A812E/A932S, R527N/T692G/W727S/L736M/A812E, R527N/T692G/W727S/L736M/S842G/L860F/V878S, R527N/W727S/L736M, R527N/L736M/A932S, R527N/ A812E, S678T/T692G/W727S/A812E/S842G, S678T/ T692G/A812E, S678T/A812E, T692G/W727S/L736M/ S842G/R913V, and T692G/A812E, wherein the positions are numbered with reference to SEQ ID NO: 2880.

The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 3104, wherein the positions are numbered with reference to SEQ ID NO: 3104. In some embodiments, the acid alpha-glucosidase comprises at least one substitution at position or set of positions selected from 62, 62/89/830, 62/248/678/830/878/932, 62/678, 62/678/785, 62/678/830, 62/678/830/860, 62/678/830/860/871/878/932, 62/678/830/ 860/878, 62/678/830/860/878/932, 62/678/830/860/932, 62/678/830/871, 62/678/830/871/932, 62/678/830/878/932, 62/678/830/932, 62/678/860, 62/678/860/878, 62/678/860/ 932, 62/678/871, 62/678/871/932, 62/678/878/932, 62/678/ 932, 62/830, 62/830/860, 62/830/860/871/873, 62/830/860/ 878/932, 62/830/860/932, 62/830/871/932, 62/830/878, 62/830/932, 62/833/860/932, 62/860, 62/860/871, 62/860/ 871/878, 62/860/871/932, 62/860/878/932, 62/860/932, 62/871/878/932, 62/871/932, 62/878, 62/878/932, 62/932, 678, 678/830/932, 678/932, and 860/932, wherein the positions are numbered with reference to SEQ ID NO: 3104. In some embodiments, the acid alpha-glucosidase comprises at least one substitution at position or set of positions selected from 62A, 62A/89D/830Q, 62A/248H/678T/830Q/878S/ 932S, 62A/678T, 62A/678T/785Q, 62A/678T/830Q, 62A/ 678T/830Q/860F, 62A/678T/830Q/860F/871L/878S/932S, 62A/678T/830Q/860F/878S, 62A/678T/830Q/860F/878S/ 932S, 62A/678T/830Q/860F/932S, 62A/678T/830Q/871L, 62A/678T/830Q/871L/932S, 62A/678T/830Q/878S/932S, 62A/678T/830Q/932S, 62A/678T/860F, 62A/678T/860F/ 878S, 62A/678T/860F/932S, 62A/678T/871L, 62A/678T/ 871L/932S, 62A/678T/878S/932S, 62A/678T/878S/932T, 62A/678T/932S, 62A/830Q, 62A/830Q/860F, 62A/830Q/ 860F/871L/873H, 62A/830Q/860F/878S/932S, 62A/830Q/ 860F/932S, 62A/830Q/871L/932S, 62A/830Q/878S, 62A/ 830Q/932S, 62A/833I/860F/932S, 62A/860F, 62A/860F/ 871L, 62A/860F/871L/878S, 62A/860F/871U/932S, 62A/ 860F/878S/932S, 62A/860F/932S, 62A/871L/878S/932S, 62A/871L/932S, 62A/878S, 62A/878S/932S, 62A/932S, 678T, 678T/830Q/932S, 678T/932S, and 860F/932S, wherein the positions are numbered with reference to SEQ ID NO: 3104. In some embodiments, the acid alpha-glucosidase comprises at least one substitution at position or set of positions selected from L62A, L62A/A89D/K830Q, L62A/Y248H/S678T/K830Q/V878S/A932S, L62A/S678T, L62A/S678T/P785Q, L62A/S678T/K830Q, L62A/S678T/ K830Q/L860F, L62A/S678T/K830Q/L860F/E8711V878S/ A932S, L62A/S678T/K830Q/L860F/V878S, L62A/S678T/ K830Q/L860F/V878S/A932S, L62A/S678T/K830Q/ L860F/A932S, L62A/S678T/K830Q/E871L, L62A/S678T/ K830Q/E871U/A932S, L62A/S678T/K830Q/V878S/ A932S, L62A/S678T/K830Q/A932S, L62A/S678T/L860F, L62A/S678T/1L860F/V878S, L62A/S678T/L860F/A932S, L62A/S678T/E871L, L62A/S678T/E871U/A932S, L62A/ S678T/V878S/A932S, L62A/S678T/V878S/A932T, L62A/ S678T/A932S, L62A/K830Q, L62A/K830Q/L860F, L62A/ K830Q/L860F/E871U/R873H, L62A/K830Q/L860F/ V878S/A932S, L62A/K830Q/L860F/A932S, L62A/ K830Q/E871L/A932S, L62A/K830Q/V878S, L62A/ K830Q/A932S, L62A/M833I/L860F/A932S, L62A/L860F, L62A/L860F/E871L, L62A/L860F/E871L/V878S, L62A/ L860F/E871L/A932S, L62A/L860F/V878S/A932S, L62A/ L860F/A932S, L62A/E871L/V878S/A932S, L62A/E871L/ A932S, L62A/V878S, L62A/V878S/A932S, L62A/A932S, S678T, S678T/K830Q/A932S, S678T/A932S, and L860F/ A932S, wherein the positions are numbered with reference to SEQ ID NO: 3104.

In some embodiments, the acid alpha-glucosidase comprises at least one substitution at position or set of positions selected from 62/89/830, 62/830, 62/830/860, 62/830/860/ 932, and 62/830/932, wherein the positions are numbered with reference to SEQ ID NO: 3104. In some embodiments, the acid alpha-glucosidase comprises at least one substitution at position or set of positions selected from 62A/89D/ 830Q, 62A/830Q, 62A/830Q/860F, 62A/830Q/860F/932S, and 62A/830Q/932S, wherein the positions are numbered with reference to SEQ ID NO: 3104. In some embodiments, the acid alpha-glucosidase comprises at least one substitution at position or set of positions selected from L62A/ A89D/K830Q, L62A/K830Q, L62A/K830Q/L860F, L62A/ K830Q/L860F/A932S, and L62A/K830Q/A932S, wherein the positions are numbered with reference to SEQ ID NO: 3104.

In some embodiments, the recombinant acid alpha glucosidase comprises at least one mutation in at least one position as provided in Tables 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9. In some additional embodiments, the recombinant acid alpha glucosidase is derived from a human acid alpha glucosidase. In yet some additional embodiments, the recombinant acid alpha glucosidase comprising the polypeptide sequence of SEQ ID NO: 2, 6, 8, 12, 14, 16, 18, 20, 946, 1956, 2496, 2880, and/or 3104.

In some additional embodiments, the recombinant acid alpha-glucosidase provided herein is thermostable. In some further embodiments, the recombinant acid alpha-glucosidase is resistant to proteolysis. In yet some additional embodiments, the recombinant acid alpha-glucosidase is resistant to at least one digestive tract protease. In some embodiments, the digestive tract protease is selected from chymotrypsin, trypsin, carboxypeptidases, and elastases. In some further embodiments, the recombinant acid alpha-glucosidase is acid stable. In some additional embodiments, the recombinant acid alpha-glucosidase is stable to acidic pH and neutral pH. In yet some additional embodiments, the recombinant acid alpha-glucosidase is purified. In some further embodiments, the recombinant acid alpha-glucosidase exhibits at least one improved property selected from: i) enhanced catalytic activity; ii) increased expression; iii) increased stability at neutral pH levels; iv) increased stability at acidic pH levels; iv) enhanced activity in cell lysates; and vi) decreased immunogenicity; or a combination of any of i), ii), iii), iv), v), and/or vi), as compared to a reference sequence. In some further embodiments, the recombinant acid alpha glucosidase exhibits at least one improved property selected from: i) enhanced catalytic activity; ii) increased tolerance to pH 7; iii) increased tolerance to pH 4; iv) increased expression; v) increased uptake into cells; vi) increased enzymatic activity in cell lysates; vii) decreased immunogenicity, or a combination of any of i), ii), iii), iv), v), vi), and/or vii), as compared to a reference sequence. In some embodiments, the reference sequence is selected from SEQ ID NO: 2, 6, 8, 12, 14, 16, 18, 20, 946, 1956, 24%, 2880, and/or 3104. In some further embodiments, the recombinant acid alpha glucosidase is more stable at pH 7 than the acid alpha glucosidase of SEQ ID NO: 2, 6, 8, 12, 14, 16, 18, 20, 946, 1956, 24%, 2880, and/or 3104. In yet some other embodiments, the recombinant acid alpha glucosidase is more stable at pH 4 than the acid alpha glucosidase of SEQ ID NO: 2, 6, 8, 12, 14, 16, 18, 20, 946, 1956, 24%, 2880, and/or 3104. In some further embodiments, the recombinant acid alpha glucosidase exhibits increased expression than the acid alpha glucosidase of SEQ ID NO: 2, 6, 8, 12, 14, 16, 18, 20, 946, 1956, 24%, 2880, and/or 3104. In still some additional embodiments, the recombinant acid alpha glucosidase is more lysosomally stable than the acid alpha glucosidase of SEQ ID NO: 2, 6, 8, 12, 14, 16, 18, 20, 946, 1956, 2496, 2880, and/or 3104. In some further embodiments, the recombinant acid alpha glucosidase is more readily taken up by cells than the acid alpha glucosidase of SEQ ID NO: 2, 6, 8, 12, 14, 16, 18, 20, 946, 1956, 2496, 2880, and/or 3104. In some additional embodiments, the recombinant acid alpha glucosidase exhibits greater enzymatic activity in cell lysates than the acid alpha glucosidase of SEQ ID NO: 2, 6, 8, 12, 14, 16, 18, 20, 946, 1956, 2496, 2880, and/or 3104. In some additional embodiments, the recombinant acid alpha glucosidase exhibits reduced or decreased immunogenicity than the acid alpha glucosidase of SEQ ID NO: 2, 6, 8, 12, 14, 16, 18, 20, 946, 1956, 2496, 2880, and/or 3104. In some embodiments, the recombinant acid alpha glucosidase is purified.

In some further embodiments, the recombinant acid alpha-glucosidase comprises a polypeptide sequence comprising at least about 85%, about 86%, about 87%, about 88%, about 89%, about 90%, about 91%, about 92%, about 93%, about 94%, about 95%, about 96%, about 97%, about 98%, or about 99% sequence identity to at least one of the even-numbered sequences of SEQ ID NOS: 8-3378. In some further embodiments, the recombinant acid alpha-glucosidase comprises a polypeptide sequence comprising at least 85%, 86%, 87%, 88%, 89%, 90%, 91%, 92%, 93%, 94%, 95%, 96%, 97%, 98%, or 99% sequence identity to at least one of the even-numbered sequences of SEQ ID NOS: 8-3378. In some embodiments the recombinant acid alpha glucosidase comprises a polypeptide sequence at least 90% identical to at least one of the even-numbered sequences of SEQ ID NOS: 8-3378. In some further embodiments, the recombinant acid alpha-glucosidase comprises a polypeptide sequence comprises at least one of the even-numbered sequences of SEQ ID NOS: 2-3378. In some further embodiments, the recombinant acid alpha-glucosidase consists of a polypeptide sequence comprising at least one of the even-numbered sequences of SEQ ID NOS: 8-3378.

The present invention also provides compositions comprising at least one recombinant acid alpha-glucosidase provided herein. In some embodiments, the compositions comprise one recombinant acid alpha-glucosidase provided herein.

The present invention also provides recombinant polynucleotide sequences encoding at least one recombinant acid alpha-glucosidase provided herein. In some embodiment, a recombinant polynucleotide sequence encodes one recombinant acid alpha-glucosidase. In some embodiments, the recombinant polynucleotide sequence is selected from DNA, RNA, and mRNA. In some embodiments, the polynucleotide sequence is codon-optimized. In some further embodiments, the recombinant polynucleotide sequence encodes a recombinant acid alpha-glucosidase comprising a polypeptide sequence comprising at least about 85%, about 86%, about 87%, about 88%, about 89%, about 90%, about 91%, about 92%, about 93%, about 94%, about 95%, about 96%, about 97%, about 98%, or about 99% sequence identity to at least one of the even-numbered sequences of SEQ ID NOS: 8-3378. In some further embodiments, the recombinant acid alpha-glucosidase encoded by the polynucleotide sequence comprises a polypeptide sequence comprising at least 85%, 86%, 87%, 88%, 89%, 90%, 91%, 92%, 93%, 94%, 95%, 96%, 97%, 98%, or 99% sequence identity to at least one of the even-numbered sequences of SEQ ID NOS: 8-3378.

In some further embodiments, the recombinant polynucleotide sequence is at least about 85%, about 86%, about 87%, about 88%, about 89%, about 90%, about 91%, about 92%, about 93%, about 94%, about 95%, about 96%, about 97%, about 98%, or about 99% sequence identity to at least one of the odd-numbered sequences of SEQ ID NOS: 7-3377. In some further embodiments, the recombinant polynucleotide sequence is at least 85%, 86%, 87%, 88%, 89%, 90%, 91%, 92%, 93%, 94%, 95%, 96%, 97%, 98%, or 99%, identical to at least one of the odd-numbered sequences of SEQ ID NOS: 7-3377. In some additional embodiments, the recombinant polynucleotide sequence comprises a sequence comprising at least 90% sequence identity to at least one of the odd-numbered sequences of SEQ ID NOS: 7-3377. In yet some further embodiments, the recombinant polynucleotide sequence comprises an odd-numbered sequence of SEQ ID NOS: 7-3377.

The present invention also provides expression vectors comprising the recombinant polynucleotide sequence encoding recombinant acid alpha-glucosidase. In some embodiments, the recombinant polynucleotide sequence is operably linked to a control sequence. In some further embodiments, the control sequence is a promoter. In some additional embodiments, the promoter is a heterologous promoter. The present invention also provides the expression vector referred to herein as pDH. In some embodiments, the pDH vector comprises at least one polynucleotide sequence encoding an acid alpha glucosidase. In some additional embodiments, the pDH vector comprises at least one polynucleotide sequence encoding an acid alpha glucosidase provided herein. In some further embodiments, the pDH vector comprises at least one polynucleotide sequence selected from the odd-numbered sequences of SEQ ID NOS: 1-3377. In some additional embodiments, the pDH vector comprises at least one polynucleotide sequence encoding an acid alpha glucosidase selected from the even-numbered sequences of SEQ ID NOS: 2-3378. In some embodiments, the pDH vector comprises SEQ ID NO: 3379, while in some other embodiments, the pDH vector comprises SEQ ID NO: 3380. In some additional embodiments, SEQ ID NO:1, which is included in SEQ ID NO: 3379 is replaced with another polynucleotide sequence. In some embodiments, the SEQ ID NO: 1 in SEQ ID NO: 3379 is replaced by at least one polynucleotide sequence selected from the odd-numbered sequences of SEQ ID NOS: 1-3377. In some additional embodiments, the pDH vector comprises the plasmid provided in the map at FIG. 9, while in some other embodiments, the pDH vector comprises the plasmid the map at FIG. 10. In some embodiments, the "stuffer sequence" (i.e., the bla sequence) in the plasmid shown in FIG. 10 is replaced by a gene of interest. In some embodiments, the "stuffer gene" ATG start codon to the last codon of the gene is numbered from base pair 724 to 1581 (for a total of 858 base pairs). As used herein, the terms "stuffer gene" and "stuffer sequence" refer to a sequence within a plasmid vector that is replaced by a gene of interest. As used herein, the term "gene of interest" refers to a gene that encodes a desired polypeptide (e.g., a "polypeptide of interest"). In some additional embodiments, the stuffer sequence is replaced by a gene of interest (i.e., a gene that is desired for expression, such that a polypeptide of interest, such as a variant acid alpha glucosidase is produced).

The present invention also provides host cells comprising at least one expression vector provided herein. In some embodiments, the expression vector provided in the host cells is pDH. In some embodiments, the host cell is selected from eukaryotes and prokaryotes. In some further embodiments, the host cell is a mammalian cell.

The present invention also provides methods of producing a recombinant acid alpha glucosidase variant, comprising culturing at least one host cell provided herein, under conditions that the acid alpha glucosidase encoded by the recombinant polynucleotide is produced. In some embodiments, the methods further comprise the step of recovering the acid alpha glucosidase. In yet some further embodiments, the methods further comprise the step of purifying the acid alpha glucosidase. The present invention also provides recombinant acid alpha glucosidase variants produced according to a method provided herein.

The present invention also provides compositions comprising at least one recombinant acid alpha glucosidase provided herein. The present invention also provides for use of the compositions provided herein. In some embodiments, the present invention provides pharmaceutical compositions for the treatment of Pompe disease, comprising at least one composition provided herein. In some additional embodiments, the pharmaceutical composition further comprises at least one pharmaceutically acceptable carrier and/or excipient. In some further embodiments, the pharmaceutical composition is suitable for parenteral injection or infusion to a human. In yet some additional embodiments, the present invention provides pharmaceutical compositions comprising at least one recombinant polynucleotide provided herein. In yet some further embodiments, the present invention provides pharmaceutical compositions comprising at least one recombinant polypeptide provided herein. In yet some additional embodiments, the present invention provides compositions comprising at least one recombinant polynucleotide and at least one recombinant polypeptide provided herein.

The present invention also provides methods for treating and/or preventing the symptoms of Pompe disease in a subject, comprising providing a subject having Pompe disease and at least one pharmaceutical composition provided herein, and administering the pharmaceutical composition to the subject. In some embodiments, the symptoms of Pompe disease are ameliorated. In some additional embodiments, the subject is an infant or child. In yet some further embodiments, the subject is an adult or young adult.

DESCRIPTION OF THE INVENTION

Figure 1:
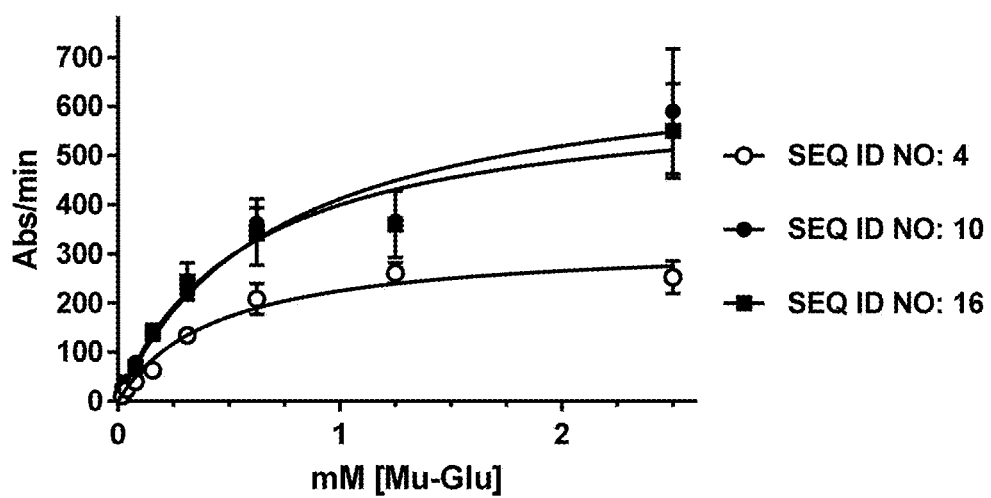
FIG. 1 provides a graph showing the kinetic assay results for three GAA variants, as described in Example 9.

The present invention provides engineered acid alpha-glucosidase (GAA) polypeptides and compositions thereof. In some embodiments, the engineered GAA polypeptides have been optimized to provide enhanced catalytic activity and enhanced acid stability, while reducing sensitivity to proteolysis. The invention also provides methods for utilization of the compositions comprising the engineered GAA polypeptides for therapeutic and other purposes.

Abbreviations and Definitions

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Tus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value. In some instances, "about" encompasses values that are within 2.5%, 3%, 3.5%, 4%, 4.5%, 5%, 5.5%, 6%, 6.5%, 7%, 7.5%, 8%, 8.5%, 9%, 9.5%, or 10% of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein, the terms "acid alpha-glucosidase," "acid α-glucosidase," "acid alpha-glucosidase polypeptide" "lysosomal alpha-glucosidase," and "GAA" refer to enzymes within a family (EC 3.2.1.20) of enzymes that break down glycogen present in lysosomes. The enzyme is also sometimes referred to as "alpha-1,4-glucosidase," α-1, 4-glucosidase," "acid maltase," "glucoinvertase," "glucosidosucrase," "lysosomal alpha-glucosidase," "lysosomal α-glucosidase," "maltase," or "maltase-glucoamylase." One reaction catalyzed by the enzyme is the hydrolysis of terminal, non-reducing (1 to 4) linked alpha-D-glucose residues with release of alpha-D-glucose.

As used herein, "Pompe disease" refers to a glycogen storage disease type II, which is an autosomal recessive genetic disorder that results in a metabolic disorder characterized by lysosomal accumulation of glycogen in skeletal muscle and other tissues. It is characterized based on age of onset, organ involvement, severity, and rate of progression. The more severe form is infantile-onset Pompe disease (IOPD), which occurs in infants. The other form, referred to as "late-onset Pompe disease" (LOPD), occurs in individuals with an onset of disease before 12 months of age, but without the cardiomyopathy associated with IOPD, and all individuals with an onset of disease after 12 months of age. Synonyms for Pompe disease include "acid alpha-glucosidase deficiency," acid maltase deficiency," "GAA deficiency," "glycogen storage disease type II," "GSD II," "GSD2," and "glycogenosis type II."

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The terms "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example, a wild-type polypeptide or polynucleotide sequence is a sequence present in an organism that can be isolated from a source in nature and which has not been intentionally modified by human manipulation.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970], by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., 1977, Nucleic Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison WI), using default parameters provided.

As used herein, the term "reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. "Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered GAA, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X27 as compared to SEQ ID NO: 2" refers to a difference of the amino acid residue at the polypeptide position corresponding to position 27 of SEQ ID NO: 2. Thus, if the reference polypeptide of SEQ ID NO: 2 has a phenylalanine at position 2, then a "residue difference at position X27 as compared to SEQ ID NO: 2" an amino acid substitution of any residue other than phenylalanine at the position of the polypeptide corresponding to position 27 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., as shown in in Tables 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X27P/X27R or X27P/R). In some embodiments, the enzyme variants comprise more than one substitution. These substitutions are separated by a slash for ease in reading (e.g., F27P/C944W). In some cases, the "X" does not precede the position number in the present application. The present application includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

A "functional fragment" or a "biologically active fragment" used interchangeably herein refers to a polypeptide that has an amino-terminal and/or carboxy-terminal deletion (s) and/or internal deletions, but where the remaining amino acid sequence is identical to the corresponding positions in the sequence to which it is being compared (e.g., a full-length engineered GAA of the present invention) and that retains substantially all of the activity of the full-length polypeptide.

"Isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The recombinant GAA polypeptides may be present within a cell, present in the cellular medium, or prepared in various forms, such as lysates or isolated preparations. As such, in some embodiments, the recombinant GAA polypeptides can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure GAA composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant GAA polypeptides are substantially pure polypeptide compositions.

"Improved enzyme property" refers to an engineered GAA polypeptide that exhibits an improvement in any enzyme property as compared to a reference GAA polypeptide and/or as a wild-type GAA polypeptide or another engineered GAA polypeptide. Improved properties include but are not limited to such properties as increased protein expression, increased thermoactivity, increased thermostability, increased pH activity, increased stability, increased enzymatic activity, increased substrate specificity or affinity, increased specific activity, increased resistance to substrate or end-product inhibition, increased chemical stability, improved chemoselectivity, improved solvent stability, increased tolerance to acidic, neutral, or basic pH, increased tolerance to proteolytic activity (i.e., reduced sensitivity to proteolysis), reduced aggregation, increased solubility, reduced immunogenicity, improved post-translational modification (e.g., glycosylation), altered temperature profile, increased lysosomal stability, etc.

"Increased enzymatic activity" or "enhanced catalytic activity" refers to an improved property of the engineered GAA polypeptides, which can be represented by an increase in specific activity (e.g., product produced/time/weight protein) or an increase in percent conversion of the substrate to the product (e.g., percent conversion of starting amount of substrate to product in a specified time period using a specified amount of GAA) as compared to the reference GAA enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring GAA or another engineered GAA from which the GAA polypeptides were derived.

In some embodiments, the engineered GAA polypeptides have a $k_{cat}$ of at least 0.1/sec, at least 0.5/sec, at least 1.0/sec, at least 5.0/sec, at least 10.0/sec and in some preferred embodiments greater than 10.0/sec. In some embodiments, the $K_m$, is in the range of about 1 µM to about 5 mM; in the range of about 5 µM to about 10 mM; in the range of about 30 µM to about 30 mM; or in the range of about 50 µM to about 50 mM. In some specific embodiments, the engineered GAA enzyme exhibits improved enzymatic activity after exposure to certain conditions in the range of 1.5 to 10 fold, 1.5 to 25 fold, 1.5 to 50 fold, 1.5 to 100 fold or greater than that of a reference GAA enzyme (e.g., a wild-type GAA or any other reference GAA, such as SEQ ID NO: 2, 6, 8, 12, 14, 16, 18, 20, 946, 1956, 2496, 2880, and/or 3104).

GAA activity can be measured by any suitable method known in the art (e.g., standard assays, such as monitoring changes in spectrophotometric properties of reactants or products). In some embodiments, the amount of products produced can be measured by High-Performance Liquid Chromatography (HPLC) separation combined with UV absorbance or fluorescent detection. In some embodiments, the amount of product produced can be measured by monitoring fluorescence (Ex. 355 nm, Em. 460 nm) after hydrolysis of a 4-methylumbelliferyl-alpha-D-glucopyranoside (4-MUGlu) molecule. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

The term "improved tolerance to acidic pH" means that a recombinant GAA according to the invention will have increased stability (higher retained activity at about pH 4.8, after exposure to an acidic pH for a specified period of time (e.g., 1 hour, up to 24 hours)) as compared to a reference GAA or another enzyme.

The term "improved tolerance to neutral pH" means that a recombinant GAA according to the invention will have increased stability (higher retained activity at about pH 7, after exposure to a neutral pH for a specified period of time (e.g., 1 hour, up to 24 hours)) as compared to a reference GAA or another enzyme.

The term "improved cellular uptake" means that a recombinant GAA provided herein exhibits increased endocytosis into cells, as compared to a reference GAA (including wild-type GAA) or another enzyme. In some embodiments, the cells are cultured Pompe patient cells (higher retained intracellular activity after incubation with cultured cells over a specified period of time, as compared to a reference GAA or another enzyme). In some additional embodiments, the recombinant GAA provided herein exhibits greater retained intracellular activity with cultured cells over a specific period of time as compared to a reference GAA (including wild-type GAA) or another enzyme. In some additional embodiments, the time period is about 4 hours, while in some other embodiments, the time period is less than 4 hours (e.g., 1, 2, or 3 hours), and in some alternative embodiments, the time period is more than 4 hours (e.g., 5, 6, 7, 8, or more hours).

The terms "reduced immunogenicity" and "decreased immunogenicity" mean that a recombinant GAA provided herein induces a reduced immune response as compared to a wild-type or another reference GAA.

"Physiological pH" as used herein means the pH range generally found in a subject's (e.g., human) blood.

The term "basic pH" (e.g., used with reference to improved stability to basic pH conditions or increased tolerance to basic pH) means a pH range of about 7 to 11.

The term "acidic pH" (e.g., used with reference to improved stability to acidic pH conditions or increased tolerance to acidic pH) means a pH range of about 1.5 to 4.5.

"Conversion" refers to the enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" of a GAA polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the GAA enzymes may be codon optimized for optimal production from the host organism selected for expression.

"Control sequence" refers herein to include all components, which are necessary or advantageous for the expression of a polynucleotide and/or polypeptide of the present application. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a GAA polypeptide of the present application is capable of converting a substrate to the desired product compound, Exemplary "suitable reaction conditions" are provided in the present application and illustrated by the Examples. "Loading", such as in "compound loading" or "enzyme loading" refers to the concentration or amount of a component in a reaction mixture at the start of the reaction. "Substrate" in the context of an enzymatic conversion reaction process refers to the compound or molecule acted on by the GAA polypeptide. "Product" in the context of an enzymatic conversion process refers to the compound or molecule resulting from the action of the GAA polypeptide on a substrate.

As used herein the term "culturing" refers to the growing of a population of microbial cells under any suitable conditions (e.g., using a liquid, gel or solid medium).

Recombinant polypeptides can be produced using any suitable methods known the art. Genes encoding the wild-type polypeptide of interest can be cloned in vectors, such as plasmids, and expressed in desired hosts, such as E. coli, S. cerevisiae, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant GAA polypeptides" (also referred to herein as "engineered GAA polypeptides," "variant GAA enzymes," and "GAA variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence. In some preferred embodiments, the pDH vector provided herein finds use.

As used herein, the term "gene therapy vector" refers to vehicles or carriers suitable for delivery of polynucleotide sequences to cells. In some embodiments, the vectors encapsulate genes (e.g., therapeutic genes) or polynucleotide sequences for delivery to cells or tissues, including but not limited to adenovirus (AV), adeno-associated virus (AAV), lentivirus (LV), and non-viral vectors, such as liposomes. It is not intended that the present invention be limited to any specific gene therapy vector, as any vehicle suitable for a given setting finds use. The gene therapy vector may be designed to deliver genes to a specific species or host, or may find more general applicability.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., the polynucleotides encoding the GAA variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, the term analogue refers to polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "therapeutic" refers to a compound administered to a subject who shows signs or symptoms of pathology having beneficial or desirable medical effects.

The term "pharmaceutical composition" refers to a composition suitable for pharmaceutical use in a mammalian subject (e.g., human) comprising a pharmaceutically effective amount of an engineered GAA polypeptide encompassed by the invention and an acceptable carrier.

The term "gene therapy" refers to the delivery of a gene, polydeoxyribonucleotide, or polynucleotide sequence(s) with a gene therapy vector to cells or tissues for the modification of those cells or tissues for the treatment of prevention of a disease. Gene therapy may include replacing a mutated gene that causes disease with a healthy copy of the gene, or inactivating, or "knocking out," a mutated gene that is functioning improperly. In some embodiments, gene therapy is used in the treatment of disease in patients.

The term "mRNA therapy" refers to the delivery of an mRNA polyribonucleotide sequence to cells or tissues for the modification of those cells or tissues for the treatment or prevention of a disease. In some embodiments, the mRNA polynucleotide sequences for delivery to cells or tissue, are formulated, for instance, but not limited to, in liposomes. In some embodiments, mRNA therapy is used in the treatment of disease in patients.

The term "cell therapy" refers to the delivery of living cells that have been modified exogenously to patients to provide a missing gene for the treatment or prevention of a disease. The modified cells are then reintroduced into the body.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

The term "subject" encompasses mammals such as humans, non-human primates, livestock, companion animals, and laboratory animals (e.g., rodents and lagomorphs). It is intended that the term encompass females as well as males.

As used herein, the term "patient" means any subject that is being assessed for, treated for, or is experiencing disease.

The term "infant" refers to a child in the period of the first month after birth to approximately one (1) year of age. As used herein, the term "newborn" refers to child in the period from birth to the 28' day of life. The term "premature infant" refers to an infant born after the twentieth completed week of gestation, yet before full term, generally weighing ~500 to ~2499 grams at birth. A "very low birth weight infant" is an infant weighing less than 1500 g at birth.

As used herein, the term "child" refers to a person who has not attained the legal age for consent to treatment or research procedures. In some embodiments, the term refers to a person between the time of birth and adolescence.

As used herein, the term "adult" refers to a person who has attained legal age for the relevant jurisdiction (e.g., 18 years of age in the United States). In some embodiments, the term refers to any fully grown, mature organism. In some embodiments, the term "young adult" refers to a person less than 18 years of age, but who has reached sexual maturity.

As used herein, "composition" and "formulation" encompass products comprising at least one engineered GAA of the present invention, intended for any suitable use (e.g., pharmaceutical compositions, dietary/nutritional supplements, feed, etc.).

The terms "administration" and "administering" a composition mean providing a composition of the present invention to a subject (e.g., to a person suffering from the effects of Pompe disease).

The term "carrier" when used in reference to a pharmaceutical composition means any of the standard pharmaceutical carrier, buffers, and excipients, such as stabilizers, preservatives, and adjuvants.

The term "pharmaceutically acceptable" means a material that can be administered to a subject without causing any undesirable biological effects or interacting in a deleterious manner with any of the components in which it is contained and that possesses the desired biological activity.

As used herein, the term "excipient" refers to any pharmaceutically acceptable additive, carrier, diluent, adjuvant, or other ingredient, other than the active pharmaceutical ingredient (API; e.g., the engineered GAA polypeptides of the present invention). Excipients are typically included for formulation and/or administration purposes.

The term "therapeutically effective amount" when used in reference to symptoms of disease/condition refers to the amount and/or concentration of a compound (e.g., engineered GAA polypeptides) that ameliorates, attenuates, or eliminates one or more symptom of a disease/condition or prevents or delays the onset of symptom(s).

The term "therapeutically effective amount" when used in reference to a disease/condition refers to the amount and/or concentration of a composition (e.g., engineered GAA polypeptides) that ameliorates, attenuates, or eliminates the disease/condition. In some embodiments, the term is use in reference to the amount of a composition that elicits the biological (e.g., medical) response by a tissue, system, or animal subject that is sought by the researcher, physician, veterinarian, or other clinician.

It is intended that the terms "treating," "treat" and "treatment" encompass preventative (e.g., prophylactic), as well as palliative treatment.

Engineered GAA Polypeptides:

In some embodiments, engineered GAA polypeptides are produced by cultivating a microorganism comprising at least one polynucleotide sequence encoding at least one engineered GAA polypeptide under conditions which are conducive for producing the engineered GAA polypeptide(s). In some embodiments, the engineered GAA polypeptide is recovered from the resulting culture medium and/or cells.

The present invention provides exemplary engineered GAA polypeptides having GAA activity. The Examples provide Tables showing sequence structural information correlating specific amino acid sequence features with the functional activity of the engineered GAA polypeptides. This structure-function correlation information is provided in the form of specific amino acid residues differences relative to a reference engineered polypeptide, as indicated in the Examples. The Examples further provide experimentally determined activity data for the exemplary engineered GAA polypeptides.

Polynucleotides Encoding Engineered Polypeptides, Expression Vectors and Host Cells:

The present invention provides polynucleotides encoding the engineered GAA polypeptides described herein. In some embodiments, the polynucleotides are operatively linked to one or more heterologous regulatory sequences that control gene expression to create a recombinant polynucleotide capable of expressing the polypeptide. Expression constructs containing a heterologous polynucleotide encoding the engineered GAA polypeptides can be introduced into appropriate host cells to express the corresponding GAA polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the engineered GAA polypeptide. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the variants provided in Tables 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9, as well as SEQ ID NOS: 2, 8, and/or 14.

In various embodiments, the codons are preferably selected to fit the host cell in which the protein is being produced. For example, preferred codons used in bacteria are used for expression in bacteria. Consequently, codon optimized polynucleotides encoding the engineered GAA polypeptides contain preferred codons at about 40%, 50%, 60%, 70%, 80%, or greater than 90% of codon positions of the full-length coding region.

In some embodiments, as described above, the polynucleotide encodes an engineered polypeptide having GAA activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 2, 6, 8, 12, 14, 16, 18, 20, 946, 1956, 2496, 2880, and/or 3104, or the amino acid sequence of any variant as disclosed in Tables 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9, and one or more residue differences as compared to the reference polypeptide of SEQ ID NO: 2, 6, 8, 12, 14, 16, 18, 20, 946, 1956, 2496, 2880, and/or 3104, or the amino acid sequence of any variant as disclosed in Table 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9 (e.g., 1, 2, 3, 4, 5, 6, 7, 8, 9, 10 or more amino acid residue positions). In some embodiments, the reference sequence is selected from SEQ ID NOS: 2, 6, 8, 12, 14, 16, 18, 20, 946, 1956, 2496, 2880, and/or 3104.

The present invention provides recombinant acid alpha-glucosidases and/or biologically active recombinant acid alpha-glucosidase fragments comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 2. The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 2. In some embodiments, the acid alpha-glucosidase comprises at least one substitution at position or set of positions selected from 27, 27/944, 28, 29/478, 30, 88, 107, 109, 109/842, 110, 113, 135, 137, 138, 148, 150, 247, 274, 276, 278, 375, 403, 414, 418, 418/499, 421, 426, 437, 444, 455, 463, 471, 471/478, 476, 489, 527, 547, 581, 610, 642, 668, 670, 692, 725/732, 750, 753, 786, 820, 862, 871, 895, 897, 930, 934, and 944, wherein the positions are numbered with reference to SEQ ID NO: 2. In some embodiments, the acid alpha-glucosidase comprises at least one substitution or substitution sets at one or more positions selected from 27P, 27P/944W, 27R, 28P, 28R, 28S, 29T/478T, 30G, 30K, 30T, 88G, 88S, 107G, 107P, 109G/842E, 109P, 110G, 110L, 113S, 135A, 135Q, 137P, 138A, 148G, 148Y, 150G, 247R, 274G, 276F, 276Y, 278A, 278G, 375E, 403W, 414P, 418E/499R, 418R, 421S, 426R, 437S, 444T, 455V, 463A, 471Q/478S, 471S, 476A, 476H, 489R, 527R, 547G, 581G, 581T, 610A, 610G, 610S, 642M, 642Q, 642S, 668H, 670N, 692Q, 725N/732I, 750P, 753T, 786P, 786Y, 820E, 862G, 871E, 895R, 897V, 930R, 934R, 944G, and 944R, wherein the positions are numbered with reference to SEQ ID NO: 2. In some embodiments, the acid alpha-glucosidase comprises at least one substitution or substitution sets at one or more positions selected from F27P, F27P/C944W, F27R, L28P, L28R, L28S, L29T/A478T, V30G, V30K, V30T, K88G, K88S, Q107G, Q107P, L109G/G842E, L109P, Q110G, Q110L, Q113S, S135A, S135Q, E137P, M138A, T148G, T148Y, T150G, Q247R, D274G, A276F, A276Y, T278A, T278G, I375E, R403W, R414P, A418E/H499R, A418R, Q421S, G426R, A437S, A444T, R455V, E463A, K471Q/A478S, K471S, S476A, S476H, A489R, N527R, A547G, K581G, K581T, W610A, W610G, W610S, L642M, L642Q, L642S, S668H, L670N, T692Q, K725N/V732I, A750P, A753T, R786P, R786Y, G820E, R862G, L871E, K895R, T897V, C930R, L934R, C944G, and C944R, wherein the positions are numbered with reference to SEQ ID NO: 2. In some embodiments, the acid alpha-glucosidase comprises at least one substitution at position or set of positions selected from 29/218/240/668/700/744/869, 29/218/240/700/869, 29/240/596/668/700/744/869, 29/240/596/668/869, 36/106/150/218/527/750/883/894, 106/112/150/218/414/527/793/883, 106/150/169/218/414/486/527/750/894, 106/150/169/218/414/486/527/894, 106/150/169/218/414/486/749/793/883/894, 106/150/169/218/414/486/750/793/883/894, 106/150/169/218/414/486/793/883, 106/150/169/218/414/486/894, 106/150/169/218/414/749/750/793/883, 106/150/169/218/414/749/793, 106/150/169/218/414/749/793/883, 106/150/169/218/486/527/749/793/894, 106/150/169/218/486/749/883, 106/150/169/218/486/883, 106/150/169/218/749/800, 106/150/169/414/486/749/750/883, 106/150/169/527749/793/883, 106/150/169/749/793/883/894, 106/150/218/331/414/486/527733/749/793, 106/150/218/414/486/642/750/793/883, 106/150/218/414/486/750/793/894, 106/150/218/414/527/749/750/883, 106/150/218/414/527/749/793/883/894, 106/150/218/414/749/750/793/883/894, 106/150/218/414/749/793/883, 106/150/218/486/527/749/894, 106/150/218/486/793/883, 106/150/218/527/749/750/793, 106/150/218/527/793/894, 106/150/218/749/750/793, 106/150/218/793, 106/150/218/793/894, 106/150/245/793/883/894, 106/150/414/749/750/793/894, 106/150/414/749/793/894, 106/150/486/527/750/793, 106/150/486/749/793/883/894, 106/150/749/793/883, 106/169/185/218/414/749/750/793, 106/191/280402/414/444727, 106/191/414/444/522/928/944, 106/191/414/489/928/944, 106/280/402/414/444/489/727/944, 150/169/218/414/527/793, 150/218/414/486/749750, 150/218/414/486/750/793, 150/218/414/486/750/793/883, 150/218/414/749/750/793/894, 150/218/414/749/793, 150/218/527/749/793, 150/218/749/750/793, 150/218/749793, 150/414/486/527/750/894, 150/414/486/749/750/793, 150/486/750/883/894, 169/486/750/793/883, 180/275/402/518/547/610/638/669/671, 180/402/431/507/547/610/669/671/793, 180/402/507/547/610/671, 191/280/402/414/444/465/842/928, 191/280/402/414/444/489/500/944, 191/280/414/444/489/500/522/842/928/944, 191/280/414/444/489/522/727/944, 191/280/414/489/842/928/944, 191/280/414/944, 191/414/522/842/944, 196/402/431/547/610/638, 218/668/700/869, 224/402/507/518/547/638/668, 269/275/431/518/547/638/668/669, 275/281/402/431/507/518/610/668, 275/281/402/431/518/547/610/669/671, 275/281/402/507/518/547/638/669/671, 275/281/402/518/547/610/638/671, 275/281/402/518/547/610/668/669/887, 275/281/402/547/610/638/669/671, 275/281/431/518/547/638/669/671, 275/281/507/

547/669/671, 275/281/610/638/668/669, 275/281/671, 275/377/402/507/518/669/671/715, 275/402/431/507/547/671, 275/402/431/518/610/638/669/671/922, 275/402/507/547/610/638/668/669, 275/402/507/547/610/638/669/671, 275/402/507/547/610/671, 275/402/547/610/638/669/671, 275/402/547/638/669/671, 275/402/638/669/671, 275/431/507/518/547/668/669/671, 275/431/507/518/610/669/671, 275/431/507/547/610/638/671, 275/431/518/547/638/668, 275/431/518/610/638/669/671, 275/431/638, 275/507/518/547/610/638/668/669, 275/507/518/547/638/669/671, 275/507/547/610/638/669/671, 275/507/547/668/669/671, 275/518/671, 280/402/536/928, 281/402/507/518/547/610/638/669/671, 281/402/507/547/638/669/671, 281/402/518/547/610/638/668/669, 281/402/518/547/668, 281/431/507/518/547/610/638/668, 402/431/518/547/610/668, 402/431/518/547/671, 402/431/518/610, 402/431/547/638/671, 431/507/518/541/547/638/669/671, 431/507/518/669/671, 507/547/610, 507/547/638/669/671, 547/610/638/671, and 547/638/668, wherein the positions are numbered with reference to SEQ ID NO: 2. In some embodiments, the acid alpha-glucosidase comprises at least one substitution or substitution sets at one or more positions selected from 29Q/218S/240I/668D/700F/V44V/869L, 29Q/240I/596P/668D/869L, 29Q/240I/596S/668D/700F/744V/869T, 29V/218S/240I/700F/869T, 36R/106P/150S/218S/527D/750P/883H/894R, 106P/112S/150S/218S/414G/527D/793K/883H, 106P/150S/169S/218S/414G/486E/527D/750P/894R, 106P/150S/169S/218S/414G/486E/527D/894R, 106P/150S/169S/218S/414G/486E/749F/793K/883H/894R, 106P/150S/169S/218S/414G/486E/750P/793K/883H/894R, 106P/150S/169S/218S/414G/486E/793K/883H, 106P/150S/169S/218S/414G/486E894R, 106P/150S/169S/218S/414G/749E/750P/793K/883H, 106P/150S/169S/218S/414G/749E/793K, 106P/150S/169S/218S/414G/749E/793K/883H, 106P/150S/169S/218S/486E/527D/749E/793K/894R, 106P/150S/169S/218S/486E/749E/883H, 106P/150S/169S/218S/486E/883H, 106P/150S/169S/218S/749E/800A, 106P/150S/169S/414G/486E/749F/750P/883H, 106P/150S/169S/527D/749E/793K/883H, 106P/150S/169S/749E/793K/883H/894R, 106P/150S/218S/331A/414G/486E/527D/733E/749E/793K, 106P/150S/218S/414G/486E/642F/750P/793K/883H, 106P/150S/218S/414G/486E/750P/793K/894R, 106P/150S/218S/414G/527D/749F750P/883H, 106P/150S/218S/414G/527D/749E/793K/883H/894G, 106P/150S/218S/414G/749E/750P/793K/883H/894R, 106P/150S/218S/414G/749E/793K/883H, 106P/150S/218S/486E/527D/749E/894R, 106P/150S/218S/486E/793K/883H, 106P/150S/218S/527D/749E/750P/793K, 106P/150S/218S/527D/793K/894G, 106P/150S/218S/749E/750P/793K, 106P/150S/218S/793K, 106P/150S/218S/793K/894R, 106P/150S/245S/793K/883H/894R, 106P/150S/414G/749E/750P/793K/894R, 106P/150S/414G/749F/793K/894R, 106P/150S/486E/527D/750P/793K, 106P/150S/486E/749E/793K/883H/894G, 106P/150S/749E/793K/883H, 106P/169S/185G/218S/414G/749E/750P/793K, 106P/191R/280D/402A/414G/444P/727P, 106P/191R/414G/444P/522V/928T/944S, 106P/191R/414G/489D/928T/944S, 106P/280D/402A/414G/444P/489D/727P/944S, 150S/169S/218S/414G/527D/793K, 150S/218S/414G/486A/750P/793K, 150S/218S/414G/486F/749E/750P, 150S/218S/414G/486E/750P/793K/883H, 150S/218S/414G/749E/750P/793K/894R, 150S/218S/414G/749E/793K, 150S/218S/527D/749E/793K, 150S/218s/749E/750P/793K, 150S/414G/486E/527D/750P/894R, 150S/414G/486E/749E/750P/793K, 150S/486E/750P/883H/894G, 169S/486E/750P/793K/883H, 180H/275M/402A/518V/547G/610R/638I/669H/671N, 180H/402A/431V/507L/547G/610R/669H/671N/793G, 180H/402A/507L/547G/610R/671N, 191R/280D/402A/414G/444P/465E/842S/928T, 191R/280D/402A/414G/444P/489D/500A/944S, 191R/280D/414G/444P/489D/500A/522V/842S/928T/944S, 191R/280D/414G/444P/489D/522V/727P/944S, 191R/280D/414G/489D/842S/928T/944S, 191R/280D/414G/944S, 191R/414G/522V/842S/944S, 196V/402A/431V/547G/610R/638I, 218S/668D/700F/869T, 224F/402A/507L/518V/547G/638I/668D, 269N/275M/431V/518V/547G/638I/668D/669H, 275M/281V/402A/431V/507L/518V/610R/668D, 275M/281V/402A/507L/518V/547G/638I/669H/671N, 275M/281V/402A/518V/547G/610R/638I/671N, 275M/281V/402A/518V/547G/610R/668D/669H/887D, 275M/281V/402A/547G/610R/638I/669H/671N, 275M/281V/507L/547G/669H/671N, 275M/281V/610R/638I/668D/669H, 275M/402A/431V/507L/547G/671N, 275M/402A/507L/547G/610R/671N, 275M/402A/547G/638I/669H/671N, 275M/431V/518V/547G/638I/668D, 275M/431V/S18V/610R/638I/669H/671N, 275M/431V/638I, 275M/507L/547G/668D/669H/671N, 275V/281V/402A/431V/518V/547G/610R/669H/671N, 275V/281V/431V/518V/547G/638I/669H/671N, 275V/281V/671N, 275V/377K/402A/507L/518V/669H/671N, 715G, 275V/402A/431V/518V/610R/638I/669H/671N/922L, 275V/402A/507L/547G/610R/638I/668D/669H, 275V/402A/507L/547G/610R/638I/669H/671N, 275V/402A/547G/610R/638I/669H/671N, 275V/402A/638I/669H/671N, 275V/431V/507L/518V/547G/668D/669H/671N, 275V/431V/507L/518V/610R/669H/671N, 275V/431V/507L/547G/610R/638I/671N, 275V/507L/518V/547G/610R/638I/668D/669H, 275V/507L/518V/547G/638I/669H/671N, 275V/507L/547G/610R/638I/669H/671N, 275V/518V/671N, 280D/402A/536I/928T, 281V/402A/507L/518V/547G/610R/638I/669H/671N, 281V/402A/507L/547G/638I/669H/671N, 281V/402A/518V/547G/610R/638I/668D/669H, 281V/402A/518V/547G/668D, 281V/431V/507L/518V/547G/610R/638I/668D, 402A/431V/518V/547G/610R/668D, 402A/431V/518V/547G/671N, 402A/431V/518V/610R, 402A/431V/547G/638I/671N, 431V/507L/518V/541E/547G/638I/669H/671N, 431V/507L/518V/669H/671N, 507L/547G/610R, 507L/547G/638I/669H/671N, 547G/610R/638I/671N, and 547G/638I/668D, wherein the positions are numbered with reference to SEQ ID NO: 2. In some embodiments, the acid alpha-glucosidase comprises at least one substitution or substitution sets at one or more positions selected from L29Q/L218S/L240U/S668D/H700F/I744V/I869L, L29Q/L240U/A596P/S668D/I869L, L29Q/L240I/A596S/S668D/H700F/I744V/I869T, L29V/L218S/L240I/H700F/I869T, G36R/K106P/T150S/L218S/N527D/A750P/R883H/Q894R, K106P/A112S/T150S/L218S/R414G/N527D/E793K/R883H, K106P/T150S/N169S/L218S/R414G/T486E/N527D/A750P/Q894R, K106P/T150S/N169S/L218S/R414G/T486E/N527D/Q894R, K106P/T150S/N169S/L218S/R414G/T486E/Q749E/E793K/R883H/Q894R, K106P/150S/N169S/L218S/R414G/T486E/A750P/E793K/R883H/Q894R, K106P/T150S/N169S/L218S/R414G/T486E/E793K/R883H, K106P/T150S/N169S/L218S/R414G/T486E/Q894R, K106P/T150S/N169S/L28S/R414G/Q749E/A750P/E793K/R883H, K106P/T150S/N169S/L218S/R414G/Q749E/E793K, K106P/T150S/N169S/L218S/R414G/Q749E/E793K/R883H, K106P/T150S/N169S/L218S/T486E/N527D/Q749E/E793K/Q894R, K106P/T150S/N169S/L218S/T486E/Q749E/R883H, K106P/T150S/N169S/L218S/T486E/R883H, K106P/T150S/N169S/L218S/Q749E/P800A, K106P/

T150S/N169S/R414G/T486E/Q749E/A750P/R883H, K106P/T150S/N169S/N527D/Q749E/E793K/R883H, K106P/T150S/N169S/Q749E/E793K/R883H/Q894R, K106P/T150S/L218S/V331A/R414G/T486E/N527D/ D733E/Q749E/E793K, K106P/T150S/L218S/R414G/ T486E/L642F/A750P/E793K/R883H, K106P/T150S/ L218S/R414G/T486E/A750P/E793K/Q894R, K106P/ T150S/L218S/R414G/N527D/Q749E/A750P/R883H, K106P/T150S/L218S/R414G/N527D/Q749E/E793K/ R883H/Q894G, K106P/T150S/L218S/R414G/Q749E/ A750P/E793K/R883H/Q894R, K106P/T150S/L218S/ R414G/Q749E/E793K/R883H, K106P/T150S/L218S/ T486E/N527D/Q749F/Q894R, K106P/150S/L218S/T486E/ E793K/R883H, K106P/T150S/L218S/N527D/Q749E/ A750P/E793K, K106P/T150S/L218S/N527D/E793K/ Q894G, K106P/T150S/L218S/Q749E/A750P/E793K, K106P/T150S/L218S/E793K, K106P/T150S/L218S/ E793K/Q894R, K106P/T150S/P245S/E793K/R883H/ Q894R, K106P/T150S/R414G/Q749E/A750P/E793K/ Q894R, K106P/T150S/R414G/Q749E/E793K/Q894R, K106P/T150S/T486E/N527D/A750P/E793K, K106P/ T150S/T486E/Q749E/E793K/R883H/Q894G, K106P/ T150S/Q749E/E793K/R883H, K106P/N169S/V185G/ L218S/R414G/Q749E/750P/E793K, K106P/H191R/ G280D/S402A/R414G/A444P/S727P, K106P/H191R/ R414G/A444P/E522V/D928T/C944S, K106P/H191R/ R414G/A489D/D928T/C944S, K106P/G280D/S402A/ R414G/A444P/A489D/S727P/C944S, T150S/N169S/ L218S/R414G/N527D/E793K, T150S/L218S/R414G/ T486A/A750P/E793K, T150S/L218S/R414G/T486E/ Q749E/A750P, T150S/L218S/R414G/T486E/A750P/ E793K/R883H, T150S/L218S/R414G/Q749E/A750P/ E793K/Q894R, T150S/L218S/R414G/Q749E/E793K, T150S/L218S/N527D/Q749E/E793K, T150S/L218S/ Q749E/A750P/E793K, T150S/L218S/Q749E/E793K, T150S/R414G/T486E/N527D/A750P/Q894R, T150S/ R414G/T486E/Q749E/A750P/E793K, T150S/T486E/ A750P/R883H/Q894G, N169S/T486E/A750P/E793K/ R883H, N180H/L275M/S402A/I518V/A547G/W610R/ V638I/L669H/S671N, N180H/S402A/M431V/M507L/ A547G/W610R/L669H/S671N/E793G, N180H/S402A/ M507L/A547G/W610R/S671N, H191R/G280D/S402A/ R414G/A444P/G465E/G842S/D928T, H191R/G280D/ S402A/R414G/A444P/A489D/D500A/C944S, H191R/ G280D/R414G/A444P/A489D/D500A/E522V/G842S/ D928T/C944S, H191R/G280D/R414G/A444P/A489D/ E522V/S727P/C944S, H191R/G280D/R414G/A489D/ G842S/D928T/C944S, H191R/G280D/R414G/C944S, H191R/R414G/E522V/G842S/C944S, A196V/S402A/ M431V/A547G/W610R/V638I, L218S/S668D/H700F/ I869T, L224F/S402A/M5071I/I518V/A547G/V638I/ S668D, T269N/L275M/M431V/I518V/A547G/V638I/ S668D/L669H, L275M/A281V/S402A/M431V/M507L/ I518V/W610R/S668D, L275M/A281V/S402A/M507L/ I518V/A547G/V638I/L669H/S671N, L275M/A281V/ S402A/I518V/A547G/W610R/V638U/S671N, L275M/ A281V/S402A/I518V/A547G/W610R/S668D/L669H/ E887D, L275M/A281V/S402A/A547G/W610R/V638I/ L669H/S671N, L275M/A281V/M507L/A547G/L669H/ S671N, L275M/A281V/W610R/V638U/S668D/L669H, L275M/S402A/M431V/M507L/A547G/S671N, L275M/ S402A/M507L/A547G/W610R/S671N, L275M/S402A/ A547G/V638I/L669H/S671N, L275M/M431V/I518V/ A547G/V638I/S668D, L275M/M431V/I518V/W610R/ V638I/L669H/S671N, L275M/M431V/V638I, L275M/ M507L/A547G/S668D/L669H/S671N, L275V/A281V/ S402A/M431V/I518V/A547G/W610R/L669H/S671N, L275V/A281V/M431V/I518V/A547G/V638V/L669H/ S671N, L275V/A281V/S671N, L275V/R377K/S402A/ M507L/I518V/L669H/S671N/V715G, L275V/S402A/ M431V/I518V/W610R/V638I/L669H/S671N/P922L, L275V/S402A/M507L/A547G/W610R/V638U/S668D/ L669H, L275V/S402A/M507L/A547G/W610R/V638I/ L669H/S671N, L275V/S402A/A547G/W610R/V638I/ L669H/S671N, L275V/S402A/V638V/L669H/S671N, L275V/M431V/M507L/I518V/A547G/S668D/L669H/ S671N, L275V/M431V/M507L/I518V/W610R/L669H/ S671N, L275V/M431V/M507L/A547G/W610R/V638I/ S671N, L275V/M507L/I518V/A547G/W610R/V638I/ S668D/L669H, L275V/M507L/I518V/A547G/V638I/ L669H/S671N, L275V/M507L/A547G/W610R/V638I/ L669H/S671N, L275V/I518V/S671N, G280D/S402A/ V536I/D928T, A281V/S402A/M507L/I518V/A547G/ W610R/V638T/L669H/S671N, A281V/S402A/M507L/ A547G/V638I/L669H/S671N, A281V/S402A/I518V/ A547G/W610R/V638I/S668D/L669H, A281V/S402A/ I518V/A547G/S668D, A281V/M431V/M507L/I518V/ A547G/W610R/V638I/S668D, S402A/M431V/I518V/ A547G/W610R/S668D, S402A/M431V/I518V/A547G/ S671N, S402A/M431V/I518V/W610R, S402A/M431V/ A547G/V638I/S671N, M431V/M507L/I518V/G541E/ A547G/V638/L669H/S671N, M431V/M507L/I518V/ L669H/S671N, M507U/A547G/W610R, M507L/A547G/ V638I/L669H/S671N, A547G/W610R/V638I/S671N, and A547G/V638I/S668D, wherein the positions are numbered with reference to SEQ ID NO: 2.

The present invention provides recombinant acid alpha-glucosidases and/or biologically active recombinant acid alpha-glucosidase fragments comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 8. The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 8. In some embodiments, the acid alpha-glucosidase comprises at least one substitution at position or set of positions selected from 4, 27, 27/28/489, 27/418/478, 28, 28/29, 28/29/113/135/138, 28/29/113/135/418, 28/29/135, 28/29/418, 29/113/126/135/ 193, 29/113/135, 29/113/135/455, 29/113/138, 29/148, 29/478, 106, 106/138/218/431/671/49, 106/218/281, 106/ 218/455, 106/218/455/507/749, 106/489/671, 106/638, 106/ 671/934, 113, 113/135/418, 113/418/455/478/581, 113/418/ 478/489/581, 135, 135/148/150/418, 135/478/489/581, 135/ 489, 135/944, 138/218/668/671, 138/218/749/934, 138/671/ 749/934, 157, 218, 218/281, 218/281/431, 218/281/671, 218/431, 218/431/489/507/749/934, 218/455, 218/507/749, 218/507/934, 218/638/671, 218/749, 281/431/489/668, 345/ 934, 418, 418/489, 431/668/671, 489/638/934, 489/671/934, 489/749, 489/934, 507/668, 507/671/934, 671/749, 671/934, and 749/784, wherein the positions are numbered with reference to SEQ ID NO: 8. In some embodiments, the acid alpha-glucosidase comprises at least one substitution or substitution sets at one or more positions selected from 4H, 27P/28S/489R, 27P/418E/478T, 27R, 28S, 28S/29T, 28S/ 29T/113S/135Q/138A, 28S/29T/113S/135Q/418E, 28S/ 29T/135Q, 28S/29T/418E, 29T/113S/126Q/135Q/193Q, 29T/113S/135Q, 29T/113S/135Q/455V, 29T/113S/138A, 29T/148G, 29T/478T, 106P, 106P/138A/218S/431V/671N/ 749E, 106P/218S/281V, 106P/218S/455V, 106P/218S/ 455V/507L749E, 106P/489R/671N, 106P/638I, 106P/ 671N/934R, 113S, 113S/135Q/418E, 113S/418E/455V/ 478T/581T, 113S/418E/478T/489R/581T, 135P/944Y, 135Q, 135Q/148G/150G/418E, 135Q/478T/489R/581T, 135Q/489R, 138A/218S/668D/671N, 138A/218S/749E/ 934R, 138A/671N/749E/934R, 157M, 218S, 218S/281V, 218S/281V/431V, 218S/281V/671N, 218S/431V, 218S/ 431V/489R/507L/749E/934R, 218S/455V, 218S/507L/ 749E, 218S/507L/934R, 218S/638I/671N, 218S/749E, 281V/431V/489R/668D, 345K/934R, 418E, 418E/489R, 431V/668D/671N, 489R/638I/934R, 489R/671N/934R, 489R/749E, 489R/934R, 507L/668D, 507L/671N/934R, 671N/749E, 671N/934R, and 749E/784T, wherein the positions are numbered with reference to SEQ ID NO: 8. In some embodiments, the acid alpha-glucosidase comprises at least one substitution or substitution sets at one or more positions selected from P4H, F27P/L28S/A489R, F27P/A418E/ A478T, F27R, L28S, L28S/L29T, L28S/L29T/Q113S/ S135Q/M138A, L28S/L29T/Q113S/S135Q/A418E, L28S/ L29T/S135Q, L28S/L29T/A418E, L29T/Q113S/P126Q/ S135Q/H193Q, L29T/Q113S/S135Q, L29T/Q113S/S135Q/ R455V, L29T/Q113S/M138A, L29T/T148G, L29T/A478T, K106P, K106P/M138A/L218S/M431V/S671N/Q749E, K106P/L218S/A281V, K106P/L218S/R455V, K106P/ L218S/R455V/M507L/Q749E, K106P/A489R/S671N, K106P/V638I, K106P/S671N/L934R, Q113S, Q113S/ S135Q/A418E, Q113S/A418E/R455V/A478T/K581T, Q113S/A418E/A478T/A489R/K581T, S135P/C944Y, S135Q, S135Q/T148G/S150G/A418E, S135Q/A478T/ A489R/K581T, S135Q/A489R, M138A/L218S/S668D/ S671N, M138A/L218S/Q749E/L934R, M138A/S671N/ Q749E/L934R, L157M, L218S, L218S/A281V, L218S/ A281V/M431V, L218S/A281V/S671N, L218S/M431V, L218S/M431V/A489R/M507L/Q749E/L934R, L218S/ R455V, L218S/M507L/Q749E, L218S/M507L/L934R, L218S/V638I/S671N, L218S/Q749E, A281V/M431V/ A489R/S668D, Q345K/L934R, A418E, A418E/A489R, M431V/S668D/S671N, A489R/V638I/L934R, A489R/ S671N/L934R, A489R/Q749E, A489R/L934R, M507L/ S668D, M507L/S671N/L934R, S671N/Q749E, S671N/ L934R, and Q749E/A784, wherein the positions are numbered with reference to SEQ ID NO: 8.

The present invention provides recombinant acid alpha-glucosidases and/or biologically active recombinant acid alpha-glucosidase fragments comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 14. The present invention provides recombinant acid alpha-glucosidases and/or biologically active recombinant acid alpha-glucosidase fragments comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 14. In some embodiments, the acid alpha-glucosidase comprises at least one substitution at position or set of positions selected from 22, 24, 27, 27/165, 30, 33, 34, 37/62, 37/62/79/196/696/862, 37/62/523, 37/62/523/793, 37/64/66/79/154/523/681/793/ 862, 37/79/154/793, 37/196, 37/528/696/793, 37/528/790, 37/528/790/793/862, 37/790/793, 39, 39/58/489/725/830/ 842/930/944, 39/70/109/830/842, 39/70/489/612, 39/70/ 725, 39/267, 39/267/489/522/612/830/842, 39/267/489/830/ 944, 39/489/500/612, 39/500/612, 40, 44/157, 47, 49, 50, 55, 60/500/612, 62/79/154/862, 62/79/196/681/862, 62/79/ 523/528/790, 6279/790/793, 62/79/862, 62/92, 62/92/790/ 793, 62/106/523/528/696/793/862, 62/154/696/793/862, 62793/862, 68, 70, 70/267/725/944, 70/267/930/944, 70/489/930, 70/725/830/860/930/944, 77, 79/154/681, 79/154/793/862, 79/862, 89, 97, 106/154, 107, 109, 109/ 522/612/725, 109/522/830/944, 109/612, 118, 149, 157, 158, 178, 179, 196/528/681/790/793, 207, 208, 217, 267/ 489/500/725/830/930, 267/522/725, 352, 385, 424, 448, 463, 489/830/944, 500, 500/612/830/860, 500/860/930, 500/ 930/944, 522/725, 523, 523/790/793, 528/681, 528/793, 528/862, 672, 673, 725, 734, 740, 753, 774, 778, 793, 830, 844, 862, 875, 880, 892, 902, 922, 925, 930, 932, 934, 938, and 944, wherein the positions are numbered with reference to SEQ ID NO: 14. In some embodiments, the acid alpha-glucosidase comprises at least one substitution or substitution sets at one or more positions selected from 22R, 24E, 24R, 24W, 27A, 27G, 27G/165I, 27K, 27R, 27S, 27V, 27W, 30D, 30L, 33G, 33P, 34D, 34M, 34T, 37F/62E, 37F/62E/ 79S/196T/696S/862Q, 37F/62E/523N, 37F/62E/523N/ 793K, 37F/64Q/66G/79S/154R/523N/681Q/793K/862Q, 37F/79S/154R/793K, 37F/196T, 37F/528S/696S/793K, 37F/528S/790V, 37F/528S/790V/793K/862Q, 37F/790V/ 793K, 39D, 39H, 39Q, 39Q/58L489D/725E/830K/842S/ 930P/944S, 39Q/70A/109P/830K/842S, 39Q/70A/489D/ 612D, 39Q/70A/725E, 39Q/267K, 39Q/267K/489D/522V/ 612D/830K/842S, 39Q/267K/489D/830K/944S, 39Q/ 489D/500A/612D, 39Q/500A/612D, 40W, 44I/157V, 47G, 47R, 49A, 49G, 50G, 50L, 50V, 55C, 55L, 60V/500A/612D, 62E/79S/154R/862Q, 62E/79S/196T/681Q/862Q, 62E/79S/ 523N/528S/790V, 62E/79S/790V/793K, 62E/79S/862Q, 62E/92R, 62E/92R/790V/793K, 62E/106R/523N/528S/ 696S/793K/862Q, 62E/154R/696S/793K/862Q, 62E/793K/ 862Q, 68N, 68S, 68W, 70A/267K/725E/944S, 70A/267K/ 930P/944S, 70A/489D/930P, 70A/725E/830K/860F/930P/ 944S, 70Q, 77W, 79S/154R/681Q, 79S/154R/793K/862Q, 79S/862Q, 89R, 97D, 97G, 106R/154R, 107G, 109D, 109P/ 522V/612D/725E, 109P/522V/830K/944S, 109P/612D, 118F, 149R, 157Q, 158E, 158F, 178G, 178V, 179L, 196T/ 528S/681Q/790V/793K, 207R, 207Y, 208G, 208I, 217A, 217D, 267K/489D/500A/725E/830K/930P, 267K/522V/ 725E, 352K, 352V, 385G, 424K, 448L, 463A, 489D/830K/ 944S, 500A, 500A/612D/830K/860F, 500A/860F/930P, 500A/930P/944S, 522V/725E, 523N, 523N/790V/793K, 528S/681Q, 528S/793K, 528S/862Q, 672E, 672K, 673N, 673R, 725F, 725V, 734K, 740G, 740Q, 753S, 774G, 774S, 778Q, 793K, 830V, 844R, 862Q, 875D, 880R, 892L, 902L, 922E, 925A, 925W, 930P, 932A, 934F, 938A, 938P, 944R, and 944S, wherein the positions are numbered with reference to SEQ ID NO: 14. In some embodiments, the acid alpha-glucosidase comprises at least one substitution or substitution sets at one or more positions selected from 122R, L24E, L24R, L24W, F27A, F27G, F27G/M165I, F27K, F27R, F27S, F27V, F27W, V30D, V30L, E33G, E33P, L34D, L34M, L34T, S37F/A62E, S37F/A62E/N79S/ A196T/A696S/R862Q, S37F/A62E/D523N, S37F/A62E/ D523N/E793K, S37F/P64Q/R66G/N79S/K154R/D523N/ E681Q/E793K/R862Q, S37F/N79S/K154R/E793K, S37F/ A196T, S37F/N528S/A696S/E793K, S37F/N528S/I790V, S37F/N528S/I790V/E793K/R862Q, S37F/I790V/E793K, P39D, P39H, P39Q, P39Q/R58L/A489D/K725E/Q830K/ G842S/C930P/C944S, P39Q/V70A/L109P/Q830K/G842S, P39Q/V70A/A489D/S612D, P39Q/V70A/K725E, P39Q/ R267K, P39Q/R267K/A489D/E522V/S612D/Q830K/

G842S, P39Q/R267K/A489D/Q830K/C944S, P39Q/ A489D/D500A/S612D, P39Q/D500A/S612D, V40W, T44I/ L157V, A47G, A47R, Q49A, Q49G, Q50G, Q50L, Q50V, P55C, P55L, A60V/D500A/S612D, A62E/N79S/K154R/ R862Q, A62E/N79S/A196T/E681Q/R862Q, A62E/N79S/ D523N/N528S/I790V, A62E/N79S/I790V/E793K, A62E/ N79S/R862Q, A62E/Q92R, A62E/Q92R/I790V/E793K, A62E/K106R/D523N/N528S/A696S/E793K/R862Q, A62E/K154R/A696S/E793K/R862Q, A62E/E793K/ R862Q, R68N, R68S, R68W, V70A/R267K/K725E/C944S, V70A/R267K/C930P/C944S, V70A/A489D/C930P, V70A/ K725E/Q830K/L860F/C930P/C944S, V70Q, P77W, N79S/ K154R/E681Q, N79S/K154R/E793K/R862Q, N79S/ R862Q, A89R, A97D, A97G, K106R/K154R, Q107G, L109D, L109P/E522V/S612D/K725E, L109P/E522V/ Q830K/C944S, L109P/S612D, W118F, P149R, L157Q, T158E, T158F, P178G, P178V, A179L, A196T/N528S/ E681Q/I790V/E793K, E207R, E207Y, E208G, E208I, Q217A, Q217D, R267K/A489D/D500A/K725E/Q830K/ C930P, R267K/E522V/K725E, Y352K, Y352V, R385G, H424K, R448L, E463A, A489D/Q830K/C944S, D500A, D500A/S612D/Q830K/L860F, D500A/L860F/C930P, D500A/C930P/C944S, E522V/K725E, D523N, D523N/ I790V/E793K, N528S/E681Q, N528S/E793K, N528S/ R862Q, L672E, L672K, P673N, P673R, K725F, K725V, H734K, E/740G, E/740Q, A753S, A774A, A774S, L778Q, E/793K, Q830V, E844R, R862Q, N875D, E880R, Q892L, A902L, P922E, K925A, K925W, C930P, S932A, L934F, Q938A, Q938P, C944R, and C944S, wherein the positions are numbered with reference to SEQ ID NO: 14.

In some embodiments, the recombinant acid alpha glucosidase comprises at least one mutation in at least one position as provided in Tables 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9. In some additional embodiments, the recombinant acid alpha glucosidase is derived from a human acid alpha glucosidase. In yet some additional embodiments, the recombinant acid alpha glucosidase comprising the polypeptide sequence of SEQ ID NO: 2, 6, 8, 12, 14, 16, 18, 20, 946, 1956, 2496, 2880, and/or 3104.

In some embodiments, the polynucleotide encoding the engineered GAA polypeptides comprises a polynucleotide sequence selected from a polynucleotide sequence encoding SEQ ID NO: 1, 5, 7, 11, 13, 15, 17, 19, 945, 1955, 2495, 2879, and/or 3103. In some embodiments, the polynucleotide encoding an engineered GAA polypeptide has at least about 80%, about 85%, about 90%, about 91%, about 92%, about 93%, about 94%, about 95%, about 96%, about 97%, about 98%, or about 99% nucleotide residue identity to SEQ ID NO: 1, 5, 7, 11, 13, 15, 17, 19, 945, 1955, 2495, 2879, and/or 3103. In some embodiments, the polynucleotide encoding an engineered GAA polypeptide has at least 80%, 85%, 90%, 91%, 92%, 93%, 94%, 95%, 96%, 97%, 98%, or 99% nucleotide residue identity to SEQ ID NO: 1, 5, 7, 11, 13, 15, 17, 19, 945, 1955, 2495, 2879, and/or 3103. In some embodiments, the polynucleotide encoding an engineered GAA polypeptide comprises SEQ ID NO: 1, 5, 7, 11, 13, 15, 17, 19, 945, 1955, 2495, 2879, and/or 3103. In some embodiments, the polynucleotide encoding an engineered GAA polypeptide consists of SEQ ID NO: 1, 5, 7, 11, 13, 15, 17, 19, 945, 1955, 2495, 2879, and/or 3103. In some embodiments, the polynucleotides are capable of hybridizing under highly stringent conditions to a reference polynucleotide sequence selected from SEQ ID NO: 1, 5, 7, 11, 13, 15, 17, 19, 945, 1955, 2495, 2879, and/or 3103, or a complement thereof, or a polynucleotide sequence encoding any of the variant GAA polypeptides provided herein.

In some embodiments, an isolated polynucleotide encoding any of the engineered GAA polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, Kozak sequence, leader sequences, polyadenylation sequences, propeptide sequences, signal peptide sequences, DNA based regulatory elements for gene therapy retention and transcription terminators. As known in the art, suitable promoters can be selected based on the host cells used. For bacterial host cells, suitable promoters for directing transcription of the nucleic acid constructs of the present application, include, but are not limited to the promoters obtained from the E. coli lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomnucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/ GAP), and *Saccharomyces cerevisiae* 3-phosphoglycerate kinase. Other useful promoters for yeast host cells are known in the art (See e.g., Romanos et al., Yeast 8:423-488 [1992]). Exemplary promoters for use in mammalian cells include, but are not limited to those from cytomegalovirus (CMV), chicken β-actin promoter fused with the CMV enhancer, Simian vacuolating virus 40 (SV40), from *Homo sapiens* phosphorglycerate kinase, beta actin, elongation factor-1a or glyceraldehyde-3-phosphate dehydrogenase, or from *Gallus gallus* β-actin.

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra). Exemplary terminators for mammalian cells include, but are not limited to those from cytomegalovirus (CMV), Simian vacuolating virus 40 (SV40), from *Homo sapiens* growth hormone hGH, from bovine growth hormone BGH, and from human or rabbit beta globulin.

In some embodiments, the control sequence is a suitable leader sequence, 5'-cap modification, 5' UTR, etc. In some embodiments, these regulatory sequence elements mediate binding to molecules involved in mRNA trafficking and translation, inhibit 5'-exonucleolytic degradation and confer resistance to de-capping. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/ glyceraldehyde-3-phosphate dehydrogenase (ADH2/GAP). Suitable leaders for mammalian host cells include but are not limited to the 5'-UTR element present in orthopoxvirus mRNA.

In some embodiments, the control sequence comprises a 3' untranslated nucleic acid region and polyadenylation tail nucleic acid sequence, sequences operably linked to the 3' terminus of the protein coding nucleic acid sequence and which mediate binding to proteins involved in mRNA trafficking and translation and mRNA half-life. Any polyadenylation sequence and 3' UTR which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Biol., 15:5983-5990 [1995]). Useful polyadenylation and 3' UTR sequences for mammalian host cells include, but are not limited to the 3'-UTIRs of α- and β-globin mRNAs that harbor several sequence elements that increase the stability and translation of mRNA.

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered GAA polypeptides provided herein. Effective signal peptide coding regions for bacterial host cells include, but are not limited to the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomiucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase. Un some embodiments, the *S. cerevisiae* a-mating factor prepro peptide (Mfalpha) finds use (e.g., SEQ ID NOS: 3383 and 3384). Useful signal peptides for mammalian host cells include, but are not limited to those from the genes for immunoglobulin gamma (IgG). Additional signal peptides useful for mammalian hosts include mouse signal peptides. In some embodiments, a synthetic mouse IG signal peptide finds use (e.g., SEQ ID NOS: 3381 and 3382).

In some embodiments, the control sequence is a propeptide coding region that codes for an amino acid sequence positioned at the amino terminus of a polypeptide. The resultant polypeptide is referred to as a "proenzyme," "propolypeptide," or "zymogen," in some cases). A propolypeptide can be converted to a mature active polypeptide by catalytic or autocatalytic cleavage of the propeptide from the propolypeptide. The propeptide coding region includes, but is not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention also provides a recombinant expression vector comprising a polynucleotide encoding an engineered GAA polypeptide, and one or more expression regulating regions such as a promoter and a terminator, a replication origin, etc., depending on the type of hosts into which they are to be introduced. in some embodiments, the various nucleic acid and control sequences described above are joined together to produce a recombinant expression vector which includes one or more convenient restriction sites to allow for insertion or substitution of the nucleic acid sequence encoding the variant GAA polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any suitable vector (e.g., a plasmid or virus including but not limited to adenovirus (AV), adeno-associated virus (AAV), lentivirus (LV), and non-viral vectors, such as liposomes), that can be conveniently subjected to recombinant DNA procedures and can result in the expression of the variant GAA polynucleotide sequence. The choice of the vector will typically depend on the compatibility of the vector with the host cell into which the vector is to be introduced. The vectors may be linear or closed circular plasmids. Indeed, it is not intended that the present invention be limited to any specific vector.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector is pDH. A plasmid map of this vector containing SEQ ID NO:1 is provided in FIG. 9. The sequence of this plasmid is provided as SEQ ID NO: 3379. A plasmid map of this vector containing a beta-lactamase stuffer sequence is provided in FIG. 10. The sequence of this plasmid is provided as SEQ ID NO: 3380. It is contemplated that the pDH vector will find use in expression of various genes, including but not limited to the polynucleotide sequences encoding the acid alpha-glucosidases provided herein. Indeed, it is contemplated that the stuffer sequence (or SEQ ID NO: 1 present in SEQ ID NO: 3379) will be substituted with any suitable gene of interest.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered GAA polypeptide of the present application, the polynucleotide being operatively linked to one or more control sequences for expression of the engineered GAA enzyme(s) in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells, fungal cells, such as yeast cells (e.g., *Saccharomyces cerevisiae* and *Pichia pastoris* [ATCC Accession No. 201178]); insect cells such as *Drosophila* S2 and *Spodoptera* Sf9 cells; animal cells (e.g., CHO, CHO-K1, COS, and BHK), and human cells (e.g., HEK293T, human fibroblast, THP-1, Jurkat and Bowes melanoma cell lines); and plant cells.

Accordingly, in another aspect, the present invention provides methods for producing the engineered GAA polypeptides, where the methods comprise culturing a host cell capable of expressing a polynucleotide encoding the engineered GAA polypeptide under conditions suitable for expression of the polypeptide. In some embodiments, the methods further comprise the steps of isolating and/or purifying the GAA polypeptides, as described herein.

Appropriate culture media and growth conditions for the above-described host cells are well known in the art. Polynucleotides for expression of the GAA polypeptides may be introduced into cells by various methods known in the art. Techniques include, among others, electroporation, biolistic particle bombardment, liposome mediated transfection, calcium chloride transfection, and protoplast fusion.

The engineered GAA with the properties disclosed herein can be obtained by subjecting the polynucleotide encoding the naturally occurring or engineered GAA polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, 9,684,771, 9,665,694; and WO 95/22625; WO 97/0078; WO 97/35966; WO 98/27230; WO 00/42651; WO 01/75767; WO 2009/152336, WO 2013/138339, WO 2015/048572, and WO 2015/048573; and all related US and non-US counterparts of these listed patents and applications; Ling et al., Anal. Biochem., 254:157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; and Stemmer, Proc. Nat. Acad. Sci. USA, 91:10747-10751 [1994]; all of which are incorporated herein by reference).

In some embodiments, the enzyme clones obtained following mutagenesis treatment are screened by subjecting the enzymes to a defined temperature (or other assay conditions) and measuring the amount of enzyme activity remaining after heat treatments or other assay conditions.

Clones containing a polynucleotide encoding a GAA polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tetra. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer), purified, annealed, ligated and cloned in appropriate vectors.

Accordingly, in some embodiments, a method for preparing the engineered GAA polypeptide can comprise: (a) synthesizing a polynucleotide encoding a polypeptide comprising an amino acid sequence selected from the amino acid sequence of any variant provided in Table 3-1, 3-2, 4-1, 6-1, 10-1, 10-2, 12-1, 13-1, 13-2, 14-1, 14-2, 15-1, 16-1, 17-1, 17-2, 17-3, 17-4, 17-5, 17-6, 17-7, 17-8, and/or 17-9, as well as SEQ ID NOS: 2, 6, 8, 12, 14, 16, 18, 20, 946, 1956, 2496, 2880, and/or 3104, and (b) expressing the GAA polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered GAA polypeptide can be measured for any desired improved property (e.g., activity, selectivity, stability, acid tolerance, protease sensitivity, etc.), using any suitable assay known in the art, including but not limited to the assays and conditions described herein.

In some embodiments, any, some, or all of the engineered GAA polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the GAA polypeptides include, among others, reverse phase chromatography high performance liquid chromatography, ion exchange chromatography, hydrophobic interaction chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved variant GAA enzymes. In some embodiments utilizing affinity chromatography purification, any antibody which specifically binds the variant GAA polypeptide finds use. For the production of antibodies, various host animals, including but not limited to rabbits, mice, rats, etc., are immunized by injection with a GAA polypeptide (e.g., a GAA variant), or a fragment thereof. In some embodiments, the GAA polypeptide or fragment is attached to a suitable carrier, such as BSA, by means of a side chain functional group or linkers attached to a side chain functional group.

In some embodiments, the engineered GAA polypeptide is produced in a host cell by a method comprising culturing a host cell (e.g., *S. cerevisiae, Daucus carota, Nicotiana tabacum, H. sapiens* [e.g., HEK293T], or *Cricetulus griseus* [e.g., CHO]) comprising a polynucleotide sequence encoding an engineered GAA polypeptide as described herein under conditions conducive to the production of the engineered GAA polypeptide and recovering the engineered GAA polypeptide from the cells and/or culture medium.

In some embodiments, the engineered GAA polypeptide is produced in a host cell by a method comprising culturing a host cell comprising a polynucleotide sequence encoding an engineered GAA polypeptide as described herein under conditions conducive to the production of the engineered GAA polypeptide and recovering the engineered GAA polypeptide from the cells and/or culture medium.

In some preferred embodiments, the invention encompasses a method of producing an engineered GAA polypeptide comprising culturing a recombinant bacterial cell comprising a polynucleotide sequence encoding an engineered GAA polypeptide having at least 85%, 90%, 95%, 96%, 97%, 98%, 99%, or 100% sequence identity to reference sequences SEQ ID NO: 2, 6, 8, 12, 14, 16, 18, 20, 946, 1956, 2496, 2880, and/or 3104, and one or more amino acid residue differences as compared to SEQ ID NO: 2, 6, 8, 12, 14, 16, 18, 20, 946, 1956, 2496, 2880, and/or 3104, and/or combinations thereof when aligned, under suitable culture conditions to allow the production of the engineered GAA polypeptide and optionally recovering the engineered GAA polypeptide from the culture and/or cultured bacterial cells.

In some embodiments, once the engineered GAA polypeptides are recovered from the recombinant host cells or cell culture and they are further purified by any suitable method(s) known in the art. In some additional embodiments, the purified GAA polypeptides are combined with other ingredients and compounds to provide compositions and formulations comprising the engineered GAA polypeptide as appropriate for different applications and uses (e.g., pharmaceutical compositions).

Compositions:

The present invention provides engineered GAA polypeptides suitable for use in pharmaceutical and other compositions, such as dietary/nutritional supplements, as well as for other purposes.

Pharmaceutical Compositions:

Depending on the mode of administration, the compositions comprising a therapeutically effective amount of an engineered GAA according to the present invention are in the form of a solid, semi-solid, gel, or liquid. In some embodiments, the compositions include other pharmaceutically acceptable components such as diluents, buffers, excipients, salts, emulsifiers, preservatives, stabilizers, fillers, and other ingredients. Details on techniques for formulation and administration are well known in the art and described in the literature.

In some embodiments, the engineered GAA polypeptides are formulated for use in oral pharmaceutical compositions. Any suitable format for use in delivering the engineered GAA polypeptides find use in the present invention, including but not limited to pills, tablets, gel tabs, capsules, lozenges, dragees, powders, soft gels, sol-gels, gels, emulsions, implants, patches, sprays, ointments, liniments, creams, pastes, jellies, paints, aerosols, chewing gums, demulcents, sticks, suspensions (including but not limited to oil-based suspensions, oil-in water emulsions, etc.), slurries, syrups, controlled release formulations, suppositories, etc. In some embodiments, the engineered GAA polypeptides are provided in a format suitable for injection (i.e., in an injectable formulation). In some embodiments, the engineered GAA polypeptides are provided in biocompatible matrices such as sol-gels, including silica-based (e.g., oxysilane) sol-gels. In some embodiments, the engineered GAA polypeptides are encapsulated. In some alternative embodiments, the engineered GAA polypeptides are encapsulated in nanostructures (e.g., nanotubes, nanotubules, nanocapsules, or microcapsules, microspheres, liposomes, etc.). Indeed, it is not intended that the present invention be limited to any particular delivery formulation and/or means of delivery. It is intended that the engineered GAA polypeptides be administered by any suitable means known in the art, including but not limited to parenteral, oral, topical, transdermal, intranasal, intraocular, intrathecal, via implants, etc.

In some embodiments, the engineered GAA polypeptides are chemically modified by glycosylation, pegylation (i.e., modified with polyethylene glycol [PEG] or activated PEG, etc.) or other compounds (See e.g., Ikeda, Amino Acids 29:283-287 [2005]; U.S. Pat. Nos. 7,531,341, 7,534,595, 7,560,263, and 7,53,653; US Pat. Appln. Publ. Nos. 2013/0039898, 2012/0177722, etc.). Indeed, it is not intended that the present invention be limited to any particular delivery method and/or mechanism.

In some additional embodiments, the engineered GAA polypeptides are provided for delivery to cells or tissues via gene therapy, including viral delivery vectors, including but not limited to adenovirus (AV), adeno-associated virus (AAV), lentivirus (LV), or non-viral vectors (e.g., liposomes). In some embodiments, the engineered GAA polypeptides are provided for delivery to cells or tissues via mRNA therapy following formulation of polyribonucleotide sequences in a encapsulated delivery, such as liposomes. In some additional embodiments, the engineered GAA polypeptides are provided for delivery to cells or tissues via cell therapy, where the polynucleotide sequence encoding the engineered GAA polypeptides is introduced into exogenous cell and that cell (or cells) are introduced into a recipient (e.g., a patient exhibiting or at risk for developing Pompe disease).

In some additional embodiments, the engineered GAA polypeptides are provided in formulations comprising matrix-stabilized enzyme crystals. In some embodiments, the formulation comprises a cross-linked crystalline engineered GAA enzyme and a polymer with a reactive moiety that adheres to the enzyme crystals. The present invention also provides engineered GAA polypeptides in polymers.

In some embodiments, compositions comprising the engineered GAA polypeptides of the present invention include one or more commonly used carrier compounds, including but not limited to sugars (e.g., lactose, sucrose, mannitol, and/or sorbitol), starches (e.g., corn, wheat, rice, potato, or other plant starch), cellulose (e.g., methyl cellulose, hydroxypropylmethyl cellulose, sodium carboxy-methylcellulose), gums (e.g., arabic, tragacanth, guar, etc.), and/or proteins (e.g., gelatin, collagen, etc.). Additional components in oral formulations may include coloring and or sweetening agents (e.g., glucose, sucrose, and mannitol) and lubricating agents (e.g., magnesium stearate), as well as enteric coatings (e.g., methacrylate polymers, hydroxyl propyl methyl cellulose phthalate, and/or any other suitable enteric coating known in the art). In some embodiments, disintegrating or solubilizing agents are included (e.g., cross-linked polyvinyl pyrrolidone, agar, alginic acid or salts thereof, such as sodium alginate). In some embodiments, the engineered GAA polypeptide are be combined with various additional components, including but not limited to preservatives, suspending agents, thickening agents, wetting agents, alcohols, fatty acids, and/or emulsifiers, particularly in liquid formulations. In some embodiments, the engineered GAA polypeptides are administered to subjects in combination with other compounds, molecules, and/or materials used in the treatment of Pompe disease, including but not limited to pharmacological chaperones, as well as any other suitable compounds. In some additional embodiments, the pharmaceutical composition is suitable for parenteral injection into a human. In some embodiments, the pharmaceutical composition comprises a pill, tablet, capsule, or gelcap that further comprises an enteric coating.

In some embodiments, the present invention provides engineered GAA polypeptides suitable for use in decreasing the concentration of glycogen in tissues. The dosages of engineered GAA polypeptide(s) administered to an animal depend upon the condition or disease, the general condition of the animal, and other factors known to those in the art. In some embodiments, the compositions are intended for single or multiple administrations to an animal. In some embodiments, it is contemplated that the concentration of engineered GAA polypeptide(s) in the composition(s) administered to an animal (e.g., a human with Pompe disease) is sufficient to effectively treat, ameliorate and/or prevent the symptoms of disease (e.g., Pompe disease and/or Pompe disease-related conditions, diseases and/or symptoms), In some embodiments, the engineered GAA polypeptides are administered in combination with other pharmaceutical and/or dietary compositions.

The foregoing and other aspects of the invention may be better understood in connection with the following non-limiting examples. The examples are provided for illustrative purposes only and are not intended to limit the scope of the present invention in any way.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); CDS (coding sequence); DNA (deoxyribonucleic acid); RNA (ribonucleic acid); E. coli W3110 (commonly used laboratory E. coli strain, available from the Coli Genetic Stock Center [CGSC], New Haven, CT); DPBS (Dulbecco's phosphate buffered saline); LB (Luria-Burtani); TB (terrific broth); 4-MUGlu (4-methylumbelliferyl α-D-glucopyranoside; SD-Ura (single drop out medium without uracil); HPLC (high pressure liquid chromatography); SDS-PAGE (sodium dodecyl sulfate polyacrylamide gel electrophoresis); MU-Glu (4-methylumbelliferyl α-D-glucopyranoside); IPTG (isopropyl β-D-1-thiogalactopyranoside); PMBS (polymyxin B sulfate); FIOPC (fold improvements over positive control); PBMC (peripheral blood mononuclear cells); LB (Luria broth); MeOH (methanol); Axygen (Axygen, Inc., Union City, CA); Athens Research (Athens Research Technology, Athens, GA); ProSpec (ProSpec Tany Technogene, East Brunswick, NJ); Sigma-Aldrich (Sigma-Aldrich, St. Louis, MO); Ram Scientific (Ram Scientific, Inc., Yonkers, NY); Pall Corp. (Pall, Corp., Pt. Washington, NY); Millipore (Millipore, Corp., Billerica MA); Difco (Difco Laboratories, BD Diagnostic Systems, Detroit, MI); Molecular Devices (Molecular Devices, LLC, Sunnyvale, CA); Kuhner (Adolf Kuhner, AG, Basel, Switzerland); Microfluidics (Microfluidics Corp., Westwood, MA); Thermotron (Thermotron, Inc., Holland, MI); Cambridge Isotope Laboratories, (Cambridge Isotope Laboratories, Inc., Tewksbury, MA); Applied Biosystems (Applied Biosystems, part of Life Technologies, Corp., Grand Island, NY); Greiner Bio-One (Greiner Bio-One North America, Monroe, NC); Agilent (Agilent Technologies, Inc., Santa Clara, CA); Thermo Scientific (part of Thermo Fisher Scientific, Waltham, MA); Corning (Corning, Inc., Palo Alto, CA); Megazyme (Megazyme International, Wicklow, Ireland); Enzo (Enzo Life Sciences, Inc., Farmingdale, NY); GE Healthcare (GE Healthcare Bio-Sciences, Piscataway, NJ); Pierce (Pierce Biotechnology (now part of Thermo Fisher Scientific), Rockford, IL); Phenomenex (Phenomenex, Inc., Torrance, CA); Optimal (Optimal Biotech Group, Belmont, CA); and Bio-Rad (Bio-Rad Laboratories, Hercules, CA).

Example 1

GAA Gene Acquisition and Construction of Expression Vectors

In this Example, GAA gene acquisition and expression vector construction are described. A synthetic gene coding for a WT human GAA (Uniprot ID P10253) with the native signal peptide removed was designed for optimized gene expression in *Saccharomyces cerevisiae* and fused to the yeast MFα signal peptide sequence (SEQ ID NO: 3383) to generate the gene sequence represented by SEQ ID NO:2, which was cloned into the yeast expression vector pYT-72, as previously described (See e.g. US Pat. Appln. Publn. No. 2017/0360900 A1). Recombination cloning and gene expression were performed in *S. cerevisiae* strain INVSc1. Directed evolution techniques were used to generate libraries of gene variants from this plasmid construct (See e.g., U.S. Pat. No. 8,383,346 and WO2010/144103).

For secreted expression and transient transfection in mammalian cells, a chimeric GAA expression construct encoding the synthetic mouse IG signal peptide (residues 1-19 of Uniprot accession number: A0N1R5; SEQ ID NO: 3381) fused to a synthetic gene coding for the different GAA variants was generated as follows. In some embodiments, the synthetic GAA gene variants are based on a GAA sequence that is codon-optimized for yeast (SEQ ID NO: 3), while in some alternative embodiments, the synthetic GAA variants are based on a GAA sequence that is codon-optimized for mammalian (SEQ ID NO: 5) expression. Oligonucleotides containing restriction enzyme flanks to enable cloning into either the BamHI/XIwI site or HindIII/XhoI site were used to amplify a fragment coding for the synthetic mouse IG signal peptide (SEQ ID NOS: 3381 and 3382) and the coding sequence for the mature form of GAA. For mammalian expression, the PCR product was ligated into the linearized vector pcDNA3.1(+) either at the BamHI/XhoI site or HindIII/XhoI site (Invitrogen). Directed evolution was used to generate specific gene variants derived from SEQ ID NOS: 18 to 828, within the pcDNA3.1(+) plasmid construct (See e.g., U.S. Pat. No. 8,383,346 and WO2010/144103, each of which is incorporated by reference in its entirety).

Figure 9:
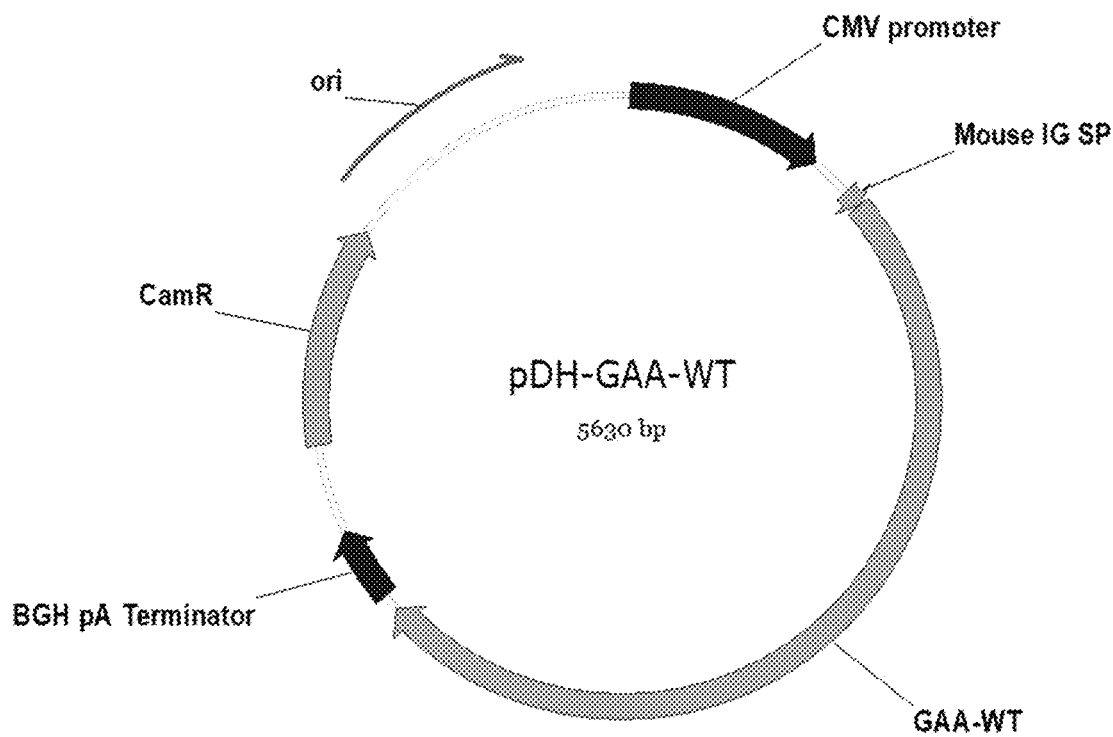
FIG. 9 provides a plasmid map of the pDH vector containing WT GAA.
Figure 10:
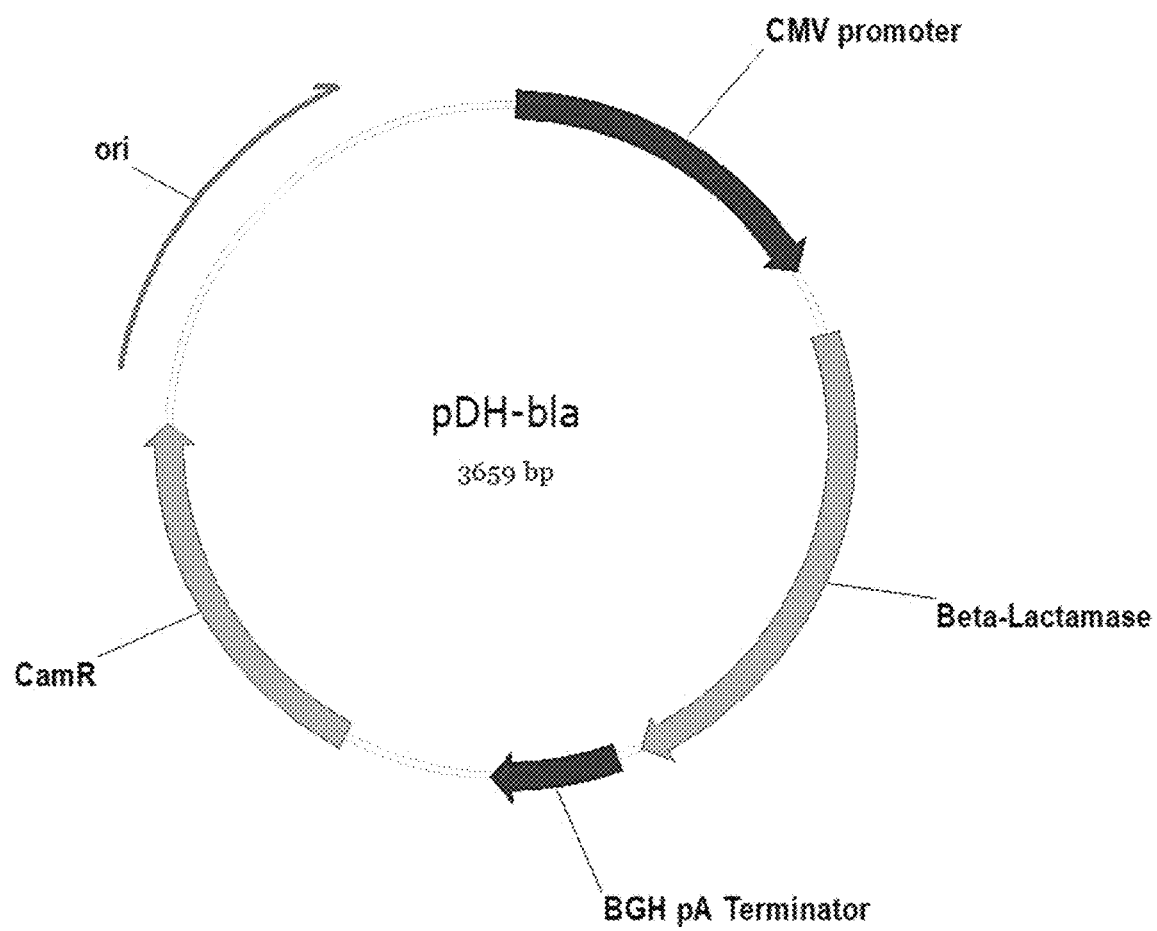
FIG. 10 provides a plasmid map showing the pDH vector comprising the stuffer sequence bla (i.e., beta-lactamase).

The pDH vector was generated to optimize for vector copy number, desired selection drug, and base pair length, to enable compatibility with library variant generation. For mammalian expression, the PCR product was ligated into the linearized vector pDH either at the BamHI/XhoI site or HindIII/XhoI site. Directed evolution was used to generate specific gene variants (SEQ ID NOS: 829 to 3378) derived from SEQ ID NO: 20, within the pDH plasmid construct. A plasmid map for pDH containing WT GAA is shown in FIG. 9 and the plasmid sequence is provided as SEQ ID NO: 3379. In addition, a plasmid map for pDH containing a beta-lactamase (bla) stuffer sequence is provided in FIG. 10 and the sequence is provided as SEQ ID NO: 3380.

In some experiments, expression of GAA variants was performed using a linear PCR amplification product of the expression cassettes described above (i.e., a chimeric expression construct composed of the synthetic mouse IG signal peptide (residues 1-19 of Uniprot accession number: A0N1R5; SEQ ID NO: 3381) fused to a synthetic gene coding for the different GAA variants) in pcDNA3.1(+) or pDH. PCR amplification was performed with optimizations generally known by those skilled in the art with primer pair (SEQ ID NOS: 3387 and 3388) for pcDNA3.1(+) and primer pair (SEQ ID NOS: 3385 and 3386; or SEQ ID NOS: 3387 and 3388) for pDH. In some cases, phosphorothioate primers were used.

Example 2

High-Throughput Growth of *Saccharomyces cerevisiae* and GAA Assays

In this Example, experiments involving high-throughput growth of cells producing GAA variants, and assays to determine GAA activity are described.
High-Throughput (HTP) Growth of *S. cerevisiae*
Yeast (INVSc1) cells transformed with vectors expressing GAA and GAA variants using the lithium acetate method as known in the art, were selected on SD-Ura agar plates. After 72 h incubation at 30° C., colonies were placed into the wells of AXYGEN® 1.1 ml 96-well deep well plates (Axygen) filled with 200 µl/well SD-Ura broth (2 g/L SD-Ura, 6.8 g/L yeast nitrogen base without amino acids [Sigma Aldrich]), 3.06 g/L sodium dihydrogen phosphate, 0.804 g/L disodium hydrogen phosphate, pH 6.0, supplemented with 6% glucose. The cells were grown for 20-24 hours in a Kuhner shaker (250 rpm, 30° C., and 85% relative humidity). Overnight culture samples (20 µL) were transferred into COSTAR® 96-well deep plates (Corning), filled with 380 µL of SD-ura broth supplemented with 2% glucose. The plates were incubated for 66-84 h in a Kuhner shaker (250 rpm, 30° C., and 85% relative humidity). The cells were then pelleted (4000 rpm×20 min), and the supernatants (conditioned media) stored at 4° C. until analyzed.
HTP-Analysis of Supernatants
GAA variant activity was determined by measuring the hydrolysis of 4-methylumbelliferyl α-D-glucopyranoside (4-MUGlu). For the unchallenged assay, 50 µL of SD-URA conditioned media produced as described above was mixed with 50 µL of 1 mM 4-MUGlu in McIlvaine Buffer (McIlvaine, J. Biol. Chem., 49:183-186 [1921]), pH 4.5, in a 96-well, black, opaque bottom plate. The reactions were mixed briefly and incubated at 37° C. for 4-24 hours, prior to quenching with 100 µL of 0.5 M sodium carbonate pH 10.5. Hydrolysis was analyzed using a SPECTRAMAX® M2 microplate reader (Molecular Devices), by monitoring fluorescence (Ex. 355 nm, Em. 460 nm).
HTP-Analysis of Supernatants Challenged with Neutral Buffer
GAA variants were challenged with neutral to near neutral (pH 6.5-7.5) buffer to simulate the pH that the variants encounter in the blood following their administration to a patient. First, 50 µL of GAA variants in SD-URA conditioned media and 50 µL of McIlvaine buffer (pH 6.5-7.4) were added to the wells of a 96-well round bottom plate. The plates were sealed and incubated at 37° C. for 1 h. Then, 50 µL of each challenged sample were mixed with 50 µL of 1 mM 4-MUGlu in McIlvaine buffer pH 4.4. The reactions were mixed briefly and incubated at 37° C. for 4-24 hrs, prior to quenching with 100 µL of 0.5 M sodium carbonate, pH 10.5. Hydrolysis was analyzed using a SPECTRAMAX® M2 microplate reader (Molecular Devices) by monitoring fluorescence (Ex. 355 nm, Em. 460 nm).
HTP-Analysis of Supernatants Pretreated with Acid
GAA variants were challenged with acidic (pH 3) buffer to simulate the pH that the variants encounter in the lysosome following their administration to a patient. First, 50 µL of GAA variants in SD-URA conditioned media and 50 µL of McIlvaine buffer (pH 3) were added to the wells of a 96-well round bottom plate. The plates were sealed and incubated at 37° C. for 1 h. Then, 50 µL of each challenged sample were mixed with 50 µL of 1 mM 4-MUGlu in McIlvaine buffer pH 4.4. The reactions were mixed briefly and incubated at 37° C. for 4-24 hrs, prior to quenching with 100 µL of 0.5 M sodium carbonate pH 10.5. Hydrolysis was analyzed using a SPECTRAMAX® M2 microplate reader (Molecular Devices) monitoring fluorescence (Ex. 355 nm, Em. 460 nm).
HTP-Analysis of Supernatants with Glycogen Substrate
The hydrolytic activity of the GAA variants was determined by measuring the hydrolysis of glycogen to glucose. For the unchallenged assay, 50 µL of SD-URA conditioned media produced as described above was mixed with 50 µL of 5 mM glycogen in pH 4.5 McIlvaine buffer (7.71 mL of 0.2 M $Na_2HPO_4$ and 12.29 of 0.1 M citric acid) in a 96-well, black, opaque bottom plate. The reactions were mixed briefly and incubated at 37° C. for 24 hours. After incubation, 20 uL of the glycogen hydrolysis reaction mixtures were mixed with 80 uL of AMPLEX® Red Glucose Assay Kit (Sigma) to determine the glucose content of each reaction. Hydrolysis was analyzed using a SPECTRAMAX® M2 microplate reader (Molecular Devices) by monitoring fluorescence (Ex. 544 nm, Em. 585 nm)

Example 3

GAA and GAA Variants

GAA and GAA variant activity was determined by assaying the enzyme activity after a series of independent challenges. The results for all of the variants and the substitutions in each of the polypeptide sequences are reported in reference to SEQ ID NO: 2. These variants were tested for GAA 4-MUGlu activity (Unchallenged Activity FIOPC), after pH 6.5 incubation (pH 6.5 Stability Activity FIOPC), and for glycogen hydrolysis (Glycogen Activity FIOPC), as described in Example 2. Tables 3-1 and 3-2 provide the results of these assays.

TABLE 3-1

Activity of GAA Variants Under Various Conditions[1]

| SEQ ID NO: (nt/aa) | Amino Acid Differences (Relative to SEQ ID NO: 2) | Unchallenged Activity FIOPC | pH 6.5 Stability Activity FIOPC | Glycogen Activity FIOPC |
|---|---|---|---|---|
| 21/22 | A276F | ++ | +++ | + |
| 23/24 | A276Y | +++ | +++ | + |
| 25/26 | A418E/H499R | | | ++ |

TABLE 3-1-continued

Activity of GAA Variants Under Various Conditions[1]

| SEQ ID NO: (nt/aa) | Amino Acid Differences (Relative to SEQ ID NO: 2) | Unchallenged Activity FIOPC | pH 6.5 Stability Activity FIOPC | Glycogen Activity FIOPC |
|---|---|---|---|---|
| 27/28 | A418R | | ++ | + |
| 29/30 | A437S | + | + | |
| 31/32 | A444T | | ++ | + |
| 33/34 | A489R | ++ | ++ | ++ |
| 35/36 | A547G | + | ++ | |
| 37/38 | A750P | + | + | + |
| 39/40 | A753T | + | + | + |
| 41/42 | C930R | + | + | + |
| 43/44 | C944G | + | + | + |
| 45/46 | C944R | + | + | + |
| 47/48 | D274G | | ++ | |
| 49/50 | E137P | + | ++ | + |
| 51/52 | E463A | | ++ | + |
| 53/54 | F27P | ++ | ++ | + |
| 55/56 | F27P/C944W | ++ | ++ | ++ |
| 57/58 | F27R | | +++ | ++ |
| 59/60 | G426R | | ++ | + |
| 61/62 | G820E | | ++ | + |
| 63/64 | I375E | ++ | ++ | + |
| 65/66 | K471Q/A478S | + | + | + |
| 67/68 | K471S | + | + | |
| 69/70 | K581G | + | | + |
| 71/72 | K581T | ++ | ++ | ++ |
| 73/74 | K725N/V732I | + | ++ | |
| 75/76 | K88G | ++ | ++ | |
| 77/78 | K88S | | ++ | |
| 79/80 | K895R | | ++ | ++ |
| 81/82 | L109G/G842E | ++ | +++ | + |
| 83/84 | L109P | + | + | + |
| 85/86 | L28P | ++ | + | + |
| 87/88 | L28R | ++ | + | ++ |
| 89/90 | L28S | ++ | ++ | ++ |
| 91/92 | L29T/A478T | + | ++ | ++ |
| 93/94 | L642M | ++ | ++ | + |
| 95/96 | L642Q | ++ | ++ | + |
| 97/98 | L642S | ++ | ++ | + |
| 99/100 | L670N | | ++ | |
| 101/102 | L871E | | ++ | + |
| 103/104 | L934R | ++ | ++ | ++ |
| 105/106 | M138A | + | + | ++ |
| 107/108 | N527R | | ++ | + |
| 109/110 | Q107G | | ++ | + |
| 111/112 | Q107P | | | + |
| 113/114 | Q110G | | +++ | + |
| 115/116 | Q110L | | ++ | + |
| 117/118 | Q113S | + | + | ++ |
| 119/120 | Q247R | | + | + |
| 121/122 | Q421S | | | + |
| 123/124 | R403W | + | + | + |
| 125/126 | R414P | + | + | ++ |
| 127/128 | R455V | | | ++ |
| 129/130 | R786P | | ++ | + |
| 131/132 | R786Y | | ++ | |
| 133/134 | R862G | | ++ | + |
| 135/136 | S135A | | ++ | + |
| 137/138 | S135Q | + | +++ | ++ |
| 139/140 | S476A | | ++ | + |
| 141/142 | S476H | | ++ | |
| 143/144 | S668H | ++ | ++++ | |
| 145/146 | T148G | ++ | ++ | + |
| 147/148 | T148Y | + | + | |
| 149/150 | T150G | ++ | ++ | ++ |
| 151/152 | T278A | + | + | |
| 153/154 | T278G | | ++ | + |
| 155/156 | T692Q | + | + | + |
| 157/158 | T897V | | ++ | |
| 159/160 | V30G | | +++ | ++ |
| 161/162 | V30K | ++ | ++ | + |
| 163/164 | V30T | ++ | ++ | + |
| 165/166 | W610A | | ++ | + |
| 167/168 | W610G | ++ | ++ | |
| 169/170 | W610S | + | ++ | + |

[1]All activities were determined relative to the reference polypeptide of SEQ ID NO: 2. Levels of increased activity are defined as follows: ""+"" = 0.9 to 1.1; "++" > 1.1; "+++" > 2; and "++++" > 3.5.

TABLE 3-2

Activity of GAA Variants Relative to SEQ ID NO: 21

| SEQ ID NO: (nt/aa) | Amino Acid Differences (Relative to SEQ ID NO: 2) | Unchallenged Activity FIOPC | pH 6.5 Stability Activity FIOPC | Glycogen Activity FIOPC |
|---|---|---|---|---|
| 171/172 | G280D/S402A/V536I/D928T | | | ++ |
| 173/174 | H191R/G280D/S402A/R414G/A444P/G465E/G842S/D928T | + | + | ++ |
| 175/176 | L275V/A281V/S671N | ++ | + | ++ |
| 177/178 | K106P/H191R/R414G/A444P/E522V/D928T/C944S | ++ | + | + |
| 179/180 | H191R/G280D/R414G/A444P/A489D/D500A/E522V/G842S/D928T/C944S | ++ | ++ | ++ |
| 181/182 | K106P/H191R/R414G/A489D/D928T/C944S | ++ | ++ | |
| 183/184 | L275M/A281V/S402A/M431V/M507L/I518V/W610R/S668D | ++ | + | ++ |
| 185/186 | L275M/M507L/A547G/S668D/L669H/S671N | ++ | ++ | + |
| 187/188 | L275M/M431V/V638I | ++ | ++ | ++ |
| 189/190 | A281V/S402A/I518V/A547G/S668D | ++ | ++ | + |
| 191/192 | L275V/I518V/S671N | ++ | ++ | + |
| 193/194 | L275V/M431V/M507L/I518V/A547G/S668D/L669H/S671N | ++ | ++ | + |
| 195/196 | S402A/M431V/I518V/W610R | ++ | ++ | + |
| 197/198 | K106P/H191R/G280D/S402A/R414G/A444P/S727P | ++ | ++ | + |
| 199/200 | M431V/M507L/I518V/L669H/S671N | ++ | ++ | + |
| 201/202 | L275V/R377K/S402A/M507L/I518V/L669H/S671N/V715G | ++ | ++ | + |
| 203/204 | H191R/R414G/E522V/G842S/C944S | ++ | ++ | + |
| 205/206 | H191R/G280D/R414G/A489D/G842S/D928T/C944S | ++ | ++ | + |
| 207/208 | L275M/A281V/W610R/V638I/S668D/L669H | ++ | ++ | + |
| 209/210 | A196V/S402A/M431V/A547G/W610R/V638I | ++ | ++ | ++ |
| 211/212 | H191R/G280D/S402A/R414G/A444P/A489D/D500A/C944S | ++ | ++ | + |
| 213/214 | L275V/S402A/V638I/L669H/S671N | ++ | ++ | + |
| 215/216 | L29Q/L240I/A596P/S668D/I869L | ++ | ++ | ++ |
| 217/218 | K106P/G280D/S402A/R414G/A444P/A489D/S727P/C944S | ++ | ++ | ++ |
| 219/220 | L29Q/L240I/A596S/S668D/H700F/I744V/I869T | ++ | ++ | + |
| 221/222 | L218S/S668D/H700F/I869T | ++ | ++ | + |
| 223/224 | M507L/A547G/W610R | ++ | ++ | |
| 225/226 | A281V/M431V/M507L/I518V/A547G/W610R/V638I/S668D | ++ | ++ | ++ |
| 227/228 | H191R/G280D/R414G/A444P/A489D/E522V/S727P/C944S | ++ | ++ | + |
| 229/230 | L275V/S402A/M431V/I518V/W610R/V638I/L669H/S671N/P922L | ++ | ++ | |

TABLE 3-2-continued

Activity of GAA Variants Relative to SEQ ID NO: 21

| SEQ ID NO: (nt/aa) | Amino Acid Differences (Relative to SEQ ID NO: 2) | Unchallenged Activity FIOPC | pH 6.5 Stability Activity FIOPC | Glycogen Activity FIOPC |
|---|---|---|---|---|
| 231/232 | L29V/L218S/L240I/H700F/I869T | ++ | ++ | + |
| 233/234 | A547G/V638I/S668D | ++ | ++ | + |
| 235/236 | H191R/G280D/R414G/C944S | ++ | ++ | + |
| 237/238 | L275V/M431V/M507L/I518V/W610R/L669H/S671N | ++ | ++ | |
| 239/240 | L275M/S402A/M431V/M507L/A547G/S671N | ++ | ++ | |
| 241/242 | S402A/M431V/A547G/V638I/S671N | ++ | ++ | + |
| 243/244 | A281V/S402A/M507L/A547G/V638I/L669H/S671N | ++ | ++ | + |
| 245/246 | L275M/A281V/M507L/A547G/L669H/S671N | ++ | ++ | |
| 247/248 | L275M/M431V/I518V/A547G/V638I/S668D | ++ | ++ | |
| 249/250 | A547G/W610R/V638I/S671N | ++ | ++ | + |
| 251/252 | L275V/M431V/M507L/A547G/W610R/V638I/S671N | ++ | ++ | + |
| 253/254 | L275M/S402A/M507L/A547G/W610R/S671N | ++ | ++ | |
| 255/256 | L275M/A281V/S402A/I518V/A547G/W610R/V638I/S671N | ++ | ++ | |
| 257/258 | A281V/S402A/I518V/A547G/W610R/V638I/S668D/L669H | ++ | ++ | |
| 259/260 | L275M/A281V/S402A/A547G/W610R/V638I/L669H/S671N | ++ | ++ | |
| 261/262 | L275M/M431V/I518V/W610R/V638I/L669H/S671N | ++ | ++ | + |
| 263/264 | L29Q/L218S/L240I/S668D/H700F/I744V/I869L | ++ | ++ | ++ |
| 265/266 | A281V/S402A/M507L/I518V/A547G/W610R/V638I/L669H/S671N | ++ | ++ | + |
| 267/268 | S402A/M431V/I518V/A547G/S671N | ++ | ++ | |
| 269/270 | L275V/A281V/S402A/M431V/I518V/A547G/W610R/L669H/S671N | ++ | ++ | |
| 271/272 | L224F/S402A/M507L/I518V/A547G/V638I/S668D | ++ | ++ | ++ |
| 273/274 | N180H/S402A/M507L/A547G/W610R/S671N | ++ | ++ | + |
| 275/276 | L275M/A281V/S402A/M507L/I518V/A547G/V638I/L669H/S671N | ++ | ++ | |
| 277/278 | K106P/T150S/T486E/Q749E/E793K/R883H/Q894G | ++ | +++ | ++ |
| 279/280 | L275V/A281V/M431V/I518V/A547G/V638I/L669H/S671N | ++ | ++ | |
| 281/282 | L275V/S402A/A547G/W610R/V638I/L669H/S671N | ++ | ++ | |
| 283/284 | L275M/S402A/A547G/V638I/L669H/S671N | ++ | ++ | + |
| 285/286 | K106P/T150S/T486E/N527D/A750P/E793K | ++ | +++ | ++ |
| 287/288 | S402A/M431V/I518V/A547G/W610R/S668D | ++ | ++ | |
| 289/290 | T150S/L218S/N527D/Q749E/E793K | ++ | +++ | ++ |
| 291/292 | L275V/M507L/I518V/A547G/V638I/L669H/S671N | ++ | ++ | + |
| 293/294 | N180H/S402A/M431V/M507L/A547G/W610R/L669H/S671N/E793G | ++ | ++ | |
| 295/296 | L275V/M507L/I518V/A547G/W610R/V638I/S668D/L669H | ++ | ++ | + |
| 297/298 | L275V/S402A/M507L/A547G/W610R/V638I/S668D/L669H | ++ | ++ | + |
| 299/300 | M507L/A547G/V638I/L669H/S671N | +++ | ++ | + |
| 301/302 | K106P/T150S/N169S/L218S/Q749E/P800A | +++ | +++ | ++ |
| 303/304 | T150S/R414G/T486E/Q749E/A750P/E793K | +++ | +++ | ++ |
| 305/306 | K106P/T150S/L218S/R414G/T486E/L642F/A750P/E793K/R883H | +++ | +++ | ++ |
| 307/308 | N180H/L275M/S402A/I518V/A547G/W610R/V638I/L669H/S671N | +++ | ++ | |
| 309/310 | T150S/L218S/R414G/Q749E/E793K | +++ | +++ | + |
| 311/312 | L275V/M507L/A547G/W610R/V638I/L669H/S671N | +++ | ++ | + |
| 313/314 | T150S/R414G/T486E/N527D/A750P/Q894R | +++ | +++ | ++ |
| 315/316 | K106P/T150S/L218S/N527D/E793K/Q894G | +++ | +++ | ++ |
| 317/318 | T150S/N169S/L218S/R414G/N527D/E793K | +++ | +++ | ++ |
| 319/320 | K106P/T150S/L218S/E793K | +++ | +++ | ++ |
| 321/322 | K106P/T150S/R414G/Q749E/A750P/E793K/Q894R | +++ | +++ | ++ |
| 323/324 | K106P/T150S/N169S/N527D/Q749E/E793K/R883H | +++ | +++ | ++ |
| 325/326 | L275V/S402A/M507L/A547G/W610R/V638I/L669H/S671N | +++ | ++ | + |
| 327/328 | K106P/T150S/L218S/Q749E/A750P/E793K | +++ | +++ | ++ |
| 329/330 | M431V/M507L/I518V/G541E/A547G/V638I/L669H/S671N | +++ | +++ | + |
| 331/332 | T150S/L218S/R414G/T486A/A750P/E793K | +++ | +++ | ++ |
| 333/334 | T150S/L218S/Q749E/A750P/E793K | +++ | +++ | ++ |
| 335/336 | K106P/T150S/N169S/L218S/R414G/T486E/Q894G | +++ | +++ | ++ |
| 337/338 | T150S/L218S/R414G/T486E/A750P/E793K/R883H | +++ | +++ | ++ |
| 339/340 | K106P/T150S/N169S/L218S/R414G/Q749E/E793K | +++ | +++ | ++ |
| 341/342 | T269N/L275M/M431V/I518V/A547G/V638I/S668D/L669H | +++ | +++ | |
| 343/344 | K106P/T150S/R414G/Q749E/E793K/Q894R | +++ | +++ | ++ |
| 345/346 | K106P/T150S/L218S/N527D/Q749E/A750P/E793K | +++ | +++ | ++ |
| 347/348 | K106P/T150S/N169S/Q749E/E793K/R883H/Q894R | +++ | +++ | ++ |
| 349/350 | K106P/T150S/L218S/E793K/Q894R | +++ | +++ | ++ |
| 351/352 | K106P/T150S/N169S/L218S/T486E/N527D/Q749E/E793K/Q894R | +++ | +++ | ++ |
| 353/354 | K106P/T150S/L218S/R414G/T486E/A750P/E793K/Q894R | +++ | +++ | ++ |
| 355/356 | K106P/T150S/N169S/L218S/R414G/T486E/Q749E/E793K/R883H/Q894R | +++ | +++ | ++ |
| 357/358 | K106P/T150S/N169S/L218S/T486E/R883H | +++ | +++ | ++ |
| 359/360 | K106P/T150S/N169S/L218S/R414G/T486E/A750P/E793K/R883H/Q894R | +++ | +++ | ++ |
| 361/362 | G36R/K106P/T150S/L218S/N527D/A750P/R883H/Q894R | +++ | +++ | ++ |
| 363/364 | K106P/T150S/N169S/L218S/T486E/Q749E/R883H | +++ | +++ | ++ |
| 365/366 | K106P/N169S/V185G/L218S/R414G/Q749E/A750P/E793K | +++ | +++ | ++ |
| 367/368 | K106P/T150S/P245S/E793K/R883H/Q894R | +++ | +++ | +++ |
| 369/370 | K106P/T150S/N169S/L218S/R414G/Q749E/A750P/E793K/R883H | +++ | +++ | ++ |

TABLE 3-2-continued

Activity of GAA Variants Relative to SEQ ID NO: 21

| SEQ ID NO: (nt/aa) | Amino Acid Differences (Relative to SEQ ID NO: 2) | Unchallenged Activity FIOPC | pH 6.5 Stability Activity FIOPC | Glycogen Activity FIOPC |
|---|---|---|---|---|
| 373/374 | T150S/L218S/Q749E/E793K | +++ | +++ | ++ |
| 375/376 | T150S/L218S/R414G/Q749E/A750P/E793K/Q894R | +++ | +++ | ++ |
| 377/378 | K106P/T150S/N169S/R414G/T486E/Q749E/A750P/R883H | +++ | +++ | ++ |
| 379/380 | K106P/T150S/N169S/L218S/R414G/T486E/E793K/R883H | +++ | +++ | ++ |
| 381/382 | K106P/T150S/L218S/T486E/N527D/Q749E/Q894R | +++ | +++ | ++ |
| 383/384 | K106P/T150S/N169S/L218S/R414G/T486E/N527D/Q894R | +++ | +++ | ++ |
| 385/386 | T150S/L218S/R414G/T486E/Q749E/A750P | +++ | +++ | ++ |
| 387/388 | K106P/T150S/L218S/R414G/Q749E/E793K/R883H | +++ | +++ | ++ |
| 389/390 | K106P/T150S/N169S/L218S/R414G/T486E/N527D/A750P/Q894R | +++ | +++ | ++ |
| 391/392 | N169S/T486E/A750P/E793K/R883H | +++ | +++ | ++ |
| 7/8 | T150S/T486E/A750P/R883H/Q894G | +++ | ++++ | +++ |
| 393/394 | K106P/T150S/L218S/R414G/N527D/Q749E/A750P/R883H | +++ | ++++ | ++ |
| 395/396 | K106P/T150S/L218S/R414G/Q749E/A750P/E793K/R883H/Q894R | +++ | +++ | ++ |
| 397/398 | K106P/T150S/N169S/L218S/R414G/Q749E/E793K/R883H | +++ | ++++ | ++ |
| 399/400 | K106P/T150S/L218S/T486E/E793K/R883H | +++ | +++ | ++ |
| 401/402 | K106P/T150S/L218S/V331A/R414G/T486E/N527D/D733E/Q749E/E793K | +++ | ++++ | ++ |
| 403/404 | L275M/A281V/S402A/I518V/A547G/W610R/S668D/L669H/E887D | +++ | +++ | ++ |
| 405/406 | K106P/T150S/L218S/R414G/N527D/Q749E/E793K/R883H/Q894G | +++ | +++ | ++ |
| 407/408 | K106P/T150S/Q749E/E793K/R883H | +++ | ++++ | +++ |
| 409/410 | K106P/A112S/T150S/L218S/R414G/N527D/E793K/R883H | ++++ | ++++ | +++ |

[1]All activities were determined relative to the reference polypeptide of SEQ ID NO: 2. Levels of increased activity are defined as follows: ""+"" = 0.9 to 1.1; "++" > 1.1; "+++" > 2; and ++++ > 3.5

Example 4

GAA Variants of SEQ ID NO: 8

In this Example, analysis of GAA variants derived from SEQ ID NO: 8 for improved GAA activity after a series of challenges are described. Directed evolution of the GAA encoded by SEQ ID NO: 8 was carried out by constructing libraries of variant genes. These libraries were then plated, grown, and screened for GAA 4-MUGlu activity after in the unchallenged, no pre-incubation, activity assay (Unchallenged Activity FIOPC), after pH 7 incubation (pH 7 Stability Activity FIOPC), or after pH 3 incubation (pH 3 Stability Activity FIOPC), as described in Example 2. The results are presented in Table 4-1.

TABLE 4-1

Activity of GAA Variants Relative to SEQ ID NO: 81

| SEQ ID NO: (nt/aa) | Amino Acid Differences (Relative to SEQ ID NO: 8) | Unchallenged Activity FIOPC | pH 3 Stability Activity FIOPC | pH 7 Stability Activity FIOPC |
|---|---|---|---|---|
| 411/412 | A281V/M431V/A489R/S668D | +++ | +++ | +++ |
| 413/414 | A418E | ++++ | +++++ | ++++ |
| 415/416 | A418E/A489R | + | ++ | + |
| 417/418 | A489R/L934R | + | + | |
| 419/420 | A489R/Q749E | + | + | |
| 421/422 | A489R/S671N/L934R | + | + | |
| 423/424 | A489R/V638I/L934R | ++ | ++ | ++ |
| 425/426 | F27P/A418E/A478T | + | + | +++ |
| 427/428 | F27P/L28S/A489R | + | +++ | ++ |
| 429/430 | F27R | + | + | ++ |
| 431/432 | K106P | ++ | +++ | ++ |
| 433/434 | K106P/A489R/S671N | +++ | ++ | +++ |
| 435/436 | K106P/L218S/A281V | ++ | +++ | ++ |
| 437/438 | K106P/L218S/R455V | +++ | +++ | +++ |
| 439/440 | K106P/L218S/R455V/M507L/Q749E | +++ | +++ | +++ |
| 441/442 | K106P/M138A/L218S/M431V/S671N/Q749E | +++ | | ++ |
| 443/444 | K106P/S671N/L934R | + | | + |
| 445/446 | K106P/V638I | + | +++ | + |
| 447/448 | L157M | +++ | +++ | +++ |
| 449/450 | L218S | + | ++ | + |
| 451/452 | L218S/A281V | ++ | +++ | ++ |
| 453/454 | L218S/A281V/M431V | +++ | +++ | +++ |
| 455/456 | L218S/A281V/S671N | + | | |
| 457/458 | L218S/M431V | + | + | |
| 459/460 | L218S/M431V/A489R/M507L/Q749E/L934R | +++ | ++ | +++ |
| 461/462 | L218S/M507L/L934R | + | + | + |
| 463/464 | L218S/M507L/Q749E | +++ | ++ | +++ |
| 465/466 | L218S/Q749E | +++ | +++ | +++ |
| 467/468 | L218S/R455V | + | + | + |
| 469/470 | L218S/V638I/S671N | +++ | +++ | +++ |
| 471/472 | L28S | + | ++ | + |
| 473/474 | L28S/L29T | + | + | + |
| 475/476 | L28S/L29T/A418E | ++ | +++ | ++ |
| 477/478 | L28S/L29T/Q113S/S135Q/A418E | + | ++++ | +++ |
| 479/480 | L28S/L29T/Q113S/S135Q/M138A | + | + | + |
| 13/14 | L28S/L29T/S135Q | +++ | ++++ | +++ |
| 481/482 | L29T/A478T | + | | + |
| 483/484 | L29T/Q113S/M138A | + | + | + |
| 485/486 | L29T/Q113S/P126Q/S135Q/H193Q | + | +++ | ++ |
| 487/488 | L29T/Q113S/S135Q | ++ | +++ | ++ |
| 489/490 | L29T/Q113S/S135Q/R455V | + | + | + |
| 491/492 | L29T/T148G | +++ | +++ | +++ |
| 493/494 | M138A/L218S/Q749E/L934R | + | + | |
| 495/496 | M138A/L218S/S668D/S671N | +++ | ++ | +++ |
| 497/498 | M138A/S671N/Q749E/L934R | +++ | +++ | +++ |
| 499/500 | M431V/S668D/S671N | + | + | + |
| 501/502 | M507L/S668D | + | + | + |
| 503/504 | M507L/S671N/L934R | +++ | +++ | +++ |
| 505/506 | P4H | + | ++ | + |
| 507/508 | Q113S | + | + | + |
| 509/510 | Q113S/A418E/A478T/A489R/K581T | + | + | + |
| 511/512 | Q113S/A418E/R455V/A478T/K581T | + | + | + |
| 513/514 | Q113S/S135Q/A418E | ++ | +++ | +++ |
| 515/516 | Q345K/L934R | + | ++ | |
| 517/518 | Q749E/A784T | +++ | +++ | ++ |
| 519/520 | S135P/C944Y | +++ | +++ | +++ |
| 521/522 | S135Q | + | ++ | + |
| 523/524 | S135Q/A478T/A489R/K581T | + | + | |
| 525/526 | S135Q/A489R | + | +++ | ++ |
| 527/528 | S135Q/T148G/S150G/A418E | + | +++ | + |

TABLE 4-1-continued

Activity of GAA Variants Relative to SEQ ID NO: 8[1]

| SEQ ID NO: (nt/aa) | Amino Acid Differences (Relative to SEQ ID NO: 8) | Unchallenged Activity FIOPC | pH 3 Stability Activity FIOPC | pH 7 Stability Activity FIOPC |
|---|---|---|---|---|
| 529/530 | S671N/L934R | +++ | ++ | +++ |
| 531/532 | S671N/Q749E | +++ | +++ | +++ |

[1]All activities were determined relative to the reference polypeptide of SEQ ID NO: 8. Levels of increased activity are defined as follows: "+" = 0.5-0.9; "++" 0.9 to 1.1; "+++" > 1.1; "++++" > 2; and "+++++" > 3.5.

Example 5

High-Throughput Growth of Adherent Mammalian Cells and GAA Assays Obtained Through Adherent Mammalian Expression High-Throughput (HTP) Growth of GAA and GAA Variants in Adherent Mammalian Cells (HEK293T)

HEK 293T cells were transfected with a pcDNA 3.1(+) vector (ThermoFisher Scientific), pDH vector, or PCR-amplified linear DNA (as described in Example 1) encoding a synthetic mouse IG signal peptide (SEQ ID NOS: 3381 and 3382) fusion to wild-type GAA or GAA variants using the lipofection method with LIPOFECTAMINE® 3000 Reagent (ThermoFisher Scientific). HEK 293T cells were cultured in standard complete growth medium (DMEM with 10% fetal bovine serum [both from Corning]) and seeded into NUNC® Edge 2.0 96-well plate (ThermoFisher Scientific), at densities of $0.5 \times 10^5$ cells/well/250 µL to adhere and grow for 24 hours at 37° C., and in the presence of 5% $CO_2$ prior to lipofection-mediated transfection. Following transfection, cells were incubated for 24-96 hours, to allow for expression and secretion of GAA variants into the conditioned media. Conditioned media (20-100 µL) from the HEK293T transfection was then transferred into new 96-well plates for activity, stability or uptake into cell analysis.

HTP-Analysis of Supernatants

GAA variant activity was determined by measuring the hydrolysis of 4-methylumbelliferyl α-D-glucopyranoside (4-MUGlu). For the unchallenged assay, 20 µL of HEK 293T conditioned media produced as described above was mixed with 50 µL of 1.5 mM 4-MUGlu in McIlvaine Buffer (McIlvaine, J. Biol. Chem., 49:183-186 [1921]), pH 4.4, in a 96-well, black, opaque bottom plate. The reactions were incubated at 25-37° C. for 30-60 minutes with agitation at 400 rpm, prior to quenching with 100 µL of 0.5 M sodium carbonate pH 10.5. Hydrolysis was analyzed using a SPECTRAMAX® M2 microplate reader (Molecular Devices) or an ENVISION® microplate reader (Perkin Elmer) monitoring fluorescence (Ex. 355 nm, Em. 460 nm).

HTP-Analysis of Supernatants Challenged with Neutral Buffer

GAA variants were challenged with neutral buffer to simulate the pH that the variants encounter in the blood following their administration to a patient. First, 20 µL of conditioned media containing GAA variants from HEK 293T expression were combined with 100 µL of DPBS buffer (pH 7.4) in a 96-well plate. The plates were sealed and incubated at 37° C. for 24-96 h. Next, 20 µL of neutral-pH-challenged sample were mixed with 50 µL of 1.5 mM 4-MUGlu in McIlvaine buffer, pH 4.4. The reactions were incubated at 37° C. for 180 minutes with agitation at 400 rpm, prior to quenching with 100 µL of 0.5 M sodium carbonate pH 10.5. Hydrolysis was analyzed using a SPECTRAMAX® M2 microplate reader or an ENVISION® microplate reader (Perkin Elmer) monitoring fluorescence (Ex. 355 nm, Em. 460 nm).

HTP-Analysis of Supernatants Challenged with Plasma

GAA variants were challenged with plasma to simulate the conditions that the variants encounter in the blood following their administration to a patient. First, 30 µL of conditioned media containing GAA variants from HEK 293T expression were combined with 30 µL of plasma (Innovative Research, Innovative Grade US Origin Monkey Cynomolgus Plasma K2 EDTA) in a 96-well plate. The plates were sealed and incubated at 37° C. for 2-4 h. Next, 10 µL of plasma-challenged sample were mixed with 50 µL of 1.5 mM 4-MUGlu in McIlvaine buffer, pH 4.4. The reactions were incubated at 25-37° C. for 15-60 minutes with agitation at 400 rpm, prior to quenching with 100 µL of 0.5 M sodium carbonate pH 10.5. Hydrolysis was analyzed using a SPECTRAMAX® M2 microplate reader or an ENVISION® microplate reader (Perkin Elmer) monitoring fluorescence (Ex. 355 nm, Em. 460 nm).

HTP-Analysis of GAA Activity in Lysates of Pompe Fibroblasts and C2C12 GAA Knockout Myoblasts GAA variants produced in HTP were incubated with target cells and assayed for residual intracellular activity after 24 hours. For these experiments, mammalian cells lacking functional GAA activity were used, namely Pompe patient-derived fibroblasts (Coriell Institute for Medical Research #GM00248) and C2C12 myoblasts whose native GAA gene had been knocked out using Crispr-Cas9 editing. In these experiments, Pompe fibroblasts or C2C12 GAA knockout myoblasts were seeded into black, clear bottom, tissue culture treated COSTAR® 96-well plates (Corning, 3904) and allowed to grow to confluency in standard complete growth medium. Upon confluency, complete growth culture media was removed from the plates using an automated BIOMEK® i5 liquid handling robot. Conditioned media produced by HEK293T cells transiently transfected as described above, were transferred to Pompe patient-derived fibroblasts and C2C12 myoblasts, and allowed to incubate for 4-24 hours at 37° C., 5% $CO_2$. Medium was removed from the cultures using an automated BIOMEK® i5 liquid handling robot. The cells were briefly washed with 150 µL 1xDPBS/well, and DPBS was removed using an automated BIOMEK® i5 liquid handling robot. Then, 200 µL standard complete growth culture medium was added to each well, and the plates were returned to the incubator for 0-72 hours. At the conclusion of incubation, standard complete growth media was removed using an automated BIOMEK® i5 liquid handling robot. The cells were washed with 150 µL 1xDPBS/well, and the DPBS removed using an automated BIOMEK® i5 liquid handling. The cells were lysed via addition of 50 µL of McIlvaine buffer, pH 4.4, supplemented with 0.2-0.5% TRITON X-100™ non-ionic surfactant (Sigma #93443) and agitation at room temperature for 30 minutes. Activity was assessed by addition of 50 µL of 1.5 mM 4-MUGlu in McIlvaine buffer, pH 4.4. The plates were sealed, incubated at 37° C. for 300-360 minutes with agitation at 400 rpm, prior to quenching with 100 µL of 0.5 M sodium carbonate, pH 10.5. Hydrolysis was analyzed using a SPECIRAMAX® M2 microplate reader or an ENVISION® microplate reader (Perkin Elmer) monitoring fluorescence (Ex. 355 nm, Em. 460 nm). Cellular uptake FIOPC was calculated by dividing normalized GAA variant intracellular activity by the activity of the reference polypeptide with the indicated SEQ ID NO.

Example 6

GAA Variants of SEQ ID NO: 16

In this Example, experiments for evolution and screening of GAA variants derived from SEQ ID NO: 16 for improved GAA activity after a series of challenges are described. The GAA synthetic gene coding for SEQ ID NO: 13 was fused to the synthetic mouse IG signal peptide polynucleotide (SEQ ID NO: 3381) (as described in Example 1) to generate the synthetic gene coding for SEQ ID NO: 15. Directed evolution of the GAA encoded by SEQ ID NO: 16 was carried out by constructing libraries of variant genes. These libraries were then plated, grown, and screened for GAA MU-Glu activity ("Unchallenged Activity FIOPC"), as well as after pH 7.4 pre-incubation ("pH 7.4 Stability and Activity FIOPC"), as described in Example 5. Variants were also tested for 4-MUGlu activity after lysis of Pompe fibroblasts ("Activity from Pompe Fibroblast Lysate FIOPC") or GAA$^{-/-}$ C2C12 cells ("Activity from C2C12 GAA-/- Lysate FIOPC"), as described in Example 5. The results of these assays are presented in Table 6-1.

TABLE 6-1

Activity of GAA Variants Relative to SEQ ID NO: 161

| SEQ ID NO: (nt/aa) | Amino Acid Differences (Relative to SEQ ID NO: 16) | Unchallenged Activity FIOPC | pH 7.4 Stability and Activity FIOPC | Activity from Pompe Fibroblast Lysate FIOPC | Activity from C2C12 GAA-/- Lysate FIOPC |
|---|---|---|---|---|---|
| 533/534 | V70A/R267K/K725E/C944S | +++ | +++ | +++ | +++ |
| 535/536 | R267K/A489D/D500A/K725E/Q830K/C930P | +++ | +++ | ++ | ++ |
| 537/538 | L109P/E522V/Q830K/C944S | +++ | +++ | +++ | +++ |
| 539/540 | V70A/R267K/C930P/C944S | +++ | +++ | +++ | ++ |
| 541/542 | V70A/K725E/Q830K/L860F/C930P/C944S | +++ | +++ | +++ | +++ |
| 545/546 | P39Q/R58L/A489D/K725E/Q830K/G842S/C930P/C944S | ++ | +++ | ++ | ++ |
| 547/548 | A60V/D500A/S612D | + | + | + | + |
| 549/550 | P39Q/D500A/S612D | +++ | +++ | +++ | +++ |
| 551/552 | E522V/K725E | +++ | +++ | +++ | +++ |
| 553/554 | P39Q/V70A/L109P/Q830K/G842S | +++ | +++ | +++ | +++ |
| 555/556 | P39Q/V70A/K725E | +++ | +++ | +++ | +++ |
| 557/558 | P39Q/R267K/A489D/Q830K/C944S | +++ | +++ | ++ | +++ |
| 559/560 | C930P | +++ | +++ | +++ | +++ |
| 561/562 | D500A/C930P/C944S | +++ | +++ | +++ | +++ |
| 563/564 | C944S | ++ | +++ | ++ | ++ |
| 565/566 | L109P/E522V/S612D/K725E | +++ | +++ | ++ | ++ |
| 19/20 | P39Q/R267K/A489D/E522V/S612D/Q830K/G842S | +++ | +++ | +++ | +++ |
| 567/568 | P39Q/R267K | +++ | + | +++ | ++ |
| 569/570 | P39Q/V70A/A489D/S612D | +++ | +++ | +++ | +++ |
| 571/572 | L109P/S612D | ++ | + | + | + |
| 573/574 | D500A/L860F/C930P | +++ | +++ | ++ | ++ |
| 575/576 | R267K/E522V/K725E | ++ | ++ | +++ | + |
| 577/578 | V70A/A489D/C930P | +++ | +++ | +++ | +++ |
| 579/580 | A489D/Q830K/C944S | +++ | +++ | +++ | +++ |
| 581/582 | D500A/S612D/Q830K/L860F | +++ | + | +++ | +++ |
| 583/584 | P39Q/A489D/D500A/S612D | +++ | + | ++ | + |
| 585/586 | P39Q | +++ | +++ | +++ | +++ |
| 587/588 | N528S/E793K | + | | ++ | |
| 589/590 | K106R/K154R | +++ | + | | ++ |
| 591/592 | A62E/K106R/D523N/N528S/A696S/E793K/R862Q | + | | + | |
| 593/594 | A196T/N528S/E681Q/I790V/E793K | + | | | |
| 595/596 | A62E/K154R/A696S/E793K/R862Q | +++ | + | + | ++ |
| 597/598 | A62E/Q92R/I790V/E793K | ++ | + | | ++ |
| 599/600 | E793K | +++ | ++ | + | +++ |
| 601/602 | S37F/N528S/I790V | + | | | |
| 603/604 | N528S/E681Q | + | | | |
| 605/606 | D523N/I790V/E793K | +++ | ++ | + | ++ |
| 607/608 | D523N | ++ | + | + | ++ |
| 609/610 | N528S/R862Q | ++ | | | |
| 611/612 | S37F/A62E | ++ | + | + | ++ |
| 613/614 | A753S | +++ | +++ | | ++ |
| 615/616 | A62E/N79S/K154R/R862Q | +++ | | | ++ |
| 617/618 | A62E/N79S/I790V/E793K | +++ | + | | +++ |
| 619/620 | A62E/N79S/R862Q | +++ | + | +++ | +++ |
| 621/622 | A62E/N79S/D523N/N528S/I790V | +++ | | + | |
| 623/624 | A62E/N79S/A196T/E681Q/R862Q | ++ | | + | + |
| 625/626 | S37F/A196T | + | | | + |
| 627/628 | S37F/A62E/D523N | +++ | + | ++ | ++ |
| 629/630 | S37F/N79S/K154R/E793K | +++ | ++ | | ++ |
| 631/632 | S37F/P64Q/R66G/N79S/K154R/D523N/E681Q/E793K/R862Q | + | | + | |
| 633/634 | S37F/A62E/N79S/A196T/A696S/R862Q | +++ | + | + | + |
| 635/636 | S37F/I790V/E793K | + | | | + |
| 637/638 | N79S/R862Q | +++ | + | ++ | ++ |
| 639/640 | N79S/K154R/E681Q | +++ | | ++ | + |
| 641/642 | S37F/A62E/D523N/E793K | ++ | + | + | + |
| 643/644 | A62E/E793K/R862Q | +++ | +++ | + | +++ |
| 645/646 | S37F/N528S/A696S/E793K | + | | | |
| 647/648 | S37F/N528S/I790V/E793K/R862Q | ++ | | | |
| 649/650 | A62E/Q92R | ++ | + | + | ++ |
| 651/652 | N79S/K154R/E793K/R862Q | +++ | + | + | + |
| 653/654 | R862Q | ++ | + | | ++ |
| 655/656 | L34D | +++ | +++ | +++ | +++ |
| 657/658 | Y352K | ++ | ++ | ++ | ++ |
| 659/660 | E207R | ++ | ++ | ++ | ++ |
| 661/662 | Q50L | + | + | ++ | + |
| 663/664 | L672K | ++ | + | ++ | + |
| 665/666 | Q938P | +++ | +++ | +++ | +++ |
| 667/668 | N875D | ++ | + | ++ | ++ |
| 669/670 | Q830V | +++ | + | ++ | ++ |
| 671/672 | P178G | ++ | | + | + |
| 673/674 | I22R | +++ | ++ | +++ | ++ |
| 675/676 | L24W | +++ | ++ | ++ | ++ |
| 677/678 | L778Q | +++ | + | + | + |
| 679/680 | E208I | ++ | ++ | ++ | + |
| 681/682 | K925A | ++ | + | + | + |
| 683/684 | A47G | ++ | | + | + |
| 685/686 | Y352V | ++ | | | |
| 687/688 | F27S | ++ | + | ++ | ++ |
| 689/690 | P149R | +++ | +++ | +++ | +++ |
| 691/692 | F27K | ++ | ++ | ++ | ++ |

TABLE 6-1-continued

Activity of GAA Variants Relative to SEQ ID NO: 161

| SEQ ID NO: (nt/aa) | Amino Acid Differences (Relative to SEQ ID NO: 16) | Unchallenged Activity FIOPC | pH 7.4 Stability and Activity FIOPC | Activity from Pompe Fibroblast Lysate FIOPC | Activity from C2C12 GAA-/- Lysate FIOPC |
|---|---|---|---|---|---|
| 693/694 | L672E | +++ | + | ++ | + |
| 695/696 | S932A | ++ | ++ | ++ | ++ |
| 697/698 | L24R | +++ | +++ | +++ | +++ |
| 699/700 | L24E | ++ | ++ | ++ | + |
| 701/702 | C944R | +++ | +++ | ++ | +++ |
| 703/704 | E740G | +++ | ++ | +++ | ++ |
| 705/706 | P55C | + | + | ++ | ++ |
| 707/708 | P673R | ++ | | | |
| 709/710 | F27G | ++++ | +++ | +++ | +++ |
| 711/712 | Q49A | + | + | ++ | ++ |
| 713/714 | L34M | +++ | ++ | ++ | ++ |
| 715/716 | E207Y | + | + | ++ | ++ |
| 717/718 | R68S | +++ | ++ | +++ | +++ |
| 719/720 | P55L | ++ | ++ | ++ | + |
| 721/722 | V70Q | +++ | +++ | +++ | +++ |
| 723/724 | P39H | +++ | +++ | +++ | +++ |
| 725/726 | P922E | +++ | ++ | +++ | ++ |
| 727/728 | R68W | ++ | ++ | ++ | ++ |
| 729/730 | P77W | ++ | + | ++ | ++ |
| 731/732 | A774G | ++ | + | ++ | ++ |
| 733/734 | Q50G | ++ | ++ | ++ | +++ |
| 735/736 | F27W | ++ | + | + | ++ |
| 737/738 | W118F | ++ | + | ++ | ++ |
| 739/740 | F27V | +++ | +++ | +++ | +++ |
| 741/742 | P178V | ++ | + | + | + |
| 743/744 | H424K | +++ | | | |
| 745/746 | R385G | +++ | + | + | + |
| 747/748 | F27G/M165I | +++ | +++ | +++ | +++ |
| 749/750 | V30D | +++ | +++ | +++ | +++ |
| 751/752 | V30L | + | ++ | + | + |
| 753/754 | V40W | ++ | + | ++ | +++ |
| 755/756 | R68N | +++ | +++ | +++ | +++ |
| 757/758 | A179L | ++ | ++ | ++ | ++ |
| 759/760 | A774S | +++ | +++ | +++ | +++ |
| 761/762 | E33G | ++ | ++ | ++ | ++ |
| 763/764 | A902L | ++ | ++ | ++ | ++ |
| 765/766 | L109D | +++ | +++ | +++ | ++ |
| 767/768 | E463A | + | + | + | + |
| 769/770 | F27A | +++ | +++ | +++ | +++ |
| 771/772 | E880R | ++ | + | ++ | ++ |
| 773/774 | T44I/L157V | +++ | ++ | ++ | ++ |
| 775/776 | T158E | +++ | ++ | ++ | ++ |
| 777/778 | L157Q | ++ | ++ | ++ | ++ |
| 779/780 | K725V | ++ | + | ++ | + |
| 781/782 | Q217A | ++ | +++ | + | + |
| 783/784 | Q938A | +++ | ++ | ++ | + |
| 785/786 | D500A | + | + | ++ | +++ |
| 787/788 | A89R | +++ | +++ | +++ | +++ |
| 789/790 | E844R | ++ | + | ++ | + |
| 791/792 | R448L | + | | | |
| 793/794 | Q107G | +++ | +++ | +++ | +++ |
| 795/796 | E208G | + | + | + | + |
| 797/798 | A47R | +++ | +++ | +++ | +++ |
| 799/800 | E740Q | ++ | + | ++ | ++ |
| 801/802 | F27R | ++ | ++ | ++ | ++ |
| 803/804 | L934F | + | + | + | + |
| 805/806 | K725F | ++ | +++ | + | + |
| 807/808 | K925W | + | ++ | ++ | ++ |
| 809/810 | Q49G | +++ | +++ | +++ | +++ |
| 811/812 | Q50V | +++ | ++ | +++ | +++ |
| 813/814 | Q217D | ++ | ++ | ++ | +++ |
| 815/816 | Q892L | ++ | +++ | ++ | ++ |
| 817/818 | L34T | +++ | +++ | +++ | +++ |
| 819/820 | A97G | +++ | +++ | +++ | +++ |
| 821/822 | P673N | + | | | |
| 823/824 | T158F | ++ | + | + | ++ |
| 825/826 | A97D | +++ | +++ | +++ | +++ |
| 827/828 | E33P | ++ | ++ | +++ | ++ |
| 371/372 | P39D | +++ | +++ | +++ | +++ |
| 543/544 | H734K | + | + | ++ | + |

[1] All activities were determined relative to the reference polypeptide of SEQ ID NO: 16. Levels of increased activity are defined as follows: ""+"" = 0.5-0.9; "++" = 0.9 to 1.1; "+++" > 1.1; and "++++" > 2.

Example 7

Production of GAA Variants

In this Example, production of GAA variants is described.
Production of GAA in EXPI293F™ Cells Milligram-scale production of GAA variants was achieved by transient transfection of EXP1293™ cells (ThermoFisher Scientific) using the lipofection method with EXPIFECTAMINE™ 293 Reagent (ThermoFisher Scientific) in EXPI293™ Expression Medium (ThermnoFisher Scientific). GAA variants fused to an N-terminal synthetic mammalian signal peptide (SEQ ID NO: 3381) were subcloned into the mammalian expression vectors pLEV113, pcDNA 3.1(+), or pDH as described in Example 1. EXPI293™ cells were transfected with plasmid DNA and grown in suspension for 4-7 days. Conditioned media was then harvested, clarified by centrifugation and filtration and stored at 4° C. until analysis.

Example 8

Purification of GAA Variants

In this Example, methods of purifying GAA variants are described.
Purification of GAA Variants From Mammalian Cell Supernatants GAA variants (SEQ ID NOS: 4, 6, 10, 12, 16, 18, 20, 946, 1894, 1924, 1950, 1956, 1984, 2034, 2054, 2066, 2074, 2178, 2202, and 2496) produced in EXPI293F™ cells as described in Example 7, were purified from mammalian culture supernatant as described in the literature (Yasuda et al., Prot. Exp. Pur., 37:499-506 [2004]). Concanavalin A resin (Sigma Aldrich) was equilibrated with 0.1 M sodium acetate, 0.1 M NaCl, 1 mM $MgCl_2$, $CaCl_2$, and $MnCl_2$, pH 6.0 (Concanavalin A binding buffer). Supernatant was sterile-filtered with a 0.2 µm bottle-top filter before it was loaded onto the column. After loading, the column was washed with 10 column volumes of Concanavalin A binding buffer and the bound protein was eluted with Concanavalin A binding buffer supplemented with 0.9 M methyl-α-D-mannopyranoside and 0.9 M methyl-α-D-glucopyranoside. Eluted protein was concentrated, and the buffer exchanged into storage buffer (20 mM sodium phosphate, 150 mM sodium chloride, 185 µM TWEEN®-20 non-ionic detergent, pH 6.0) using an AMICON® Ultra 15 mL filtration unit with a 50 kDa molecular weight cut off membrane (Millipore). The GAA in storage buffer was sterile filtered through ANOTOP® 0.2 µm syringe filters (Whatman), and stored at −80° C. Based on BCA quantitation (described below), the purification process produced 2.4-50 ng of purified protein/ml of culture supernatant.

Protein Quantification by BCA Assay

A bicinchoninic acid (BCA) protein assay (Sigma Aldrich) was used to quantify purified GAA variants produced as described above. In a microtiter plate, 25 µL of protein standards and purified GAA with proper dilution were mixed with 200 µL of working reagent containing 50 parts of BCA reagent A and 1 part of BCA reagent B. The plate was thoroughly mixed on a plate shaker for 30 seconds and incubated at 37° C. for 30 minutes. Absorbance was measured at 562 nm on a plate reader.

Example 9

In Vitro Characterization of GAA Variants

In this Example, experiments conducted to characterize GAA variants produced as indicated herein are described.

Kinetic Characterization of rhGAA and GAA Variants

GAA variant activity was determined by measuring the hydrolysis of 4-methylumbelliferyl α-D-glucopyranoside (4-MUGlu). Purified enzyme produced as described above was mixed with 50 µL of 0-2.5 mM 4-MUGlu in McIlvaine Buffer (McIlvaine, J. Biol. Chem., 49:183-186 [1921]), pH 4.5, in a 96-well, black, opaque bottom plate. The reactions were mixed briefly and incubated at 37° C. for 15-30 min, prior to quenching with 100 µL of 0.5 M sodium carbonate pH 10.5. Hydrolysis was analyzed using a SPECTRAMAX® M2 microplate reader monitoring fluorescence (Ex. 355 nm, Em. 460 nm), plotted and analyzed using the Michaelis-Menten equation. The results from this assay are presented in FIG. 1.

Stability at Neutral DH of rhGAA and GAA Variants

Figure 11:
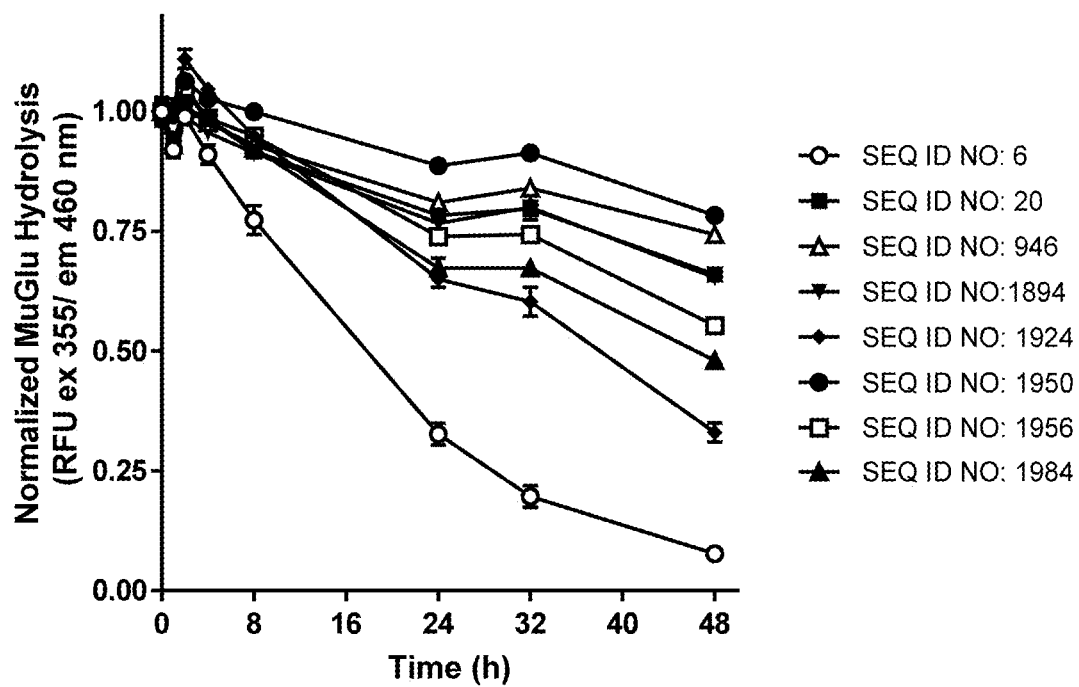
FIG. 11 provides a graph showing the stability at neutral pH and 37° C., expressed as normalized residual RFU activity, of eight GAA variants.
Figure 12:
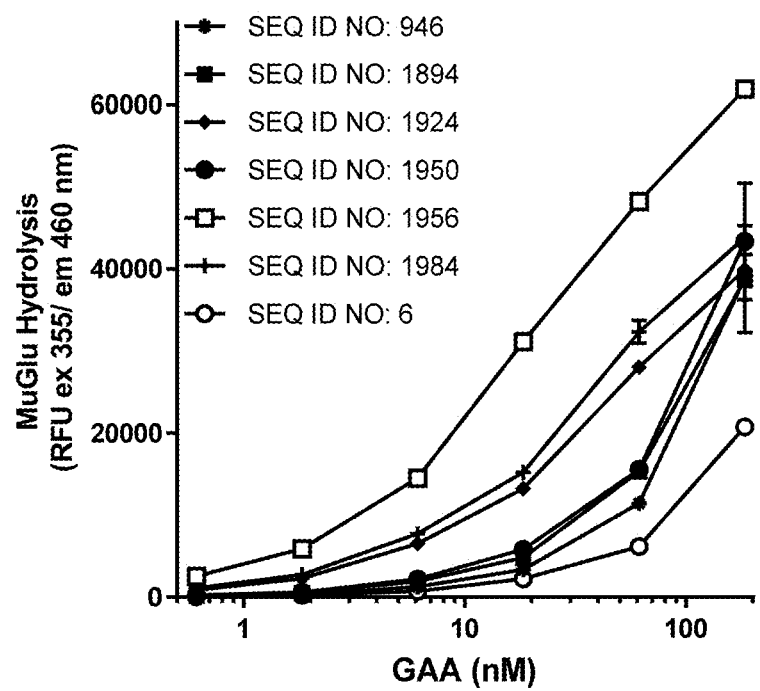
FIG. 12 provides a graph showing the cellular uptake of different purified GAA variants, expressed as RFU activity, after 24 hours incubation at 37° C. with cultured Pompe patient fibroblasts.
Figure 13:
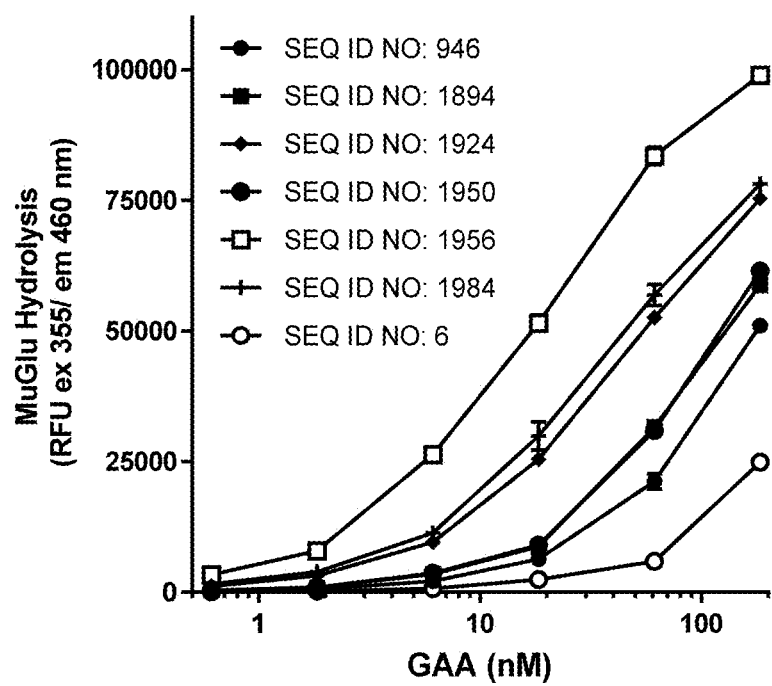
FIG. 13 provides a graph showing the cellular uptake of different purified GAA variants, expressed as RFU activity, after 72 hours incubation at 37° C. with cultured Pompe patient fibroblasts.
Figure 14:
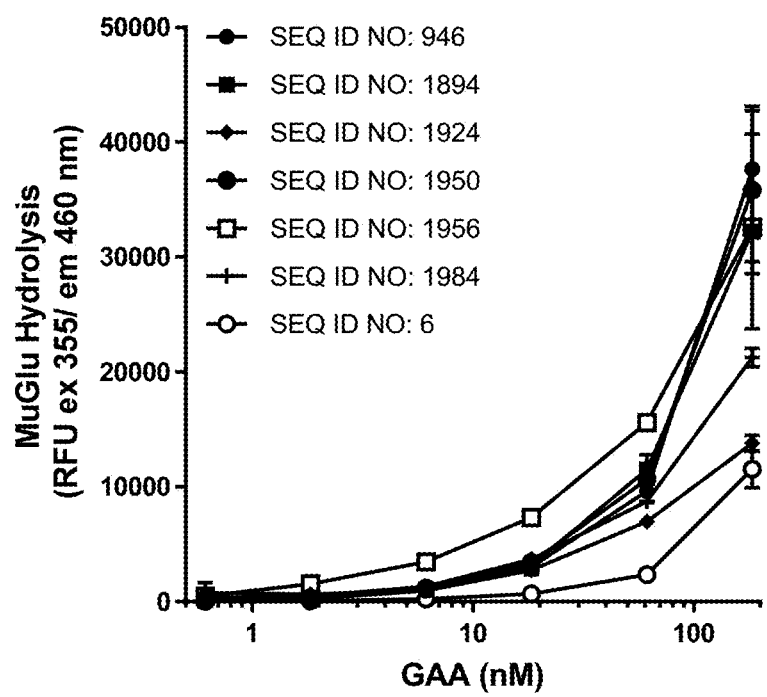
FIG. 14 provides a graph showing the cellular uptake of different purified GAA variants, expressed as RFU activity, after 24 hours incubation at 37° C. with cultured C2C12 GAA−/− myoblasts.
Figure 15:
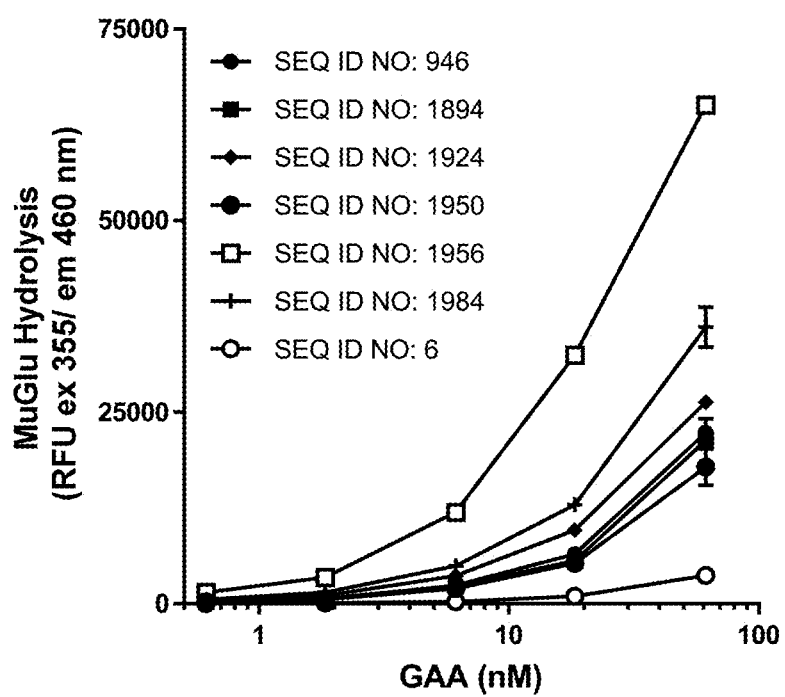
FIG. 15 provides a graph showing the cellular uptake of different purified GAA variants, expressed as RFU activity, after 72 hours incubation at 37° C. with cultured C2C12 GAA−/− myoblasts.
Figure 16:
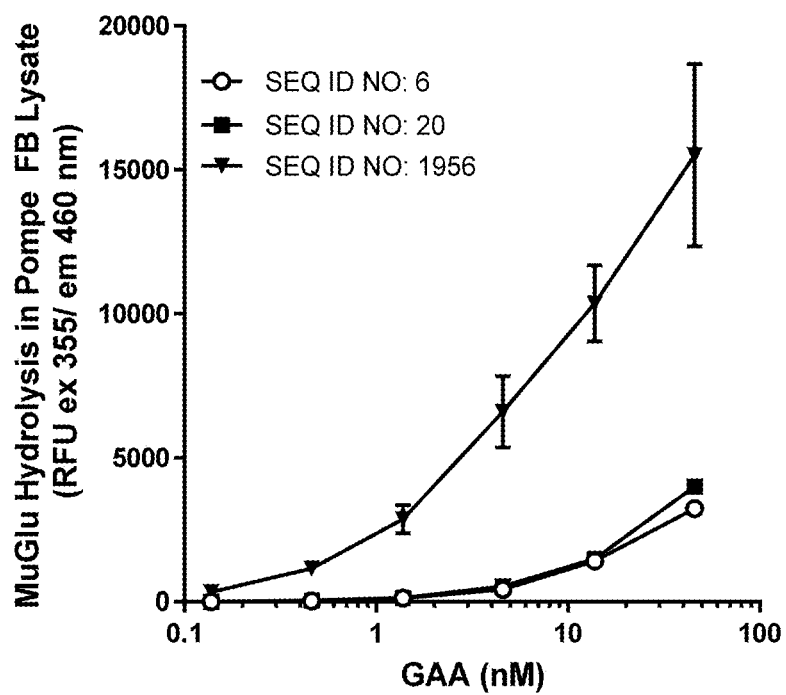
FIG. 16 provides a graph showing the cellular uptake of different purified GAA variants, expressed as RFU activity, after 4 hours incubation at 37° C. with cultured Pompe patient fibroblasts, followed by cell washing and an additional 20 hr incubation.
Figure 17:
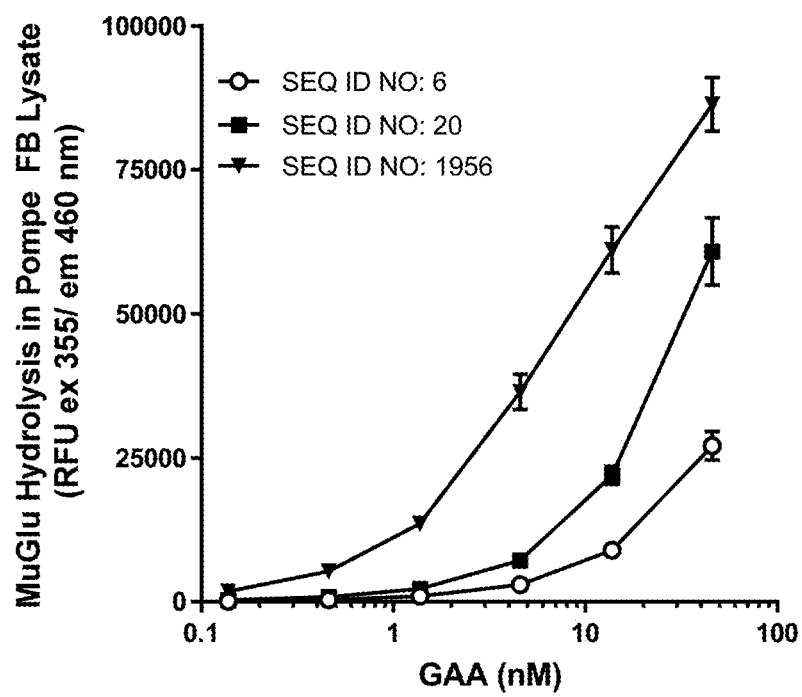
FIG. 17 provides a graph showing the cellular uptake of different purified GAA variants, expressed as RFU activity, after 24 hours incubation at 37° C. with cultured Pompe patient fibroblasts.
Figure 18:
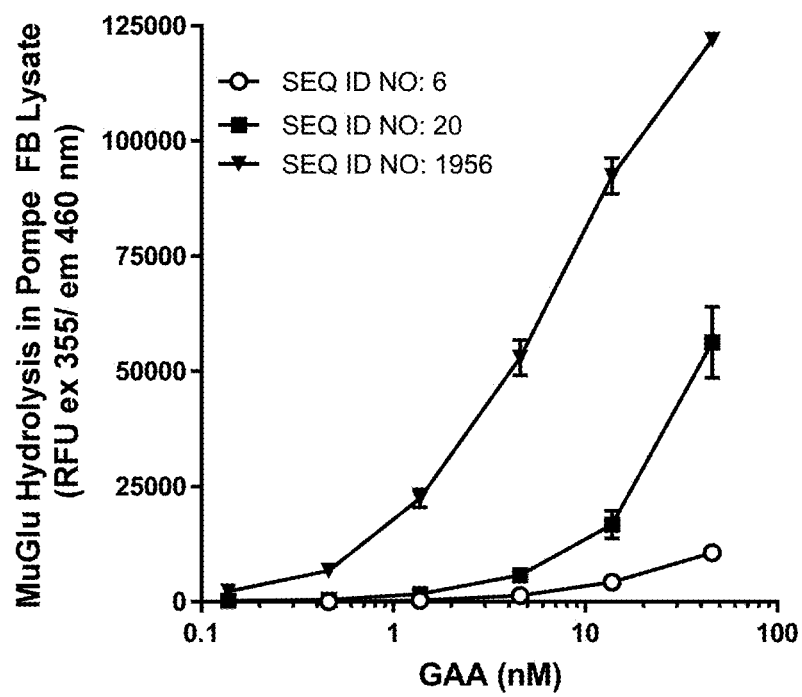
FIG. 18 provides a graph showing the cellular uptake of different purified GAA variants, expressed as RFU activity, after 72 hours incubation at 37° C. with cultured Pompe patient fibroblasts.
Figure 19:
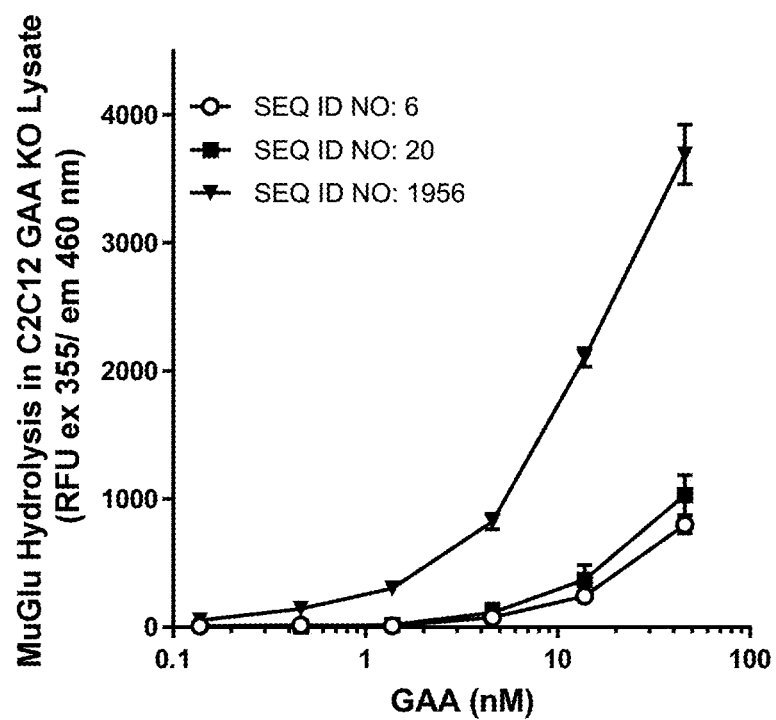
FIG. 19 provides a graph showing the cellular uptake of different purified GAA variants, expressed as RFU activity, after 4 hours incubation at 37° C. with cultured C2C12 GAA−/− myoblasts, followed by cell washing and an additional 20 hr incubation.
Figure 20:
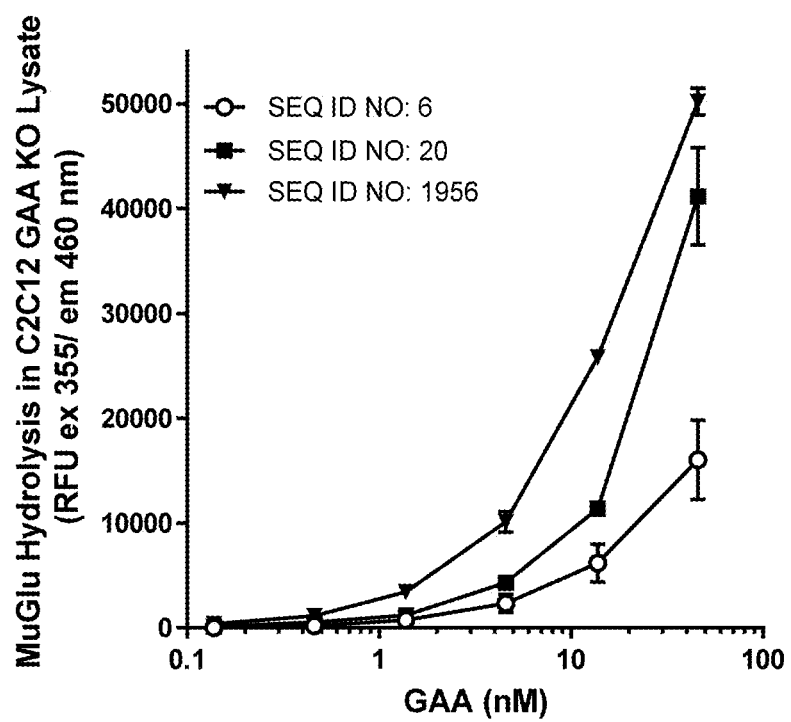
FIG. 20 provides a graph showing the cellular uptake of different purified GAA variants, expressed as RFU activity, after 24 hours incubation at 37° C. with cultured C2C12 GAA−/− myoblasts.
Figure 21:
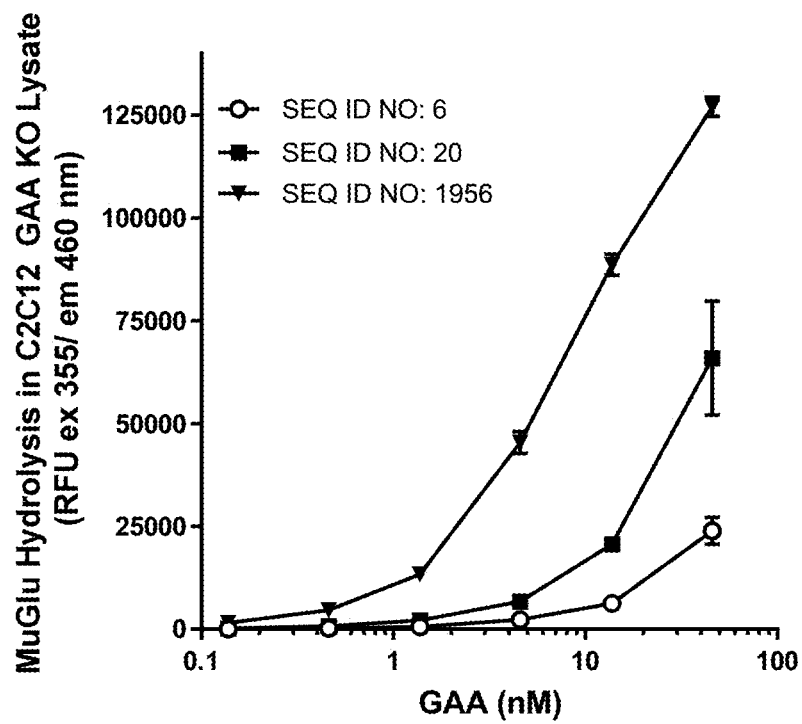
FIG. 21 provides a graph showing the cellular uptake of different purified GAA variants, expressed as RFU activity, after 72 hours incubation at 37° C. with cultured C2C12 GAA−/− myoblasts.
Figure 22:
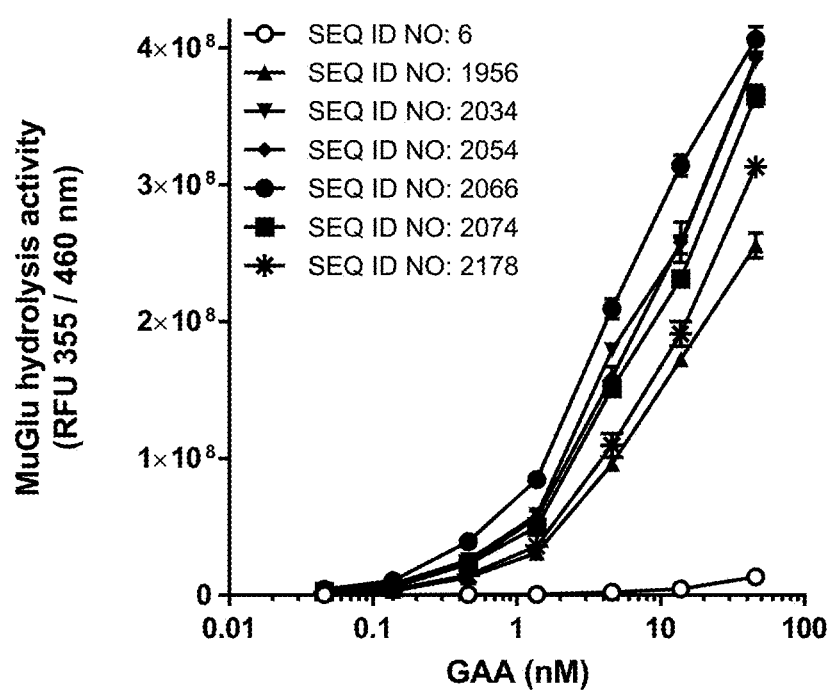
FIG. 22 provides a graph showing the cellular uptake of different purified GAA variants, expressed as RFU activity, after 96 hours incubation at 37° C. with cultured Pompe patient fibroblasts.
Figure 23:
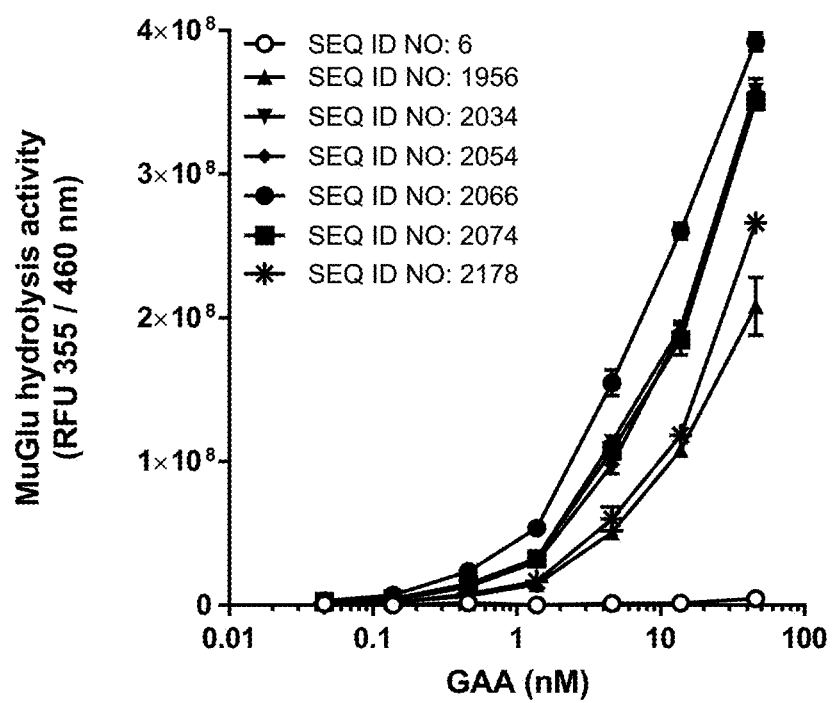
FIG. 23 provides a graph showing the cellular uptake of different purified GAA variants, expressed as RFU activity, after 96 hours incubation at 37° C. with cultured C2C12 GAA−/− myoblasts.
Figure 24:
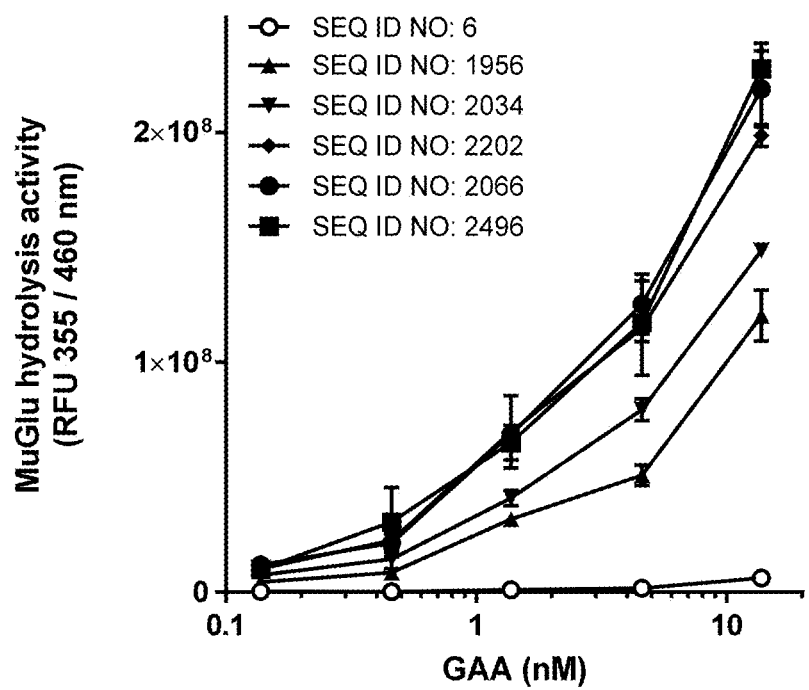
FIG. 24 provides a graph showing the cellular uptake of different purified GAA variants, expressed as RFU activity, after 48 hours incubation at 37° C. with cultured Pompe patient fibroblasts.
Figure 25:
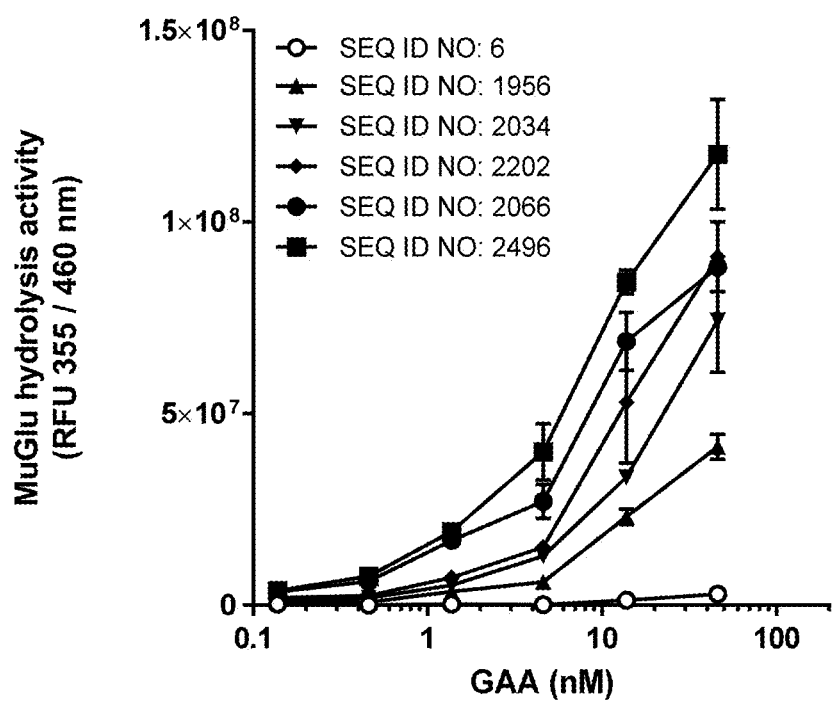
FIG. 25 provides a graph showing the cellular uptake of different purified GAA variants, expressed as RFU activity, after 48 hours incubation at 37° C. with cultured C2C12 GAA−/− myoblasts.
Figure 26:
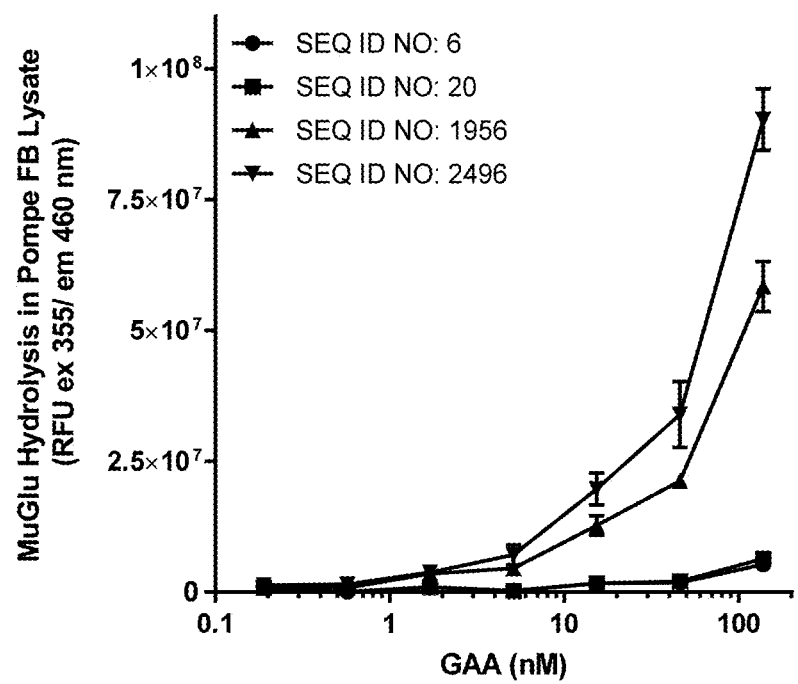
FIG. 26 provides a graph showing the cellular uptake of different purified GAA variants, expressed as RFU activity, after 1 hour incubation at 37° C. with cultured Pompe patient fibroblasts, followed by cell washing and an additional 71 hr incubation.
Figure 27:
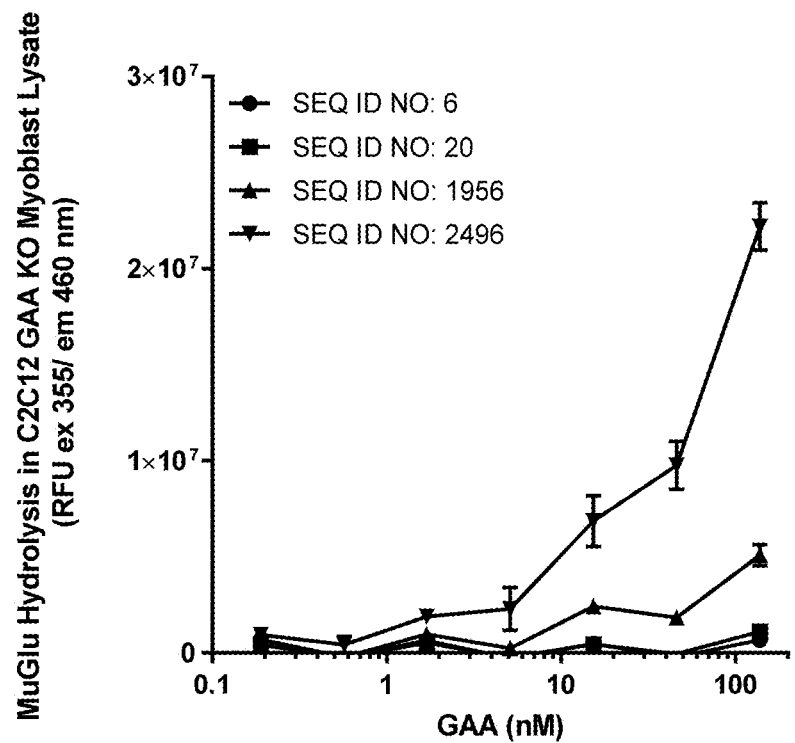
FIG. 27 provides a graph showing the cellular uptake of different purified GAA variants, expressed as RFU activity, after 1 hour incubation at 37° C. with cultured C2C12 GAA−/− myoblasts, followed by cell washing and an additional 71 hr incubation.

GAA variant stability to neutral pH was determined by incubating variants in 100 µL of MEM complete growth medium (pH 7.4) in a 96-well plate. The plates were sealed and incubated at 37° C. for up to 48 h. Next, 10 µL of neutral-pH-challenged sample were mixed with 50 µL of 1.5 mM 4-MUGlu in McIlvaine buffer, pH 4.4 in a 96-well, black, opaque bottom plate. The reactions were incubated at room temperature for 30 minutes with agitation, prior to quenching with 100 µL of 0.5 M sodium carbonate pH 10.5. Hydrolysis was analyzed using a SPECTRAMAX® M2 microplate reader or an ENVISION® microplate reader (Perkin Elmer) monitoring fluorescence (Ex. 355 nm, Em. 460 nm measuring the hydrolysis of 4-methylumbelliferyl α-D-glucopyranoside (4-MUGlu). The results from this assay are presented in FIG. 11.

Figure 8:
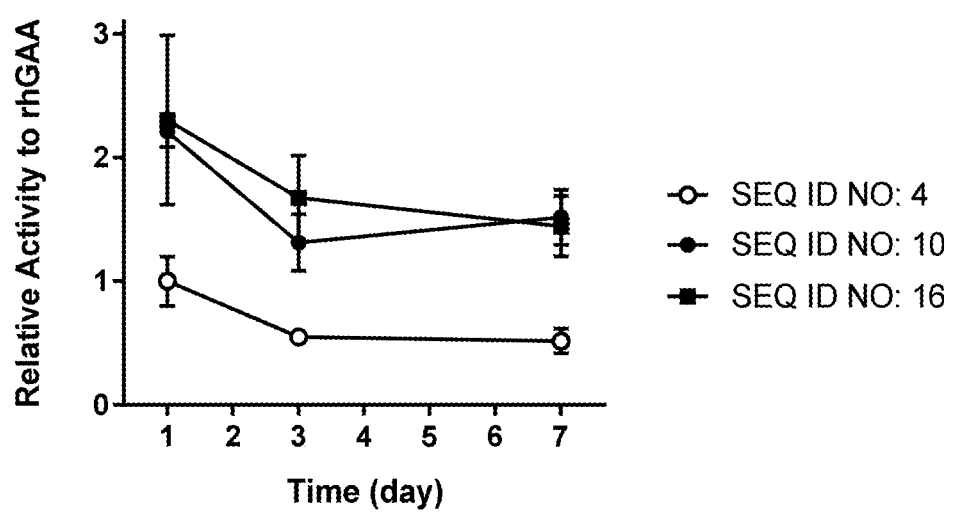
FIG. 8 provides a graph showing the cellular uptake of different purified GAA variants, expressed as relative activity, after 1-7 days incubation at 37° C. with cultured Pompe patient fibroblasts.

Cellular Uptake in Pompe Fibroblasts or C2C12 GAA Knockout Myoblasts of Purified GAA Variants Expressed in Expi293F Cells The cellular uptake of GAA variants as compared to reference enzymes (SEQ ID NOS: 4 and 6), was determined to assess their overall ability to be endocytosed into cultured cells. Pompe fibroblasts (GM00248, Coriell Institute for Medical Research) or C2C12 GAA knockout cells were seeded into a black walled, clear bottom 96-well plate (Costar, #3603) in standard complete growth medium and allowed to reach confluency (2-3 days at 37° C., 5% $CO_2$). After reaching confluency, standard complete growth medium was removed using an automated BIOMEK® i5 liquid handling robot. Enzymes purified as described in Example 8, were added to cells at 0-10 ug GAA/mL in standard complete growth media and allowed to incubate for acute (1-6 hours) or extended (16-96 hours) treatments at 37° C., 5% $CO_2$. Media containing GAA variants were aspirated using an automated BIOMEK® i5 liquid handling robot. The cells were briefly washed with 150 µL 1×DPBS/well, and the DPBS was removed by an automated BIOMEK® i5 liquid handling robot. Then, 200 µL standard complete growth medium was added to each well, and the plates were returned to the incubator for 0-72 hours. At the conclusion of incubation, MEM complete growth media was removed using an automated BIOMEK® i5 liquid handling robot. The cells were washed with 150 µL 1×DPBS/well, and the DPBS was removed using an automated BIOMEK® i5 liquid handling robot. Cells were lysed via addition of 50 µL of McIlvaine buffer, pH 4.4, supplemented with 0.2-0.5% TRITON X-100™ non-ionic surfactant (Sigma #93443)) and agitation at room temperature for 30 minutes. GAA activity was assessed by addition of 50 µL of 1.5 mM 4-MUGlu in McIlvaine buffer, pH 4.4. The plates were sealed, incubated at 37° C. for 300-360 minutes with agitation at 400 rpm, prior to quenching with 100 µL of 0.5 M sodium carbonate pH 10.5. Hydrolysis was analyzed using a SPECTRAMAX® M2 microplate reader monitoring fluorescence (Ex. 355 nm, Em. 460 nm). Cellular uptake FIOPC was calculated by dividing the normalized GAA variant intracellular activity by the control (WT) activity. FIGS. 4, 5, 8, 12, 13, 16-18, 22, 24, and 26, provide graphs showing the cellular uptake in Pompe fibroblasts of purified GAA variants after treatments of 1 to 96 hours. FIGS. 6, 7, 14, 15, 19-21, 23, 25, and 27 provide graphs showing the cellular uptake in C2C12 GAA KO myoblasts of purified GAA variants after treatments of 1 to 96 hours. FIG. 8 provides a graph showing the cellular uptake and stability of GAA variants after 1-7 days.

Glycogen Degradation Activity of GAA Variants Expressed in EXPI293F™ Cells

Figure 2:
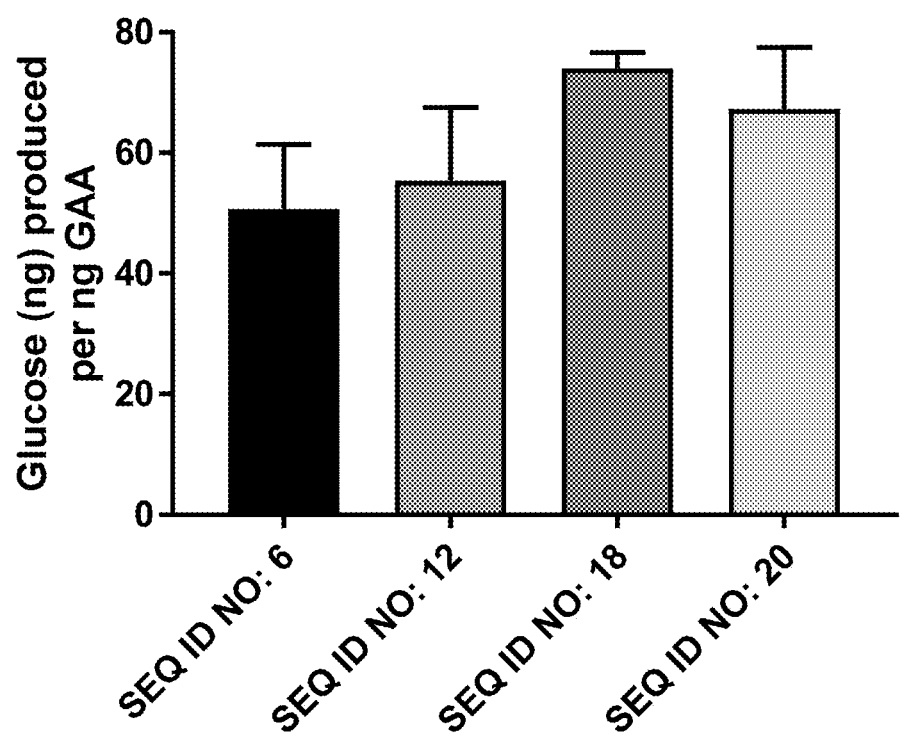
FIG. 2 provides a graph showing the glycogen hydrolysis to glucose activity of four GAA variants, as described in Example 9.
Figure 3:
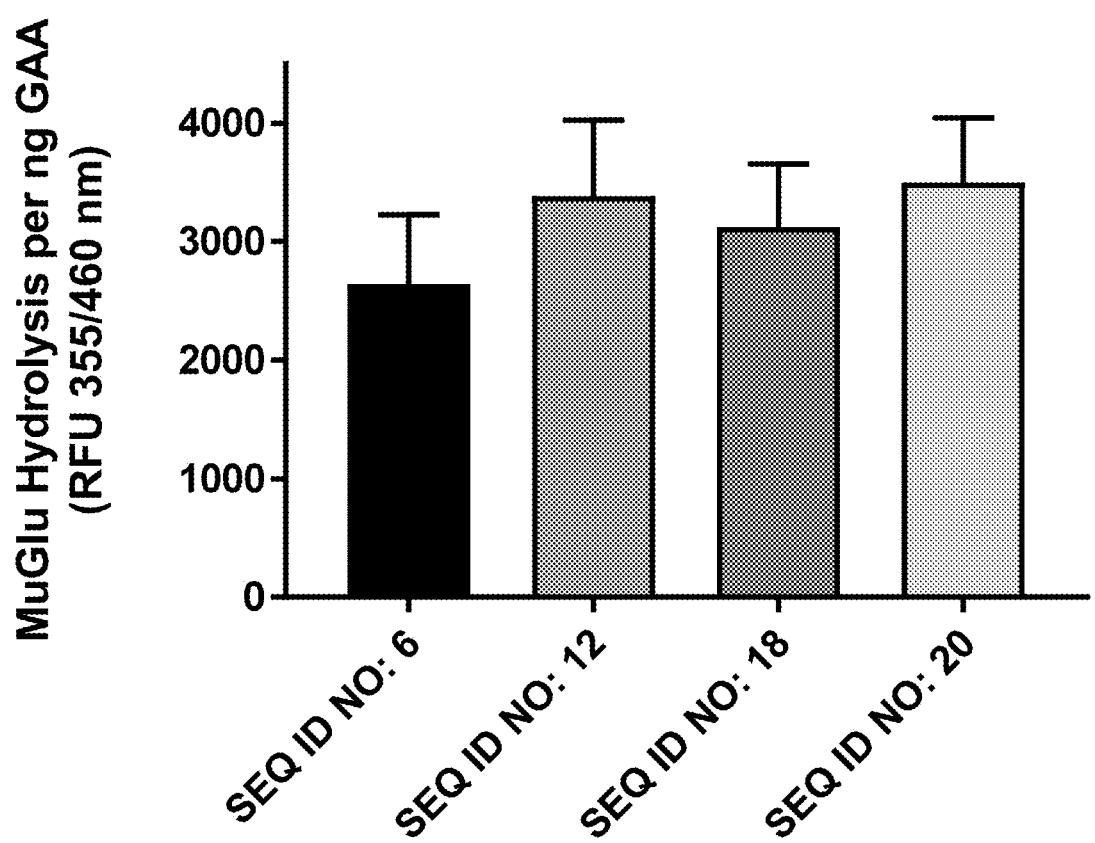
FIG. 3 provides a graph showing the 4-MuGlu hydrolysis levels of four GAA variants, as described in Example 9.
Figure 4:
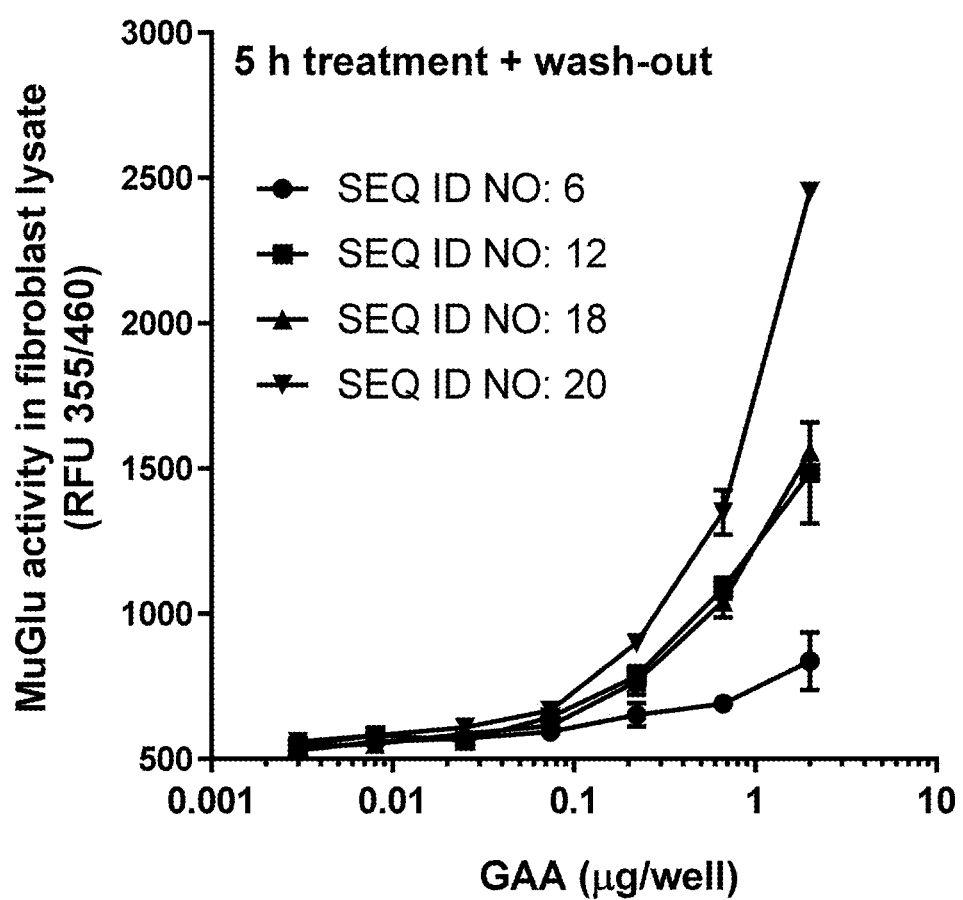
FIG. 4 provides a graph showing the cellular uptake of different purified GAA variants, expressed as RFU activity, after 5 hours incubation at 37° C. with cultured Pompe patient fibroblasts, followed by 24 hr incubation.
Figure 5:
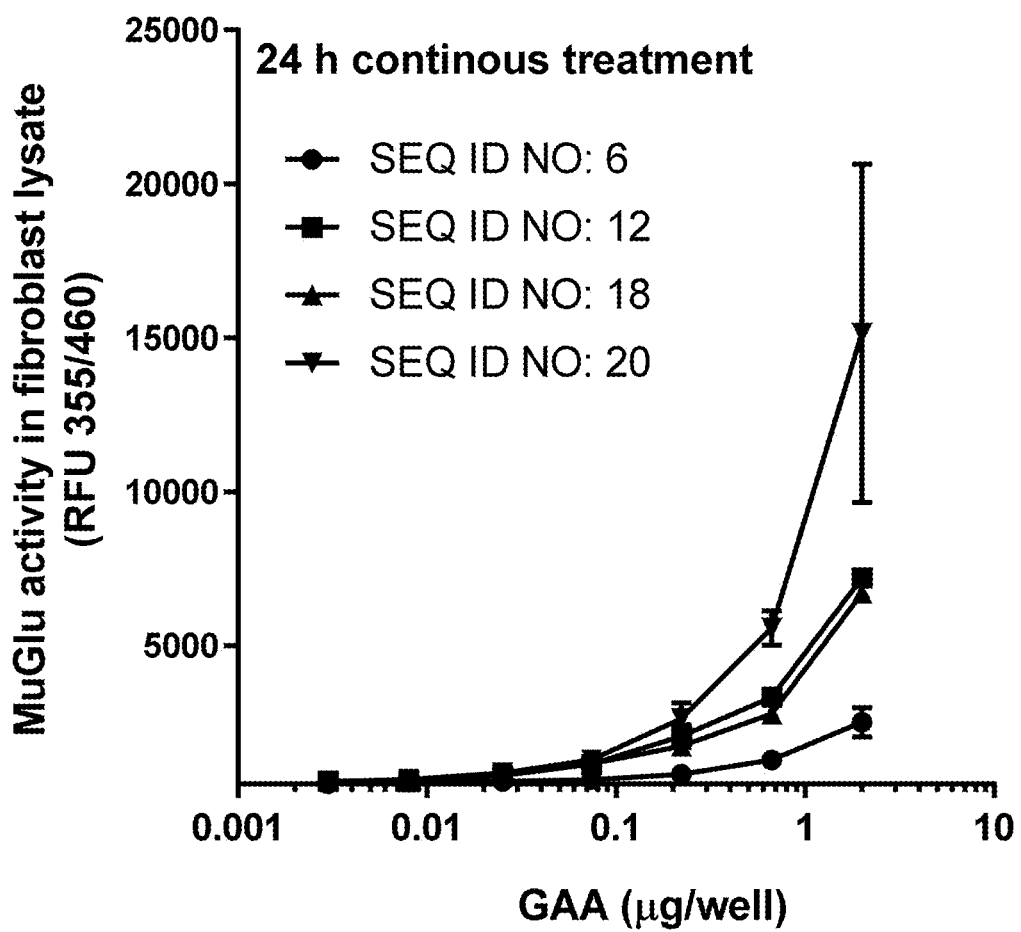
FIG. 5 provides a graph showing the cellular uptake of different purified GAA variants, expressed as RFU activity, after 24 hours incubation at 37° C. with cultured Pompe patient fibroblasts.
Figure 6:
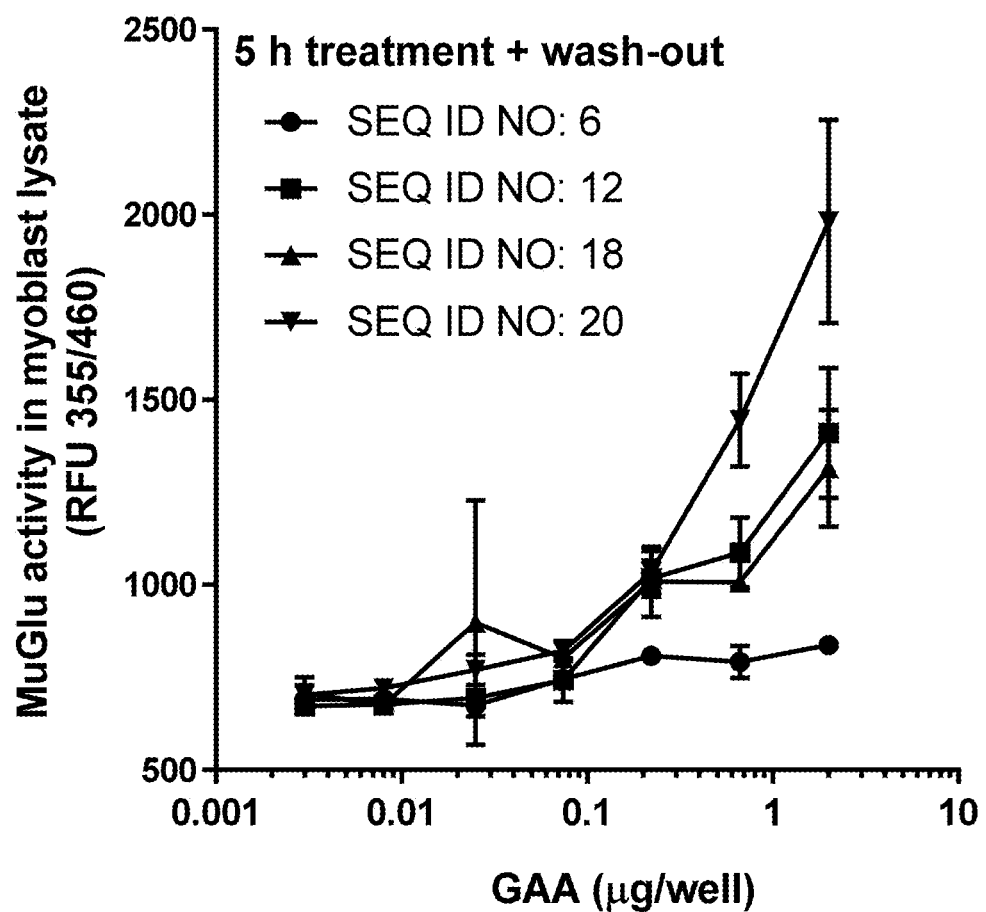
FIG. 6 provides a graph showing the cellular uptake of different purified GAA variants, expressed as RFU activity, after 5 hours incubation at 37° C. with cultured C2C12 GAA−/− myoblasts, followed by 24 hr incubation.
Figure 7:
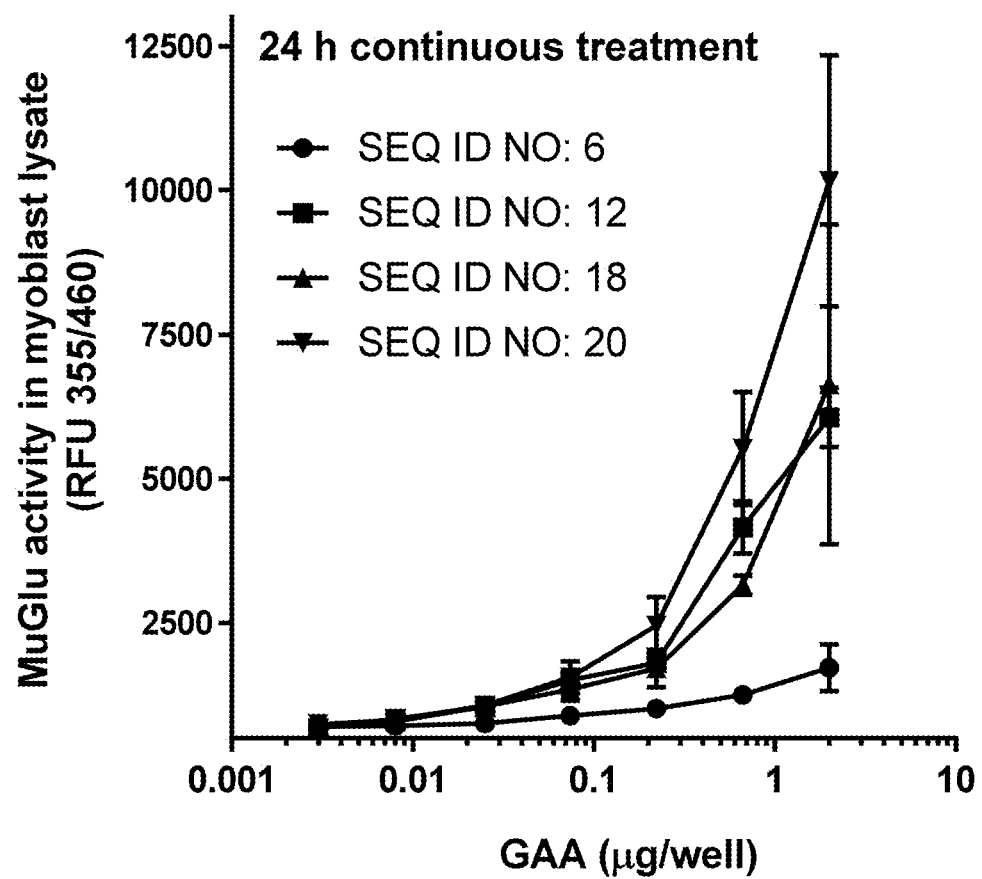
FIG. 7 provides a graph showing the cellular uptake of different purified GAA variants, expressed as RFU activity, after 24 hours incubation at 37° C. with cultured C2C12 GAA−/− myoblasts.

The relative glycogen hydrolysis activity of GAA variants was assessed using an AMPLEX® Red Glucose/Glucose Oxidase Kit (Invitrogen, #A22189) following the manufacturer's instructions with the modifications described herein. Briefly, GAA variants were diluted to an appropriate concentration range (0-2 µg/mL) in 50 µL reactions with 10 mM glycogen in McIlvaine buffer pH 4.4, in a COSTAR® black walled, clear bottom 96-well plate (#3603, Corning). The plates were sealed and gently shaken at room temperature for 30 minutes. Reactions were neutralized by addition of 25 µL of 0.5 M sodium carbonate, pH 10.5. 50 µL of the AMPLEX® Red/Horseradish Peroxidase/Glucose oxidase solution prepared as per manufacturer's instructions, was added to each well. The plates were sealed and gently shaken at room temperature for 30 minutes. Reactions were quantified to a standard curve of free glucose using a SPECTRAMAX® M2 microplate reader monitoring fluorescence (Ex. 530 nm, Em. 590 nm). The results are shown in FIG. 2.

Example 10

GAA Variants of SEQ ID NO: 20

In this Example, experiments for evolution and screening of GAA variants derived from SEQ ID NO: 20 for improved GAA activity after a series of challenges are described. Libraries of variant genes GAA encoded based off of by SEQ ID NO: 20 were constructed, plated, grown, and screened for GAA MU-Glu activity ("Unchallenged Activity FIOPC"), as well as after plasma challenge ("Plasma Stability and Activity FIOPC"), as described in Example 5. Variants were also tested for 4-MUGlu activity after lysis of Pompe fibroblasts ("Activity from Pompe Fibroblast Lysate FIOPC") or GAA$^{-/-}$ C2C12 cells ("Activity from C2C12 GAA-/- Lysate FIOPC"), as described in Example 5. The results, of these assays are presented in Table 10-1 and 10-2.

TABLE 10-1

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC | Activity from C2C12 GAA-/- Lysate FIOPC |
|---|---|---|---|---|---|
| 19/20 | | + | + | + | + |
| 829/830 | L24R/F27G/A89R/D500A/S842G | | ++ | ++ | ++ |
| 831/832 | L24R/F27G/D500A/S842G | + | ++ | ++ | + |
| 833/834 | D500A/S932A | | + | ++ | + |
| 835/836 | L24R/Q39H/S842G/S932A | | + | + | ++ |
| 837/838 | Q39D/A89R/A97G/D500A | | + | ++ | ++ |
| 839/840 | D500A/S842G | | ++ | ++ | + |
| 841/842 | S842G/S932A | | | + | ++ |
| 843/844 | A89R/A97G/Q107G | | ++ | ++ | ++ |
| 845/846 | A89R/A97G/D500A | | | ++ | ++ |
| 847/848 | F27G/Q39H/Q49G/A97G/D500A/S842G | | ++ | ++ | ++ |
| 849/850 | R68N/A89R/A97G/S932A | | + | ++ | + |
| 851/852 | A89R/S842G | | + | ++ | + |
| 853/854 | L24R/Q39D/R68S/A89R/Q107G/D500A/S842G | + | ++ | ++ | ++ |
| 855/856 | L24R/F27G/D500A/S842G/S932A | | | ++ | ++ |
| 857/858 | L24R/Q39H/Q49G/A89R/A97G/S842G/S932A | | | ++ | ++ |
| 859/860 | L24R/S842G/S932A | + | + | ++ | ++ |
| 861/862 | L24R/A89R/D500A | | + | ++ | ++ |
| 863/864 | L24R/Q39H/A89R/A97D/S842G/S932A | | | ++ | ++ |
| 865/866 | L24R | + | + | ++ | ++ |
| 867/868 | F27G/Q49G/R68S/D500A/S842G | | + | ++ | ++ |
| 869/870 | Q107G/D500A/S842G | | | ++ | ++ |
| 871/872 | L34T/Q39D/D500A/S932A | + | + | ++ | ++ |
| 873/874 | R68S | + | + | ++ | + |
| 875/876 | L24W/L109D/D612S | | + | ++ | ++ |
| 877/878 | L24W/V70A/K267R/A774S | | + | ++ | ++ |
| 879/880 | I22R/L24W/D612S/K725E/C944R | + | + | ++ | ++ |
| 881/882 | L24W | | | ++ | + |
| 883/884 | I22R/L24W/F27A/D489A | | + | ++ | + |
| 885/886 | D489A | | | + | + |
| 887/888 | I22R/L24W/F27A/Q50V/Q107G/L109D/D489A/D612S/K725E | | + | ++ | + |
| 889/890 | Q50V/D612S/C944S | + | | ++ | + |
| 891/892 | D612S/K725E/C944S | ++ | ++ | ++ | |
| 893/894 | L109D/D612S/A774S/C944S | + | ++ | + | ++ |
| 895/896 | I22R/L24W/F27A/D612S/C944R | + | + | ++ | + |
| 897/898 | Q50V/D489A/A774S | | | ++ | ++ |
| 899/900 | Q50V/L109D/D489A/D612S | | | + | + |
| 901/902 | I22R/L24W/Q50V/L109D/K267R/D489A/A774S/C944R | | + | ++ | ++ |
| 903/904 | I22R/L24W | + | | ++ | ++ |
| 905/906 | L24W/Q50V/D489A/C944S | | + | ++ | ++ |
| 907/908 | I22R/Q50V/L109D/K267R/D489A | | ++ | ++ | + |

TABLE 10-1-continued

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC | Activity from C2C12 GAA−/− Lysate FIOPC |
|---|---|---|---|---|---|
| 909/910 | L24W/D489A/C944R | | | ++ | ++ |
| 911/912 | L24W/K725E | | | ++ | + |
| 913/914 | L24W/L109D/C944S | + | + | ++ | + |
| 915/916 | D612S/P922E | | + | + | + |
| 917/918 | L24W/K267R/K725E/C944S | + | + | ++ | ++ |
| 919/920 | Q107G/L109D | | | | ++ |
| 921/922 | D489A/C944R | + | + | + | + |
| 923/924 | I22R/L24W/Q50V/K267R/D612S/P922E/C944R | | | ++ | ++ |
| 925/926 | I22R/L24W/F27A/D489A/D612S/A774S | + | | +++ | + |
| 927/928 | L24W/F27A/Q107G/K267R/D612S/C944S | + | | ++ | + |
| 929/930 | L24W/F27A/K267R/C944R | | | + | + |
| 931/932 | I22R/L24W/D489A | | | ++ | ++ |
| 933/934 | I22R/Q50V/Q107G/K267R/D489A/D612S/C944S | + | + | ++ | + |
| 935/936 | L24W/V70A/Q107G/L109D/D489A/D612S/K725E | + | + | ++ | ++ |
| 937/938 | I22R/L24W/Q107G/K267R/D489A/P922E | + | | +++ | ++ |
| 939/940 | L24W/Q107G/L109D/K267R/D489A/D612S/K725E/A774S | + | + | ++ | ++ |
| 941/942 | L24W/F27A/C944R | + | + | ++ | + |
| 943/944 | D612S | | | + | ++ |
| 945/946 | L24W/Q50V/D612S | + | | ++ | ++ |
| 947/948 | I22R/K267R/D489A/D612S | | + | ++ | ++ |
| 949/950 | L24W/F27A/Q50V/Q107G/K267R/A774S/C944S | + | + | ++ | + |
| 951/952 | L24W/C944S | + | | ++ | ++ |
| 953/954 | E614W | | | ++ | + |
| 955/956 | N527R | + | + | ++ | + |
| 957/958 | E381W | | | ++ | + |
| 959/960 | R862Y | + | | ++ | + |
| 961/962 | D923L | | | ++ | ++ |
| 963/964 | A62L | + | ++ | ++ | ++ |
| 965/966 | S916R | | | ++ | + |
| 967/968 | P914G | | | + | + |
| 969/970 | D523E | + | | ++ | + |
| 971/972 | D923W | | | ++ | |
| 973/974 | A62F | | | +++ | + |
| 975/976 | E188W | | | ++ | + |
| 977/978 | P71V | | | + | |
| 979/980 | P71W | | | ++ | + |
| 981/982 | L742V | + | + | ++ | + |
| 983/984 | N527V | | | + | + |
| 985/986 | P123V | | | + | + |
| 987/988 | H193P | + | ++ | ++ | |
| 989/990 | P123L | | ++ | ++ | + |
| 991/992 | P914Q | | | + | ++ |
| 993/994 | S124V | | | ++ | + |
| 995/996 | E858C | | | ++ | + |
| 997/998 | P57M | | | + | ++ |
| 999/1000 | S264M | + | + | ++ | + |
| 1001/1002 | T148K | | | + | |
| 1003/1004 | P57F | + | + | ++ | ++ |
| 1005/1006 | E614Q | + | | ++ | ++ |
| 1007/1008 | A112H | ++ | + | ++ | + |
| 1009/1010 | R862Q | + | + | ++ | + |
| 1011/1012 | H48W | | | ++ | ++ |
| 1013/1014 | P914T | | | + | |
| 1015/1016 | S916G | | | ++ | + |
| 1017/1018 | K88R | | + | ++ | + |
| 1019/1020 | P914K | | | ++ | ++ |

TABLE 10-1-continued

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC | Activity from C2C12 GAA-/- Lysate FIOPC |
|---|---|---|---|---|---|
| 1021/1022 | G820A | | | ++ | + |
| 1023/1024 | V913W | | | ++ | + |
| 1025/1026 | D923V | | ++ | ++ | ++ |
| 1027/1028 | P832A | | | | + |
| 1029/1030 | P71L | + | ++ | ++ | + |
| 1031/1032 | A253M | | ++ | + | ++ |
| 1033/1034 | L823F | | + | ++ | + |
| 1035/1036 | L305F | | | ++ | + |
| 1037/1038 | P914S | | | + | + |
| 1039/1040 | S727W | + | | ++ | ++ |
| 1041/1042 | L940Q | + | + | ++ | + |
| 1043/1044 | E188R | | | + | + |
| 1045/1046 | H48V | + | | + | + |
| 1047/1048 | P832R | | + | ++ | ++ |
| 1049/1050 | H48Q | + | + | + | |
| 1051/1052 | H193E | + | + | + | + |
| 1053/1054 | T148R | + | | +++ | ++ |
| 1055/1056 | G820V | | | ++ | |
| 1057/1058 | E381R | | | ++ | |
| 1059/1060 | S402N | + | + | ++ | ++ |
| 1061/1062 | L823V | | + | ++ | ++ |
| 1063/1064 | R862M | | + | ++ | + |
| 1065/1066 | K88L | | | | + |
| 1067/1068 | A62W | | ++ | ++ | ++ |
| 1069/1070 | G108R | + | ++ | + | + |
| 1071/1072 | L748V | | + | ++ | + |
| 1073/1074 | E42G | | + | ++ | + |
| 1075/1076 | E858W | | + | ++ | ++ |
| 1077/1078 | P57L | + | + | ++ | ++ |
| 1079/1080 | I333L | | | + | |
| 1081/1082 | V312A | | | + | |
| 1083/1084 | P197G | ++ | ++ | + | + |
| 1085/1086 | S916H | + | ++ | ++ | + |
| 1087/1088 | P914I | | | ++ | |
| 1089/1090 | N911R | | | ++ | |
| 1091/1092 | E381V | | | ++ | + |
| 1093/1094 | P71Y | | | ++ | + |
| 1095/1096 | R862I | + | ++ | ++ | ++ |
| 1097/1098 | S124M | + | + | ++ | + |
| 1099/1100 | P71G | + | | + | + |
| 1101/1102 | P914R | + | + | ++ | ++ |
| 1103/1104 | S124G | | | ++ | + |
| 1105/1106 | N911G | | | + | + |
| 1107/1108 | E614R | | | ++++ | ++ |
| 1109/1110 | V913R | + | ++ | ++ | ++ |
| 1111/1112 | E937K | | + | +++ | ++ |
| 1113/1114 | E204A | | + | | |
| 1115/1116 | S402V/P781Q | + | ++ | ++ | + |
| 1117/1118 | V913G | + | + | ++ | + |

[1]All activities were determined relative to the reference polypeptide of SEQ ID NO: 20. Levels of increased activity are defined as follows: "+" = 0.9 to 1.1; "++" >1.1; "+++" >2; and "++++" >3.5.

TABLE 10-2

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC |
|---|---|---|---|---|
| 19/20 | | + | + | + |
| 1119/1120 | K88G | ++ | ++ | + |
| 1121/1122 | L818V | + | | ++ |
| 1123/1124 | T148E | + | + | + |
| 1125/1126 | A741D | + | | + |
| 1127/1128 | N527P | + | + | ++ |
| 1129/1130 | L737M | ++ | ++ | ++ |
| 1131/1132 | G445L | + | | |
| 1133/1134 | P197L | + | + | + |
| 1135/1136 | M260V | + | + | |
| 1137/1138 | A112W | + | | ++ |
| 1139/1140 | H45M | + | + | + |
| 1141/1142 | G108S | + | + | ++ |
| 1143/1144 | L259N | | | + |
| 1145/1146 | P71Q | + | + | ++ |
| 1147/1148 | E42C | | | + |
| 1149/1150 | P57T | + | + | |
| 1151/1152 | P197I | + | + | + |

TABLE 10-2-continued

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC |
|---|---|---|---|---|
| 1153/1154 | L238Q | + | | |
| 1155/1156 | I816L | + | + | ++ |
| 1157/1158 | E858V | | + | + |
| 1159/1160 | S916A | + | + | + |
| 1161/1162 | P682A | + | + | + |
| 1163/1164 | M260F | + | | + |
| 1165/1166 | H255Q | + | | + |
| 1167/1168 | M432C | + | + | ++ |
| 1169/1170 | P71D | + | | ++ |
| 1171/1172 | T325A | + | | |
| 1173/1174 | E188Q/R377Q | + | + | |
| 1175/1176 | K106G | + | + | |
| 1177/1178 | K106N | ++ | + | + |
| 1179/1180 | L244I | + | | + |
| 1181/1182 | A319F | | | + |
| 1183/1184 | I815M | | | + |
| 1185/1186 | F237L | + | | + |
| 1187/1188 | H63A | ++ | + | + |
| 1189/1190 | P832E | + | + | + |
| 1191/1192 | A741T | | + | + |
| 1193/1194 | S124F | ++ | + | ++ |
| 1195/1196 | T325V | + | ++ | ++ |
| 1197/1198 | P832V | ++ | + | + |
| 1199/1200 | P682K | ++ | ++ | + |
| 1201/1202 | H387R | + | + | + |
| 1203/1204 | R862G | + | + | ++ |
| 1205/1206 | H63K | + | + | + |
| 1207/1208 | S243R | | | + |
| 1209/1210 | H255R | + | | + |
| 1211/1212 | E204G | + | + | ++ |
| 1213/1214 | V312F | + | | + |
| 1215/1216 | S727T | ++ | ++ | ++ |
| 1217/1218 | L240I | ++ | ++ | ++ |
| 1219/1220 | L261T | + | | |
| 1221/1222 | S264F | + | + | ++ |
| 1223/1224 | E614V | + | | ++ |
| 1225/1226 | T91I | | | + |
| 1227/1228 | L240M | ++ | + | ++ |
| 1229/1230 | S727A | + | + | + |
| 1231/1232 | V913A | + | | + |
| 1233/1234 | P832K | | + | ++ |
| 1235/1236 | L940G | + | | ++ |
| 1237/1238 | Q61V | + | + | + |
| 1239/1240 | R455T | + | + | + |
| 1241/1242 | H193S | ++ | + | ++ |
| 1243/1244 | M260R | + | | |
| 1245/1246 | E204Q | | | + |
| 1247/1248 | S262L | + | | + |
| 1249/1250 | T91K | + | + | ++ |
| 1251/1252 | S127G/P914F | | | + |
| 1253/1254 | R455V | ++ | + | |
| 1255/1256 | A62P | + | + | |
| 1257/1258 | E42Q | + | | + |
| 1259/1260 | E614L | + | | + |
| 1261/1262 | L305Y | + | + | ++ |
| 1263/1264 | S264L | + | + | + |
| 1265/1266 | P186G | + | + | |
| 1267/1268 | G820K | + | + | + |
| 1269/1270 | P832M | + | + | ++ |
| 1271/1272 | S264R | + | + | ++ |
| 1273/1274 | H63T | + | + | + |
| 1275/1276 | S262F | | | + |
| 1277/1278 | F237M | + | | |
| 1279/1280 | K88V | + | + | + |
| 1281/1282 | S124R | + | + | + |
| 1283/1284 | Q61M | + | + | + |
| 1285/1286 | H193V | + | + | + |
| 1287/1288 | H63C | + | | ++ |
| 1289/1290 | T148V | + | + | |
| 1291/1292 | N911M | | | + |
| 1293/1294 | N527F | + | | ++ |
| 1295/1296 | K88E | + | + | |
| 1297/1298 | L305G | + | | |
| 1299/1300 | Q61G | + | + | ++ |
| 1301/1302 | S124D | + | + | ++ |
| 1303/1304 | F237V | + | | |
| 1305/1306 | A253L | + | ++ | + |
| 1307/1308 | I815A | | | + |
| 1309/1310 | R862C | + | + | ++ |
| 1311/1312 | Q421R | + | + | ++ |
| 1313/1314 | H255T | + | | |
| 1315/1316 | H63D | + | + | + |
| 1317/1318 | P832W | + | + | ++ |
| 1319/1320 | P57R | + | + | ++ |
| 1321/1322 | T148S | | + | + |
| 1323/1324 | S262T | + | + | + |
| 1325/1326 | A62G | | | + |
| 1327/1328 | P914E | + | + | + |
| 1329/1330 | K88M | + | + | + |
| 1331/1332 | R862K | + | + | ++ |
| 1333/1334 | R455G | + | | |
| 1335/1336 | S264C | | | + |
| 1337/1338 | K88I | + | + | |
| 1339/1340 | Y248A | + | | |
| 1341/1342 | L305R | + | + | ++ |
| 1343/1344 | P279G | + | | |
| 1345/1346 | A62S | + | + | ++ |
| 1347/1348 | R455H | + | + | + |
| 1349/1350 | L320M | + | ++ | ++ |
| 1351/1352 | L736V | + | + | + |
| 1353/1354 | A309C | + | + | + |
| 1355/1356 | E204D | + | + | + |
| 1357/1358 | S264A | ++ | ++ | ++ |
| 1359/1360 | H193R | + | + | ++ |
| 1361/1362 | E614G | + | + | ++ |
| 1363/1364 | K154R | + | + | + |
| 1365/1366 | K154E | + | + | + |
| 1367/1368 | T29S | + | + | ++ |
| 1369/1370 | Q421Y | | | + |
| 1371/1372 | P197V | + | + | |
| 1373/1374 | E188G | + | + | ++ |
| 1375/1376 | K88S | | + | |
| 1377/1378 | Y248F | + | + | + |
| 1379/1380 | K88W | | + | + |
| 1381/1382 | H45N | ++ | + | + |
| 1383/1384 | P914M | + | | ++ |
| 1385/1386 | S727Q | + | + | + |
| 1387/1388 | P71A | + | + | + |
| 1389/1390 | P197T | + | + | + |
| 1391/1392 | T148A | + | + | |
| 1393/1394 | E858M | + | | + |
| 1395/1396 | L823A | + | + | ++ |
| 1397/1398 | P57S | + | ++ | + |
| 1399/1400 | E204S | + | | + |
| 1401/1402 | P186S | + | | |
| 1403/1404 | K106V | + | + | |
| 1405/1406 | L736W | + | + | |
| 1407/1408 | E614I | | | + |
| 1409/1410 | S916I | + | + | + |
| 1411/1412 | R862A | + | + | + |
| 1413/1414 | V913E | + | + | + |
| 1415/1416 | H63R | + | | ++ |
| 1417/1418 | E937S | + | + | ++ |
| 1419/1420 | S262A | + | + | |
| 1421/1422 | P71R | + | + | ++ |
| 1423/1424 | E858R | + | | |
| 1425/1426 | H63P | + | + | |
| 1427/1428 | L305V | ++ | ++ | |
| 1429/1430 | E42W | + | + | ++ |
| 1431/1432 | H48I | + | + | + |
| 1433/1434 | K154A | + | | |
| 1435/1436 | Y248V | + | | |
| 1437/1438 | A112F | + | | + |
| 1439/1440 | L818T | | | + |
| 1441/1442 | A741C | + | + | + |
| 1443/1444 | P123Y | + | + | + |

TABLE 10-2-continued

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC |
|---|---|---|---|---|
| 1445/1446 | F556S | + | + | ++ |
| 1447/1448 | D523L | + | + |  |
| 1449/1450 | R862L | + |  | + |
| 1451/1452 | A62V | + | + | + |
| 1453/1454 | Q61P | + | + | + |
| 1455/1456 | H193A | + | + |  |
| 1457/1458 | H255V | + |  |  |
| 1459/1460 | L748I | + | + | + |
| 1461/1462 | M260W | ++ |  | ++ |
| 1463/1464 | R455L | + | + | + |
| 1465/1466 | I249L | + | + | + |
| 1467/1468 | G108N | + | + | ++ |
| 1469/1470 | Q421G | + | + | ++ |
| 1471/1472 | I816V | + | + | + |
| 1473/1474 | L818M | + | + | + |
| 1475/1476 | R195Y | + | + |  |
| 1477/1478 | P832C |  |  | ++ |
| 1479/1480 | L748T | + |  |  |
| 1481/1482 | N527W |  |  | ++ |
| 1483/1484 | T148R/V772I | + | + | ++ |
| 1485/1486 | K106T | + | + |  |
| 1487/1488 | L240W/A374T |  | + |  |
| 1489/1490 | F556Y |  | + |  |
| 1491/1492 | P914F |  |  | + |
| 1493/1494 | P57Y | ++ | ++ | ++ |
| 1495/1496 | M432L | + | ++ | ++ |
| 1497/1498 | P123S | + | + | + |
| 1499/1500 | G108V | + | + |  |
| 1501/1502 | P279R | + |  |  |
| 1503/1504 | R195V | + | + |  |
| 1505/1506 | E42D | + | + |  |
| 1507/1508 | F205L | + | + |  |
| 1509/1510 | H45S | + | + | ++ |
| 1511/1512 | Q421M |  |  | ++ |
| 1513/1514 | A112R | + | + | ++ |
| 1515/1516 | S916V | + | + | ++ |
| 1517/1518 | E381T | + |  | ++ |
| 1519/1520 | A253S | + |  |  |
| 1521/1522 | F205V | + | + | + |
| 1523/1524 | E858S | + | ++ | + |
| 1525/1526 | E858G | + | ++ | ++ |
| 1527/1528 | E937Q | + | + | + |
| 1529/1530 | P914W |  |  | + |
| 1531/1532 | P197R | + | ++ | ++ |
| 1533/1534 | S264V | + | + | ++ |
| 1535/1536 | S727R |  |  | + |
| 1537/1538 | E858K |  | + | + |
| 1539/1540 | P832G | ++ | + | ++ |
| 1541/1542 | V913H |  |  | ++ |
| 1543/1544 | T148M | + |  | ++ |
| 1545/1546 | L252V | + |  | + |
| 1547/1548 | P123M | + | + | ++ |
| 1549/1550 | E937R |  |  | + |
| 1551/1552 | S243G |  |  | + |
| 1553/1554 | R455S |  |  | + |
| 1555/1556 | A741E |  |  | + |
| 1557/1558 | S243V |  |  | + |
| 1559/1560 | S402R | + | + | + |
| 1561/1562 | P832I | + | + | ++ |
| 1563/1564 | P57C | + | + | + |
| 1565/1566 | E614P |  |  | + |
| 1567/1568 | P279E | + |  | + |
| 1569/1570 | V913Q | + | + | ++ |
| 1571/1572 | P682W |  |  | ++ |
| 1573/1574 | E381G |  |  | ++ |
| 1575/1576 | N527S | + | + | + |
| 1577/1578 | E614Y | + | ++ | ++ |
| 1579/1580 | I816M |  |  | + |
| 1581/1582 | H45C | + | + | + |
| 1583/1584 | L259G | + |  |  |
| 1585/1586 | S243E |  |  | + |
| 1587/1588 | E204V | + | + | + |
| 1589/1590 | P57N | + | + | + |
| 1591/1592 | H45Y |  |  | + |
| 1593/1594 | F237A |  |  | + |
| 1595/1596 | P71C | + |  | ++ |
| 1597/1598 | H48G | + | + | ++ |
| 1599/1600 | A253G | + |  | ++ |
| 1601/1602 | L736M | ++ | + | ++ |
| 1603/1604 | L940W | + |  | ++ |
| 1605/1606 | L823G |  |  | ++ |
| 1607/1608 | S262E | ++ | ++ | + |
| 1609/1610 | E188S | + | ++ | + |
| 1611/1612 | T325L | + | + | ++ |
| 1613/1614 | N527G |  |  | + |
| 1615/1616 | P197A | + | + | + |
| 1617/1618 | H193L | + | + |  |
| 1619/1620 | S727G | + | + | ++ |
| 1621/1622 | F556R | + | + | ++ |
| 1623/1624 | L261E | + |  | + |
| 1625/1626 | A309G | ++ |  | ++ |
| 1627/1628 | E42Y |  |  | + |
| 1629/1630 | K154L | + |  | + |
| 1631/1632 | F556H | + | + | + |
| 1633/1634 | K106A | + | + |  |
| 1635/1636 | S402G | ++ | ++ | ++ |
| 1637/1638 | H45T | ++ | ++ | + |
| 1639/1640 | E858P | + | + | ++ |
| 1641/1642 | S262P | + | ++ | + |
| 1643/1644 | P914H |  | + | ++ |
| 1645/1646 | P71E | ++ | ++ | + |
| 1647/1648 | P682L | + | + | + |
| 1649/1650 | E188T |  | ++ | + |
| 1651/1652 | L329F | + | ++ | ++ |
| 1653/1654 | S246G |  |  | + |
| 1655/1656 | H63M | + | ++ | + |
| 1657/1658 | H63L | + | + | + |
| 1659/1660 | R323A |  |  | + |
| 1661/1662 | T148G | ++ | ++ | ++ |
| 1663/1664 | S124C |  |  | ++ |
| 1665/1666 | R323L |  |  | + |
| 1667/1668 | P682V | + | ++ | ++ |
| 1669/1670 | G445Y | + |  | ++ |
| 1671/1672 | E858Y | + | ++ | ++ |
| 1673/1674 | P279L | + |  | ++ |
| 1675/1676 | R862N | ++ | ++ | + |
| 1677/1678 | P186A | + | + |  |
| 1679/1680 | S262M | + | + | ++ |
| 1681/1682 | E937F |  |  | ++ |
| 1683/1684 | A741G | ++ | ++ | + |
| 1685/1686 | P123G | + | + | ++ |
| 1687/1688 | H45L |  | + | ++ |
| 1689/1690 | H63W | + | ++ | ++ |
| 1691/1692 | S246A | + |  | + |
| 1693/1694 | L940T | ++ | ++ | + |
| 1695/1696 | P57E | + | ++ | + |
| 1697/1698 | P123A | + | + | ++ |
| 1699/1700 | H63V | + | + | + |
| 1701/1702 | H255S | + |  |  |
| 1703/1704 | H387L | + | ++ | + |
| 1705/1706 | K106W |  |  | + |
| 1707/1708 | P832S | ++ | ++ | ++ |
| 1709/1710 | S727C | ++ | + | + |
| 1711/1712 | S124L | ++ | ++ | ++ |
| 1713/1714 | P914V | ++ | ++ | ++ |
| 1715/1716 | S124N | + | + | + |
| 1717/1718 | L244V |  |  | ++ |
| 1719/1720 | R323M | + |  | ++ |
| 1721/1722 | S402D | + | + | + |
| 1723/1724 | S402M | + |  | ++ |
| 1725/1726 | L259M | + |  | + |
| 1727/1728 | D523W | + |  | + |
| 1729/1730 | R195G | ++ | ++ | + |
| 1731/1732 | Q421F |  |  | ++ |
| 1733/1734 | T148H | + | ++ | ++ |
| 1735/1736 | Y248R | + |  |  |

TABLE 10-2-continued

Activity of GAA Variants Relative to SEQ ID NO: 20[1]

| SEQ ID NO: (nt/aa) | Amino Acid Differences (Relative to SEQ ID NO: 20) | Unchallenged Activity FIOPC | Plasma Stability and Activity FIOPC | Activity from Pompe Fibroblast Lysate FIOPC |
|---|---|---|---|---|
| 1737/1738 | A62T | + | + | + |
| 1739/1740 | P279A | + |  | + |
| 1741/1742 | R455E |  | + |  |
| 1743/1744 | P682G | ++ | ++ | + |
| 1745/1746 | E188M | + | ++ | ++ |
| 1747/1748 | P57Q | + | + | + |
| 1749/1750 | H193Y | + | + | + |
| 1751/1752 | Q421A | + | + | ++ |
| 1753/1754 | R195P | + | + | + |
| 1755/1756 | L320V | ++ | + | + |
| 1757/1758 | A253P | + | ++ | + |
| 1759/1760 | S298P/Q421R |  |  | ++ |
| 1761/1762 | H63G | ++ | ++ | ++ |
| 1763/1764 | A319M |  |  | ++ |
| 1765/1766 | P682F | + | + | ++ |
| 1767/1768 | H48R | + | + | ++ |
| 1769/1770 | I333V | + | + | ++ |
| 1771/1772 | A112P |  | + | + |
| 1773/1774 | Q61D | + |  |  |
| 1775/1776 | R323K |  | + | + |
| 1777/1778 | P71F | + | + | + |
| 1779/1780 | V913L | + | + | + |
| 1781/1782 | E614S | + | ++ | + |
| 1783/1784 | M260L |  |  | ++ |
| 1785/1786 | L259S |  |  | + |
| 1787/1788 | L823R |  |  | ++ |
| 1789/1790 | L240Y |  |  | + |
| 1791/1792 | S402W | + |  | ++ |
| 1793/1794 | E937G |  |  | + |
| 1795/1796 | H63Y |  | + | ++ |
| 1797/1798 | I249V/S777N | + |  | ++ |
| 1799/1800 | E42M |  |  | + |
| 1801/1802 | E188V | + | + | + |
| 1803/1804 | S402L | + | + | + |
| 1805/1806 | A112V | ++ | ++ | ++ |
| 1807/1808 | G108H | + | ++ | ++ |
| 1809/1810 | P682R | ++ | + | + |
| 1811/1812 | M432I |  |  | + |
| 1813/1814 | Q61S | + | + | + |
| 1815/1816 | N527A | + | + | + |
| 1817/1818 | A741I |  |  | + |
| 1819/1820 | G251C |  |  | + |
| 1821/1822 | H63E | ++ | ++ | + |
| 1823/1824 | T91V |  |  | + |
| 1825/1826 | Q421P |  |  | + |
| 1827/1828 | E937L |  |  | + |

[1]All activities were determined relative to the reference polypeptide of SEQ ID NO: 20. Levels of increased activity are defined as follows: "+" = 0.9 to 1.1; and "++" > 1.1.

Example 11

High-Throughput Growth of Suspension Mammalian Cells and GAA Assays Obtained Through Suspension Mammalian Expression High-Throughput (HTP) Growth of GAA and GAA Variants in Suspension Mammalian Cells (Expi293F)

EXPI293F™ cells (ThermoFisher Scientific) were transfected with pDH or PCR-amplified linear DNA (as described in Example 1) encoding a synthetic mouse IG signal peptide (SEQ ID NOS: 3381 and 3382) fusion to wild-type GAA or GAA variants using the lipofection method with EXPI-FECTAMINE™ 293 Reagent (ThermoFisher Scientific) in EXPI293™ Expression Medium (ThermoFisher Scientific). EXPI293F™ cells (ThermoFisher Scientific) were cultured in EXPI293™ Expression Medium (ThermoFisher Scientific) and seeded into Axygen 1.1 mL deep well plate (Corning, P-DW-11-C-S), at densities of 1×10⁶ cells/well/ 400 µL. Cells were subjected to lipofection-mediated transfection and returned to a shaking incubator with 8% $CO_2$ and 70% humidity for 3-4 days to allow for expression and secretion of GAA variants into the conditioned media. Conditioned media was harvested by centrifugation of expression plates and transfer of conditioned media into a BioRad Hardshell PCR Plate (BioRad, HSP9601). Plates were centrifuged again and clarified conditioned media was transferred into new 96-well plates for activity, stability or uptake into cell analysis.

HTP-Analysis of Supernatants

GAA variant activity was determined by measuring the hydrolysis of 4-methylumbelliferyl α-D-glucopyranoside (4-MUGlu). For the unchallenged assay, 5-10 µL of EXP1293F™ clarified conditioned media produced as described above was mixed with 50 µL of 1.5 mM 4-MUGlu in McIlvaine Buffer (McIlvaine, J. Biol. Chem., 49:183-186 [1921]), pH 4.4, in a 96-well, black, opaque bottom plate. The reactions were incubated at 25-37° C. for 10-60 minutes with agitation at 400 rpm, prior to quenching with 100 µL of 0.5 M sodium carbonate pH 10.5. Hydrolysis was analyzed using a SPECTRAMAX® M2 microplate reader (Molecular Devices) or an ENVISION® microplate reader (Perkin Elmer) monitoring fluorescence (Ex. 355 nm, Em. 460 nm). Unchallenged activity FIOPC was calculated by dividing normalized GAA variant by the activity of the reference polypeptide with the indicated SEQ ID NO.

HTP-Analysis of Supernatants Challenged with Plasma

GAA variants were challenged with plasma to simulate the conditions that the variants encounter in the blood following their administration to a patient. First, 30 µL of GAA variants in EXPI293F™ clarified conditioned media were combined with 30 µL of plasma (Innovative Research, Innovative Grade US Origin Monkey Cynomolgus Plasma K2 EDTA) in a 96-well plate. The plates were sealed and incubated at 37° C. for 2-4 h. Next, 10 µL of plasma-challenged sample were mixed with 50 µL of 1.5 mM 4-MUGlu in McIlvaine buffer, pH 4.4. The reactions were incubated at 25-37° C. for 15-60 minutes with agitation at 400 rpm, prior to quenching with 100 µL of 0.5 M sodium carbonate pH 10.5. Hydrolysis was analyzed using a SPECTRAMAX® M2 microplate reader or an ENVISION® microplate reader (Perkin Elmer) monitoring fluorescence (Ex. 355 nm, Em. 460 nm). Plasma stability FIOPC was calculated by dividing normalized GAA variant activity following challenge by the activity of the reference polypeptide with the indicated SEQ ID NO following challenge.

HTP-Analysis of GAA Activity in Lysates of Pone Fibroblasts and C2C12 GAA Knockout Myoblasts GAA variants from HTP EXP1293F™ expression in clarified conditioned media were incubated with target cells and assayed for residual intracellular activity after 24-72 hours. For these experiments, mammalian cells lacking functional GAA activity were used, namely Pompe patient-derived fibroblasts (Coriell Institute for Medical Research #GM00248) and C2C12 myoblasts whose native GAA gene had been knocked out using Crispr-Cas9 editing. In these experiments, Pompe fibroblasts or C2C12 GAA knockout myoblasts were seeded into 96-well plates COSTAR® (3904, Corning) and allowed to grow to confluency in standard complete growth medium. Upon confluency, complete growth culture media was removed from the plates using an automated BIOMEK® i5 liquid handling robot. Clarified conditioned media from transient HPT transfections in EXPI293F™, were transferred to Pompe patient-derived fibroblasts and C2C12 myoblasts, and allowed to incubate for 4-24 hours at 37° C., 5% $CO_2$. Medium was removed from the cultures using an automated BIOMEK® i5 liquid handling robot. The cells were briefly washed with 150 μL 1×DPBS/well, and DPBS was removed using an automated BIOMEK® i5 liquid handling robot. Then, 200 μL standard complete growth culture medium was added to each well, and the plates were returned to the incubator for 0-72 hours. At the conclusion of incubation, standard complete growth media was removed using an automated BIOMEK® i5 liquid handling robot. The cells were washed with 150 μL 1×DPBS/well, and the DPBS removed using an automated BIOMEK® i5 liquid handling. The cells were lysed via addition of 50 μL of McIlvaine buffer, pH 4.4, supplemented with 0.2-0.5% TRITON X-100™ non-ionic surfactant (Sigma #93443) and agitation at room temperature for 30 minutes. Activity was assessed by addition of 50 μL of 1.5 mM 4-MUGlu in McIlvaine buffer, pH 4.4. The plates were sealed, incubated at 37° C. for 300-360 minutes with agitation at 400 rpm, prior to quenching with 100 μL of 0.5 M sodium carbonate, pH 10.5. Hydrolysis was analyzed using a SPECTRAMAX® M2 microplate reader or an ENVISION® microplate reader (Perkin Elmer) monitoring fluorescence (Ex. 355 nm, Em. 460 nm). Cellular uptake FIOPC was calculated by dividing normalized GAA variant intracellular activity by the activity of the reference polypeptide with the indicated SEQ ID NO.

Example 12

GAA Variants of SEQ ID NO: 946

In this Example, experiments for evolution and screening of GAA variants derived from SEQ ID NO: 946 for improved GAA activity after a series of challenges are described. Libraries of variant genes GAA encoded based off of by SEQ ID NO: 946 were constructed, plated, grown, and screened for GAA MU-Glu activity ("Unchallenged Activity FIOPC"), as well as after plasma challenge ("Plasma Stability and Activity FIOPC"), as described in Example 11. Variants were also tested for 4-MUGlu activity after lysis of Pompe fibroblasts treated for 24 hours ("Lysate Activity from Extended Treatment of Pompe Fibroblast FIOPC") or GAA$^{-/-}$ C2C12 cells ("Lysate Activity from Extended Treatment C2C12 GAA-/- FIOPC") or 6 hour treatments hours ("Lysate Activity from Acute Treatment of Pompe Fibroblast FIOPC") or ("Lysate Activity from Acute Treatment C2C12 GAA-/- FIOPC"), as described in Example 11. The results of these assays are presented in Table 12-1.

TABLE 12-1

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 945/946 | | + | + | + | + | + | + |
| 1829/1830 | A62W/ A89R/ E188W/ D489A/ D500A/ S727W/ L823F | | | +++ | ++ | +++ | |
| 1831/1832 | S124V/ D500A/ S842G/ R862Q | + | | ++ | ++ | ++ | |
| 1833/1834 | W24R/ D489A/ D500A/ S842G | + | + | | ++ | + | ++ |
| 1835/1836 | W24R/ Q39H/ D489A/ R862Q | ++ | + | | ++ | | |
| 1837/1838 | W24R/ P57L/ L823F/ R862Q | + | + | + | + | ++ | |
| 1839/1840 | P57L | + | + | ++ | + | ++ | |
| 1841/1842 | W24R/ A89R/ D489A | + | + | | + | | |
| 1843/1844 | W24R/ A89R/ D489A/ S727W/ R862Q | + | + | ++ | ++ | + | |
| 1845/1846 | Q39H/ P57L/ A62W/ E188W/ D500A/ S842G | | | +++ | ++ | +++ | |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 1847/1848 | W24R/ P57L/ A62W/ A89R/ D489A/ L823F/ R862Q | + | | ++ | ++ | ++ | |
| 1849/1850 | W24R/ A62W/ A89R/ E188W/ L823V/ S842G/ R862Q | | | + | | ++ | |
| 1851/1852 | P57L/ E188W/ D489A/ L823F/ R862Q | | | ++ | ++ | +++ | |
| 1853/1854 | Q39H/ P57L/ D500A/ R862Q | + | + | ++ | ++ | ++ | |
| 1855/1856 | A62W/ S124V/ E188W/ L823F/ S842G/ R862Q | | | ++ | ++ | +++ | |
| 1857/1858 | P57F/ A62L/ L305F/ D500A/ V913R/ S916G | | | +++ | ++ | +++ | |
| 1859/1860 | P57F/ E614Q/ S916G/ S932A | | | ++ | | ++ | |
| 1861/1862 | P57F/ A62L/ L305F/ V913R | | | ++ | + | ++ | ++ |
| 1863/1864 | P57F/ A62L/ A437G/ D500A/ L761F/ P914K/ S916R | | + | +++ | ++ | + | |
| 1865/1866 | A62L/ A437G/ V913R/ S916R | | + | ++ | ++ | | |
| 1867/1868 | A62L/ D489A/ E614Q/ S916R | | | ++ | + | ++ | |
| 1869/1870 | P57F/ A62L/ V913R/ S916R/ S932A | | | +++ | ++ | ++ | |
| 1871/1872 | A62L/ N527R/ S727W/ S916G | | | +++ | | | |
| 1873/1874 | P57F/ A62W/ | | | +++ | +++ | ++ | |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| | L305F/ A437G/ D500A/ S727W/ V913R/ S916R | | | | | | |
| 1875/1876 | P57F/ A437G/ D500A/ E614Q/ S727W/ P914R | | | +++ | ++ | | |
| 1877/1878 | D500A/ S727W/ V913R/ S916R | | | +++ | ++ | + | |
| 1879/1880 | E381V | | | ++ | + | + | |
| 1881/1882 | S124V/ T148R/ E381W/ S727W/ E858W/ E937K | | | +++ | | ++ | |
| 1883/1884 | E381W/ E858C/ E937K | | | +++ | ++ | ++ | |
| 1885/1886 | A62F/ E614R | | | +++ | ++ | +++ | ++ |
| 1887/1888 | A89R/ T148R/ P149R/ E381W | + | | +++ | ++ | ++ | ++ |
| 1889/1890 | A62F/ P149R/ E381V/ E858W/ E937K | | | +++ | ++ | +++ | |
| 1891/1892 | A62F/ P149R/ S727W | | | +++ | ++ | +++ | ++ |
| 1893/1894 | A89R/ T148R/ P149R | + | + | +++ | ++ | +++ | +++ |
| 1895/1896 | A62F/ A89R/ S124V/ T148R/ E381W/ E858W | | | ++++ | ++ | +++ | ++ |
| 1897/1898 | A62F/ A89R/ T148R/ E381V/ E614R/ E858W | | | +++ | ++ | +++ | ++ |
| 1899/1900 | A62W/ S124V/ P149R/ E381V/ P832R/ E858C/ E937K | | | +++ | + | ++ | |
| 1901/1902 | S124V/ P832R/ E937K | | | +++ | ++ | ++ | + |
| 1903/1904 | A62W/ A89R/ E381V | + | + | +++ | ++ | ++ | + |
| 1905/1906 | A62W/ | | | +++ | ++ | +++ | + |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| | P149R/ E381W/ E614R/ E937K | | | | | | |
| 1907/1908 | S124V/ E381W/ E614R | | | +++ | + | ++ | + |
| 1909/1910 | A62F/ E96K/ E614R | | | +++ | + | ++ | |
| 1911/1912 | T148R/ P832R/ E858W/ E937K | | | +++ | ++ | +++ | |
| 1913/1914 | A62F/ A89R/ E381V/ D923W | | | +++ | + | ++ | ++ |
| 1915/1916 | A62F/ E381V | | | +++ | + | + | |
| 1917/1918 | A62W/ T148R/ P149R/ E381V/ E858C/ E937K | | | ++++ | ++ | ++ | + |
| 1919/1920 | A62W/ T148R/ E381W/ E858C | | | +++ | ++ | ++ | ++ |
| 1921/1922 | A62F/ A89R/ P149R/ E381W/ P832R | | | ++++ | ++ | ++ | + |
| 1923/1924 | A62W/ A89R/ P149R/ E381W | + | | +++ | ++ | ++ | + |
| 1925/1926 | D923W | | | ++ | | | |
| 1927/1928 | A62W/ A89R/ S124V/ E381W/ E858C | | | +++ | ++ | ++ | |
| 1929/1930 | E381V/ E614R/ P832R | | | +++ | + | ++ | ++ |
| 1931/1932 | A62W/ A89R/ E381W/ E858C | | | +++ | + | ++ | ++ |
| 1933/1934 | A89R/ E381W | + | + | ++ | ++ | ++ | |
| 1935/1936 | A62W/ S124V/ T148R/ P149R/ E381W/ E614R | | | +++ | + | ++ | +++ |
| 1937/1938 | A62F/ S124V/ E381W/ P832R | | | +++ | + | ++ | |
| 1939/1940 | S19T/ S124V/ P149R/ E381V/ S727W | | | +++ | + | ++ | |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 1941/1942 | A62W/ T148R/ E381W/ E614R/ E937K | | | +++ | ++ | ++ | + |
| 1943/1944 | A62F/ A89R/ T148R/ D923W | | | +++ | ++ | +++ | ++++ |
| 1945/1946 | A62W/ T148R/ E381W/ S727W | | | ++++ | ++ | ++ | +++ |
| 1947/1948 | A62W/ E381V | | | ++ | + | | |
| 1949/1950 | A62F/ A89R | + | + | +++ | ++ | + | ++ |
| 1951/1952 | A62F/ A89R/ E858C | | | +++ | ++ | ++ | ++ |
| 1953/1954 | A62W/ A437G/ D489A/ E614Q/ S727W/ V913R | | | ++ | ++ | + | |
| 1955/1956 | A62L/ A437G/ D489A/ N527R/ S727W/ V913R/ S932A | | | +++ | +++ | ++ | + |
| 1957/1958 | P57F/ A62W/ L305F/ D489A/ Q907K/ V913R/ S916G | | | +++ | ++ | +++ | ++ |
| 1959/1960 | P57F/ A62W/ L305F/ S916R | | | ++ | ++ | +++ | ++ |
| 1961/1962 | P57F/ A437G/ D500A/ N527R/ S727W/ S916R | | | +++ | +++ | ++ | ++ |
| 1963/1964 | A62L/ L305F/ S727W | | | ++ | | +++ | ++ |
| 1965/1966 | P57F/ A62L/ L305F/ A437G/ E614Q/ A683S/ V913R/ S916R/ S932A | | | +++ | ++ | ++ | + |
| 1967/1968 | P57F/ L305F | | + | ++ | + | ++ | + |
| 1969/1970 | D489A/ E614Q/ S916G | | | ++ | + | ++ | |
| 1971/1972 | D489A/ D500A | + | ++ | ++ | ++ | ++ | |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 1973/1974 | P57F/ A62W/ A437G/ V913R/ S916G | | | ++ | ++ | ++ | ++ |
| 1975/1976 | P57F/ A62W/ L305F/ D489A/ V913R/ S916G | | | +++ | ++ | ++ | ++ |
| 1977/1978 | A62W/ S727W | | | ++ | | ++ | ++ |
| 1979/1980 | A62L/ N527R | | | ++ | + | ++ | + |
| 1981/1982 | P57F/ L305F/ A437G/ S916G | | + | +++ | ++ | | |
| 1983/1984 | A62L/ A437G/ N527R/ S727W | + | + | ++++ | +++ | | |
| 1985/1986 | P57F/ A62L/ A437G/ N527R/ S727W | | + | ++++ | +++ | | |
| 1987/1988 | A62W/ D489A/ N527R/ S916R/ S932A | | | +++ | +++ | | |
| 1989/1990 | A62L/ D489A/ D500A/ S932A | + | ++ | ++ | ++ | | |
| 1991/1992 | D500A/ P914R/ S916G | | + | +++ | ++ | | |
| 1993/1994 | A62W/ D500A | | + | ++ | ++ | | |
| 1995/1996 | A62L/ L305F/ A437G/ D500A/ S727W/ V913R | | | +++ | ++ | ++ | |
| 1997/1998 | A437G | + | + | + | + | | |
| 1999/2000 | P57F/ A62L/ S916G | + | ++ | +++ | ++ | | |
| 2001/2002 | P57F/ A62L/ L305F/ A437G/ D500A/ E614Q/ S727W/ S916R | | | ++++ | +++ | ++ | +++ |
| 2003/2004 | A437G/ D489A/ P914R/ S916R | + | + | ++ | ++ | | |
| 2005/2006 | P57F/ A62W/ F120I/ N527R/ | | | ++ | | ++ | ++ |

TABLE 12-1-continued

Activity of GAA Variants Relative to SEQ ID NO: 946[1]

| SEQ ID NO: (nt/aa) | Amino Acid Differences (Relative to SEQ ID NO: 946) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 2007/2008 | V913R/ S916R A62L/ A437G/ N527R/ S916G/ S932A | | + | +++ | ++ | | ++ |
| 2009/2010 | A437G/ S727W/ P914K | | + | +++ | ++ | | |
| 2011/2012 | P57F/ A437G/ V913R/ P914R | + | ++ | ++ | +++ | | ++ |
| 2013/2014 | A62W/ S916G | + | ++ | ++ | + | | |
| 2015/2016 | P57F/ D489A/ N527R/ P914R/ S916G | | | +++ | ++ | | |
| 2017/2018 | A437G/ P914R/ S916G | | + | ++ | ++ | | |

[1]All activities were determined relative to the reference polypeptide of SEQ ID NO: 946. Levels of increased activity are defined as follows: "+" = 0.9 to 1.1; "++" > 1.1; "+++" > 2; and "++++" > 3.5.

Example 13

GAA Variants of SEQ ID NO: 1956

In this Example, experiments for evolution and screening of GAA variants derived from SEQ ID NO: 1956 for improved GAA activity after a series of challenges are described. Libraries of variant genes GAA encoded based off of by SEQ ID NO: 1956 were constructed, plated, grown, and screened for GAA MU-Glu activity ("Unchallenged Activity FIOPC"), as well as after plasma challenge ("Plasma Stability and Activity FIOPC"), as described in Example 11. Variants were also tested for 4-MUGlu activity after lysis of Pompe fibroblasts treated for 24 hours ("Lysate Activity from Extended Treatment of Pompe Fibroblast FIOPC") or GAA−/− C2C12 cells ("Lysate Activity from Extended Treatment C2C12 GAA−/− FIOPC") or 6 hour treatments hours ("Lysate Activity from Acute Treatment of Pompe Fibroblast FIOPC") or ("Lysate Activity from Acute Treatment C2C12 GAA−/− FIOPC"), as described in Example 11. The results of these assays are presented in Tables 13-1 and 13-2.

TABLE 13-1

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 1955/1956 | | + | + | + | + | + | + |
| 2019/2020 | Q795E | + | | ++ | ++ | + | ++ |
| 2021/2022 | P78E/S372T/ L390Q | | | | ++ | | |
| 2023/2024 | D87E/T266N/ S372T/T483S | | ++ | ++ | ++ | | ++ |
| 2025/2026 | D87E/Q795E | + | + | +++ | ++ | ++ | +++ |
| 2027/2028 | T266N/S372T/ T924N | | ++ | + | ++ | ++ | ++ |
| 2029/2030 | P78E | + | ++ | ++ | + | + | |
| 2031/2032 | P78E/D87E/ V536T | ++ | ++ | ++ | +++ | | |

TABLE 13-1-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 2033/2034 | D87E/T266N/T483S | + | ++ | ++ | +++ | + | ++ |
| 2035/2036 | D87E | + | + | ++ | ++ | + | ++ |
| 2037/2038 | P78E/D87E/K176T/T266N/V536T/Q615D | + | ++ | + | ++ | + | ++ |
| 2039/2040 | P78E/D87E/T266N/T483S/T924N | | ++ | ++ | +++ | | ++ |
| 2041/2042 | D87E/S372T/S777G | + | | + | | ++ | + |
| 2043/2044 | T266N/S372T/V536T/Q615D/T763L/S777G | | | | | | + |
| 2045/2046 | P78E/V536T/Q615D | + | | ++ | | | |
| 2047/2048 | P78E/T266N/T483S/V536T/Q615D | + | + | | ++ | | |
| 2049/2050 | T266N | + | ++ | ++ | +++ | + | ++ |
| 2051/2052 | D87E/Q615D | | | ++ | +++ | ++ | + |
| 2053/2054 | P78E/T266N/T763L | + | ++ | ++ | +++ | | |
| 2055/2056 | P78E/D87E/T266N/S372T/A386Y/S777G | + | +++ | ++ | ++ | | + |
| 2057/2058 | D87E/V536T/S777G | + | + | ++ | | + | + |
| 2059/2060 | L390Q/Q615D | + | | + | | ++ | |
| 2061/2062 | P78E/T266N/T483S/Q795E | + | +++ | ++ | +++ | | ++ |
| 2063/2064 | P78E/D87E/T483S/S777G | + | + | | | | ++ |
| 2065/2066 | D87E/T266N | + | +++ | +++ | +++ | ++ | +++ |
| 2067/2068 | P78E/L390Q | + | | ++ | + | | |
| 2069/2070 | T266N/V536T/Q615D/Q795E | + | + | ++ | +++ | + | + |
| 2071/2072 | D87E/T266N/T924N | | ++ | ++ | ++ | | + |
| 2073/2074 | P78E/D87E/T266N/S372T/V536T | + | +++ | ++ | +++ | + | ++ |
| 2075/2076 | S202K | + | | ++ | + | ++ | ++ |
| 2077/2078 | T44G | + | | + | ++ | | ++ |
| 2079/2080 | S446T | + | + | ++ | | ++ | ++ |
| 2081/2082 | Q344M | + | ++ | ++ | + | ++ | +++ |
| 2083/2084 | L41I/S53M | + | + | | ++ | | ++ |
| 2085/2086 | L488M | + | + | + | ++ | + | ++ |
| 2087/2088 | Q615G | | | + | ++ | + | ++ |
| 2089/2090 | P779E | + | | + | | ++ | ++ |
| 2091/2092 | S777G | ++ | + | ++ | | ++ | ++ |
| 2093/2094 | T141W | + | | | | + | + |
| 2095/2096 | G65L | + | | | + | ++ | ++ |
| 2097/2098 | L857T | + | | | | + | + |
| 2099/2100 | P779R | + | ++ | ++ | ++ | ++ | ++ |
| 2101/2102 | S202N | + | | + | | ++ | ++ |
| 2103/2104 | S678H | + | ++ | | | + | + |
| 2105/2106 | Q425R/S678I/G894C | | | ++ | + | ++ | +++ |
| 2107/2108 | T543C | + | | + | + | + | + |
| 2109/2110 | T543S | + | ++ | ++ | ++ | ++ | ++ |
| 2111/2112 | V859Y | | | | | + | + |
| 2113/2114 | P199V | + | ++ | ++ | ++ | ++ | ++ |
| 2115/2116 | G412Y | + | | | | + | + |
| 2117/2118 | L909F | + | ++ | ++ | ++ | ++ | ++ |

TABLE 13-1-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 2119/2120 | F679W | + | + | | | | |
| 2121/2122 | G65V | + | | | | + | + |
| 2123/2124 | P503S | + | + | | | ++ | ++ |
| 2125/2126 | G56L | + | ++ | + | ++ | ++ | + |
| 2127/2128 | G56A | + | + | + | | ++ | + |
| 2129/2130 | L423V | + | + | | | + | |
| 2131/2132 | S777I | + | | + | + | + | + |
| 2133/2134 | V797L | | | | ++ | | ++ |
| 2135/2136 | S678Y | ++ | ++ | + | + | + | ++ |
| 2137/2138 | N484L | | | | | | ++ |
| 2139/2140 | Q768S | + | | ++ | ++ | ++ | ++ |
| 2141/2142 | T145R | + | + | ++ | | ++ | ++ |
| 2143/2144 | I156L | | | | | + | ++ |
| 2145/2146 | V797M | | | | + | + | + |
| 2147/2148 | T44P/L347I | | | | | + | |
| 2149/2150 | E773V | ++ | | ++ | | ++ | ++ |
| 2151/2152 | A105T | + | ++ | | + | + | + |
| 2153/2154 | L530V | | | | | + | ++ |
| 2155/2156 | T543Q | ++ | | ++ | | ++ | + |
| 2157/2158 | T543V | + | | + | ++ | ++ | ++ |
| 2159/2160 | L488K | + | ++ | ++ | ++ | ++ | ++ |
| 2161/2162 | T826G | | | | | | + |
| 2163/2164 | V859T | + | | + | + | ++ | ++ |
| 2165/2166 | T141S | ++ | | ++ | + | ++ | ++ |
| 2167/2168 | S202L | + | | + | ++ | | ++ |
| 2169/2170 | S202R | + | | + | + | | + |
| 2171/2172 | A834H | + | | | | | + |
| 2173/2174 | L488G | | ++ | | | | |
| 2175/2176 | S777R | + | | + | + | | + |
| 2177/2178 | T44R | ++ | ++ | ++ | + | ++ | ++ |
| 2179/2180 | S136G | | | | | + | + |
| 2181/2182 | T44E | ++ | + | ++ | ++ | ++ | ++ |
| 2183/2184 | T145I | + | | + | + | ++ | ++ |
| 2185/2186 | D726E | | | | | | + |
| 2187/2188 | S202T | + | | + | + | + | ++ |
| 2189/2190 | P779H | | | | | ++ | + |
| 2191/2192 | A496G | + | | + | + | | + |
| 2193/2194 | S678L | + | ++ | | | ++ | +++ |
| 2195/2196 | G56R | + | ++ | + | ++ | ++ | + |
| 2197/2198 | D348G | + | | ++ | ++ | ++ | ++ |
| 2199/2200 | Q344G | | + | | | | + |
| 2201/2202 | S678T | ++ | ++ | ++ | +++ | ++ | ++ |
| 2203/2204 | T44L | ++ | | ++ | + | ++ | ++ |
| 2205/2206 | L656V | | + | | ++ | | + |
| 2207/2208 | L693F | | | | | | + |
| 2209/2210 | V710N | | | | | | + |
| 2211/2212 | V710L | | + | | | | |
| 2213/2214 | M663A | | | | | | + |
| 2215/2216 | V710M | + | | | | | |
| 2217/2218 | L670I | + | | ++ | + | | + |
| 2219/2220 | L670F | + | ++ | + | ++ | | + |
| 2221/2222 | L670R | + | + | ++ | | + | ++ |
| 2223/2224 | V710S | | | | | | + |
| 2225/2226 | F588L | + | | | | | |
| 2227/2228 | F705M | | + | | | | + |
| 2229/2230 | L670Q | + | + | + | + | | |
| 2231/2232 | L670T | + | ++ | + | ++ | | ++ |
| 2233/2234 | K154R/F588L | + | | | | | + |
| 2235/2236 | L693Y | | | + | | | |
| 2237/2238 | V710K | | + | + | | | + |
| 2239/2240 | A708C | | | + | + | | ++ |
| 2241/2242 | Y430F | | | + | | | + |
| 2243/2244 | I816L | | | ++ | | | |
| 2245/2246 | L656M | | | ++ | | | |
| 2247/2248 | L670W | | | + | + | ++ | ++ |
| 2249/2250 | L670V | + | | | | + | |
| 2251/2252 | L693I | | | ++ | + | | ++ |
| 2253/2254 | V589I/M663F | + | + | | + | ++ | ++ |
| 2255/2256 | F588V | | | ++ | | | |

TABLE 13-1-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 2257/2258 | M663F | + | + | ++ | | + | + |
| 2259/2260 | M687L | | | ++ | | + | ++ |
| 2261/2262 | L670E | + | | + | | | + |
| 2263/2264 | L670S | ++ | ++ | ++ | | | + |
| 2265/2266 | L628M | + | + | + | ++ | + | + |
| 2267/2268 | V580I | ++ | ++ | ++ | ++ | ++ | ++ |
| 2269/2270 | V580L | + | | + | | | |
| 2271/2272 | R583L | + | | + | | + | + |
| 2273/2274 | W3L/L569F | + | + | | | + | + |
| 2275/2276 | L629I | + | | | | ++ | ++ |
| 2277/2278 | T692L | + | + | + | | + | |
| 2279/2280 | A711C | | | | | | + |
| 2281/2282 | R577T | + | | | | | |
| 2283/2284 | H499Y/A711F | | | | | + | |
| 2285/2286 | P503T | + | ++ | | | | + |
| 2287/2288 | A690V | | | + | | | ++ |
| 2289/2290 | L628V | | | | | | + |
| 2291/2292 | L569I | + | + | | | | + |
| 2293/2294 | L691V | | ++ | | | | |
| 2295/2296 | T692V | | ++ | ++ | | | |
| 2297/2298 | L569Y | + | ++ | ++ | + | | ++ |
| 2299/2300 | I573Q | + | ++ | | | | ++ |
| 2301/2302 | A711F | | + | + | + | | + |
| 2303/2304 | T692Y | + | + | + | ++ | | ++ |
| 2305/2306 | L629C | | | | | | + |
| 2307/2308 | T692I | | | + | | | |
| 2309/2310 | L157S | | | + | | | |
| 2311/2312 | S671A | | + | | | | + |
| 2313/2314 | R577M | | + | | | | + |
| 2315/2316 | L569S | | ++ | | | | + |
| 2317/2318 | I573M | + | ++ | | | | + |
| 2319/2320 | R577V | + | | | | | |
| 2321/2322 | T692C | + | + | | | | |
| 2323/2324 | I573H | + | | | | | |
| 2325/2326 | S671T | ++ | ++ | | | | ++ |
| 2327/2328 | I573D | ++ | | | | | |
| 2329/2330 | S671M | + | ++ | | | | |
| 2331/2332 | R577D | + | + | | | | + |
| 2333/2334 | L629A | | + | | | + | + |
| 2335/2336 | T692G | + | + | + | | ++ | ++ |
| 2337/2338 | A711R | + | ++ | ++ | + | | ++ |
| 2339/2340 | R577A | + | + | | | | |
| 2341/2342 | L628I | + | ++ | ++ | + | + | ++ |
| 2343/2344 | T692F | + | + | + | | | ++ |
| 2345/2346 | R583G | | | | | | + |
| 2347/2348 | R583K | + | + | + | | | + |
| 2349/2350 | V580Y | | | | | | + |
| 2351/2352 | A572G | | | | | | + |
| 2353/2354 | A711W | | | + | | | |
| 2355/2356 | L629G | | | | | | + |
| 2357/2358 | I573C | + | | | | | + |
| 2359/2360 | L569V | | | | | | + |
| 2361/2362 | L669R | | | ++ | | | |
| 2363/2364 | L579V | | | | | | + |
| 2365/2366 | A572S | ++ | ++ | + | | | ++ |
| 2367/2368 | T692S | + | ++ | ++ | | | + |
| 2369/2370 | T692R | + | + | ++ | | | ++ |
| 2371/2372 | V580E | + | + | + | | | ++ |
| 2373/2374 | A574S | | + | | | | + |
| 2375/2376 | V631I | | + | + | | | + |
| 2377/2378 | A711H | + | ++ | | | + | ++ |
| 2379/2380 | L691F | + | | + | + | | ++ |
| 2381/2382 | V580G | + | | | | | + |
| 2383/2384 | V580W | + | | | | | |
| 2385/2386 | R577E | ++ | | | | | + |
| 2387/2388 | R583C | | | | | | + |
| 2389/2390 | A711L | + | | + | | | |
| 2391/2392 | S671G | | | + | | | |
| 2393/2394 | A711G | | | | + | | + |

TABLE 13-1-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 2395/2396 | V631L | | | ++ | | | + |
| 2397/2398 | L569T | + | ++ | ++ | + | | ++ |
| 2399/2400 | L569H | ++ | | | | + | + |
| 2401/2402 | L569Q | + | | | | | |
| 2403/2404 | V631M | | | ++ | | | + |
| 2405/2406 | H709S | + | | + | | | ++ |
| 2407/2408 | T227A | | | + | | | + |
| 2409/2410 | V878R | + | + | ++ | + | | |
| 2411/2412 | A578S | + | | | | | |
| 2413/2414 | T585L | + | | ++ | + | + | + |
| 2415/2416 | L871E | + | + | + | + | | |
| 2417/2418 | V222C | + | | ++ | + | | + |
| 2419/2420 | K581Y | | | | | | + |
| 2421/2422 | V878G | | | | | | ++ |
| 2423/2424 | T585V | | + | | | | |
| 2425/2426 | K581H | | | | | | ++ |
| 2427/2428 | I877L | | + | + | | | + |
| 2429/2430 | V868L | | + | | | | + |
| 2431/2432 | V878A | + | + | | ++ | + | + |
| 2433/2434 | R873Y | | + | + | + | | + |
| 2435/2436 | H706V | | | | | | + |
| 2437/2438 | K581G | | | | | | + |
| 2439/2440 | V222P | | + | | | | + |
| 2441/2442 | T585M | | | + | + | | ++ |
| 2443/2444 | T585Q | | + | | + | | + |
| 2445/2446 | L633V | | | + | | | |
| 2447/2448 | A229C | | | ++ | | | |
| 2449/2450 | L871R | | | | | | + |
| 2451/2452 | V878L | + | ++ | + | | | + |
| 2453/2454 | V868I | | + | ++ | | | + |
| 2455/2456 | K581V | | | | | | + |
| 2457/2458 | K581F | | | | | | + |
| 2459/2460 | T585F | | + | | | | + |
| 2461/2462 | V878K | | | ++ | | | + |
| 2463/2464 | R873A | + | + | + | | | |
| 2465/2466 | K581L | + | ++ | | | | + |
| 2467/2468 | K581T | + | + | | | | |
| 2469/2470 | I869L | + | + | ++ | + | | + |
| 2471/2472 | K581S | + | ++ | | | | + |
| 2473/2474 | V878S | ++ | ++ | | ++ | ++ | ++ |
| 2475/2476 | H706M | | ++ | | | | + |
| 2477/2478 | V878Q | ++ | ++ | ++ | | | |
| 2479/2480 | R873F | | | + | | | |
| 2481/2482 | I877V | + | ++ | + | | | |
| 2483/2484 | V878F | ++ | ++ | + | + | | + |
| 2485/2486 | I869S | + | ++ | + | | | |
| 2487/2488 | V878W | ++ | ++ | | | | + |
| 2489/2490 | H706F | + | + | ++ | | | |
| 2491/2492 | N225D | | + | ++ | | | |
| 2493/2494 | L871K | ++ | ++ | | + | ++ | + |
| 2495/2496 | P78E/D87E/T266N | + | + | + | + | + | + |

[1]All activities were determined relative to the reference polypeptide of SEQ ID NO: 1956. Levels of increased activity are defined as follows:

"+" = 0.9 to 1.1;

"++" >1.1; and

"+++" >2.

TABLE 13-2

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC |
|---|---|---|---|---|---|
| 2497/2498 | A142G | + |  | + | + |
| 2499/2500 | P788N |  | + |  | + |
| 2501/2502 | D493L |  | ++ | ++ | ++ |
| 2503/2504 | P788L |  | ++ |  |  |
| 2505/2506 | S612T | + | ++ | + | + |
| 2507/2508 | W265H |  |  |  | + |
| 2509/2510 | K129E |  |  |  | + |
| 2511/2512 | K752N | + | +++ |  |  |
| 2513/2514 | H499E | + |  |  | ++ |
| 2515/2516 | V185L |  | ++ |  |  |
| 2517/2518 | L857E | + |  |  |  |
| 2519/2520 | K752S | + | + |  |  |
| 2521/2522 | G56S | ++ | + | ++ | ++ |
| 2523/2524 | T145L |  | ++ |  | + |
| 2525/2526 | T44F | + |  |  | + |
| 2527/2528 | T543K | + |  |  | ++ |
| 2529/2530 | P788T |  | + |  | + |
| 2531/2532 | K176R | + | ++ |  |  |
| 2533/2534 | V859A | ++ | + |  | + |
| 2535/2536 | K129V | ++ | ++ |  | ++ |
| 2537/2538 | T44A | ++ |  | ++ |  |
| 2539/2540 | P779S | + |  | ++ |  |
| 2541/2542 | L857A | + |  |  | ++ |
| 2543/2544 | S202Q | + | + | + |  |
| 2545/2546 | F354S | ++ | ++ |  |  |
| 2547/2548 | H499I |  |  |  | + |
| 2549/2550 | S446K | + |  |  |  |
| 2551/2552 | K752G | + | ++ |  |  |
| 2553/2554 | G65F |  | + |  |  |
| 2555/2556 | P503N | + | ++ |  | + |
| 2557/2558 | T44W | + |  | ++ | + |
| 2559/2560 | A834S | + | + | ++ | + |
| 2561/2562 | S446D | + |  |  |  |
| 2563/2564 | Q615M | + |  | + |  |
| 2565/2566 | L857V | ++ |  |  |  |
| 2567/2568 | F152W | + | + | + |  |
| 2569/2570 | F152S |  |  |  | + |
| 2571/2572 | S136K |  | ++ |  |  |
| 2573/2574 | K129S | + | ++ |  |  |
| 2575/2576 | T373S | + | ++ |  |  |
| 2577/2578 | G822R | + | ++ |  | + |
| 2579/2580 | T826M | + |  |  |  |
| 2581/2582 | G936S | + |  |  | +++ |
| 2583/2584 | F679Y | + | ++ |  |  |
| 2585/2586 | H63N | ++ | + |  |  |
| 2587/2588 | V931L | + | + |  |  |
| 2589/2590 | I156C | + | ++ |  |  |
| 2591/2592 | H499V |  |  |  | ++ |
| 2593/2594 | P788A | + | + |  |  |
| 2595/2596 | K752W |  |  |  | ++ |
| 2597/2598 | W730L |  |  | ++ | +++++ |
| 2599/2600 | P788Q |  | + |  |  |
| 2601/2602 | H499M | + |  | ++ |  |
| 2603/2604 | S202D | + | ++ |  |  |
| 2605/2606 | T543L | ++ | ++ | ++ |  |
| 2607/2608 | P199A | ++ | + | ++ |  |
| 2609/2610 | S612G |  |  |  | +++ |
| 2611/2612 | S856A | ++ |  | + |  |
| 2613/2614 | K129W |  |  | ++ | ++ |
| 2615/2616 | I156R | + | + |  |  |
| 2617/2618 | S136V | ++ |  | ++ |  |
| 2619/2620 | F354L | ++ |  | ++ |  |
| 2621/2622 | P186H | + |  |  |  |
| 2623/2624 | Y677T | + |  |  |  |
| 2625/2626 | P199W | ++ |  | + |  |
| 2627/2628 | S136R | + | ++ | + |  |
| 2629/2630 | K129T | ++ | ++ | + |  |
| 2631/2632 | P337H |  |  |  | +++ |
| 2633/2634 | I469M | ++ |  | ++ |  |
| 2635/2636 | H499A | + |  |  | +++ |
| 2637/2638 | Q344C |  |  | ++ | ++++ |

TABLE 13-2-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC |
|---|---|---|---|---|---|
| 2639/2640 | D177Q | | | + | ++ |
| 2641/2642 | S202Y | | ++ | | |
| 2643/2644 | A105V | + | ++ | | |
| 2645/2646 | E773P | ++ | ++ | ++ | ++ |
| 2647/2648 | W730K | | | | + |
| 2649/2650 | L857R | + | | | + |
| 2651/2652 | A834W | | ++ | | |
| 2653/2654 | L488C | + | +++ | + | + |
| 2655/2656 | L860S | + | | ++ | ++ |
| 2657/2658 | L488E | + | +++ | | |
| 2659/2660 | L649M | | + | | |
| 2661/2662 | K267E | | | | + |
| 2663/2664 | K752L | ++ | ++ | | |
| 2665/2666 | S678R | | + | | |
| 2667/2668 | E855G | + | | | |
| 2669/2670 | N484A | | ++ | | |
| 2671/2672 | P788I | + | + | | ++ |
| 2673/2674 | D348E | ++ | ++ | + | |
| 2675/2676 | L488S | ++ | +++ | | + |
| 2677/2678 | Q615S | + | + | | |
| 2679/2680 | V859G | ++ | ++ | + | ++ |
| 2681/2682 | T141K | | | + | |
| 2683/2684 | Q768I | | ++ | ++ | +++ |
| 2685/2686 | V926T | + | + | + | |
| 2687/2688 | P788H | + | ++ | + | + |
| 2689/2690 | S446C | + | ++ | + | |
| 2691/2692 | P779I | + | ++ | + | |
| 2693/2694 | V797F | + | ++ | ++ | |
| 2695/2696 | S372D | + | | | ++ |
| 2697/2698 | V350F | | | | + |
| 2699/2700 | Y765W | | | | ++ |
| 2701/2702 | T44V | ++ | | ++ | ++ |
| 2703/2704 | T373A | + | | | |
| 2705/2706 | G936N | ++ | | | + |
| 2707/2708 | S446I | + | | | |
| 2709/2710 | S678Q | + | | + | ++ |
| 2711/2712 | P526L | | | ++ | |
| 2713/2714 | P199G | + | ++ | + | |
| 2715/2716 | P199R | + | | + | |
| 2717/2718 | L187I | + | | + | |
| 2719/2720 | K267R | + | | ++ | ++ |
| 2721/2722 | I469T | ++ | | | |
| 2723/2724 | T826I | ++ | ++ | ++ | +++ |
| 2725/2726 | S856G | ++ | + | ++ | +++ |
| 2727/2728 | P503C | + | ++ | ++ | |
| 2729/2730 | V797I | + | ++ | | |
| 2731/2732 | G412W | + | | + | ++ |
| 2733/2734 | S202A | ++ | ++ | ++ | + |
| 2735/2736 | T145A | + | + | + | |
| 2737/2738 | S777W | + | | ++ | ++ |
| 2739/2740 | G412R | + | | + | ++ |
| 2741/2742 | D348W | | | | ++ |
| 2743/2744 | P199T | ++ | + | ++ | ++ |
| 2745/2746 | W265D | | | | +++ |
| 2747/2748 | K267G | | | + | ++++ |
| 2749/2750 | W265F | + | + | | |
| 2751/2752 | H499Q | ++ | + | | + |
| 2753/2754 | E855L | + | | | ++ |
| 2755/2756 | A496M | + | + | ++ | ++ |
| 2757/2758 | S202G | ++ | | ++ | ++ |
| 2759/2760 | Q768V | | | | ++ |
| 2761/2762 | T543H | ++ | ++ | ++ | ++ |
| 2763/2764 | Y125W | | ++ | | |
| 2765/2766 | N484K | + | + | | ++ |
| 2767/2768 | N484R | | | | ++ |
| 2769/2770 | Q768K | | | + | ++ |
| 2771/2772 | S612L | | | | +++ |
| 2773/2774 | A834V | + | | | ++ |
| 2775/2776 | S678V | + | ++ | ++ | ++ |
| 2777/2778 | V926M | + | ++ | + | ++ |
| 2779/2780 | G139E | | | | ++ |

TABLE 13-2-continued

Activity of GAA Variants Relative to SEQ ID NO: 1956[1]

| SEQ ID NO: (nt/aa) | Amino Acid Differences (Relative to SEQ ID NO: 1956) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC |
|---|---|---|---|---|---|
| 2781/2782 | Y125H | | | ++ | ++ |
| 2783/2784 | P503H | + | | + | ++ |
| 2785/2786 | V797R | | | + | +++ |
| 2787/2788 | F152L | ++ | | ++ | |
| 2789/2790 | W730R | | | ++ | + |
| 2791/2792 | T924A | + | | ++ | + |
| 2793/2794 | V797W | | | | ++ |
| 2795/2796 | V797E | | ++ | | + |
| 2797/2798 | T141R | + | + | + | ++ |
| 2799/2800 | S678W | ++ | | ++ | ++ |
| 2801/2802 | G65Y | + | | ++ | + |
| 2803/2804 | G936R | ++ | | | |
| 2805/2806 | T44Y | ++ | + | ++ | ++ |
| 2807/2808 | P788S | + | | + | |
| 2809/2810 | P199V/L775I | ++ | + | ++ | ++ |
| 2811/2812 | S777M | | + | ++ | ++ |
| 2813/2814 | I156K | | | | ++ |
| 2815/2816 | P526V | + | + | | |
| 2817/2818 | G56W | ++ | ++ | ++ | |
| 2819/2820 | P199I | + | + | + | |
| 2821/2822 | D401G | + | | | |
| 2823/2824 | G412S | ++ | | ++ | |
| 2825/2826 | A834G | + | | ++ | ++ |
| 2827/2828 | P788Y | + | ++ | + | +++ |
| 2829/2830 | S612R | + | | | ++ |
| 2831/2832 | S202H | + | + | | + |
| 2833/2834 | K129I | + | ++ | | ++ |
| 2835/2836 | D401S | + | | | + |
| 2837/2838 | A496W | | ++ | | + |
| 2839/2840 | T543R | + | | + | +++ |
| 2841/2842 | S446G | + | | | + |
| 2843/2844 | I156S | | + | | ++ |
| 2845/2846 | G65R | + | ++ | ++ | ++ |
| 2847/2848 | G65A | + | | + | ++ |
| 2849/2850 | P779M | ++ | + | ++ | ++ |
| 2851/2852 | K752F | ++ | ++ | | |
| 2853/2854 | D162T | | + | | |
| 2855/2856 | I469V | ++ | | + | ++ |
| 2857/2858 | S53I | + | | + | ++ |
| 2859/2860 | A105W | ++ | + | ++ | ++ |
| 2861/2862 | L857S | + | | | |
| 2863/2864 | T543G | ++ | | | ++ |
| 2865/2866 | V350I | ++ | | + | ++ |

[1]All activities were determined relative to the reference polypeptide of SEQ ID NO: 1956. Levels of increased activity are defined as follows: "+" = 0.9 to 1.1; "++" >1.1; "+++" >2; "++++" > 3.5; and "+++++" >5.

Example 14

GAA Variants of SEQ ID NO: 24%

In this Example, experiments for evolution and screening of GAA variants derived from SEQ ID NO: 2496 for improved GAA activity after a series of challenges are described. Libraries of variant genes GAA encoded based off of by SEQ ID NO: 2496 were constructed, plated, grown, and screened for GAA MU-Glu activity ("Unchallenged Activity FIOPC"), as well as after plasma challenge ("Plasma Stability and Activity FIOPC"), as described in Example 11. Variants were also tested for 4-MUGlu activity after lysis of Pompe fibroblasts treated for 24 hours ("Lysate Activity from Extended Treatment of Pompe Fibroblast FIOPC") or GAA$^{-/-}$ C2C12 cells ("Lysate Activity from Extended Treatment C2C12 GAA-/- FIOPC") or 6 hour treatments hours ("Lysate Activity from Acute Treatment of Pompe Fibroblast FIOPC") or ("Lysate Activity from Acute Treatment C2C12 GAA-/- FIOPC"), as described in Example 11. The results of these assays are presented in Table 14-1 and Table 14-2.

TABLE 14-1

Activity of GAA Variants Relative to SEQ ID NO: 2496[1]

| SEQ ID NO: (nt/aa) | Amino Acid Differences (Relative to SEQ ID NO: 2496) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|---|
| 2495/2496 | | + | + | + | + | + | + |
| 2867/2868 | L569T/L628M/ T692Y | ++ | + | | ++ | ++ | + |
| 2869/2870 | L569Y/L670T/ A711H | ++ | | + | ++ | + | + |
| 2871/2872 | L569Y/L628M/ L670T/T692Y/ A711H/L871S | ++ | + | + | ++ | ++ | + |
| 2873/2874 | V589I/L670T/ Q795E/L871S | | | | + | + | + |
| 2875/2876 | L628M/L670F | + | | ++ | ++ | ++ | ++ |
| 2877/2878 | L569H/L628M/ L670T | ++ | + | + | ++ | + | ++ |
| 2879/2880 | L569T/L670T/ A711H/L871E | ++ | + | | ++ | ++ | ++ |
| 2881/2882 | L628M/L670T/ T692G/A711H/ Q795E | ++ | | ++ | ++ | ++ | ++ |
| 2883/2884 | L569Y/L628M/ L670T/A711H | ++ | + | + | ++ | ++ | ++ |
| 2885/2886 | L569Y/V589I/ L628M/T692G/ A711H/Q795E | + | + | + | ++ | ++ | ++ |
| 2887/2888 | L569H/T692G | + | | | + | + | + |
| 2889/2890 | L569Y/V589I/ L670T/S678T/ T692G/A711H/ Q795E | ++ | ++ | ++ | ++ | ++ | ++ |
| 2891/2892 | L569T/L871K | ++ | ++ | + | ++ | ++ | ++ |
| 2893/2894 | L569Y/V589I/ L628M/L670T/ T692Y/A711H | ++ | ++ | + | + | ++ | + |
| 2895/2896 | V589I/L871E | + | | | | + | |
| 2897/2898 | L670T/S678T/ T692Y/L871S | | + | + | + | + | ++ |
| 2899/2900 | L628M/A711H/ Q795E | ++ | | + | ++ | ++ | ++ |
| 2901/2902 | T692G/A711H | + | | ++ | + | ++ | ++ |
| 2903/2904 | V589I/L670T/ T692G/Q795E/ L871K | | | + | + | + | ++ |
| 2905/2906 | L569Y/V589I/ A711H/L871K | + | + | | ++ | + | ++ |
| 2907/2908 | L670T/T692G/ L871K | ++ | | + | ++ | ++ | + |
| 2909/2910 | L569H/T692Y | + | | | + | + | + |
| 2911/2912 | L569H/L628M/ L670T/T692Y/ A711H/L871K | ++ | + | ++ | ++ | ++ | + |
| 2913/2914 | L670T/S678T | ++ | | + | ++ | ++ | ++ |
| 2915/2916 | L569T/L670T/ S678T/T692G/ L871K | ++ | ++ | ++ | ++ | ++ | ++ |
| 2917/2918 | V589I | | | | | | ++ |
| 2919/2920 | L569H/V589I/ L628M/L670T/ S678T/T692G/ A711H/Q795E/ L871S | ++ | ++ | ++ | + | ++ | ++ |
| 2921/2922 | L569H/L670F/ S678T/T692G/ L871S | + | ++ | + | + | + | ++ |
| 2923/2924 | L569T/V589I/ L628M/L670F/ T692G/A711H | ++ | ++ | ++ | ++ | ++ | ++ |
| 2925/2926 | L569H/L670T/ T692G | ++ | + | | | + | |
| 2927/2928 | L569Y/L871E | ++ | + | | | + | |

TABLE 14-1-continued

Activity of GAA Variants Relative to SEQ ID NO: 2496[1]

| SEQ ID NO: (nt/aa) | Amino Acid Differences (Relative to SEQ ID NO: 2496) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 2929/2930 | L569H/L628M/L670F/S678T | ++ | + | + | | + | ++ |
| 2931/2932 | L569Y/L670F/S678T | + | ++ | | | | ++ |
| 2933/2934 | L569Y/V589I/L670F | ++ | ++ | | + | + | ++ |
| 2935/2936 | L569Y/V589I/L670T/L871K | ++ | ++ | + | + | + | ++ |
| 2937/2938 | L569T/L871S | + | ++ | | | + | + |
| 2939/2940 | L871K | + | | + | | ++ | ++ |
| 2941/2942 | L569Y/L670T | | | | ++ | + | ++ |
| 2943/2944 | L569Y/T692Y/A711H | ++ | ++ | | + | | + |
| 2945/2946 | L871S | + | | | | + | ++ |
| 2947/2948 | L569Y/A711H | ++ | ++ | | | | ++ |
| 2949/2950 | L628M/L871S | + | | | + | ++ | ++ |
| 2951/2952 | L569T/V589I/L871S | ++ | + | | + | + | ++ |
| 2953/2954 | T692G/A711H/I869L/V878S | ++ | | ++ | ++ | ++ | ++ |
| 2955/2956 | A572S/F588L/S678T/T692G/I869L/V878A | + | | | + | + | + |
| 2957/2958 | A711H | ++ | | + | ++ | ++ | ++ |
| 2959/2960 | T692G/I859S | | | | + | ++ | + |
| 2961/2962 | A572S/T692L/I869S/V878S | + | + | + | ++ | ++ | ++ |
| 2963/2964 | L629I/I869L/V878S | | | + | | ++ | + |
| 2965/2966 | A572S/F588L/Q795E | | | | | | + |
| 2967/2968 | A711H/I869S/V878S | + | | | | + | + |
| 2969/2970 | V878S | ++ | + | | ++ | + | + |
| 2971/2972 | S678T/T692G/A711H/I869S | ++ | + | + | ++ | ++ | ++ |
| 2973/2974 | A572S/T692G/I869S/V878S | + | | | | + | |
| 2975/2976 | A572S/T692G/V878S | + | | | + | ++ | ++ |
| 2977/2978 | A711H/Q795E/I869S/V878S | + | | | | + | ++ |
| 2979/2980 | Q795E/V878S | + | + | | | + | |
| 2981/2982 | T692G/A711H/Q795E/I869S | + | | + | | + | + |
| 2983/2984 | S678T/T692G/Q795E/I869S | | | | + | ++ | ++ |
| 2985/2986 | T692G/A711H/I869S/V878A | | | | + | ++ | |
| 2987/2988 | L569T/A711H | ++ | | | + | + | |
| 2989/2990 | L569T/L628M/S678T/A711H | + | + | | | + | + |
| 2991/2992 | L569T/V589I/T692G/Q795E/L871K/V878S | ++ | ++ | | ++ | ++ | |
| 2993/2994 | L569T/V589I/S678T/L871K/V878S | ++ | ++ | | ++ | ++ | + |
| 2995/2996 | L569H/A711H/I869S/V878S | + | | | | ++ | |
| 2997/2998 | S678T/Q795E/L871K/V878A | + | | | | + | ++ |
| 2999/3000 | L569H/S678T/T692G/Q795E | + | | | + | + | |
| 3001/3002 | F588L/V589I/L628M/S678T | ++ | | | + | + | + |
| 3003/3004 | T692Y | ++ | + | + | + | ++ | + |
| 3005/3006 | L569T | ++ | + | | + | ++ | + |
| 3007/3008 | T692G/L871K | + | | + | + | ++ | |

TABLE 14-1-continued

Activity of GAA Variants Relative to SEQ ID NO: 2496[1]

| SEQ ID NO: (nt/aa) | Amino Acid Differences (Relative to SEQ ID NO: 2496) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|---|
| 3009/3010 | L569T/F588L/V878S | ++ | ++ | + | ++ | ++ | + |
| 3011/3012 | L569H/A711H/L871K | ++ | | | ++ | + | |
| 3013/3014 | L569T/F588L/S678T/T692Y | ++ | ++ | | + | + | + |
| 3015/3016 | L569T/F588L/A711H/I869L/L871K/V878S | + | | | + | ++ | |
| 3017/3018 | L569T/F588L | ++ | ++ | | | + | ++ |
| 3019/3020 | L569T/T692Y | + | ++ | ++ | ++ | ++ | + |
| 3021/3022 | L569T/S678T/I869S/V878S | ++ | + | | ++ | + | ++ |
| 3023/3024 | L628M/L629I/T692Y/L871S/V878S | + | | | + | ++ | + |
| 3025/3026 | L569T/S678T/V878S | ++ | ++ | + | ++ | ++ | ++ |
| 3027/3028 | L569H/A711H/Q795E/L871S/V878S | ++ | ++ | | + | ++ | ++ |
| 3029/3030 | A711H/L871K | ++ | | | | + | + |
| 3031/3032 | T692G/A711H/Q795E/I869L/L871K/V878A | + | | | + | ++ | + |
| 3033/3034 | L569T/F588L/V589I/L628M/L629I/T692Y/A711H | | + | + | + | | ++ |
| 3035/3036 | S678T/T692G/I869S | ++ | | | + | ++ | + |
| 3037/3038 | T692G/I869L/L871K/V878S/S916R | + | | | + | ++ | + |
| 3039/3040 | L569H/L628M | ++ | + | | | + | + |
| 3041/3042 | L628M/V878S | ++ | | | + | + | + |
| 3043/3044 | T692G/A711H/L871S/V878A | ++ | | + | ++ | ++ | ++ |
| 3045/3046 | L569T/Q795E | ++ | ++ | | + | + | ++ |
| 3047/3048 | L569T/T692Y/A711H/I869L/L871K/V878A | ++ | ++ | + | ++ | ++ | ++ |
| 3049/3050 | S246T | ++ | | | + | + | + |
| 3051/3052 | T585K | ++ | | | | + | ++ |
| 3053/3054 | G584E | + | | | | + | |
| 3055/3056 | A812E | ++ | + | | + | + | + |
| 3057/3058 | V313L | + | | | | + | |
| 3059/3060 | L304M | ++ | | | + | ++ | ++ |
| 3061/3062 | V313I | ++ | | | + | ++ | ++ |
| 3063/3064 | A582T | ++ | | | ++ | ++ | ++ |

[1]All activities were determined relative to the reference polypeptide of SEQ ID NO: 2496. Levels of increased activity are defined as follows:
"+" = 0.9 to 1.1; and
"++" >1.1.

TABLE 14-2

Activity of GAA Variants Relative to SEQ ID NO: 2496[1]

| SEQ ID NO: (nt/aa) | Amino Acid Differences (Relative to SEQ ID NO: 2496) | Unchallenged Activity FIOPC | Plasma Stability and Activity FIOPC | Lysate Activity from Extended Treatment of Pompe Fibroblast FIOPC | Lysate Activity from Extended Treatment C2C12 GAA-/- FIOPC |
|---|---|---|---|---|---|
| 2495/2496 | | + | + | + | + |
| 3065/3066 | L810V | | ++ | | |

TABLE 14-2-continued

Activity of GAA Variants Relative to SEQ ID NO: 2496[1]

| SEQ ID NO: (nt/aa) | Amino Acid Differences (Relative to SEQ ID NO: 2496) | Unchallenged Activity FIOPC | Plasma Stability and Activity FIOPC | Lysate Activity from Extended Treatment of Pompe Fibroblast FIOPC | Lysate Activity from Extended Treatment C2C12 GAA−/− FIOPC |
|---|---|---|---|---|---|
| 3067/3068 | A60V/V589A | | | | + |
| 3069/3070 | S307T | | | | |
| 3071/3072 | V313T | | | + | |
| 3073/3074 | G584C | | | | + |

[1] All activities were determined relative to the reference polypeptide of SEQ ID NO: 2496. Levels of increased activity are defined as follows: "+" = 0.9 to 1.1; and "++" > 1.1.

Example 15

GAA Variants of SEQ ID NO: 2880

In this Example, experiments for evolution and screening offgas variants derived from SEQ ID NO: 2880 for improved GAA activity after a series of challenges are described. Libraries of variant genes GA encoded based off of by SEQ ID NO: 2880 were constructed, plated, grown, and screened for GAA MU-Glu activity ("Unchallenged Activity FIOPC"), as well as after plasma challenge ("Plasma Stability and Activity FIOPC"), as described in Example 11. Variants were also tested for 4-MUGlu activity after lysis of GAA$^{−/−}$ C2C12 cells ("Lysate Activity from Extended Treatment C2C12 GAA−/− FIOPC") or 6 hour treatments hours of Pompe fibroblasts ("Lysate Activity from Acute Treatment of Pompe Fibroblast FIOPC") or GAA$^{−/−}$ C2C12 cells ("Lysate Activity from Acute Treatment C2C12 GAA−/− FIOPC"), as described in Example 11. The results, of these assays are presented in Table 15-1.

TABLE 15-1

Activity of GAA Variants Relative to SEQ ID NO: 2880[1]

| SEQ ID NO: (nt/aa) | Amino Acid Differences (Relative to SEQ ID NO: 2880) | Unchallenged Activity FIOPC | Plasma Stability and Activity FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|
| 2879/2880 | | + | + | + | + | + |
| 3075/3076 | R527N/L736M/A932S | ++ | ++ | + | ++ | ++ |
| 3077/3078 | L109D/S678T/A812E | ++ | ++ | ++ | + | ++ |
| 3079/3080 | A89R/S842G/V878S | ++ | + | + | + | + |
| 3081/3082 | R403H/R527N/S678T/T692G/L736M/A812E/S842G/L860F | ++ | ++ | ++ | ++ | ++ |
| 3083/3084 | S678T/T692G/A812E | ++ | ++ | + | + | ++ |
| 3085/3086 | L109D/W727S/L860F/V878S | ++ | ++ | ++ | + | ++ |
| 3087/3088 | A89R/R527N/W727S/A812E/L860F | ++ | ++ | ++ | + | ++ |
| 3089/3090 | A89R/S678T/T692G/L736M/A932S | ++ | ++ | ++ | ++ | ++ |
| 3091/3092 | L109D/R527N/S678T/A812E | ++ | ++ | + | + | ++ |
| 3093/3094 | S678T/L860F/V878S | ++ | ++ | ++ | + | ++ |
| 3095/3096 | L109D/A812E | ++ | ++ | + | | ++ |
| 3097/3098 | T692G/W727S/L736M/S842G/R913V | ++ | ++ | ++ | ++ | ++ |
| 3099/3100 | A89R/L109D/W727S/A932S | ++ | ++ | ++ | + | ++ |
| 3101/3102 | R527N/S678T/T692G/W727S/L736M/V878S | ++ | ++ | ++ | + | ++ |

TABLE 15-1-continued

Activity of GAA Variants Relative to SEQ ID NO: 2880[1]

| SEQ ID NO: (nt/aa) | Amino Acid Differences (Relative to SEQ ID NO: 2880) | Unchallenged Activity FIOPC | Plasma Stability and Activity FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|
| 3103/3104 | R527N/T692G/ W727S/L736M/ A812E | ++ | ++ | ++ | + | ++ |
| 3105/3106 | A89R/R527N | ++ | ++ | + | | + |
| 3107/3108 | A89R/L109D/ A932S | ++ | ++ | + | | + |
| 3109/3110 | L109D/S842G | + | | + | + | ++ |
| 3111/3112 | S678T/R913V | ++ | ++ | ++ | ++ | ++ |
| 3113/3114 | A89R/L109D/ S678T/W727S/ L736M/A812E/ V878S | ++ | ++ | ++ | + | ++ |
| 3115/3116 | L109D/T692G/ W727S/A812E/ S842G/L860F | ++ | ++ | ++ | ++ | ++ |
| 3117/3118 | T692G/A812E | ++ | + | ++ | + | + |
| 3119/3120 | S678T/A932S | ++ | + | ++ | + | ++ |
| 3121/3122 | L109D/S678T/ L736M/A812E/ V878S | ++ | ++ | ++ | ++ | ++ |
| 3123/3124 | L109D/A932S | ++ | ++ | ++ | + | ++ |
| 3125/3126 | R527N/T692G/ W727S/L736M/ S842G/L860F/ V878S | ++ | ++ | + | + | ++ |
| 3127/3128 | R527N/W727S/ L736M | ++ | ++ | + | | ++ |
| 3129/3130 | L109D/S678T/ S842G/V878S | ++ | + | + | ++ | ++ |
| 3131/3132 | L109D/S678T/ W727S/L860F | ++ | ++ | ++ | + | ++ |
| 3133/3134 | R527N/S678T/ T692G/A812E/ A932S | ++ | ++ | ++ | ++ | +++ |
| 3135/3136 | A89R/S678T/ A812E/V878S | ++ | + | ++ | ++ | ++ |
| 3137/3138 | R527N/A812E | ++ | ++ | + | | ++ |
| 3139/3140 | S678T/T692G/ W727S/A812E/ S842G | ++ | + | + | | ++ |
| 3141/3142 | L109D/L736M/ A932S | ++ | ++ | ++ | ++ | ++ |
| 3143/3144 | A89R/L109D/ R527N/S678T/ W727S/S842G | ++ | ++ | ++ | | ++ |
| 3145/3146 | W727S | ++ | + | ++ | + | ++ |
| 3147/3148 | A89R/R527N/ S678T/A932S | ++ | ++ | ++ | ++ | +++ |
| 3149/3150 | L109D/S678T/ T692G/S842G/ L860F/V878S/ A932S | ++ | ++ | ++ | ++ | +++ |
| 3151/3152 | A89R/R527N/ S678T/T692G/ L736M/S842G/ V878S/A932S | ++ | + | ++ | + | ++ |
| 3153/3154 | R527N | ++ | | + | | + |
| 3155/3156 | L109D/T692G/ W727S/L736M/ A812E | ++ | ++ | + | + | ++ |
| 3157/3158 | W727S/A932S | ++ | ++ | ++ | + | ++ |
| 3159/3160 | V878S/A932S | ++ | ++ | ++ | + | ++ |
| 3161/3162 | S678T/A812E | ++ | + | ++ | ++ | +++ |
| 3163/3164 | W24L/S28L/ T29L/Q39P/ V50Q/L62A/ E78P/E87D/ Q135S/S150T/ N266T/K267R/ | ++ | ++ | + | | ++ |

TABLE 15-1-continued

Activity of GAA Variants Relative to SEQ ID NO: 2880[1]

| SEQ ID NO: (nt/aa) | Amino Acid Differences (Relative to SEQ ID NO: 2880) | Unchallenged Activity FIOPC | Plasma Stability and Activity FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|
| | V522E/R527N/ A551V/T670L/ W727S/P750A/ K830Q/S842G/ E871L/H883R/ G894Q/A932S | | | | | |
| 3165/3166 | S28L/V50Q/ E78P/E87D/ Q135S/N266T/ K267R/G437A/ E486T/R527N/ A551V/T670L/ W727S/P750A/ K830Q/S842G/ E871L/H883R/ G894Q/R913V/ A932S | ++ | ++ | + | | + |
| 3167/3168 | W24L/S28L/ Q39P/V50Q/ L62A/E78P/ E87D/Q135S/ S150T/N266T/ K267R/V522E/ R527N/A551V/ T569L/W727S/ K830Q/S842G/ E871L/H883R/ G894Q/R913V | ++ | + | | | + |
| 3169/3170 | T29L/Q39P/ V50Q/L62A/ G65R/E78P/ E87D/Q135S/ S150T/G437A/ A551V/T569L/ T670L/W727S/ P750A/K830Q/ S842G/H883R/ G894Q/A932S | ++ | + | ++ | | |
| 3171/3172 | W24L/V50Q/ E78P/E87D/ Q135S/S150T/ K267R/E486T/ V522E/R527N/ A551V/T670L/ W727S/P750A/ K830Q/S842G/ E871L/H883R/ G894Q/R913V/ A932S | ++ | ++ | ++ | | ++ |
| 3173/3174 | W24L/T29L/ Q39P/V50Q/ L62A/E78P/ E87D/Q135S/ S150T/K267R/ G437A/E486T/ V522E/R527N/ A551V/H711A/ W727S/P750A/ K830Q/S842G/ E871L/H883R/ G894Q/R913V/ A932S | ++ | ++ | + | | ++ |
| 3175/3176 | L62A/Q135S/ V522E/H711A/ W727S/P750A/ S842G/E871L/ G894Q | ++ | ++ | ++ | + | ++ |
| 3177/3178 | E87D/P750A | + | ++ | ++ | | ++ |

TABLE 15-1-continued

Activity of GAA Variants Relative to SEQ ID NO: 2880[1]

| SEQ ID NO: (nt/aa) | Amino Acid Differences (Relative to SEQ ID NO: 2880) | Unchallenged Activity FIOPC | Plasma Stability and Activity FIOPC | Lysate Activity from Extended Treatment C2C12 GAA-/- FIOPC | Lysate Activity from Acute Treatment of Pompe Fibroblast FIOPC | Lysate Activity from Acute Treatment C2C12 GAA-/- FIOPC |
|---|---|---|---|---|---|---|
| 3179/3180 | Q135S/H711A/ P750A/A932S | + | + | ++ | + | ++ |
| 3181/3182 | V522E/K830Q | ++ | ++ | ++ | | ++ |
| 3183/3184 | S28L/G437A/ R527N/E871L | ++ | ++ | ++ | ++ | ++ |
| 3185/3186 | L62A/G437A | ++ | ++ | + | | ++ |
| 3187/3188 | G437A/P750A/ K830Q/A932S | ++ | ++ | + | ++ | ++ |
| 3189/3190 | T29L/E78P/ Q135S/W727S/ K830Q | ++ | ++ | ++ | + | ++ |
| 3191/3192 | L62A | ++ | ++ | ++ | ++ | ++ |
| 3193/3194 | V50Q/H711A | + | + | ++ | + | ++ |
| 3195/3196 | S150T/E871L/ A932S | + | ++ | + | ++ | + |
| 3197/3198 | Q39P/V50Q | + | + | ++ | + | ++ |
| 3199/3200 | E78P/E87D/ E486T/R527N/ T670L/W727S/ P750A/K830Q/ S842G/E871L/ R913V/A932S | + | + | ++ | | ++ |
| 3201/3202 | W24L/R527N/ W727S/S842G/ E871L/H883R/ R913V/A932S | ++ | ++ | ++ | | +++ |
| 3203/3204 | W24L/T670L/ W727S/P750A/ S842G/E871L | ++ | ++ | ++ | ++ | ++ |
| 3205/3206 | V50Q/W727S/ P750A/H883R/ G894Q | ++ | ++ | ++ | ++ | ++ |
| 3207/3208 | T29L/Q135S/ S150T/R527N/ T670L/W727S/ H883R | + | + | ++ | + | ++ |
| 3209/3210 | Q39P/W727S/ P750A/A932S | ++ | ++ | ++ | + | ++ |
| 3211/3212 | S150T/H883R/ A932S | + | + | + | + | |
| 3213/3214 | Q135S/T670L/ W727S | + | + | +++ | ++ | ++ |
| 3215/3216 | T29L/E78P/ E87D/S150T/ R527N/W727S | + | + | +++ | ++ | ++ |
| 3217/3218 | W24L/S28L/ V50Q/Q135S/ S150T/G437A/ V522E/R527N/ E871L/H883R/ G894Q/A932S | ++ | ++ | +++ | | ++ |
| 3219/3220 | W24L/L62A/ E87D/E486T/ W727S | + | + | +++ | + | + |
| 3221/3222 | T29L/V522E/ T670L/H711A/ E871L | + | + | +++ | | + |
| 3223/3224 | S28L/V522E/ R527N/T569L/ H711A/K830Q/ G894Q | + | + | ++ | | |
| 3225/3226 | S28L/W727S/ E871L | + | + | +++ | ++ | +++ |
| 3227/3228 | T670L/H711A/ E871L | | | +++ | + | ++ |
| 3229/3230 | T29L/S150T/ G437A/W727S | + | | ++ | | + |
| 3231/3232 | K267R/R527N/ W727S | ++ | + | +++ | ++ | ++ |

TABLE 15-1-continued

Activity of GAA Variants Relative to SEQ ID NO: 2880[1]

| SEQ ID NO: (nt/aa) | Amino Acid Differences (Relative to SEQ ID NO: 2880) | Unchallenged Activity FIOPC | Plasma Stability and Activity FIOPC | Lysate Activity from Extended Treatment C2C12 GAA−/− FIOPC | Lysate Activity from Acute Treatment of Pompe Fibroblast FIOPC | Lysate Activity from Acute Treatment C2C12 GAA−/− FIOPC |
|---|---|---|---|---|---|---|
| 3233/3234 | S150T/R527N/ S842G/E871L/ R913V | + | + | +++ | ++ | ++ |
| 3235/3236 | T29L/S150T/ K267R/W727S/ P750A/E871L/ H883R/A932S | + | + | ++ | ++ | ++ |
| 3237/3238 | S28L/W727S | + | | +++ | ++ | ++ |
| 3239/3240 | T29L/E87D | + | | +++ | ++ | ++ |
| 3241/3242 | T29L/L62A/ G437A/R527N | + | | ++ | + | + |
| 3243/3244 | V50Q/Q135S/ S150T/A932S | + | + | +++ | ++ | ++ |
| 3245/3246 | V50Q/G437A/ V522E/R527N | + | + | ++ | | + |
| 3247/3248 | S28L/L62A | ++ | ++ | ++ | ++ | ++ |
| 3249/3250 | S28L/L62A/ K267R/A932S | ++ | ++ | ++ | ++ | ++ |
| 3251/3252 | W24L/V50Q/ E486T/R527N/ H711A/W727S | ++ | ++ | + | + | ++ |
| 3253/3254 | L62A/E87D/ S150T/W727S | ++ | +++ | ++ | ++ | ++ |
| 3255/3256 | S28L | ++ | ++ | ++ | +++ | ++ |
| 3257/3258 | W24L/L62A/ W727S/K830Q/ A932S | +++ | +++ | ++ | ++ | ++ |
| 3259/3260 | V522E/R527N/ T569L/W727S | ++ | ++ | + | + | ++ |
| 3261/3262 | T29L/T670L/ A932S | ++ | ++ | ++ | ++ | ++ |
| 3263/3264 | E871L | ++ | +++ | ++ | +++ | ++ |
| 3265/3266 | G437A/V522E/ R527N/T670L/ E871L | ++ | ++ | + | | + |
| 3267/3268 | V522E | ++ | ++ | ++ | + | ++ |
| 3269/3270 | L62A/E87D/ S150T | ++ | ++ | ++ | ++ | ++ |
| 3271/3272 | W24L/S28L/ L62A/V522E/ T569L/A932S | ++ | ++ | ++ | ++ | + |
| 3273/3274 | W24L/E87D/ Q135S/V522E/ T670L/H711A/ K830Q/S842G/ R913V | ++ | +++ | ++ | ++ | ++ |
| 3275/3276 | W24L/S150T/ V522E/R527N/ W727S/H883R/ G894Q | ++ | +++ | ++ | ++ | ++ |
| 3277/3278 | T670L/K830Q/ E871L | ++ | +++ | ++ | + | ++ |
| 3279/3280 | L62A/G437A/ W727S | +++ | +++ | ++ | ++ | ++ |
| 3281/3282 | S28L/V50Q/ V522E/R527N/ H711A/W727S/ E871L | +++ | +++ | ++ | ++ | ++ |
| 3283/3284 | W24L/S28L/ G437A/E486T/ R527N | ++ | ++ | ++ | ++ | ++ |

[1] All activities were determined relative to the reference polypeptide of SEQ ID NO: 2880. Levels of increased activity are defined as follows:
"+" = 0.9 to 1.1;
"++" >1.1;
"+++" >2; and
"++++" >3.5.

Example 16

GAA Variants of SEQ ID NO: 3104

In this Example, experiments for evolution and screening of GAA variants derived from SEQ ID NO: 3104 for improved GAA activity after a series of challenges are described. Libraries of variant genes GAA encoded based off of by SEQ ID NO: 3104 were constructed, plated, grown, and screened for GAA MU-Glu activity ("Unchallenged Activity FIOPC"), as well as after plasma challenge ("Plasma Stability and Activity FIOPC"), as described in Example 11. Variants were also tested for 4-MUGlu activity after lysis of Pompe fibroblasts treated for 20 hours ("Lysate Activity from Extended Treatment of Pompe Fibroblast FIOPC") or GAA$^{-/-}$ C2C12 cells ("Lysate Activity from Extended Treatment C2C12 GAA-/- FIOPC") or 4 hour treatments hours ("Lysate Activity from Acute Treatment of Pompe Fibroblast FIOPC") or ("Lysate Activity from Acute Treatment C2C12 GAA-/- FIOPC"), as described in Example 11. The results of these assays are presented in Table 16-1.

TABLE 16-1

Activity of GAA Variants Relative to SEQ ID NO: 3104[1]

| SEQ ID NO: (nt/aa) | Amino Acid Differences (Relative to SEQ ID NO: 3104) | Unchallenged Activity FIOPC | Plasma Stability and Activity FIOPC | Lysate Activity from Extended Treatment of Pompe Fibroblast FIOPC | Lysate Activity from Acute Treatment of Pompe Fibroblast FIOPC | Lysate Activity from Extended Treatment C2C12 GAA-/- FIOPC | Lysate Activity from Acute Treatment C2C12 GAA-/- FIOPC |
|---|---|---|---|---|---|---|---|
| 3285/3286 | L62A/L860F/A932S | + | + | + | + | + | ++ |
| 3287/3288 | L62A/S678T/K830Q/L860F/V878S/A932S | + | + | + | + | + | +++ |
| 3289/3290 | L62A/K830Q/L860F/V878S/A932S | + | + | + | + | + | + |
| 3291/3292 | S678T/A932S | + | + | + | + | + | + |
| 3293/3294 | L62A/M833I/L860F/A932S | + | + | + | + | + | + |
| 3295/3296 | L62A/L860F/E871L/V878S | + | + | + | + | + | + |
| 3297/3298 | L62A/S678T/P785Q | + | + | + | + | + | + |
| 3299/3300 | L62A/V878S/A932S | + | + | + | + | + | ++ |
| 3301/3302 | L62A/K830Q/L860F/E871L/R873H | + | + | + | + | + | + |
| 3303/3304 | L62A/Y248H/S678T/K830Q/V878S/A932S | + | + | + | + | + | + |
| 3305/3306 | L62A/L860F/E871L | + | + | + | + | + | + |
| 3307/3308 | S678T | + | + | + | + | + | + |
| 3309/3310 | L62A/S678T/K830Q/E871L/A932S | + | + | + | + | + | + |
| 3311/3312 | L62A/S678T/L860F | + | + | + | + | + | ++ |
| 3313/3314 | L62A/A89D/K830Q | + | + | + | + | + | + |
| 3315/3316 | L62A/V878S | + | + | + | + | + | + |
| 3317/3318 | L62A/K830Q/A932S | + | + | + | + | + | +++ |
| 3319/3320 | L62A/S678T/K830Q/L860F/A932S | + | + | + | + | + | ++ |
| 3321/3322 | L62A/A932S | + | + | + | + | + | ++ |
| 3323/3324 | L62A/S678T/L860F/V878S | + | + | + | + | + | + |
| 3325/3326 | L62A/S678T/E871L | + | + | + | + | + | +++ |
| 3327/3328 | L62A | + | + | + | + | + | ++ |
| 3329/3330 | L62A/S678T/K830Q/L860F | + | + | + | + | + | +++ |
| 3331/3332 | L62A/K830Q/V878S | + | + | + | + | + | + |
| 3333/3334 | L62A/E871L/A932S | + | + | + | + | + | +++ |
| 3335/3336 | L62A/K830Q/E871L/A932S | + | + | + | + | + | + |

TABLE 16-1-continued

Activity of GAA Variants Relative to SEQ ID NO: 3104[1]

| SEQ ID NO: (nt/aa) | Amino Acid Differences (Relative to SEQ ID NO: 3104) | Unchallenged Activity FIOPC | Plasma Stability and Activity FIOPC | Lysate Activity from Extended Treatment of Pompe Fibroblast FIOPC | Lysate Activity from Acute Treatment of Pompe Fibroblast FIOPC | Lysate Activity from Extended Treatment C2C12 GAA-/- FIOPC | Lysate Activity from Acute Treatment C2C12 GAA-/- FIOPC |
|---|---|---|---|---|---|---|---|
| 3337/3338 | L62A/S678T/K830Q/E871L | + | + | + | + | + | ++ |
| 3339/3340 | L860F/A932S | + | + | + | + | + | ++ |
| 3341/3342 | L62A/S678T/V878S/A932S | + | + | + | + | + | + |
| 3343/3344 | L62A/S678T/K830Q | + | + | + | + | + | + |
| 3345/3346 | L62A/L860F | + | + | + | + | + | +++ |
| 3347/3348 | L62A/S678T/V878S/A932T | + | + | + | + | + | +++ |
| 3349/3350 | L62A/S678T/K830Q/L860F/V878S | + | + | + | + | + | + |
| 3351/3352 | L62A/L860F/V878S/A932S | + | + | + | + | + | + |
| 3353/3354 | L62A/S678T/L860F/A932S | + | + | + | + | + | + |
| 3355/3356 | L62A/S678T | + | + | + | + | + | ++ |
| 3357/3358 | L62A/S678T/A932S | + | + | + | + | + | + |
| 3359/3360 | L62A/S678T/E871L/A932S | + | + | + | + | + | ++ |
| 3361/3362 | L62A/K830Q/L860F/A932S | + | + | + | + | + | ++ |
| 3363/3364 | L62A/S678T/K830Q/V878S/A932S | + | + | + | + | + | + |
| 3365/3366 | L62A/E871L/V878S/A932S | + | + | + | + | + | +++ |
| 3367/3368 | L62A/K830Q/L860F | + | + | + | + | + | ++ |
| 3369/3370 | L62A/S678T/K830Q/A932S | + | + | + | + | + | ++ |
| 3371/3372 | L62A/L860F/E871L/A932S | + | + | + | + | + | + |
| 3373/3374 | L62A/S678T/K830Q/L860F/E871L/V878S/A932S | + | + | + | + | + | +++ |
| 3375/3376 | L62A/K830Q | + | + | + | + | + | ++ |
| 3377/3378 | S678T/K830Q/A932S | + | + | + | + | + | + |

[1]All activities were determined relative to the reference polypeptide of SEQ ID NO: 3104. Levels of increased activity are defined as follows:
""+"" = 0.9 to 1.1;
"++" >1.1;
"+++" >2; and
"++++" >3.5.

Example 17

Identification of Active GAA Variants with Reduced Immunogenicity

Putative T-cell epitopes in a WT GAA (SEQ ID NO:6) were identified using the Immune Epitope Database (IEDB; Immune Epitope Database and Analysis Resource website) tools, as known in the art and proprietary statistical analysis tools (See e.g., iedb.org and Vita et al., Nucl. Acids Res., 38 (Database issue): D854-62 [2010]. Epub 2009 Nov. 11]). The WT GAA was parsed into all possible 15-mer analysis frames, with each frame overlapping the last by 14 amino acids. The 15-mer analysis frames were evaluated for immunogenic potential by scoring their 9-mer core regions for predicted binding to eight common class II HLA-DR alleles (DRB1*0101, DRB1*0301, DRB1*0401, DRB1*0701, DRB1*0801, DRB1*1101, DRB1*1301, and DRB1*1501) that collectively cover nearly 95% of the human population (See e.g., Southwood et al., J. Immunol., 160:3363-3373 [1998]), using methods recommended on the IEDB website. Potential T-cell epitope clusters contained within the enzyme (i.e., sub-regions contained within GAA which have an unusually high potential for immunogenicity) were identified using statistical analysis tools, as known in the art.

GAA variants that were identified in Examples 3, 4, 6, 10, and 12-16 to be active in assays described in Examples 5 and 11 were analyzed for their levels of predicted immunogenicity by evaluating their binding to the eight common Class II HLA-DR alleles. The total immunogenicity score and immunogenic hit count were calculated for each variant. The total immunogenicity score (TIS) reflects the overall predicted immunogenicity of the variant (i.e., a higher score indicates a higher level of predicted immunogenicity). The immunogenic "hit count" (IHC) indicates the number of 15-mer analysis frames with an unusually high potential for immunogenicity (i.e., a higher score indicates a higher potential for immunogenicity). Mutations resulting in a reduced total immunogenicity score and/or an immunogenic hit count compared to the reference sequence were considered to be potential "deimmunizing mutations" and are shown in Tables 17-1, 17-2, 17-3, 17-4, 17-5, 17-6, 17-7, 17-8, and 17-9. A collection of the most deimmunizing mutations were recombined to generate a number of variants that were active and predicted to be significantly less immunogenic than WT GAA.

TABLE 17-1

Reduction of Total Immunogenicity Score (TIS) and Immunogenic Hit Count (IHC) for GAA Variants Relative to SEQ ID NO: 2[1]

| SEQ ID NO: (nt/aa) | Amino Acid Differences (Relative to SEQ ID NO: 2) | TIS Reduction (Relative to SEQ ID NO: 2) | IHC Reduction (Relative to SEQ ID NO: 2) |
| --- | --- | --- | --- |
| 7/8 | T150S/T486E/A750P/R883H/Q894G | +++ | ++++ |
| 101/102 | L871E | +++ | +++ |
| 105/106 | M138A | + | |
| 109/110 | Q107G | ++ | |
| 113/114 | Q110G | ++ | |
| 115/116 | Q110L | + | |
| 123/124 | R403W | + | |
| 125/126 | R414P | + | |
| 137/138 | S135Q | + | |
| 145/146 | T148G | + | |
| 147/148 | T148Y | + | |
| 149/150 | T150G | + | |
| 155/156 | T692Q | ++ | + |
| 159/160 | V30G | +++ | +++ |
| 161/162 | V30K | ++ | + |
| 163/164 | V30T | +++ | +++ |
| 183/184 | L275M/A281V/S402A/M431V/M507L/I518V/W610R/S668D | ++ | |
| 185/186 | L275M/M507L/A547G/S668D/L669H/S671N | +++ | + |
| 187/188 | L275M/M431V/V638I | ++ | |
| 189/190 | A281V/S402A/I518V/A547G/S668D | ++ | |
| 193/194 | L275V/M431V/M507L/I518V/A547G/S668D/L669H/S671N | +++ | + |
| 195/196 | S402A/M431V/I518V/W610R | + | |
| 197/198 | K106P/H191R/G280D/S402A/R414G/A444P/S727P | ++ | |
| 199/200 | M431V/M507L/I518V/L669H/S671N | ++ | + |
| 201/202 | L275V/R377K/S402A/M507L/I518V/L669H/S671N/V715G | ++ | + |
| 203/204 | H191R/R414G/E522V/G842S/C944S | + | |
| 207/208 | L275M/A281V/W610R/V638I/S668D/L669H | ++ | |
| 209/210 | A196V/S402A/M431V/A547G/W610R/V638I | ++ | |
| 211/212 | H191R/G280D/S402A/R414G/A444P/A489D/D500A/C944S | ++ | |
| 213/214 | L275V/S402A/V638I/L669H/S671N | + | + |
| 215/216 | L29Q/L240I/A596P/S668D/I869L | ++++ | ++++ |
| 217/218 | K106P/G280D/S402A/R414G/A444P/A489D/S727P/C944S | +++ | |
| 219/220 | L29Q/L240I/A596S/S668D/H700F/I744V/I869T | ++++ | +++ |
| 221/222 | L218S/S668D/H700F/I869T | +++ | + |
| 223/224 | M507L/A547G/W610R | + | |
| 225/226 | A281V/M431V/M507L/I518V/A547G/W610R/V638I/S668D | ++ | |
| 227/228 | H191R/G280D/R414G/A444P/A489D/E522V/S727P/C944S | ++ | |
| 229/230 | L275V/S402A/M431V/I518V/W610R/V638I/L669H/S671N/P922L | + | |
| 23/24 | A276Y | + | |
| 231/232 | L29V/L218S/L240I/H700F/I869T | ++ | + |
| 233/234 | A547G/V638I/S668D | +++ | + |
| 235/236 | H191R/G280D/R414G/C944S | + | |
| 237/238 | L275V/M431V/M507L/I518V/W610R/L669H/S671N | + | + |
| 239/240 | L275M/S402A/M431V/M507L/A547G/S671N | +++ | |
| 241/242 | S402A/M431V/A547G/V638I/S671N | +++ | |
| 243/244 | A281V/S402A/M507L/A547G/V638I/L669H/S671N | + | |

TABLE 17-1-continued

Reduction of Total Immunogenicity Score (TIS) and Immunogenic Hit Count (IHC) for GAA Variants Relative to SEQ ID NO: 2[1]

| SEQ ID NO: (nt/aa) | Amino Acid Differences (Relative to SEQ ID NO: 2) | TIS Reduction (Relative to SEQ ID NO: 2) | IHC Reduction (Relative to SEQ ID NO: 2) |
|---|---|---|---|
| 245/246 | L275M/A281V/M507L/A547G/L669H/S671N | ++ | |
| 247/248 | L275M/M431V/I518V/A547G/V638I/S668D | +++ | + |
| 249/250 | A547G/W610R/V638I/S671N | ++ | |
| 25/26 | A418E/H499R | + | |
| 251/252 | L275V/M431V/M507L/A547G/W610R/V638I/S671N | ++ | |
| 253/254 | L275M/S402A/M507L/A547G/W610R/S671N | +++ | |
| 255/256 | L275M/A281V/S402A/I518V/A547G/W610R/V638I/S671N | ++ | |
| 257/258 | A281V/S402A/I518V/A547G/W610R/V638I/S668D/L669H | ++ | |
| 259/260 | L275M/A281V/S402A/A547G/W610R/V638I/L669H/S671N | ++ | |
| 261/262 | L275M/M431V/I518V/W610R/V638I/L669H/S671N | ++ | + |
| 263/264 | L29Q/L218S/L240I/S668D/H700F/I744V/I869L | +++ | + |
| 265/266 | A281V/S402A/M507L/I518V/A547G/W610R/V638I/L669H/S671N | + | |
| 267/268 | S402A/M431V/I518V/A547G/S671N | +++ | |
| 269/270 | L275V/A281V/S402A/M431V/I518V/A547G/W610R/L669H/S671N | + | |
| 271/272 | L224F/S402A/M507L/I518V/A547G/V638I/S668D | +++ | ++ |
| 273/274 | N180H/S402A/M507L/A547G/W610R/S671N | ++ | |
| 275/276 | L275M/A281V/S402A/M507L/I518V/A547G/V638I/L669H/S671N | ++ | |
| 277/278 | K106P/T150S/T486E/Q749E/E793K/R883H/Q894G | +++ | +++ |
| 279/280 | L275V/A281V/M431V/I518V/A547G/V638I/L669H/S671N | + | |
| 281/282 | L275V/S402A/A547G/W610R/V638I/L669H/S671N | ++ | + |
| 283/284 | L275M/S402A/A547G/V638I/L669H/S671N | +++ | + |
| 285/286 | K106P/T150S/T486E/N527D/A750P/E793K | + | |
| 287/288 | S402A/M431V/I518V/A547G/W610R/S668D | +++ | + |
| 29/30 | A437S | ++ | ++ |
| 291/292 | L275V/M507L/I518V/A547G/V638I/L669H/S671N | ++ | + |
| 293/294 | N180H/S402A/M431V/M507L/A547G/W610R/L669H/S671N/E793G | +++ | |
| 295/296 | L275V/M507L/I518V/A547G/W610R/V638I/S668D/L669H | +++ | + |
| 297/298 | L275V/S402A/M507L/A547G/W610R/V638I/S668D/L669H | +++ | + |
| 299/300 | M507L/A547G/V638I/L669H/S671N | ++ | + |
| 303/304 | T150S/R414G/T486E/Q749E/A750P/E793K | ++ | |
| 305/306 | K106P/T150S/L218S/R414G/T486E/L642F/A750P/E793K/R883H | +++ | |
| 307/308 | N180H/L275M/S402A/I518V/A547G/W610R/V638I/L669H/S671N | +++ | + |
| 309/310 | T150S/L218S/R414G/Q749E/E793K | + | |
| 311/312 | L275V/M507L/A547G/W610R/V638I/L669H/S671N | + | + |
| 313/314 | T150S/R414G/T486E/N527D/A750P/Q894R | ++ | |
| 315/316 | K106P/T150S/L218S/N527D/E793K/Q894G | ++ | + |
| 321/322 | K106P/T150S/R414G/Q749E/A750P/E793K/Q894R | ++ | |
| 323/324 | K106P/T150S/N169S/N527D/Q749E/E793K/R883H | ++ | |
| 325/326 | L275V/S402A/M507L/A547G/W610R/V638I/L669H/S671N | ++ | + |

TABLE 17-1-continued

Reduction of Total Immunogenicity Score (TIS) and Immunogenic Hit Count (IHC) for GAA Variants Relative to SEQ ID NO: 2[1]

| SEQ ID NO: (nt/aa) | Amino Acid Differences (Relative to SEQ ID NO: 2) | TIS Reduction (Relative to SEQ ID NO: 2) | IHC Reduction (Relative to SEQ ID NO: 2) |
|---|---|---|---|
| 329/330 | M431V/M507L/I518V/G541E/A547G/V638I/L669H/S671N | +++ | + |
| 331/332 | T150S/L218S/R414G/T486A/A750P/E793K | + | |
| 335/336 | K106P/T150S/N169S/L218S/R414G/T486E/Q894R | + | |
| 337/338 | T150S/L218S/R414G/T486E/A750P/E793K/R883H | ++ | |
| 339/340 | K106P/T150S/N169S/L218S/R414G/Q749E/E793K | + | |
| 341/342 | T269N/L275M/M431V/I518V/A547G/V638I/S668D/L669H | +++ | + |
| 343/344 | K106P/T150S/R414G/Q749E/E793K/Q894R | ++ | |
| 347/348 | K106P/T150S/N169S/Q749E/E793K/R883H/Q894R | ++ | |
| 35/36 | A547G | + | |
| 353/354 | K106P/T150S/L218S/R414G/T486E/A750P/E793K/Q894R | + | |
| 355/356 | K106P/T150S/N169S/L218S/R414G/T486E/Q749E/E793K/R883H/Q894R | ++ | |
| 357/358 | K106P/T150S/N169S/L218S/T486E/R883H | ++ | + |
| 359/360 | K106P/T150S/N169S/L218S/R414G/T486E/A750P/E793K/R883H/Q894R | ++ | |
| 361/362 | G36R/K106P/T150S/L218S/N527D/A750P/R883H/Q894R | + | |
| 363/364 | K106P/T150S/N169S/L218S/T486E/Q749E/R883H | ++ | + |
| 365/366 | K106P/N169S/V185G/L218S/R414G/Q749E/A750P/E793K | + | |
| 367/368 | K106P/T150S/P245S/E793K/R883H/Q894R | + | |
| 369/370 | K106P/T150S/N169S/L218S/R414G/Q749E/A750P/E793K/R883H | ++ | |
| 37/38 | A750P | + | |
| 375/376 | T150S/L218S/R414G/Q749E/A750P/E793K/Q894R | + | |
| 377/378 | K106P/T150S/N169S/R414G/T486E/Q749E/A750P/R883H | +++ | + |
| 379/380 | K106P/T150S/N169S/L218S/R414G/T486E/E793K/R883H | ++ | |
| 381/382 | K106P/T150S/L218S/T486E/N527D/Q749E/Q894R | + | |
| 383/384 | K106P/T150S/N169S/L218S/R414G/T486E/N527D/Q894R | + | |
| 385/386 | T150S/L218S/R414G/T486E/Q749E/A750P | ++ | |
| 387/388 | K106P/T150S/L218S/R414G/Q749E/E793K/R883H | ++ | |
| 389/390 | K106P/T150S/N169S/L218S/R414G/T486E/N527D/A750P/Q894R | ++ | |
| 39/40 | A753T | + | |
| 391/392 | N169S/T486E/A750P/E793K/R883H | ++ | |
| 393/394 | K106P/T150S/L218S/R414G/N527D/Q749E/A750P/R883H | +++ | + |
| 395/396 | K106P/T150S/L218S/R414G/Q749E/A750P/E793K/R883H/Q894R | ++ | |
| 397/398 | K106P/T150S/N169S/L218S/R414G/Q749E/E793K/R883H | ++ | |
| 399/400 | K106P/T150S/L218S/T486E/E793K/R883H | + | |
| 401/402 | K106P/T150S/L218S/V331A/R414G/T486E/N527D/D733E/Q749E/E793K | ++ | |
| 403/404 | L275M/A281V/S402A/I518V/A547G/W610R/S668D/L669H/E887D | +++ | + |
| 405/406 | K106P/T150S/L218S/R414G/N527D/Q749E/E793K/R883H/Q894G | +++ | ++ |
| 407/408 | K106P/T150S/Q749E/E793K/R883H | ++ | |
| 409/410 | K106P/A112S/T150S/L218S/R414G/N527D/E793K/R883H | ++ | |
| 43/44 | C944G | + | |
| 47/48 | D274G | + | |

TABLE 17-1-continued

Reduction of Total Immunogenicity Score (TIS) and Immunogenic Hit Count (IHC) for GAA Variants Relative to SEQ ID NO: 2[1]

| SEQ ID NO: (nt/aa) | Amino Acid Differences (Relative to SEQ ID NO: 2) | TIS Reduction (Relative to SEQ ID NO: 2) | IHC Reduction (Relative to SEQ ID NO: 2) |
|---|---|---|---|
| 53/54 | F27P | + | + |
| 55/56 | F27P/C944W | + | + |
| 57/58 | F27R | + | + |
| 61/62 | G820E | + | |
| 63/64 | I375E | + | |
| 65/66 | K471Q/A478S | + | |
| 69/70 | K581G | ++ | + |
| 71/72 | K581T | + | |
| 81/82 | L109G/G842E | + | |
| 83/84 | L109P | + | |
| 85/86 | L28P | ++ | ++ |
| 89/90 | L28S | ++ | ++ |
| 91/92 | L29T/A478T | +++ | ++ |
| 95/96 | L642Q | + | |
| 97/98 | L642S | + | |
| 99/100 | L670N | +++ | + |

[1]TIS reduction was measured as a reduction in the number of counts compared to the reference polypeptide of SEQ ID NO: 2, and defined as follows: "+" = 1-10; "++" >10; "+++" >20; and "++++" >50. IHC reduction was measured as a reduction in the number of counts compared to the reference polypeptide of SEQ ID NO: 2, and defined as follows: "+" = 1-3; "++" >3; "+++" >5; and "++++" >8.

TABLE 17-2

Reduction of Total Immunogenicity Score (TIS) and Immunogenic Hit Count (IHC) for GAA Variants Relative to SEQ ID NO: 8[1]

| SEQ ID NO: (nt/aa) | Amino Acid Differences (Relative to SEQ ID NO: 8) | TIS Reduction (Relative to SEQ ID NO: 8) | IHC Reduction (Relative to SEQ ID NO: 8) |
|---|---|---|---|
| 13/14 | L28S/L29T/S135Q | ++++ | +++ |
| 413/414 | A418E | +++ | + |
| 415/416 | A418E/A489R | +++ | + |
| 431/432 | K106P | +++ | + |
| 433/434 | K106P/A489R/S671N | +++ | + |
| 445/446 | K106P/V638I | +++ | + |
| 447/448 | L157M | +++ | + |
| 469/470 | L218S/V638I/S671N | +++ | |
| 509/510 | Q113S/A418E/A478T/A489R/K581T | +++ | |
| 511/512 | Q113S/A418E/R455V/A478T/K581T | +++ | |
| 519/520 | S135P/C944Y | +++ | + |
| 521/522 | S135Q | +++ | + |
| 523/524 | S135Q/A478T/A489R/K581T | +++ | |
| 531/532 | S671N/Q749E | +++ | + |
| 441/442 | K106P/M138A/L218S/M431V/S671N/Q749E | +++ | |
| 513/514 | Q113S/S135Q/A418E | +++ | + |
| 527/528 | S135Q/T148G/S150G/A418E | +++ | + |
| 429/430 | F27R | +++ | + |
| 425/426 | F27P/A418E/A478T | +++ | + |
| 501/502 | M507L/S668D | +++ | + |
| 495/496 | M138A/L218S/S668D/S671N | +++ | + |
| 499/500 | M431V/S668D/S671N | ++++ | ++ |
| 471/472 | L28S | +++ | ++ |
| 481/482 | L29T/A478T | +++ | +++ |
| 483/484 | L29T/Q113S/M138A | +++ | +++ |
| 485/486 | L29T/Q113S/P126Q/S135Q/H193Q | +++ | +++ |
| 487/488 | L29T/Q113S/S135Q | +++ | +++ |
| 489/490 | L29T/Q113S/S135Q/R455V | +++ | +++ |
| 491/492 | L29T/T148G | +++ | +++ |
| 473/474 | L28S/L29T | +++ | +++ |
| 475/476 | L28S/L29T/A418E | ++++ | +++ |
| 477/478 | L28S/L29T/Q113S/S135Q/A418E | ++++ | +++ |
| 479/480 | L28S/L29T/Q113S/S135Q/M138A | ++++ | +++ |

[1]TIS reduction was measured as a reduction in the number of counts compared to the reference polypeptide of SEQ ID NO: 8, and defined as follows: "+" = 1-10; "++" >10; "+++" >20; and "++++" >50. IHC reduction was measured as a reduction in the number of counts compared to the reference polypeptide of SEQ ID NO: 8, and defined as follows: "+" = 1-3; "++" >5; and "+++" >8.

TABLE 17-3

Reduction of Total Immunogenicity Score (TIS) and Immunogenic Hit Count (IHC) for GAA Variants Relative to SEQ ID NO: 18[1]

| SEQ ID NO: (nt/aa) | Amino Acid Differences (Relative to SEQ ID NO: 18) | TIS Reduction (Relative to SEQ ID NO: 18) | IHC Reduction (Relative to SEQ ID NO: 18) |
|---|---|---|---|
| 19/20 | P39Q/R267K/A489D/E522V/S612D/Q830K/G842S | + | |
| 371/372 | P39D | + | |
| 533/534 | V70A/R267K/K725E/C944S | + | |
| 535/536 | R267K/A489D/D500A/K725E/Q830K/C930P | + | |
| 537/538 | L109P/E522V/Q830K/C944S | + | |
| 539/540 | V70A/R267K/C930P/C944S | + | |
| 543/544 | H734K | + | |
| 553/554 | P39Q/V70A/L109P/Q830K/G842S | + | |
| 555/556 | P39Q/V70A/K725E | + | |
| 557/558 | P39Q/R267K/A489D/Q830K/C944S | + | |
| 559/560 | C930P | + | |
| 561/562 | D500A/C930P/C944S | + | |
| 567/568 | P39Q/R267K | + | |
| 575/576 | R267K/E522V/K725E | + | |
| 577/578 | V70A/A489D/C930P | + | |
| 585/586 | P39Q | + | |
| 601/602 | S37F/N528S/I790V | + | |
| 611/612 | S37F/A62E | + | |
| 625/626 | S37F/A196T | + | |
| 627/628 | S37F/A62E/D523N | + | |
| 633/634 | S37F/A62E/N79S/A196T/A696S/R862Q | + | |
| 655/656 | L34D | + | |
| 657/658 | Y352K | + | |
| 667/668 | N875D | ++ | ++ |
| 673/674 | I22R | + | |
| 675/676 | L24W | ++ | |
| 677/678 | L778Q | + | |
| 685/686 | Y352V | + | |
| 691/692 | F27K | + | |
| 695/696 | S932A | + | |
| 697/698 | L24R | + | |
| 699/700 | L24E | ++ | |
| 709/710 | F27G | + | |
| 713/714 | L34M | + | |
| 731/732 | A774G | + | |
| 735/736 | F27W | + | |
| 745/746 | R385G | + | |
| 747/748 | F27G/M165I | + | |
| 749/750 | V30D | + | |
| 753/754 | V40W | + | |
| 761/762 | E33G | + | |
| 765/766 | L109D | + | |
| 793/794 | Q107G | ++ | |
| 801/802 | F27R | + | |
| 803/804 | L934F | + | |
| 813/814 | Q217D | + | |
| 817/818 | L34T | + | |
| 821/822 | P673N | + | |

[1] TIS reduction was measured as a reduction in the number of counts compared to the reference polypeptide of SEQ ID NO: 18, and defined as follows: "+" = 1-10; "++" >10; "+++" >20; and "++++" >50. IHC reduction was measured as a reduction in the number of counts compared to the reference polypeptide of SEQ ID NO: 18, and defined as follows: "+" = 1-2; "++" >2; and "+++" >5.

TABLE 17-4

Reduction of Total Immunogenicity Score (TIS) and Immunogenic Hit Count (IHC) for GAA Variants Relative to SEQ ID NO: 20[1]

| SEQ ID NO: (nt/aa) | Amino Acid Differences (Relative to SEQ ID NO: 20) | TIS Reduction (Relative to SEQ ID NO: 20) | IHC Reduction (Relative to SEQ ID NO: 20) |
|---|---|---|---|
| 829/830 | L24R/F27G/A89R/D500A/S842G | + | |
| 831/832 | L24R/F27G/D500A/S842G | + | |
| 833/834 | D500A/S932A | + | |
| 835/836 | L24R/Q39H/S842G/S932A | + | |
| 839/840 | D500A/S842G | + | |
| 841/842 | S842G/S932A | + | |
| 843/844 | A89R/A97G/Q107G | ++ | |

TABLE 17-4-continued

Reduction of Total Immunogenicity Score (TIS) and Immunogenic Hit Count
(IHC) for GAA Variants Rel TABLE 17-4-continued Reduction of Total Immunogenicity Score (TIS) and Immunogenic Hit Count (IHC) for GAA Variants Relative to SEQ ID NO: 20[1]

| SEQ ID NO: (nt/aa) | Amino Acid Differences (Relative to SEQ ID NO: 20) | TIS Reduction (Relative to SEQ ID NO: 20) | IHC Reduction (Relative to SEQ ID NO: 20) |
|---|---|---|---|
| 1189/1190 | P832E | + | |
| 1191/1192 | A741T | + | |
| 1207/1208 | S243R | + | |
| 1215/1216 | S727T | + | |
| 1217/1218 | L240I | + | |
| 1231/1232 | V913A | ++ | |
| 965/966 | S916R | + | |
| 1235/1236 | L940G | + | |
| 967/968 | P914G | ++ | |
| 1261/1262 | L305Y | + | + |
| 971/972 | D923W | + | |
| 1297/1298 | L305G | +++ | +++ |
| 981/982 | L742V | + | |
| 1307/1308 | I815A | + | |
| 991/992 | P914Q | + | |
| 1327/1328 | P914E | + | |
| 1335/1336 | S264C | + | |
| 1339/1340 | Y248A | + | |
| 1341/1342 | L305R | + | + |
| 1001/1002 | T148K | + | |
| 1349/1350 | L320M | | + |
| 1351/1352 | L736V | + | |
| 1353/1354 | A309C | ++ | + |
| 1385/1386 | S727Q | + | |
| 1007/1008 | A112H | + | |
| 1395/1396 | L823A | + | |
| 1405/1406 | L736W | + | |
| 1409/1410 | S916I | + | |
| 1413/1414 | V913E | ++ | |
| 1427/1428 | L305V | ++ | + |
| 1435/1436 | Y248V | + | |
| 1439/1440 | L818T | ++ | |
| 1441/1442 | A741C | ++ | |
| 1445/1446 | F556S | ++ | |
| 1013/1014 | P914T | + | |
| 1015/1016 | S916G | ++ | |
| 1459/1460 | L748I | + | |
| 1461/1462 | M260W | + | |
| 1467/1468 | G108N | ++ | |
| 1019/1020 | P914K | + | |
| 1471/1472 | I816V | + | ++ |
| 1479/1480 | L748T | + | |
| 1023/1024 | V913W | ++ | |
| 1483/1484 | T148R/V772I | + | |
| 1485/1486 | K106T | + | |
| 1487/1488 | L240W/A374T | ++ | + |
| 1489/1490 | F556Y | + | |
| 1499/1500 | G108V | + | |
| 1515/1516 | S916V | + | |
| 1033/1034 | L823F | + | |
| 1527/1528 | E937Q | + | |
| 1035/1036 | L305F | + | + |
| 1539/1540 | P832G | + | |
| 1541/1542 | V913H | ++ | |
| 1545/1546 | L252V | + | |
| 1551/1552 | S243G | ++ | + |
| 1555/1556 | A741E | ++ | |
| 1557/1558 | S243V | + | |
| 1037/1038 | P914S | + | |
| 1039/1040 | S727W | + | |
| 1041/1042 | L940Q | + | |
| 1567/1568 | P279E | + | |
| 1569/1570 | V913Q | ++ | |
| 1583/1584 | L259G | + | |
| 1585/1586 | S243E | +++ | ++ |
| 1059/1060 | S402N | + | |
| 1599/1600 | A253G | + | |
| 1601/1602 | L736M | ++ | |
| 1603/1604 | L940W | + | |
| 1069/1070 | G108R | + | |
| 1605/1606 | L823G | + | |
| 1071/1072 | L748V | + | |
| 1619/1620 | S727G | + | |

TABLE 17-4-continued

Reduction of Total Immunogenicity Score (TIS) and Immunogenic Hit Count (IHC) for GAA Variants Relative to SEQ ID NO: 20[1]

| SEQ ID NO: (nt/aa) | Amino Acid Differences (Relative to SEQ ID NO: 20) | TIS Reduction (Relative to SEQ ID NO: 20) | IHC Reduction (Relative to SEQ ID NO: 20) |
|---|---|---

TABLE 17-5-continued

Reduction of Total Immunogenicity Score (TIS) and Immunogenic Hit Count (IHC) for GAA Variants Relative to SEQ ID NO: 946[1]

| SEQ ID NO: (nt/aa) | Amino Acid Differences (Relative to SEQ ID NO: 946) | TIS Reduction (Relative to SEQ ID NO: 946) | IHC Reduction (Relative to SEQ ID NO: 946) |
|---|---|---|---|
| 1863/1864 | P57F/A62L/A437G/D500A/L761F/P914K/S916R | + | ++ |
| 1865/1866 | A62L/A437G/V913R/S916R | +++ | ++ |
| 1873/1874 | P57F/A62W/L305F/A437G/D500A/S727W/V913R/S916R | +++ | ++ |
| 1875/1876 | P57F/A437G/D500A/E614Q/S727W/P914R | ++ | ++ |
| 1953/1954 | A62W/A437G/D489A/E614Q/S727W/V913R | ++ | ++ |
| 1955/1956 | A62L/A437G/D489A/N527R/S727W/V913R/S932A | +++ | ++ |
| 1957/1958 | P57F/A62W/L305F/D489A/Q907K/V913R/S916G | ++ | + |
| 1959/1960 | P57F/A62W/L305F/S916R | ++ | + |
| 1961/1962 | P57F/A437G/D500A/N527R/S727W/S916R | +++ | ++ |
| 1963/1964 | A62L/L305F/S727W | ++ | + |
| 1965/1966 | P57F/A62L/L305F/A437G/E614Q/A683S/V913R/S916R/S932A | +++ | ++ |
| 1967/1968 | P57F/L305F | + | + |
| 1973/1974 | P57F/A62W/A437G/V913R/S916G | +++ | ++ |
| 1975/1976 | P57F/A62W/L305F/D489A/V913R/S916G | +++ | + |
| 1981/1982 | P57F/L305F/A437G/S916G | +++ | ++ |
| 1983/1984 | A62L/A437G/N527R/S727W | ++ | ++ |
| 1985/1986 | P57F/A62L/A437G/N527R/S727W | ++ | ++ |
| 1995/1996 | A62L/L305F/A437G/D500A/S727W/V913R | +++ | ++ |
| 1997/1998 | A437G | ++ | ++ |
| 2001/2002 | P57F/A62L/L305F/A437G/D500A/E614Q/S727W/S916R | +++ | ++ |
| 2003/2004 | A437G/D489A/P914R/S916R | ++ | ++ |
| 2007/2008 | A62L/A437G/N527R/S916G/S932A | +++ | ++ |
| 2009/2010 | A437G/S727W/P914K | +++ | ++ |
| 2011/2012 | P57F/A437G/V913R/P914R | ++ | ++ |
| 2017/2018 | A437G/P914R/S916G | +++ | ++ |

[1]TIS reduction was measured as a reduction in the number of counts compared to the reference polypeptide of SEQ ID NO: 946, and defined as follows: "+" = 1-10; "++" >10; "+++" >20; and "++++" >50. IHC reduction was measured as a reduction in the number of counts compared to the reference polypeptide of SEQ ID NO: 946, and defined as follows: "+" = 1-3; "++" >3; "+++" >5; and "++++" >8.

TABLE 17-6

Reduction of Total Immunogenicity Score (TIS) and Immunogenic Hit Count (IHC) for GAA Variants Relative to SEQ ID NO: 1956[1]

| SEQ ID NO: (nt/aa) | Amino Acid Differences (Relative to SEQ ID NO: 1956) | TIS Reduction (Relative to SEQ ID NO: 1956) | IHC Reduction (Relative to SEQ ID NO: 1956) |
|---|---|---|---|
| 2021/2022 | P78E/S372T/L390Q | + | |
| 2023/2024 | D87E/T266N/S372T/T483S | + | |
| 2027/2028 | T266N/S372T/T924N | + | |
| 2037/2038 | P78E/D87E/K176T/T266N/V536T/Q615D | + | |
| 2041/2042 | D87E/S372T/S777G | + | |
| 2043/2044 | T266N/S372T/V536T/Q615D/T763L/S777G | + | |
| 2053/2054 | P78E/T266N/T763L | + | |
| 2055/2056 | P78E/D87E/T266N/S372T/A386Y/S777G | + | |
| 2073/2074 | P78E/D87E/T266N/S372T/V536T | + | |
| 2497/2498 | A142G | + | |
| 2501/2502 | D493L | + | |
| 2509/2510 | K129E | + | |
| 2513/2514 | H499E | + | |
| 2517/2518 | L857E | + | |
| 2089/2090 | P779E | + | |
| 2541/2542 | L857A | + | |
| 2547/2548 | H499I | + | |
| 2559/2560 | A834S | + | |
| 2565/2566 | L857V | + | |
| 2567/2568 | F152W | + | |
| 2097/2098 | L857T | + | |
| 2569/2570 | F152S | + | |
| 2571/2572 | S136K | + | |
| 2573/2574 | K129S | + | |
| 2589/2590 | I156C | + | |
| 2601/2602 | H499M | + | |

TABLE 17-6-continued

Reduction of Total Immunogenicity Score (TIS) and Immunogenic Hit Count (IHC) for GAA Variants Relative to SEQ ID NO: 1956[1]

| SEQ ID NO: (nt/aa) | Amino Acid Differences (Relative to SEQ ID NO: 1956) | TIS Reduction (Relative to SEQ ID NO: 1956) | IHC Reduction (Relative to SEQ ID NO: 1956) |
|---|---|---|---|
| 2617/2618 | S136V | + | |
| 2117/2118 | L909F | + | |
| 2133/2134 | V797L | + | |
| 2143/2144 | I156L | + | |
| 2145/2146 | V797M | + | |
| 2651/2652 | A834W | + | |
| 2661/2662 | K267E | + | |
| 2667/2668 | E855G | + | |
| 2151/2152 | A105T | ++ | |
| 2683/2684 | Q768I | + | |
| 2685/2686 | V926T | ++ | |
| 2693/2694 | V797F | + | |
| 2695/2696 | S372D | + | |
| 2699/2700 | Y765W | + | |
| 2161/2162 | T826G | + | |
| 2725/2726 | S856G | + | |
| 2729/2730 | V797I | ++ | |
| 2165/2166 | T141S | + | |
| 2751/2752 | H499Q | + | |
| 2171/2172 | A834H | + | |
| 2763/2764 | Y125W | + | |
| 2777/2778 | V926M | + | |
| 2779/2780 | G139E | + | |
| 2791/2792 | T924A | + | |
| 2179/2180 | S136G | + | |
| 2793/2794 | V797W | ++ | |
| 2795/2796 | V797E | ++ | |
| 2191/2192 | A496G | + | |
| 2821/2822 | D401G | + | |
| 2825/2826 | A834G | + | |
| 2859/2860 | A105W | + | |
| 2861/2862 | L857S | + | |
| 2207/2208 | L693F | + | + |
| 2209/2210 | V710N | ++ | ++ |
| 2211/2212 | V710L | + | |
| 2213/2214 | M663A | ++ | + |
| 2215/2216 | V710M | +++ | ++ |
| 2217/2218 | L670I | + | |
| 2219/2220 | L670F | + | |
| 2221/2222 | L670R | + | + |
| 2223/2224 | V710S | + | + |
| 2225/2226 | F588L | ++ | + |
| 2229/2230 | L670Q | +++ | + |
| 2231/2232 | L670T | + | + |
| 2233/2234 | K154R/F588L | + | + |
| 2235/2236 | L693Y | + | + |
| 2237/2238 | V710K | + | ++ |
| 2239/2240 | A708C | +++ | ++ |
| 2247/2248 | L670W | ++ | + |
| 2249/2250 | L670V | + | |
| 2251/2252 | L693I | ++ | + |
| 2253/2254 | V589I/M663F | + | |
| 2255/2256 | F588V | ++ | + |
| 2257/2258 | M663F | + | |
| 2261/2262 | L670E | +++ | + |
| 2263/2264 | L670S | + | + |
| 2275/2276 | L629I | ++ | + |
| 2277/2278 | T692L | + | + |
| 2279/2280 | A711C | + | ++ |
| 2281/2282 | R577T | + | + |
| 2289/2290 | L628V | + | |
| 2293/2294 | L691V | + | |
| 2297/2298 | L569Y | + | |
| 2299/2300 | I573Q | ++ | + |
| 2303/2304 | T692Y | ++ | + |
| 2305/2306 | L629C | +++ | ++ |
| 2307/2308 | T692I | + | + |
| 2311/2312 | S671A | + | |
| 2315/2316 | L569S | + | + |
| 2317/2318 | I573M | + | + |
| 2321/2322 | T692C | +++ | +++ |
| 2323/2324 | I573H | ++ | + |
| 2325/2326 | S671T | + | |

TABLE 17-6-continued

Reduction of Total Immunogenicity Score (TIS) and Immunogenic Hit Count (IHC) for GAA Variants Relative to SEQ ID NO: 1956[1]

| SEQ ID NO: (nt/aa) | Amino Acid Differences (Relative to SEQ ID NO: 1956) | TIS Reduction (Relative to SEQ ID NO: 1956) | IHC Reduction (Relative to SEQ ID NO: 1956) |
|---|---|---

TABLE 17-7-continued

Reduction of Total Immunogenicity Score (TIS) and Immunogenic Hit Count (IHC) for GAA Variants Relative to SEQ ID NO: 2496[1]

| SEQ ID NO: (nt/aa) | Amino Acid Differences (Relative to SEQ ID NO: 2496) | TIS Reduction (Relative to SEQ ID NO: 2496) | IHC Reduction (Relative to SEQ ID NO: 2496) |
|---|---|---|---|
| 2875/2876 | L628M/L670F | + | |
| 2877/2878 | L569H/L628M/L670T | +++ | ++ |
| 2879/2880 | L569T/L670T/A711H/L871E | ++++ | ++++ |
| 2881/2882 | L628M/L670T/T692G/A711H/Q795E | +++ | ++++ |
| 2883/2884 | L569Y/L628M/L670T/A711H | ++ | +++ |
| 2885/2886 | L569Y/V589I/L628M/T692G/A711H/Q795E | +++ | +++ |
| 2887/2888 | L569H/T692G | +++ | +++ |
| 2889/2890 | L569Y/V589I/L670T/S678T/T692G/A711H/Q795E | +++ | ++++ |
| 2891/2892 | L569T/L871K | ++ | ++ |
| 2893/2894 | L569Y/V589I/L628M/L670T/T692Y/A711H | +++ | ++++ |
| 2895/2896 | V589I/L871E | +++ | +++ |
| 2897/2898 | L670T/S678T/T692Y/L871S | +++ | +++ |
| 2899/2900 | L628M/A711H/Q795E | + | ++ |
| 2901/2902 | T692G/A711H | +++ | +++ |
| 2903/2904 | V589I/L670T/T692G/Q795E/L871K | +++ | +++ |
| 2905/2906 | L569Y/V589I/A711H/L871K | ++ | ++ |
| 2907/2908 | L670T/T692G/L871K | +++ | +++ |
| 2909/2910 | L569H/T692Y | +++ | +++ |
| 2911/2912 | L569H/L628M/L670T/T692Y/A711H/L871K | +++ | ++++ |
| 2913/2914 | L670T/S678T | + | + |
| 2915/2916 | L569T/L670T/S678T/T692G/L871K | +++ | ++++ |
| 2917/2918 | V589I | + | |
| 2919/2920 | L569H/V589I/L628M/L670T/S678T/T692G/A711H/Q795E/L871S | ++++ | ++++ |
| 2921/2922 | L569H/L670F/S678T/T692G/L871S | ++++ | +++ |
| 2923/2924 | L569T/V589I/L628M/L670F/T692G/A711H | ++++ | ++++ |
| 2925/2926 | L569H/L670T/T692G | +++ | +++ |
| 2927/2928 | L569Y/L871E | +++ | +++ |
| 2929/2930 | L569H/L628M/L670F/S678T | ++ | + |
| 2931/2932 | L569Y/L670F/S678T | + | |
| 2933/2934 | L569Y/V589I/L670F | ++ | |
| 2935/2936 | L569Y/V589I/L670T/L871K | ++ | + |
| 2937/2938 | L569T/L871S | +++ | ++ |
| 2939/2940 | L871K | + | + |
| 2941/2942 | L569Y/L670T | + | + |
| 2943/2944 | L569Y/T692Y/A711H | ++ | +++ |
| 2945/2946 | L871S | ++ | + |
| 2947/2948 | L569Y/A711H | + | ++ |
| 2949/2950 | L628M/L871S | ++ | + |
| 2951/2952 | L569T/V589I/L871S | +++ | ++ |
| 2953/2954 | T692G/A711H/I869L/V878S | +++ | +++ |
| 2955/2956 | A572S/F588L/S678T/T692G/I869L/V878A | +++ | ++ |
| 2957/2958 | A711H | + | ++ |
| 2959/2960 | T692G/I869S | +++ | +++ |
| 2961/2962 | A572S/T692L/I869S/V878S | +++ | +++ |
| 2963/2964 | L629I/1869L/V878S | ++ | + |
| 2965/2966 | A572S/F588L/Q795E | +++ | + |
| 2967/2968 | A711H/I869S/V878S | +++ | ++++ |
| 2969/2970 | V878S | + | + |
| 2971/2972 | S678T/T692G/A711H/I869S | +++ | ++++ |
| 2973/2974 | A572S/T692G/I869S/V878S | ++++ | ++++ |
| 2975/2976 | A572S/T692G/V878S | +++ | ++ |
| 2977/2978 | A711H/Q795E/I869S/V878S | +++ | ++++ |
| 2979/2980 | Q795E/V878S | + | + |
| 2981/2982 | T692G/A711H/Q795E/I869S | +++ | ++++ |
| 2983/2984 | S678T/T692G/Q795E/I869S | +++ | +++ |
| 2985/2986 | T692G/A711H/I869S/V878A | ++++ | ++++ |
| 2987/2988 | L569T/A711H | ++ | +++ |
| 2989/2990 | L569T/L628M/S678T/A711H | ++ | +++ |
| 2991/2992 | L569T/V589I/T692G/Q795E/L871K/V878S | +++ | +++ |
| 2993/2994 | L569T/V589I/S678T/L871K/V878S | +++ | ++ |
| 2995/2996 | L569H/A711H/I869S/V878S | ++++ | ++++ |
| 2997/2998 | S678T/Q795E/L871K/V878A | + | + |
| 2999/3000 | L569H/S678T/T692G/Q795E | +++ | +++ |
| 3001/3002 | F588L/V589I/L628M/S678T | + | |
| 3003/3004 | T692Y | ++ | + |
| 3005/3006 | L569T | ++ | + |
| 3007/3008 | T692G/L871K | +++ | ++ |
| 3009/3010 | L569T/F588L/V878S | +++ | ++ |
| 3011/3012 | L569H/A711H/L871K | +++ | +++ |
| 3013/3014 | L569T/F588L/S678T/T692Y | +++ | +++ |
| 3015/3016 | L569T/F588L/A711H/I869L/L871K/V878S | +++ | ++++ |

TABLE 17-7-continued

Reduction of Total Immunogenicity Score (TIS) and Immunogenic Hit Count (IHC) for GAA Variants Relative to SEQ ID NO: 2496[1]

| SEQ ID NO: (nt/aa) | Amino Acid Differences (Relative to SEQ ID NO: 2496) | TIS Reduction (Relative to SEQ ID NO: 2496) | IHC Reduction (Relative to SEQ ID NO: 2496) |
| --- | --- | --- | --- |
| 3017/3018 | L569T/F588L | +++ | ++ |
| 3019/3020 | L569T/T692Y | +++ | +++ |
| 3021/3022 | L569T/S678T/I869S/V878S | +++ | ++++ |
| 3023/3024 | L628M/L629I/T692Y/L871S/V878S | +++ | +++ |
| 3025/3026 | L569T/S678T/V878S | ++ | ++ |
|

TABLE 17-8-continued

Reduction of Total Immunogenicity Score (TIS) and Immunogenic Hit Count (IHC) for GAA Variants Relative to SEQ ID NO: 2880[1]

| SEQ ID NO: (nt/aa) | Amino Acid Differences (Relative to SEQ ID NO: 2880) | TIS Reduction (Relative to SEQ ID NO: 2880) | IHC Reduction (Relative to SEQ ID NO: 2880) |
|---|---|---|---|
| 3133/3134 | R527N/S678T/T692G/A812E/A932S | +++ | +++ |
| 3135/3136 | A89R/S678T/A812E/V878S | + | ++ |
| 3137/3138 | R527N/A812E | ++ | ++ |
| 3139/3140 | S678T/T692G/W727S/A812E/S842G | +++ | +++ |
| 3149/3150 | L109D/S678T/T692G/S842G/L860F/V878S/A932S | ++ | + |
| 3151/3152 | A89R/R527N/S678T/T692G/L736M/S842G/V878S/A932S | +++ | + |
| 3155/3156 | L109D/T692G/W727S/L736M/A812E | +++ | +++ |
| 3161/3162 | S678T/A812E | ++ | ++ |

[1]TIS reduction was measured as a reduction in the number of counts compared to the reference polypeptide of SEQ ID NO: 2880, and defined as follows: "+" = 1-10; "++" >10; "+++" >20; and "++++" >50. IHC reduction was measured as a reduction in the number of counts compared to the reference polypeptide of SEQ ID NO: 2880, and defined as follows: "+" = 1-3; "++" >3; "+++" >5; and "++++" >8.

TABLE 17-9

Reduction of Total Immunogenicity Score (TIS) and Immunogenic Hit Count (IHC) for GAA Variants Relative to SEQ ID NO: 3104[1]

| SEQ ID NO: (nt/aa) | Amino Acid Differences (Relative to SEQ ID NO: 3104) | TIS Reduction (Relative to SEQ ID NO: 3104) |
|---|---|---|
| 3313/3314 | L62A/A89D/K830Q | + |
| 3317/3318 | L62A/K830Q/A932S | + |
| 3361/3362 | L62A/K830Q/L860F/A932S | + |
| 3367/3368 | L62A/K830Q/L860F | + |
| 3375/3376 | L62A/K830Q | + |

[1]TIS reduction was measured as a reduction in the number of counts compared to the reference polypeptide of SEQ ID NO: 3104, and defined as follows: "+" = 1-10.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

SEQUENCE LISTING

The patent contains a lengthy sequence listing. A copy of the sequence listing is available in electronic form from the USPTO web site (https://seqdata.uspto.gov/?pageRequest=docDetail&DocID=US11970722B2). An electronic copy of the sequence listing will also be available from the USPTO upon request and payment of the fee set forth in 37 CFR 1.19(b)(3).

What is claimed is:

1. A recombinant acid alpha glucosidase comprising an amino acid sequence comprising at least at least 85% sequence identity to the sequence of residues 20 to 944 of SEQ ID NO: 2, wherein the amino acid sequence comprises at least a substitution S135Q/P, V913G/H/L/Q/R/W/E, P39Q/D/H, Q50V, or T266N, or a substitution at amino acid position 150, or combinations thereof, wherein the amino acid positions are relative to SEQ ID NO: 2.

2. The recombinant acid alpha glucosidase of claim 1, wherein said amino acid sequence of said recombinant acid alpha glucosidase comprises at least the substitution S135Q/P.

3. The recombinant acid alpha glucosidase of claim 1, wherein said amino acid sequence of said recombinant acid alpha glucosidase comprises at least the substitution T150G/S.

4. The recombinant acid alpha glucosidase of claim 1, wherein said amino acid sequence of said recombinant acid alpha glucosidase comprises residues 20-944 of SEQ ID NO: 6, 8, 12, 14, 16, 18, 20, 946, 1956, 2496, 2880, or 3104.

5. The recombinant acid alpha glucosidase of claim 1, wherein said recombinant acid alpha glucosidase is more thermostable than the acid alpha glucosidase of SEQ ID NO: 2.

6. The recombinant acid alpha glucosidase of claim 1, wherein said recombinant acid alpha glucosidase is more stable at pH 7 than the acid alpha glucosidase of SEQ ID NO: 2.

7. The recombinant acid alpha glucosidase of claim 1, wherein said recombinant acid alpha glucosidase is more stable at pH 4 than the acid alpha glucosidase of SEQ ID NO: 2.

8. The recombinant acid alpha glucosidase of claim 1, wherein said recombinant acid alpha glucosidase exhibits increased expression than the acid alpha glucosidase of SEQ ID NO: 2.

9. The recombinant acid alpha glucosidase of claim 1, wherein said recombinant acid alpha glucosidase is more lysosomally stable than the acid alpha glucosidase of SEQ ID NO: 2.

10. The recombinant acid alpha glucosidase of claim 1, wherein said recombinant acid alpha glucosidase is more readily taken up by cells than the acid alpha glucosidase of SEQ ID NO: 2.

11. The recombinant acid alpha glucosidase of claim 1, wherein said recombinant acid alpha glucosidase exhibits greater enzymatic activity in cell lysates than the acid alpha glucosidase of SEQ ID NO: 2.

12. The recombinant acid alpha glucosidase of claim 1, wherein said recombinant acid alpha glucosidase exhibits reduced immunogenicity, as compared to the acid alpha glucosidase of SEQ ID NO: 2.

13. The recombinant acid alpha glucosidase of claim 1, wherein said recombinant acid alpha glucosidase is purified.

14. The recombinant acid alpha glucosidase of claim 1, wherein said recombinant acid alpha glucosidase exhibits at least one improved property selected from: i) enhanced catalytic activity; ii) increased tolerance to pH 7; iii) increased tolerance to pH 4; iv) increased expression; v) increased uptake into cells; vi) increased enzymatic activity in cell lysates; vii) reduced immunogenicity; or a combination of any of i), ii), iii), iv), v), v), and/or vii), as compared to a reference acid alpha glucosidase of SEQ ID NO: 2.

15. A composition comprising at least one recombinant acid alpha glucosidase of claim 1.

16. The recombinant acid alpha glucosidase of claim 1, wherein said amino acid sequence of said recombinant acid alpha glucosidase comprises at least the substitution V913G/H/L/Q/R/W/E.

17. The recombinant acid alpha glucosidase of claim 16, wherein said amino acid sequence of said recombinant acid alpha glucosidase comprises at least the substitution the substitution V913Q/R/W/E.

18. The recombinant acid alpha glucosidase of claim 1, wherein said amino acid sequence of said recombinant acid alpha glucosidase comprises at least the substitution P39Q/D/H.

19. The recombinant acid alpha glucosidase of claim 1, wherein said amino acid sequence of said recombinant acid alpha glucosidase comprises at least the substitution Q50V.

20. The recombinant acid alpha glucosidase of claim 1, wherein said amino acid sequence of said recombinant acid alpha glucosidase comprises at least the substitution T266N.

21. The recombinant acid alpha glucosidase of claim 1, wherein said amino acid sequence of said recombinant acid alpha glucosidase comprises at least the substitution S135Q, T150S, V913R, P39Q/D/H, Q50V, or T266N, or combinations thereof.

22. The recombinant acid alpha glucosidase of claim 1, wherein said amino acid sequence of said recombinant acid alpha glucosidase comprises residues 20-944 of SEQ ID NO: 8, 14, 20, 136, 138, 150, 278, 286, 290, 302, 304, 306, 310, 314, 316, 318, 320, 322, 324, 328, 332, 334, 336, 338, 340, 344, 346, 348, 350, 352, 354, 356, 358, 350, 362, 364, 368, 370, 372, 374, 376, 378, 380, 382, 384, 386, 388, 390, 394, 396, 398, 400, 402, 406, 408, 410, 478, 480, 486, 488, 490, 514, 520, 522, 524, 526, 528, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, or 828.

23. The recombinant acid alpha glucosidase of claim 1, wherein said amino acid sequence of said recombinant acid alpha glucosidase comprises residues 20-944 of SEQ ID NO: 830, 832, 834, 836, 838, 840, 842, 844, 846, 848, 850.852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, or 1828.

24. The recombinant acid alpha glucosidase of claim 1, wherein said amino acid sequence of said recombinant acid alpha glucosidase comprises residues 20-944 of SEQ ID NO: 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, or 2018.

25. The recombinant acid alpha glucosidase of claim 1, wherein said amino acid sequence of said recombinant acid alpha glucosidase comprises residues 20-944 of SEQ ID NO: 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, or 2866.

26. The recombinant acid alpha glucosidase of claim 1, wherein said amino acid sequence of said recombinant acid alpha glucosidase comprises residues 20-944 of SEQ ID NO: 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018, 3020, 3022, 3024, 3026, 3028, 3030, 3032, 3034, 3036, 3038, 3040, 3042, 3044, 3046, 3048, 3050, 3052, 3054, 3056, 3058, 3060, 3062, 3064, 3066, 3068, 3070, 3072, 3074, 3076, 3078, 3080, 3082, 3084, 3086, 3088, 3090, 3092, 3094, 3096, 3098, 3100, 3102, 3104, 3106, 3108, 3110, 3112, 3114, 3116, 3118, 3120, 3122, 3124, 3126, 3128, 3130, 3132, 3134, 3136, 3138, 3140, 3142, 3144, 3146, 3148, 3150, 3152, 3154, 3156, 3158, 3160, 3162, 3164, 3166, 3168, 3170, 3172, 3174, 3176, 3178, 3180, 3182, 3184, 3186, 3188, 3190, 3192, 3194, 3196, 3198, 3200, 3202, 3204, 3206, 3208, 3210, 3212, 3214, 3216, 3218, 3220, 3222, 3224, 3226, 3228, 3230, 3232, 3234, 3236, 3238, 3240, 3242, 3244, 3246, 3248, 3250, 3252, 3254, 3256, 3258, 3260, 3262, 3264, 3266, 3268, 3270, 3272, 3274, 3276, 3278, 3280, 3282, or 3284.

27. The recombinant acid alpha glucosidase of claim 1, wherein said amino acid sequence of said recombinant acid alpha glucosidase comprises residues 20-944 of SEQ ID NO: 3286, 3288, 3290, 3292, 3294, 3296, 3298, 3300, 3302, 3304, 3306, 3308, 3310, 3312, 3314, 3316, 3318, 3320, 3322, 3324, 3326, 3328, 3330, 3332, 3334, 3336, 3338, 3340, 3342, 3344, 3346, 3348, 3350, 3352, 3354, 3356, 3358, 3360, 3362, 3364, 3366, 3368, 3370, 3372, 3374, 3376, or 3378.

28. The recombinant acid alpha glucosidase of claim 1, wherein the amino acid sequence further comprises a signal peptide.

29. The recombinant acid alpha glucosidase of claim 28, wherein the signal peptide is a mammalian signal peptide or a synthetic signal peptide.

30. The recombinant acid alpha glucosidase of claim 1, comprising an amino acid sequence comprising at least 90% sequence identity to the sequence of residues 20 to 944 of SEQ ID NO: 2.

31. The recombinant acid alpha glucosidase of claim 1, comprising an amino acid sequence comprising at least 91% sequence identity to the sequence of residues 20 to 944 of SEQ ID NO: 2.

32. The recombinant acid alpha glucosidase of claim 1, comprising an amino acid sequence comprising at least 92% sequence identity to the sequence of residues 20 to 944 of SEQ ID NO: 2.

33. The recombinant acid alpha glucosidase of claim 1, comprising an amino acid sequence comprising at least 93% sequence identity to the sequence of residues 20 to 944 of SEQ ID NO: 2.

34. The recombinant acid alpha glucosidase of claim 1, comprising an amino acid sequence comprising at least 94% sequence identity to the sequence of residues 20 to 944 of SEQ ID NO: 2.

35. The recombinant acid alpha glucosidase of claim 1, comprising an amino acid sequence comprising at least 95% sequence identity to the sequence of residues 20 to 944 of SEQ ID NO: 2.

36. The recombinant acid alpha glucosidase of claim 1, comprising an amino acid sequence comprising at least 96% sequence identity to the sequence of residues 20 to 944 of SEQ ID NO: 2.

37. The recombinant acid alpha glucosidase of claim 1, comprising an amino acid sequence comprising at least 97% sequence identity to the sequence of residues 20 to 944 of SEQ ID NO: 2.

38. The recombinant acid alpha glucosidase of claim 1, comprising an amino acid sequence comprising at least 98% sequence identity to the sequence of residues 20 to 944 of SEQ ID NO: 2.

39. The recombinant acid alpha glucosidase of claim 1, comprising an amino acid sequence comprising at least 99% sequence identity to the sequence of residues 20 to 944 of SEQ ID NO: 2.

* * * * *